(12) United States Patent
Learmonth et al.

(10) Patent No.: US 9,458,111 B2
(45) Date of Patent: Oct. 4, 2016

(54) PROCESS FOR THE SYNTHESIS OF SUBSTITUTED UREA COMPOUNDS

(75) Inventors: David Alexander Learmonth, S. Mamede do Coronado (PT); Brian Broadbelt, Oxfordshire (GB); Jorge Bruno Reis Wahnon, S. Mamede do Coronado (PT)

(73) Assignee: BIAL—PORTELA & CA, S.A., Sao Mamede do Coronado (PT)

( * ) Notice: Subject to any disclaimer, the term of this patent is extended or adjusted under 35 U.S.C. 154(b) by 0 days.

(21) Appl. No.: 13/811,577

(22) PCT Filed: Jul. 28, 2011

(86) PCT No.: PCT/PT2011/000025
§ 371 (c)(1),
(2), (4) Date: Jan. 22, 2013

(87) PCT Pub. No.: WO2012/015324
PCT Pub. Date: Feb. 2, 2012

(65) Prior Publication Data
US 2013/0123493 A1     May 16, 2013

Related U.S. Application Data

(60) Provisional application No. 61/368,942, filed on Jul. 29, 2010.

(51) Int. Cl.
C07D 233/90 (2006.01)
C07D 401/14 (2006.01)
C07D 405/14 (2006.01)
C07D 413/12 (2006.01)
C07D 401/12 (2006.01)
(Continued)

(52) U.S. Cl.
CPC ........... *C07D 233/90* (2013.01); *C07D 233/60* (2013.01); *C07D 233/61* (2013.01); *C07D 233/64* (2013.01); *C07D 401/04* (2013.01); *C07D 401/06* (2013.01); *C07D 401/12* (2013.01); *C07D 401/14* (2013.01); *C07D 403/10* (2013.01); *C07D 403/12* (2013.01); *C07D 405/12* (2013.01); *C07D 405/14* (2013.01); *C07D 413/12* (2013.01)

(58) Field of Classification Search
CPC  C07D 233/90; C07D 405/12; C07D 401/04; C07D 405/14; C07D 401/14; C07D 403/10
See application file for complete search history.

(56) References Cited
U.S. PATENT DOCUMENTS
2004/0019065 A1   1/2004   Romines, III et al.

FOREIGN PATENT DOCUMENTS
CH   WO 9804531 A1 * 2/1998 ............ C07D 233/54
PT   WO 2010074588 A2 * 7/2010 ............ C07D 231/12
(Continued)

OTHER PUBLICATIONS
Wang et al. J. Org. Chem. 1997, 62, 7288.*
(Continued)

*Primary Examiner* — Nyeemah A Grazier
*Assistant Examiner* — Amanda L Aguirre
(74) *Attorney, Agent, or Firm* — Banner & Witcoff, Ltd.

(57) ABSTRACT

A process for preparing a substitute urea of Formula (II) or Formula (I), or a pharmaceutically acceptable salt or ester thereof:

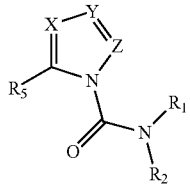

Formula II

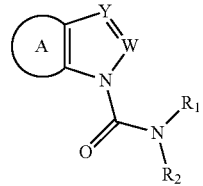

Figure 1:
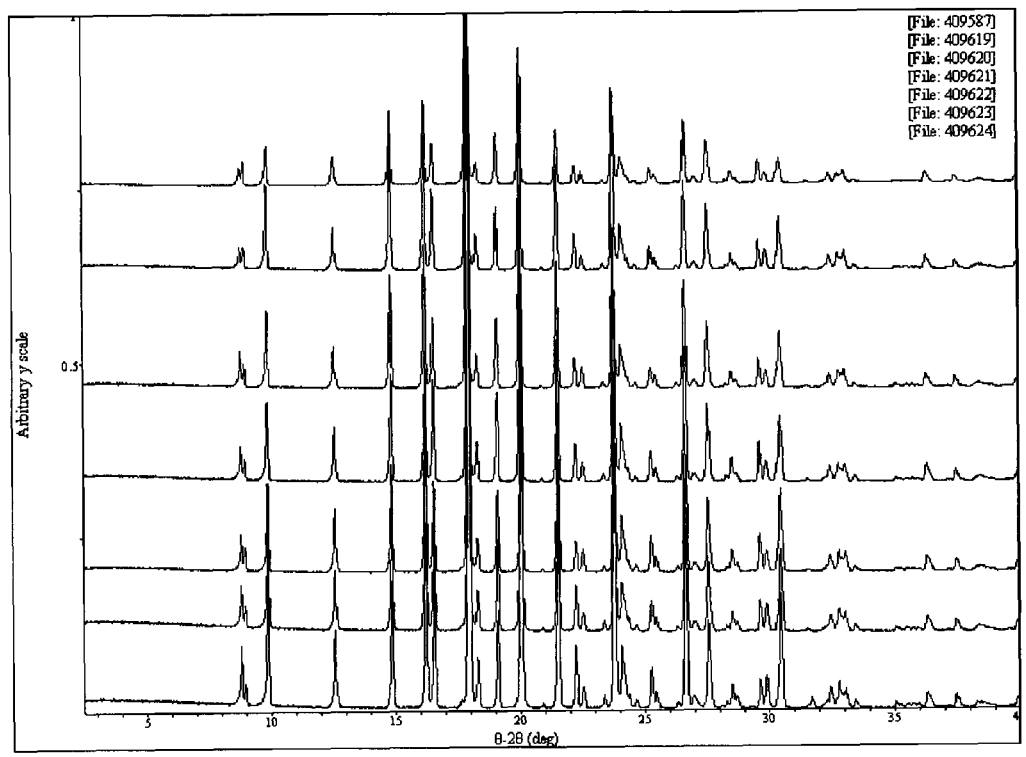

Formula I the process comprising the reaction of a carbamate of Formula (II'): Formula (I'):

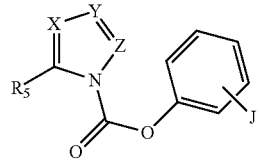

Formula II'

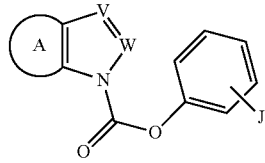

Formula I' with a primary or secondary amine of the formula R1R2NH, wherein ring A, and R1, R2, R5, V, W, X, Y and Z are as defined herein.

26 Claims, 2 Drawing Sheets

(51) Int. Cl.
  *C07D 405/12*  (2006.01)
  *C07D 403/12*  (2006.01)
  *C07D 233/60*  (2006.01)
  *C07D 233/61*  (2006.01)
  *C07D 233/64*  (2006.01)
  *C07D 401/04*  (2006.01)
  *C07D 401/06*  (2006.01)
  *C07D 403/10*  (2006.01)

(56) References Cited

FOREIGN PATENT DOCUMENTS

| WO | WO 98/04531 | 2/1998 |
| WO | WO 2007/109783 A2 | 9/2007 |
| WO | WO 2010/074588 A2 | 7/2010 |

OTHER PUBLICATIONS

Curtin et al., "Discovery an Evaluation of a Series of 3-Acylindole Imidazopyridine Platelet-Activating Factor Antagonists," Journal of Medicinal Chemistry, vol. 41, No. 1, Jan. 1, 1998, pp. 74-95.

Lee et al., "The direct conversion of carbamates to ureas using aluminum amides," Tetrahedron, vol. 60, 2004, pp. 3439-3443.

Porcs-Makkay et al., "Versatile synthesis of oxindole-1,3-dicarboxamides," Tetrahedron, vol. 66, No. 34, Jun. 12, 2010, pp. 7017-7027.

Wang et al., "Antitumor Imidazotetrazines. 35. New Synthetic Routes to the Antitumor Drug Temozolomide," Journal of Organic Chemistry, vol. 21, No. 62, Jan. 1, 1997, pp. 7288-7294.

Kanzian et al., "Nucleophilic Reactivities of Primary and Secondary Amines in Acetonitrile," Eur. J. Org. Chem. 6379-85, 2009.

* cited by examiner

PROCESS FOR THE SYNTHESIS OF SUBSTITUTED UREA COMPOUNDS

The present invention relates to processes for the synthesis of substituted urea compounds. In particular, though not exclusively, it relates to processes for synthesising certain active pharmaceutical ingredients having a heteroaryl N-carboxamide core, and novel intermediates used in such processes.

Molecules containing urea functional groups are of interest in medicinal chemistry. A common method for their preparation is to convert a first amine component to an isocyanate or activated carbamate, followed by reaction with a second amine component. However, this approach is not available when neither of the amine components is a primary amine. In particular, secondary amines cannot be converted to isocyanates, and secondary carbamates are known to suffer from low reactivity in the required nucleophilic substitution reaction with the second amine component (see Lee et al. (2004) *Tetrahedron* 60, 3439). Complex or harsh approaches have thus been used in these circumstances, e.g. formation of a carbamoyl chloride, or the aluminium amide approach described by Lee et al. (above).

A number of molecules having fatty acid amide hydrolase (FAAH) inhibitory activity and containing urea groups are disclosed in WO 2010/074588, the entire contents of which, and in particular the details of the compounds claimed therein, are hereby incorporated herein. For example, a subgroup of the compounds disclosed in this document contain an imidazole-1-carboxamide motif. These compounds are generally prepared using an approach comprising carbamoylation of 1H-imidazole derivatives with carbamoyl chlorides. For illustrative purposes, 3-(1-(cyclohexyl (methyl)carbamoyl)-1H-imidazol-4-yl)pyridine-1-oxide, hereinafter sometimes referred to as compound A, is prepared by reaction of the imidazolylpyridine hydrochloride with potassium 2-methylpropan-2-olate, followed by treatment with pyridine and N,N-dimethylpyridine-4-amine, this step being followed by addition of cyclohexyl(methyl)carbamic chloride. This mixture is kept at elevated temperature overnight, following which a non-oxidised intermediate can be extracted in low yield. This intermediate is then oxidised to give compound A.

The limitations of some of the prior art procedures disclosed in WO 2010/074588, particularly that disclosed for the synthesis of compound A, include the very low overall yield, the fairly harsh reaction conditions, and (in the case of compounds such as compound A which contain a heteroaryl N-oxide moiety) the need to purify the non-oxidised intermediate using chromatography. In addition, the use of a carbamoyl chloride entails the use of a potentially toxic and/or carcinogenic reagent, owing to the high reactivity of such carbamoylating agents. Furthermore, the particular carbamoyl chloride used for synthesis of compound A can only be prepared by reaction of N-methyl-N-cyclohexylamine with phosgene (or phosgene-generating reagents), itself a highly toxic reagent whose handling entails significant potential safety concerns.

Therefore, there exists a need to provide an efficient approach for the formation of substituted ureas, particularly (but not exclusively) those containing an imidazole-1-carboxamide core.

According to one aspect of the present invention, there is provided a process for preparing a substituted urea compound of Formula II or Formula I, or a pharmaceutically acceptable salt or ester thereof,

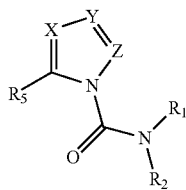

Formula II

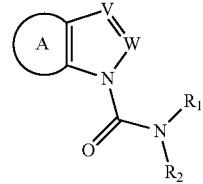

Formula I the process comprising the reaction of a carbamate of Formula I' or Formula II',

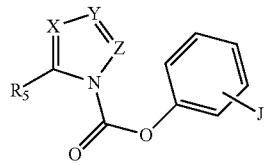

Formula II'

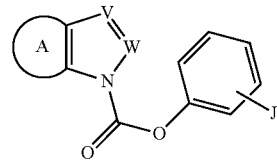

Formula I' with a primary or secondary amine of the formula: R1R2NH, wherein R1 and R2 can each be independently selected from H, $C_{1-20}$ alkyl, $C_{1-6}$ alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, R1a, halogen, OH, OR1a, OCOR1a, SH, SR1a, SCOR1a, $NH_2$, NHR1a, $NHSO_2NH_2$, $NHSO_2R1a$, NR1aCOR1b, NHCOR1a, NR1aR1b, COR1a, CSR1a, CN, COOH, COOR1a, $CONH_2$, CONHOH, CONHR1a, CONHOR1a, $SO_2R1a$, $SO_3H$, $SO_2NH_2$, CONR1aR1b, $SO_2NR1aR1b$, wherein R1a and R1b are independently selected from $C_{1-6}$ alkyl, substituted $C_{1-6}$ alkyl, aryl, heteroaryl, $C_{3-8}$ cycloalkyl and heterocyclyl, or R1a and R1b, together with the heteroatom to which they are joined, can form heterocyclyl, wherein, when R1 or R2 is $C_{1-20}$ alkyl (such as $C_{1-6}$ alkyl), alkoxy, aryl, heteroaryl, heterocyclyl, $C_{3-10}$ cycloalkyl (such as $C_{3-8}$ cycloalkyl), aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, or is a group containing one or more of these moieties, each of these moieties may optionally be substituted with one or more groups selected from R1c, halogen, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-10}$ alkyl, OH, OR1c, OCOR1c, SH, SR1c, SCOR1c, $NH_2$, $NO_2$, NHR1c, $NHSO_2NH_2$, $NHSO_2R1c$, NR1cCOR1d, NHC(NH)NH$_2$, NHCOR1c, NR1cR1d, COR1c, CSR1c, CN, COOH, COOR1c, CONH$_2$, CONHOH, CONHR1c, CONHOR1c, C(NOH)NH$_2$, CONR1cR1d, SO$_2$R1c, SO$_3$H, SO$_2$NH$_2$, SO$_2$NR1cR1d, wherein R1c and R1d are independently selected from C$_{1-6}$ alkyl, substituted C$_{1-6}$ alkyl, aryl, heteroaryl, C$_{3-8}$ cycloalkyl and heterocyclyl, or R1c and R1d, together with the heteroatom to which they are joined, can form heterocyclyl, wherein, when the substituent of R1 or R2 is C$_{1-10}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-6}$ alkyl, C$_{3-8}$ cycloalkyl or is a group containing one or more of these moieties, each of these moieties may optionally be substituted with one or more groups selected from R1e, halogen, C$_{1-10}$ alkyl, OH, OR1e, OCOR1e, SH, SR1e, SCOR1e, NH$_2$, NO$_2$, NHR1e, NHSO$_2$NH$_2$, NHSO$_2$R1e, NR1eCOR1f, NHC(NH)NH$_2$, NHCOR1e, NR1eR1f, COR1e, CSR1e, CN, COOH, COOR1e, CONH$_2$, CONHOH, CONHR1e, CONHOR1e, C(NOH)NH$_2$, CONR1eR1f, SO$_2$R1e, SO$_3$H, SO$_2$NH$_2$, SO$_2$NR1eR1f, wherein R1e and R1f are independently selected from C$_{1-6}$ alkyl, substituted C$_{1-6}$ alkyl, aryl, heteroaryl, C$_{3-8}$ cycloalkyl and heterocyclyl, or R1e and R1f, together with the heteroatom to which they are joined, can form heterocyclyl, with the exception that R1 and R2 are not both H;

or

R1 and R2, together with the N to which they are attached, can form a heteroaryl or heterocyclyl group, each of which may optionally be substituted with one or more oxygen atoms or one or more groups selected from aryl, heteroaryl, partially or fully saturated heterocyclyl, C$_{3-8}$ cycloalkyl, C$_{1-6}$ alkyl, aryl C$_{1-6}$ alkyl, heteroaryl C$_{1-6}$ alkyl, heterocyclyl C$_{1-6}$ alkyl, C$_{3-8}$ cycloalkyl C$_{1-6}$ alkyl, C$_{1-6}$ alkoxy, aryloxy, heteroaryloxy, heterocyclyloxy, R2a, halogen, OH, OR2a, OCOR2a, SH, SR2a, SCOR2a, NH$_2$, NO$_2$, NHR2a, NHSO$_2$NH$_2$, NHSO$_2$R2a, NR2aCOR2b, NHC(NH)NH$_2$, NHCOR2a, NR2aR2b, COR2a, CSR2a, CN, COOH, COOR2a, CONH$_2$, CONHOH, CONHR2a, CONHOR2a, C(NOH)NH$_2$, CONR2aR2b, SO$_2$R2a, SO$_3$H, SO$_2$NH$_2$, SO$_2$NR2aR2b, wherein R2a and R2b are independently selected from C$_{1-6}$ alkyl, substituted C$_{1-6}$ alkyl, aryl, heteroaryl, C$_{3-8}$ cycloalkyl and heterocyclyl, or R2a and R2b, together with the heteroatom to which they are joined, can form heterocyclyl, wherein, when the substituent of the heteroaryl or heterocyclyl formed by R1 and R2 together is aryl, heteroaryl, heterocyclyl, C$_{3-8}$ cycloalkyl, C$_{1-6}$ alkyl, aryl C$_{1-6}$ alkyl, heteroaryl C$_{1-6}$ alkyl, heterocyclyl C$_{1-6}$ alkyl, C$_{3-8}$ cycloalkyl C$_{1-6}$ alkyl, C$_{1-6}$ alkoxy, aryloxy, heteroaryloxy, heterocyclyloxy, or a group containing one or more of these moieties, each of these moieties may optionally be substituted with one or more groups selected from halogen, hydroxyl, C$_{1-6}$ alkyl, aryl, heteroaryl, heterocyclyl, C$_{3-8}$ cycloalkyl, C$_{1-4}$ alkoxy, aryloxy, heteroaryloxy, heterocyclyloxy, C$_{3-8}$ cycloalkyloxy, aryl C$_{1-4}$ alkoxy, heteroaryl C$_{1-6}$ alkoxy, heterocyclyl C$_{1-4}$ alkoxy, C$_{3-8}$ cycloalkyl C$_{1-4}$ alkoxy, R2c, OR2c, OCOR2c, SH, SR2c, SCOR2c, NH$_2$, NO$_2$, NHR2c, NHSO$_2$NH$_2$, NHSO$_2$R2c, NR2cCOR2d, NHC(NH)NH$_2$, NHCOR2c, NR2cR2d, COR2c, CSR2c, CN, COOH, COOR2c, CONH$_2$, CONHOH, CONHR2c, CONHOR2c, C(NOH)NH$_2$, CONR2cR2d, SO$_2$R2c, SO$_3$H, SO$_2$NH$_2$, SO$_2$NR2cR2d, wherein R2c and R2d are independently selected from C$_{1-6}$ alkyl, substituted C$_{1-6}$ alkyl, aryl, heteroaryl, C$_{3-8}$ cycloalkyl and heterocyclyl, or R2c and R2d, together with the heteroatom to which they are joined, can form heterocyclyl, wherein, when the substituent of the substituent of the heteroaryl or heterocyclyl formed by R1 and R2 together is C$_{1-6}$ alkyl, aryl, heteroaryl, heterocyclyl, C$_{3-8}$ cycloalkyl, C$_{1-6}$ alkoxy, aryloxy, heteroaryloxy, heterocyclyloxy, C$_{3-8}$ cycloalkyloxy, aryl C$_{1-4}$ alkoxy, heteroaryl C$_{1-4}$ alkoxy, heterocyclyl C$_{1-4}$ alkoxy, C$_{3-8}$ cycloalkyl C$_{1-4}$ alkoxy, or is a group containing one or more of these moieties, each of these moieties may optionally be substituted with one or more groups selected from C$_{1-4}$ alkoxy, R2e, halogen, OH, OR2e, OCOR2e, SH, SR2e, SCOR2e, NH$_2$, NO$_2$, NHR2e, NHSO$_2$NH$_2$, NHSO$_2$R2e, NR2eCOR2f, NHC(NH)NH$_2$, NR2eR2f, NHCOR2e, COR2e, CSR2e, CN, COOH, COOR2e, CONH$_2$, CONHOH, CONHR2e, CONHOR2e, C(NOH)NH$_2$, CONR2eR2f, SO$_2$R2e, SO$_3$H, SO$_2$NH$_2$, SO$_2$NR2eR2f, wherein R2e and R2f are independently selected from C$_{1-6}$ alkyl, substituted C$_{1-6}$ alkyl, aryl, heteroaryl, C$_{3-8}$ cycloalkyl and heterocyclyl, or R2e and R2f, together with the heteroatom to which they are joined, can form heterocyclyl;

J is H or a nitro group, and is attached at any available position on the phenyl ring;

Ring A is selected from aryl, heteroaryl and heterocyclyl moieties, each of which may optionally be substituted with one or more groups selected from halogen, C$_{1-6}$ alkyl, aryl, heteroaryl, heterocyclyl, C$_{1-6}$ alkoxy, aryloxy, heteroaryloxy, heterocyclyloxy, Ra, C$_{1-10}$ alkyl, OH, ORa, OCORa, SH, SRa, SCORa, NH$_2$, NO$_2$, NHRa, NHSO$_2$NH$_2$, NHSO$_2$Ra, NRaCORb, NHCORa, NHC(NH)NH$_2$, NRaRb, CORa, CSRa, CN, COOH, COORa, CONH$_2$, CONHRa, CONHOH, CONHORa, C(NOH)NH$_2$, CONRaRb, SO$_2$Ra, SO$_3$H, SO$_2$NH$_2$, SO$_2$NRaRb, wherein Ra and Rb are independently selected from C$_{1-6}$ alkyl, substituted C$_{1-6}$ alkyl, aryl, heteroaryl, C$_{3-8}$ cycloalkyl and heterocyclyl, or Ra and Rb, together with the heteroatom to which they are joined, can form heterocyclyl, wherein, when Ring A is substituted with C$_{1-6}$ alkyl, aryl, heteroaryl, heterocyclyl, C$_{1-6}$ alkoxy, aryloxy, heteroaryloxy, heterocyclyloxy, C$_{1-10}$ alkyl, C$_{3-8}$ cycloalkyl or is substituted with a group containing one or more of these moieties, each of these moieties may optionally be substituted with one or more groups selected from halogen, Rc, C$_{1-10}$ alkyl, aryl C$_{1-6}$ alkyl, heteroaryl C$_{1-6}$ alkyl, heterocyclyl C$_{1-6}$ alkyl, OH, ORc, OCORc, SH, SRc, SCORc, NH$_2$, NO$_2$, NHRc, NHSO$_2$NH$_2$, NHSO$_2$Rc, NRcCORd, NHCORc, NHC(NH)NH$_2$, NRcRd, CORc, CSRc, CN, COOH, COORc, CONH$_2$, CONHOH, CONHRc, CONHORc, C(NOH)NH$_2$, CONRcRd, SO$_2$Rc, SO$_3$H, SO$_2$NH$_2$, SO$_2$NRcRd, wherein Rc and Rd are independently selected from C$_{1-6}$ alkyl, substituted C$_{1-6}$ alkyl, aryl, heteroaryl, C$_{3-8}$ cycloalkyl and heterocyclyl, or Rc and Rd, together with the heteroatom to which they are joined, can form heterocyclyl;

V can be N, CH or C—R3, wherein R3 is halogen, C$_{1-10}$ alkyl, aryl, heteroaryl, heterocyclyl, C$_{3-8}$ cycloalkyl, C$_{1-6}$ alkoxy, aryloxy, heteroaryloxy, heterocyclyloxy, R3a, OH, OR3a, SH, SR3a, OCOR3a, SCOR3a, NH$_2$, NO$_2$, NHR3a, NHSO$_2$NH$_2$, NHSO$_2$R3a, NR3aCOR3b, NHCOR3a, NHC(NH)NH$_2$, NR3aR3b, COR3a, CSR3a, CN, COOH, COOR3a, CONH$_2$, CONHOH, CONHR3a, CONHOR3a, C(NOH)NH$_2$, CONR3aR3b, SO$_2$R3a, SO$_3$H, SO$_2$NH$_2$, SO$_2$NR3aR3b, wherein R3a and R3b are independently selected from C$_{1-6}$ alkyl, substituted C$_{1-6}$ alkyl, aryl, heteroaryl, C$_{3-8}$ cycloalkyl and heterocyclyl, or R3a and R3b, together with the heteroatom to which they are joined, can form heterocyclyl, wherein, when R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R3c, $C_{1-10}$ alkyl, OH, OR3c, OCOR3c, SH, SR3c, SCOR3c, $NH_2$, $NO_2$, NHR3c, $NHSO_2NH_2$, $NHSO_2R3c$, NR3cCOR3d, NHCOR3c, NHC(NH)$NH_2$, NR3cR3d, COR3c, CSR3c, CN, COOH, COOR3c, $CONH_2$, CONHOH, CONHR3c, CONHOR3c, C(NOH)$NH_2$, CONR3cR3d, $SO_2R3c$, $SO_3H$, $SO_2NH_2$, $SO_2NR3cR3d$, wherein R3c and R3d are independently selected from $C_{1-6}$ alkyl, substituted $C_{1-6}$ alkyl, aryl, heteroaryl, $C_{3-8}$ cycloalkyl and heterocyclyl, or R3c and R3d, together with the heteroatom to which they are joined, can form heterocyclyl, wherein, when the substituent of R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R3e, $C_{1-10}$ alkyl, OH, OR3e, OCOR3e, SH, SR3e, SCOR3e, $NH_2$, $NO_2$, NHR3e, $NHSO_2NH_2$, $NHSO_2R3e$, NR3eCOR3f, NHCOR3e, NHC(NH)$NH_2$, NR3eR3f, COR3e, CSR3e, CN, COOH, COOR3e, $CONH_2$, CONHOH, CONHR3e, CONHOR3e, C(NOH)$NH_2$, CONR3eR3f, $SO_2R3e$, $SO_3H$, $SO_2NH_2$, $SO_2NR3eR3f$, wherein R3e and R3f are independently selected from $C_{1-6}$ alkyl, substituted $C_{1-6}$ alkyl, aryl, heteroaryl, $C_{3-8}$ cycloalkyl and heterocyclyl, or R3e and R3f, together with the heteroatom to which they are joined, can form heterocyclyl;

W can be N, CH or C—R4, wherein R4 is halogen, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, R4a, OH, OR4a, SH, SR4a, OCOR4a, SCOR4a, $NH_2$, $NO_2$, NHR4a, $NHSO_2NH_2$, $NHSO_2R4a$, NR4aCOR4b, NHCOR4a, NHC(NH)$NH_2$, NR4aR4b, COR4a, CSR4a, CN, COOH, COOR4a, $CONH_2$, CONHOH, CONHR4a, CONHOR4a, C(NOH)$NH_2$, CONR4aR4b, $SO_2R4a$, $SO_3H$, $SO_2NH_2$, $SO_2NR4aR4b$, wherein R4a and R4b are independently selected from $C_{1-6}$ alkyl, substituted $C_{1-6}$ alkyl, aryl, heteroaryl, $C_{3-8}$ cycloalkyl and heterocyclyl, or R4a and R4b, together with the heteroatom to which they are joined, can form heterocyclyl, wherein, when R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R4c, $C_{1-10}$ alkyl, OH, OR4c, OCOR4c, SH, SR4c, SCOR4c, $NH_2$, $NO_2$, NHR4c, $NHSO_2NH_2$, $NHSO_2R4c$, NR4cCOR4d, NHCOR4c, NHC(NH)$NH_2$, NR4cR4d, COR4c, CSR4c, CN, COOH, COOR4c, $CONH_2$, CONHOH, CONHR4c, CONHOR4c, C(NOH)$NH_2$, CONR4cR4d, $SO_2R4c$, $SO_3H$, $SO_2NH_2$, $SO_2NR4cR4d$, wherein R4c and R4d are independently selected from $C_{1-6}$ alkyl, substituted $C_{1-6}$ alkyl, aryl, heteroaryl, $C_{3-8}$ cycloalkyl and heterocyclyl, or R4c and R4d, together with the heteroatom to which they are joined, can form heterocyclyl, wherein, when the substituent of R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R4e, $C_{1-10}$ alkyl, OH, OR4e, OCOR4e, SH, SR4e, SCOR4e, $NH_2$, $NO_2$, NHR4e, $NHSO_2NH_2$, $NHSO_2R4e$, NR4eCOR4f, NHCOR4e, NHC(NH)$NH_2$, NR4eR4f, COR4e, CSR4e, CN, COOH, COOR4e, $CONH_2$, CONHOH, CONHR4e, CONHOR4e, C(NOH)$NH_2$, CONR4eR4f, $SO_2R4e$, $SO_3H$, $SO_2NH_2$, $SO_2NR4eR4f$, wherein R4e and R4f are independently selected from $C_{1-6}$ alkyl, substituted $C_{1-6}$ alkyl, aryl, heteroaryl, $C_{3-8}$ cycloalkyl and heterocyclyl, or R4e and R4f, together with the heteroatom to which they are joined, can form heterocyclyl;

R5 together with the C to which it is attached, can form a carbonyl group with the double bonds in Formula II rearranged accordingly, or R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, $NHSO_2NH_2$, $NHSO_2R5a$, NR5aCOR5b, NHCOR5a, NHC(NH)$NH_2$, NR5aR5b, COR5a, CSR5a, CN, COOH, COOR5a, $CONH_2$, CONHOH, CONHR5a, CONHOR5a, C(NOH)$NH_2$, CONR5aR5b, $SO_2R5a$, $SO_3H$, $SO_2NH_2$, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, $NO_2$, NHR5c, $NHSO_2NH_2$, $NHSO_2R5c$, NR5cCOR5d, NHCOR5c, NHC(NH)$NH_2$, NR5cR5d, COR5c, CSR5c, CN, COOH, COOR5c, $CONH_2$, CONHOH, CONHR5c, CONHOR5c, C(NOH)$NH_2$, CONR5cR5d, $SO_2R5c$, $SO_3H$, $SO_2NH_2$, $SO_2NR5cR5d$, wherein R5c and R5d are independently selected from $C_{1-6}$ alkyl, substituted $C_{1-6}$ alkyl, aryl, heteroaryl, $C_{3-8}$ cycloalkyl and heterocyclyl, or R5c and R5d, together with the heteroatom to which they are joined, can form heterocyclyl, wherein, when the substituent of R5 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R5e, $C_{1-6}$ alkyl, OH, OR5e, OCOR5e, SH, SR5e, SCOR5e, $NH_2$, $NO_2$, NHR5e, $NHSO_2NH_2$, $NHSO_2R5e$, NR5eCOR5f, NHCOR5e, NHC(NH)$NH_2$, NR5eR5f, COR5e, CSR5e, CN, COOH, COOR5e, $CONH_2$, CONHOH, CONHR5e, CONHOR5e, C(NOH)$NH_2$, CONR5eR5f, $SO_2R5e$, $SO_3H$, $SO_2NH_2$, $SO_2NR5eR5f$, wherein R5e and R5f are independently selected from $C_{1-6}$ alkyl, substituted $C_{1-6}$ alkyl, aryl, heteroaryl, $C_{3-8}$ cycloalkyl and heterocyclyl, or R5e and R5f, together with the heteroatom to which they are joined, can form heterocyclyl;

X can be O (with the double bonds in Formula II rearranged accordingly), N, CH or C—R6, wherein R6 is selected from $C_{1-6}$ alkyl, aryl, heteroaryl, heterocyclyl, $C_{1-6}$ alkoxy, aryloxy, heteroaryloxy, heterocyclyloxy, R6a, halogen, OH, OR6a, SH, SR6a, OCOR6a, SCOR6a, $NH_2$, $NO_2$, NHR6a, $NHSO_2NH_2$, $NHSO_2R6a$, NR6aCOR6b, NHCOR6a, NHC(NH)$NH_2$, NR6aR6b, COR6a, CSR6a, CN, COOH, COOR6a, CONH$_2$, CONHOH, CONHR6a, CONHOR6a, C(NOH)NH$_2$, CONR6aR6b, SO$_2$R6a, SO$_3$H, SO$_2$NH$_2$, SO$_2$NR6aR6b, wherein R6a and R6b are independently selected from C$_{1-6}$ alkyl, substituted C$_{1-6}$ alkyl, aryl, heteroaryl, C$_{3-8}$ cycloalkyl and heterocyclyl, or R6a and R6b, together with the heteroatom to which they are joined, can form heterocyclyl, wherein, when R6 is heteroaryl or heterocyclyl, each of these moieties may optionally be substituted with one or more oxygen atoms, and when R6 is C$_{1-6}$ alkyl, aryl, heteroaryl, heterocyclyl, C$_{1-6}$ alkoxy, aryloxy, heteroaryloxy, heterocyclyloxy, C$_{3-8}$ cycloalkyl, or is a group containing one or more of these moieties, each of these moieties may optionally be substituted with one or more groups selected from halogen, R6c, C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, OH, OR6c, OCOR6c, SH, SR6c, SCOR6c, NH$_2$, NO$_2$, NHR6c, NHSO$_2$NH$_2$, NHC(NH)NH$_2$, NHSO$_2$R6c, NR6cCOR6d, NHCOR6c, NR6cR6d, COR6c, CSR6c, CN, COOH, COOR6c, CONH$_2$, CONHR6c, CONHOR6c, CONHOH, C(NOH)NH$_2$, CONR6cR6d, SO$_2$R6c, SO$_3$H, SO$_2$NH$_2$, SO$_2$NR6cR6d, wherein R6c and R6d are independently selected from C$_{1-6}$ alkyl, substituted C$_{1-6}$ alkyl, aryl, heteroaryl, C$_{3-8}$ cycloalkyl and heterocyclyl, or R6c and R6d, together with the heteroatom to which they are joined, can form heterocyclyl, wherein, when the substituent of R6 is heteroaryl or heterocyclyl, each of these moieties may optionally be substituted with one or more oxygen atoms, or when the substituent of R6 is C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{3-8}$ cycloalkyl, or is a group containing one or more of these moieties, each of these moieties may optionally be substituted with one or more groups selected from halogen, R6e, C$_{1-6}$ alkyl, C$_{1-4}$ alkoxy, OH, OR6e, OCOR6e, SH, SR6e, SCOR6e, NH$_2$, NO$_2$, NHR6e, NHSO$_2$NH$_2$, NHC(NH)NH$_2$, NHSO$_2$R6e, NR6eCOR6f, NHCOR6e, NR6eR6f, COR6e, CSR6e, CN, COOH, COOR6e, CONH$_2$, CONHOH, CONHR6e, CONHOR6e, C(NOH)NH$_2$, CONR6eR6f, SO$_2$R6e, SO$_3$H, SO$_2$NH$_2$, SO$_2$NR6eR6f, wherein R6e and R6f are independently selected from C$_{1-6}$ alkyl, substituted C$_{1-6}$ alkyl, aryl, heteroaryl, C$_{3-8}$ cycloalkyl and heterocyclyl, or R6e and R6f, together with the heteroatom to which they are joined, can form heterocyclyl;

Y can be N, CH or C—R7, wherein R7 is selected from C$_{1-6}$ alkyl, aryl, heteroaryl, heterocyclyl, C$_{1-6}$ alkoxy, aryloxy, heteroaryloxy, heterocyclyloxy, R7a, halogen, OH, OR7a, SH, SR7a, OCOR7a, SCOR7a, NH$_2$, NO$_2$, NHR7a, NHSO$_2$NH$_2$, NHSO$_2$R7a, NR7aCOR7b, NHCOR7a, NHC(NH)NH$_2$, NR7aR7b, COR7a, CSR7a, CN, COOH, COOR7a, CONH$_2$, CONHOH, CONHR7a, CONHOR7a, C(NOH)NH$_2$, CONR7aR7b, SO$_2$R7a, SO$_3$H, SO$_2$NH$_2$, SO$_2$NR7aR7b, wherein R7a and R7b are independently selected from C$_{1-6}$ alkyl, substituted C$_{1-6}$ alkyl, aryl, heteroaryl, C$_{3-8}$ cycloalkyl and heterocyclyl, or R7a and R7b, together with the heteroatom to which they are joined, can form heterocyclyl, wherein, when R7 is heteroaryl or heterocyclyl, each of these moieties may optionally be substituted with one or more oxygen atoms, and when R7 is C$_{1-6}$ alkyl, aryl, heteroaryl, heterocyclyl, C$_{1-6}$ alkoxy, aryloxy, heteroaryloxy, heterocyclyloxy, C$_{3-8}$ cycloalkyl or is a group containing one or more of these moieties, each of these moieties may optionally be substituted with one or more groups selected from halogen, R7c, C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, OH, O7c, OCOR7c, SH, SR7c, SCOR7c, NH$_2$, NO$_2$, NHR7c, NHSO$_2$NH$_2$, NHC(NH)NH$_2$, NHSO$_2$R7c, NR7cCOR7d, NHCOR7c, NR7cR7d, COR7c, CSR7c, CN, COOH, COOR7c, CONH$_2$, CONHR7c, CONHOR7c, CONHOH, C(NOH)NH$_2$, CONR7cR7d, SO$_2$R7c, SO$_3$H, SO$_2$NH$_2$, SO$_2$NR7cR7d, wherein R7c and R7d are independently selected from C$_{1-6}$ alkyl, substituted C$_{1-6}$ alkyl, aryl, heteroaryl, C$_{3-8}$ cycloalkyl and heterocyclyl, or R7c and R7d, together with the heteroatom to which they are joined, can form heterocyclyl, wherein, when the substituent of R7 is heteroaryl or heterocyclyl, each of these moieties may optionally be substituted with one or more oxygen atoms, or when the substituent of R7 is C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{3-8}$ cycloalkyl, or is a group containing one or more of these moieties, each of these moieties may optionally be substituted with one or more groups selected from halogen, aryl, heteroaryl, heterocyclyl, aryl C$_{1-6}$ alkyl, heteroaryl C$_{1-6}$ alkyl, heterocyclyl C$_{1-6}$ alkyl, C$_{1-4}$ alkoxy, R7e, C$_{1-6}$ alkyl, OH, OR7e, OCOR7e, SH, SR7e, SCOR7e, NH$_2$, NO$_2$, NHR7e, NHSO$_2$NH$_2$, NHSO$_2$R7e, NHC(NH)NH$_2$, NR7eCOR7f, NHCOR7e, NR7eR7f, COR7e, CSR7e, CN, COOH, COOR7e, CONH$_2$, CONHOH, CONHR7e, CONHOR7e, C(NOH)NH$_2$, CONR7eR7f, SO$_2$R7e, SO$_3$H, SO$_2$NH$_2$, SO$_2$NR7eR7f, wherein R7e and R7f are independently selected from C$_{1-6}$ alkyl, substituted C$_{1-6}$ alkyl, aryl, heteroaryl, C$_{3-8}$ cycloalkyl and heterocyclyl, or R7e and R7f, together with the heteroatom to which they are joined, can form heterocyclyl;

Z can be N, CH or C—R8, wherein R8 is selected from C$_{1-10}$ alkyl, aryl, heteroaryl, heterocyclyl, C$_{1-6}$ alkoxy, aryloxy, heteroaryloxy, heterocyclyloxy, R8a, halogen, OH, OR8a, SH, SR8a, OCOR8a, SCOR8a, NH$_2$, NO$_2$, NHR8a, NHSO$_2$NH$_2$, NHSO$_2$R8a, NR8aCOR8b, NHCOR8a, NHC(NH)NH$_2$, NR8aR8b, COR8a, CSR8a, CN, COOH, COOR8a, CONH$_2$, CONHOH, CONHR8a, CONHOR8a, C(NOH)NH$_2$, CONR8aR8b, SO$_2$R8a, SO$_3$H, SO$_2$NH$_2$, SO$_2$NR8aR8b, wherein R8a and R8b are independently selected from C$_{1-6}$ alkyl, substituted C$_{1-6}$ alkyl, aryl, heteroaryl, C$_{3-8}$ cycloalkyl and heterocyclyl, or R8a and R8b, together with the heteroatom to which they are joined, can form heterocyclyl, wherein, when R8 is C$_{1-6}$ alkyl, C$_{1-10}$ alkyl, aryl, heteroaryl, heterocyclyl, C$_{1-6}$ alkoxy, aryloxy, heteroaryloxy, heterocyclyloxy, C$_{3-8}$ cycloalkyl, or is a group containing one or more of these moieties, each of these moieties may optionally be substituted with one or more groups selected from halogen, R8c, C$_{1-6}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, OH, OR8c, OCOR8c, SH, SR8c, SCOR8c, NH$_2$, NO$_2$, NHR8c, NHSO$_2$NH$_2$, NHSO$_2$R8c, NR8cCOR8d, NHCOR8c, NHC(NH)NH$_2$, NR8cR8d, COR8c, CSR8c, CN, COOH, COOR8c, CONH$_2$, CONHOH, CONHR8c, CONHOR8c, C(NOH)NH$_2$, CONR8cR8d, SO$_2$R8c, SO$_3$H, SO$_2$NH$_2$, SO$_2$NR8cR8d, wherein R8c and R8d are independently selected from C$_{1-6}$ alkyl, substituted C$_{1-6}$ alkyl, aryl, heteroaryl, $C_{3-8}$ cycloalkyl and heterocyclyl, or R8c and R8d, together with the heteroatom to which they are joined, can form heterocyclyl, wherein, when the substituent of R8 is $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, R8e, $C_{1-6}$ alkyl, OH, OR8e, OCOR8e, SH, SR8e, SCOR8e, $NH_2$, $NO_2$, NHR8e, $NHSO_2NH_2$, $NHSO_2R8e$, NR8eCOR8f, NHCOR8e, NHC(NH)$NH_2$, NR8eR8f, COR8e, CSR8e, CN, COOH, COOR8e, $CONH_2$, CONHOH, CONHR8e, CONHOR8e, C(NOH)$NH_2$, CONR8eR8f, $SO_2R8e$, $SO_3H$, $SO_2NH_2$, $SO_2NR8eR8f$, wherein R8e and R8f are independently selected from $C_{1-6}$ alkyl, substituted $C_{1-6}$ alkyl, aryl, heteroaryl, $C_{3-8}$ cycloalkyl and heterocyclyl, or R8e and R8f, together with the heteroatom to which they are joined, can form heterocyclyl;

wherein, at most, two of the atoms or groups denoted X, Y and Z can be N;

wherein, when W is N, the CONR1R2 group may be joined to W instead, with the double bonds in Formula I rearranged accordingly.

Compared to the processes described in the prior art, the process of the present invention provides a simpler approach to the production of ureas of Formula II or Formula I. It allows the facile conversion of simple, unactivated O-phenyl carbamates to substituted ureas simply by addition of an amine, with reaction between the carbamate and amine proceeding at room temperature. The process of the invention thus uses fewer steps, fewer reagents, less hazardous reagents, and/or less harsh conditions than prior art processes. In addition, compared to the process described in WO2010/074588, the process of the present invention provides a significantly greater yield under a significantly more straightforward isolation protocol. The simplicity of the process of the present invention is surprising given the processes described previously.

The term '$C_{x-y}$ alkyl' as used herein refers to a linear or branched saturated hydrocarbon group containing from x to y carbon atoms. For example, $C_{1-6}$ alkyl refers to a linear or branched saturated hydrocarbon group containing from 1 to 6 carbon atoms. Examples of $C_{1-6}$ alkyl groups include methyl, ethyl, n-propyl, isopropyl, n-butyl, isobutyl, sec-butyl, tert butyl, n-pentyl, isopentyl, neopentyl and hexyl. Preferably, the hydrocarbon group is linear. The group $C_{1-10}$ alkyl is preferably $C_{1-6}$ alkyl. The term '$C_{x-y}$ alkyl' is also used to mean a linear or branched saturated hydrocarbon group containing from x to y carbon atoms and in which a terminal methyl group is further substituted, i.e. so as to render a $C_{x-y}$ alkylene group.

The term '$C_{x-y}$ alkynyl' as used herein refers to a linear or branched hydrocarbon group containing from x to y carbon atoms and at least one carbon-carbon triple bond. For example, $C_{1-6}$ alkynyl refers to a linear or branched hydrocarbon group containing from 1 to 6 carbon atoms. Examples of $C_{1-6}$ alkynyl groups include, ethynyl, methylbutynyl (e.g. 3-methyl-1-butynyl), 1,3-butadiynyl and 1,3,5-hexatriynyl.

The term 'aryl' as used herein refers to a $C_{6-12}$ monocyclic or bicyclic hydrocarbon ring wherein at least one ring is aromatic. Examples of such groups include phenyl, naphthalenyl and tetrahydronaphthalenyl.

The term 'heteroaryl' as used herein refers to a 5-6 membered monocyclic aromatic or a fused 8-10 membered bicyclic aromatic ring which monocyclic or bicyclic ring contains 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such bicyclic aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridyl, furopyridyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and imidazopyridyl.

The term 'heteroaryl substituted with one or more oxygen atoms' refers to a heteroaryl ring which has one or more oxygen atoms bonded to the ring. It does not mean that the heteroaryl ring contains one or more oxygen atoms as ring atoms, although in some embodiments, this may be the case. Preferably, the one or more oxygen atoms is bonded to a nitrogen heteroatom in the heteroaryl ring. A heteroaryl substituted with an oxygen atom may contain an N-oxide. An example of a heteroaryl substituted with one or more oxygen atoms is 1-oxidopyridyl in which the pyridyl nitrogen is oxidised.

The term 'heterocyclyl' refers to a 3-8 (preferably 4-8 and, more preferably, 4-7) membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulphur. Examples of such monocyclic rings include oxaziridinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1H-3-benzazepine, 4-(benzo[d][1,3]dioxol-5-ylmethyl)piperazin-1-yl, and, tetrahydroisoquinolinyl.

The term 'heterocyclyl substituted with one or more oxygen atoms' refers to a heterocyclyl ring which has one or more oxygen atoms bonded to the ring. It does not mean that the heterocyclyl ring contains one or more oxygen atoms as ring atoms, although in some embodiments, this may be the case. Preferably, the one or more oxygen atoms is bonded to a heteroatom, such as nitrogen or sulphur, in the heterocyclyl ring. An example of a heterocyclyl substituted with one or more oxygen atoms is 1,1-dioxido-1,3-thiazolidinyl.

The terms 'bicyclic ring' and 'fused' in the context of a bicyclic ring refers to two rings which are joined together across a bond between two atoms (e.g. naphthalene), across a sequence of atoms to form a bridge (e.g. quinuclidine) or together at a single atom to form a Spiro compound (e.g. 1,4-dioxa-8-aza-spiro[4.5]decane and N,3,3-dimethyl-1,5-dioxaspirol[5.5]undecan-9-yl).

The term '$C_{x-y}$ cycloalkyl' as used herein refers to a saturated hydrocarbon ring of x to y carbon atoms which can be mono, bi or tricyclic. For example, $C_{3-10}$ cycloalkyl refers to a saturated mono, bi or tricyclic hydrocarbon ring of 3 to 10 carbon atoms. Examples of $C_{3-10}$ cycloalkyl groups include cyclopropyl, cyclobutyl, cyclopentyl, cyclohexyl, cycloheptyl, cyclooctyl and adamantyl.

The term 'aryl $C_{x-y}$ alkyl' as used herein refers to an aryl group as defined above attached to a $C_{x-y}$ alkyl as defined above. For example, aryl $C_{1-6}$ alkyl refers to an aryl group attached to a linear or branched saturated hydrocarbon group containing from 1 to 6 carbon atoms. Examples of aryl $C_{1-6}$ alkyl groups include benzyl, phenylethyl, phenylpropyl, phenylbutyl, phenylpentyl and phenylhexyl.

The terms 'heteroaryl $C_{x-y}$ alkyl', 'heterocyclyl $C_{x-y}$ alkyl' and '$C_{x-y}$ cycloalkyl $C_{x-y}$ alkyl' as used herein refers to a heteroaryl, heterocyclyl or $C_{x-y}$ cycloalkyl group as defined above attached to a $C_{x-y}$ alkyl as defined above.

The term '$C_{x-y}$ alkoxy' as used herein refers to an —O—$C_{x-y}$ alkyl group wherein $C_{x-y}$ alkyl is as defined above. Examples of such groups include methoxy, ethoxy, propoxy, butoxy, pentoxy and hexoxy.

The term 'aryloxy' as used herein refers to an —O-aryl group. Examples of such groups include phenoxy. The terms 'heteroaryloxy' and 'heterocyclyloxy' as used herein refer to an —O-heteroaryl and —O-heterocyclyl group respectively.

The term 'halogen' as used herein refers to a fluorine, chlorine, bromine or iodine atom, unless otherwise specified.

The term '$C_{x-y}$ alkylamino' as used herein refers to a secondary amine group (—NH(R)) of which the R group is selected from a linear or branched saturated hydrocarbon group containing from x to y carbon atoms. Examples of $C_{x-y}$ alkylamino groups include methylamino, ethylamino and propylamino.

The term '$C_{x-y}$ dialkylamino' as used herein refers to a tertiary amine group (—NR(R*)) of which the R and R* groups are each independently selected from a linear or branched saturated hydrocarbon group containing from x to y carbon atoms. Examples of $C_{x-y}$ dialkylamino groups include dimethylamino, methylethylamino and diethylamino.

The term 'substituted $C_{1-6}$ alkyl' used herein with reference to the identity of the various groups identified as R (for example, in the phrase 'wherein R8e and R8f are independently selected from $C_{1-6}$ alkyl, substituted $C_{1-6}$ alkyl, aryl, heteroaryl, $C_{3-8}$ cycloalkyl and heterocyclyl') means that the particular R group (e.g. R1a, R2c, R4d, R5e, etc.) can be substituted with one or more groups selected from R', halogen, OH, OR', SH, SR', OCOR', SCOR', NH$_2$, NO$_2$, NHR', NHSO$_2$NH$_2$, NHSO$_2$R', NR'COR", NHC(NH)NH$_2$, NHCOR', NR'R", COR', CSR', CN, COOH, COOR', CONH$_2$, CONHOH, CONHR', CONR'R", CONHOR', C(NOH)NH$_2$, SO$_2$R', SO$_3$H, SO$_2$NH$_2$, SO$_2$NR'R", wherein R' and R" are independently selected from $C_{1-6}$ alkyl, aryl, heteroaryl, $C_{3-8}$ cycloalkyl and heterocyclyl, or R' and R", together with the heteroatom to which they are joined, can form heterocyclyl.

'Pharmaceutically acceptable salts' of compounds prepared according to the present invention include salts with inorganic bases, salts with organic bases, salts with inorganic acids, salts with organic acids and salts with basic or acidic amino acids. Salts with acids may, in particular, be employed in some instances. Exemplary salts include hydrochloride salt, acetate salt, trifluoroacetate salt, methanesulfonate salt, 2-hydroxypropane-1,2,3-tricarboxylate salt, (2R, 3R)-2,3-dihydroxysuccinate salt, phosphate salt and oxalate salt. The compound of the present invention may be in either solvate (e.g. hydrate) or non-solvate (e.g. non-hydrate) form. When in a solvate form, additional solvents may be alcohols such as propan-2-ol.

'Pharmaceutically acceptable esters' of compounds prepared according to the invention are derivatives in which one or more carboxyl (i.e. —C(O)OH) groups of the said compounds are modified by reaction with an alcoholic moiety U—OH so as to yield —C(O)OU groups, wherein U may be $C_{1-18}$ alkyl (e.g. $C_{1-6}$ alkyl), aryl, heteroaryl, $C_{3-8}$ cycloalkyl or combinations thereof.

General methods for the preparation of salts and esters are well known to the person skilled in the art. Pharmaceutical acceptability of salts and esters will depend on a variety of factors, including formulation processing characteristics and in vivo behaviour, and the skilled person would readily be able to assess such factors having regard to the present disclosure.

Where compounds prepared according to the invention exist in different enantiomeric and/or diastereoisomeric forms (including geometric isomerism about a double bond), these compounds may be prepared as isomeric mixtures or racemates, although the invention relates to all such enantiomers or isomers, whether present in an optically pure form or as mixtures with other isomers. Individual enantiomers or isomers may be obtained by methods known in the art, such as optical resolution of products or intermediates (for example chiral chromatographic separation (e.g. chiral HPLC)), or an enantiomeric synthesis approach. Similarly, where compounds prepared according to the invention may exist as alternative tautomeric forms (e.g. keto/enol, amide/imidic acid), the invention relates to preparation of the individual tautomers in isolation, and of mixtures of the tautomers in all proportions.

In particular embodiments of the process of the invention, compounds according to Formula II are prepared.

In an embodiment, when R1 and R2 together form piperidinyl in compounds having Formula I, the piperidinyl is not substituted with methyl, dimethyl, ethyl, isopropyl, tert-butyl, methoxycarbonyl, trifluoromethyl, chloro, bromo or benzyl. In another embodiment, R1 and R2 together in compounds having Formula I do not form 6,7-dimethoxy-3,4-dihydro-1H-isoquinolin-2-yl, 6-methoxy-3,4-dihydro-1H-isoquinolin-2-yl, 7-methoxy-3,4-dihydro-1H-isoquinolin-2-yl, 7-amino-3,4-dihydro-1H-isoquinolin-2-yl, 7-nitro-3,4-dihydro-1H-isoquinolin-2-yl, 3,4-dihydro-1H-isoquinolin-2-yl, 3,4-dihydro-1H-isoquinolin-1-yl, 3,4-dihydro-2H-quinolin-1-yl, pyrrolidin-1-yl, 3,6-dihydro-2H-pyridin-1-yl, 8-aza-spiro[4.5]dec-8-yl, 1,3-dihydroisoindol-2-yl, octahydroisoindol-2-yl, 1,2,6-triaza-spiro[2.5]oct-1-en-6-yl or azepan-1-yl. In a further embodiment, when R1 or R2 is methyl, the other of R1 or R2 is not 4-chlorobutyl, 4-azidobutyl, or 4-isothiocyanatobutyl. In another embodiment, Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl. In a further embodiment, the compound prepared by the process of the invention is not (4-phenyl-1H-imidazol-1-yl)(4-(quinolin-2-ylmethyl)piperazin-1-yl)methanone.

In compounds of Formula II, zero, one or two of the atoms or groups denoted X, Y and Z can be N.

In a particular embodiment, the process of the invention is used to prepare a compound having a formula selected from Formula I or Formula II:

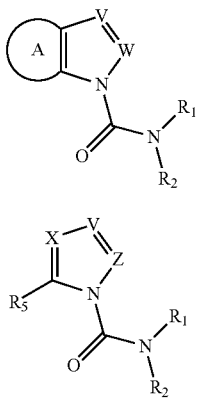

Formula I

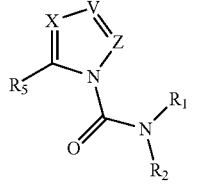

Formula II wherein:

R1 and R2 can each be independently selected from H, $C_{1-20}$ alkyl, alkoxy, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which, with the exception of H, may optionally be substituted with one or more groups selected from halogen, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, amino, $C_{1-6}$ alkylamino and $C_{1-6}$ dialkylamino, with the exception that R1 and R2 are not both H, or R1 and R2, together with the N to which they are attached, can form a heteroaryl or heterocyclyl group, each of which may optionally be substituted with one or more groups selected from hydroxy, aryl, heteroaryl, heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, and heterocyclyloxy, each of which may optionally be substituted with a group selected from halogen, hydroxyl, $C_{1-4}$ alkyl, aryl, heteroaryl, $C_{1-4}$ alkoxy, aryloxy, heteroaryloxy, aryl $C_{1-4}$ alkoxy and heteroaryl $C_{1-4}$ alkoxy, each of which, with the exception of halogen and hydroxyl, may optionally be substituted with $C_{1-4}$ alkoxy;

Ring A is selected from aryl, heteroaryl and heterocyclyl moiety, each of which may optionally be substituted with one or more groups selected from halogen, hydroxyl, aryl, heteroaryl, heterocyclyl, $C_{1-6}$ alkoxy, aryloxy, heteroaryloxy and heterocyclyloxy, each of which, with the exception of halogen and hydroxyl, may optionally be substituted with halogen, cyano, amide and carboxylic acid;

V can be N, CH or C—R3, wherein R3 is halogen, aryl, heteroaryl, heterocyclyl or $C_{3-8}$ cycloalkyl, each of which, with the exception of halogen, may optionally be substituted with halogen;

W can be N, CH or C—R4, wherein R4 is $C_{1-10}$ alkyl, aryl, heteroaryl, heterocyclyl or $C_{3-8}$ cycloalkyl, each of which may optionally be substituted with halogen;

R5 is selected from H, $C_{1-6}$ alkyl, aryl, heteroaryl, heterocyclyl and $C_{3-8}$ cycloalkyl, each of which, with the exception of H, may optionally be substituted with halogen;

X can be N, CH or C—R6, wherein R6 is selected from $C_{1-6}$ alkyl, aryl, heteroaryl and heterocyclyl, each of which, with the exception of H, may optionally be substituted with one or more groups selected from halogen, hydroxyl, amine, nitro, amide, cyano, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy and heterocyclyl $C_{1-6}$ alkoxy;

Y can be N, CH or C—R7, wherein R7 is selected from $C_{1-6}$ alkyl, aryl, heteroaryl and heterocyclyl, each of which, with the exception of H, may optionally be substituted with one or more groups selected from halogen, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy and heterocyclyl $C_{1-6}$ alkoxy, each of which may optionally be substituted with $C_{1-4}$ alkyl, cyano, amine, amide, halogen, aryl, heteroaryl, heterocyclyl, aryl $C_{1-6}$ alkyl, heteroaryl $C_{1-6}$ alkyl and heterocyclyl $C_{1-6}$ alkyl;

Z can be N, CH or C—R8, wherein R8 is selected from $C_{1-10}$ alkyl, aryl, heteroaryl, heterocyclyl or $C_{3-8}$ cycloalkyl, each of which may optionally be substituted with halogen;

or a pharmaceutically acceptable salt or ester thereof;

provided that when R1 and R2 together form piperidinyl in compounds having Formula I, the piperidinyl is not substituted with methyl, dimethyl, ethyl, isopropyl, tert-butyl, trifluoromethyl, chloro, bromo or benzyl.

In an embodiment of the invention, the process is used to prepare a compound having Formula I or Formula II:

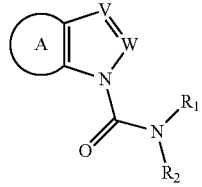

Formula I

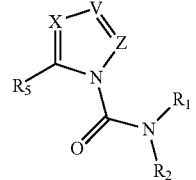

Formula II wherein:

R1 and R2 can each be independently selected from H, $C_{1-20}$ alkyl, alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, R1a, halogen, OH, OR1a, SH, SR1a, OCOR1a, SCOR1a, NH$_2$, NHR1a, NR1aR1b, COR1a, CSR1a, CN, COOH, COOR1a, CONH$_2$, SO$_2$R1a, SO$_3$H, SO$_2$NH$_2$, CONR1aR1b, SO$_2$NR1aR1b, wherein R1a and R1b are independently selected from $C_{1-6}$ alkyl, substituted $C_{1-6}$ alkyl, $C_{3-8}$ cycloalkyl and heterocyclyl, and R1a and R1b, together with the adjacent heteroatom, can form heterocyclyl, wherein, when R1 or R2 is $C_{1-20}$ alkyl (such as $C_{1-6}$ alkyl), alkoxy, aryl, heteroaryl, heterocyclyl, $C_{3-10}$ cycloalkyl (such as $C_{3-8}$ cycloalkyl), aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, or is a group containing one or more of these moieties, each of these moieties may optionally be substituted with R1c, halogen, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-10}$ alkyl, OH, OR1c, OCOR1c, SH, SR1c, SCOR1c, $NH_2$, NHR1c, NR1cR1d, COR1c, CSR1c, CN, COOH, COOR1c, $CONH_2$, $SO_2R1c$, $SO_3H$, $SO_2NH_2$, CONR1cR1d, $SO_2NR1cR1d$, wherein R1c and R1d are independently selected from $C_{1-6}$ alkyl, substituted $C_{1-6}$ alkyl, $C_{3-8}$ cycloalkyl and heterocyclyl, and R1c and R1d, together with the adjacent heteroatom, can form heterocyclyl, wherein, when the substituent of R1 or R2 is $C_{1-10}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-6}$ alkyl, $C_{3-8}$ cycloalkyl or is a group containing one or more of these moieties, each of these moieties may optionally be substituted with R1e, $C_{1-10}$ alkyl, OH, OR1e, OCOR1e, SH, SR1e, SCOR1e, $NH_2$, NHR1e, NR1eR1f, COR1e, CSR1e, CN, COOH, COOR1e, $CONH_2$, $SO_2R1e$, $SO_3H$, $SO_2NH_2$, CONR1eR1f, $SO_2NR1eR1f$, wherein R1e and R1f are independently selected from $C_{1-6}$ alkyl, substituted $C_{1-6}$ alkyl, $C_{3-8}$ cycloalkyl and heterocyclyl, and R1e and R1f, together with the adjacent heteroatom, can form heterocyclyl, with the exception that R1 and R2 are not both H, or R1 and R2, together with the N to which they are attached, can form a heteroaryl or heterocyclyl group, each of which may optionally be substituted with one or more groups selected from hydroxy, aryl, heteroaryl, partially or fully saturated heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, R2a, halogen, OH, OR2a, SH, SR2a, OCOR2a, SCOR2a, $NH_2$, NHR2a, NR2aR2b, COR2a, CSR2a, CN, COOH, COOR2a, $CONH_2$, $SO_2R2a$, $SO_3H$, $SO_2NH_2$, CONR2aR2b, $SO_2NR2aR2b$, wherein R2a and R2b are independently selected from $C_{1-6}$ alkyl, substituted $C_{1-6}$ alkyl, $C_{3-8}$ cycloalkyl and heterocyclyl, and R2a and R2b, together with the adjacent heteroatom, can form heterocyclyl, wherein, when the substituent of the heteroaryl or heterocyclyl formed by R1 and R2 together is aryl, heteroaryl, heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, or a group containing one or more of these moieties, each of these moieties may optionally be substituted with a group selected from halogen, hydroxyl, $C_{1-6}$ alkyl, aryl, heteroaryl, heterocyclyl, $C_{3-8}$ cycloalkyl, $C_{1-4}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, R2c, OR2c, SH, SR2c, OCOR2c, SCOR2c, $NH_2$, NHR2c, NR2cR2d, COR2c, CSR2c, CN, COOH, COOR2c, $CONH_2$, $SO_2R2c$, $SO_3H$, $SO_2NH_2$, CONR2cR2d, $SO_2NR2cR2d$, wherein R2c and R2d are independently selected from $C_{1-6}$ alkyl, substituted $C_{1-6}$ alkyl, $C_{3-8}$ cycloalkyl and heterocyclyl, and R2c and R2d, together with the adjacent heteroatom, can form heterocyclyl, wherein, when the substituent of the substituent of the heteroaryl or heterocyclyl of R1 and R2 together is $C_{1-4}$ alkyl, aryl, heteroaryl, heterocyclyl, $C_{3-8}$ cycloalkyl, $C_{1-4}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, or is a group containing one or more of these moieties, each of these moieties may optionally be substituted with $C_{1-4}$ alkoxy, R2e, halogen, OH, OR2e, SH, SR2e, OCOR2e, SCOR2e, $NH_2$, NHR2e, NR2eR2f, COR2e, CSR2e, CN, COOH, COOR2e, $CONH_2$, $SO_2R2e$, $SO_3H$, $SO_2NH_2$, CONR2eR2f, $SO_2NR2eR2f$, wherein R2e and R2f are independently selected from $C_{1-6}$ alkyl, substituted $C_{1-6}$ alkyl, $C_{3-8}$ cycloalkyl and heterocyclyl, and R2e and R2f, together with the adjacent heteroatom, can form heterocyclyl;

Ring A is selected from aryl, heteroaryl and heterocyclyl moiety, each of which may optionally be substituted with one or more groups selected from halogen, $C_{1-6}$ alkyl, hydroxyl, aryl, heteroaryl, heterocyclyl, $C_{1-6}$ alkoxy, aryloxy, heteroaryloxy, heterocyclyloxy, Ra, $C_{1-10}$ alkyl, OH, ORa, OCORa, SH, SRa, SCORa, $NH_2$, NHRa, NRaRb, CORa, CSRa, CN, COOH, COORa, $CONH_2$, $SO_2Ra$, $SO_3H$, $SO_2NH_2$, CONRaRb, $SO_2NRaRb$, wherein Ra and Rb are independently selected from $C_{1-6}$ alkyl, substituted $C_{1-6}$ alkyl, $C_{3-8}$ cycloalkyl and heterocyclyl, and Ra and Rb, together with the adjacent heteroatom, can form heterocyclyl, wherein, when Ring A is substituted with $C_{1-6}$ alkyl, aryl, heteroaryl, heterocyclyl, $C_{1-6}$ alkoxy, aryloxy, heteroaryloxy, heterocyclyloxy, $C_{1-10}$ alkyl, $C_{3-8}$ cycloalkyl or is substituted with a group containing one or more of these moieties, each of these moieties may optionally be substituted with Rc, $C_{1-10}$ alkyl, OH, ORc, OCORc, SH, SRc, SCORc, $NH_2$, NHRc, NRcRd, CORc, CSRc, CN, COOH, COORc, $CONH_2$, $SO_2Rc$, $SO_3H$, $SO_2NH_2$, CONRcRd, $SO_2NRcRd$, wherein Rc and Rd are independently selected from $C_{1-6}$ alkyl, substituted $C_{1-6}$ alkyl, $C_{3-8}$ cycloalkyl and heterocyclyl, and Rc and Rd, together with the adjacent heteroatom, can form heterocyclyl;

V can be N, CH or C—R3, wherein R3 is halogen, $C_{1-10}$ alkyl, aryl, heteroaryl, heterocyclyl, $C_{3-8}$ cycloalkyl, $C_{1-6}$ alkoxy, aryloxy, heteroaryloxy, heterocyclyloxy, R3a, OH, OR3a, SH, SR3a, OCOR3a, SCOR3a, $NH_2$, NHR3a, NR3aR3b, COR3a, CSR3a, CN, COOH, COOR3a, $CONH_2$, $SO_2R3a$, $SO_3H$, $SO_2NH_2$, CONR3aR3b, $SO_2NR3aR3b$, wherein R3a and R3b are independently selected from $C_{1-6}$ alkyl, substituted $C_{1-6}$ alkyl, $C_{3-8}$ cycloalkyl and heterocyclyl, and R3a and R3b, together with the adjacent heteroatom, can form heterocyclyl, wherein, when R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with aryl, heteroaryl, heterocyclyl, $C_{1-6}$ alkoxy, aryloxy, heteroaryloxy, heterocyclyloxy, R3c, $C_{1-10}$ alkyl, OH, OR3c, OCOR3c, SH, SR3c, SCOR3c, $NH_2$, NHR3c, NR3cR3d, COR3c, CSR3c, CN, COOH, COOR3c, $CONH_2$, $SO_2R3c$, $SO_3H$, $SO_2NH_2$, CONR3cR3d, $SO_2NR3cR3d$, wherein R3c and R3d are independently selected from $C_{1-6}$ alkyl, substituted $C_{1-6}$ alkyl, $C_{3-8}$ cycloalkyl and heterocyclyl, and R3c and R3d, together with the adjacent heteroatom, can form heterocyclyl, wherein, when the substituent of R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with R3e, $C_{1-10}$ alkyl, OH, OR3e, OCOR3e, SH, SR3e, SCOR3e, $NH_2$, NHR3e, NR3eR3f, COR3e, CSR3e, CN, COOH, COOR3e, $CONH_2$, $SO_2R3e$, $SO_3H$, $SO_2NH_2$, CONR3eR3f, $SO_2NR3eR3f$, wherein R3e and R3f are independently selected from $C_{1-6}$ alkyl, substituted $C_{1-6}$ alkyl, $C_{3-8}$ cycloalkyl and heterocyclyl, and R3e and R3f, together with the adjacent heteroatom, can form heterocyclyl;

W can be N, CH or C—R4, wherein R4 is halogen, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, R4a, OH, OR4a, SH, SR4a, OCOR4a, SCOR4a, $NH_2$, NHR4a, NR4aR4b, COR4a, CSR4a, CN, COOH, COOR4a, $CONH_2$, $SO_2R4a$, $SO_3H$, $SO_2NH_2$, CONR4aR4b, $SO_2NR4aR4b$, wherein R4a and R4b are independently selected from $C_{1-6}$ alkyl, substituted $C_{1-6}$ alkyl, $C_{3-8}$ cycloalkyl and heterocyclyl, and R4a and R4b, together with the adjacent heteroatom, can form heterocyclyl, wherein, when R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with aryl, heteroaryl, heterocyclyl, $C_{1-6}$ alkoxy, aryloxy, heteroaryloxy, heterocyclyloxy, R4c, $C_{1-10}$ alkyl, OH, OR4c, OCOR4c, SH, SR4c, SCOR4c, $NH_2$, NHR4c, NR4cR4d, COR4c, CSR4c, CN, COOH, COOR4c, $CONH_2$, $SO_2R4c$, $SO_3H$, $SO_2NH_2$, CONR4cR4d, $SO_2NR4cR4d$, wherein R4c and R4d are independently selected from $C_{1-6}$ alkyl, substituted $C_{1-6}$ alkyl, $C_{3-8}$ cycloalkyl and heterocyclyl, and R4c and R4d, together with the adjacent heteroatom, can form heterocyclyl, wherein, when the substituent of R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with R4e, $C_{1-10}$ alkyl, OH, OR4e, OCOR4e, SH, SR4e, SCOR4e, $NH_2$, NHR4e, NR4eR4f, COR4e, CSR4e, CN, COOH, COOR4e, $CONH_2$, $SO_2R4e$, $SO_3H$, $SO_2NH_2$, CONR4eR4f, $SO_2NR4eR4f$, wherein R4e and R4f are independently selected from $C_{1-6}$ alkyl, substituted $C_{1-6}$ alkyl, $C_{3-8}$ cycloalkyl and heterocyclyl, and R4e and R4f, together with the adjacent heteroatom, can form heterocyclyl;

R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, $C_{3-8}$ cycloalkyl and heterocyclyl, and R5a and R5b, together with the adjacent heteroatom, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, NHR5c, NR5cR5d, COR5c, CSR5c, CN, COOH, COOR5c, $CONH_2$, $SO_2R5c$, $SO_3H$, $SO_2NH_2$, CONR5cR5d, $SO_2NR5cR5d$, wherein R5c and R5d are independently selected from $C_{1-6}$ alkyl, substituted $C_{1-6}$ alkyl, $C_{3-8}$ cycloalkyl and heterocyclyl, and R5c and R5d, together with the adjacent heteroatom, can form heterocyclyl, wherein, when the substituent of R5 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with R5e, $C_{1-6}$ alkyl, OH, OR5e, OCOR5e, SH, SR5e, SCOR5e, $NH_2$, NHR5e, NR5eR5f, COR5e, CSR5e, CN, COOH, COOR5e, $CONH_2$, $SO_2R5e$, $SO_3H$, $SO_2NH_2$, CONR5eR5f, $SO_2NR5eR5f$, wherein R5e and R5f are independently selected from $C_{1-6}$ alkyl, substituted $C_{1-6}$ alkyl, $C_{3-8}$ cycloalkyl and heterocyclyl, and R5e and R5f, together with the adjacent heteroatom, can form heterocyclyl;

X can be N, CH or C—R6, wherein R6 is selected from $C_{1-6}$ alkyl, aryl, heteroaryl, heterocyclyl, $C_{1-6}$ alkoxy, aryloxy, heteroaryloxy, heterocyclyloxy, R6a, halogen, OH, OR6a, SH, SR6a, OCOR6a, SCOR6a, $NH_2$, NHR6a, NR6aR6b, COR6a, CSR6a, CN, COOH, COOR6a, $CONH_2$, $SO_2R6a$, $SO_3H$, $SO_2NH_2$, CONR6aR6b, $SO_2NR6aR6b$, wherein R6a and R6b are independently selected from $C_{1-6}$ alkyl, substituted $C_{1-6}$ alkyl, $C_{3-8}$ cycloalkyl and heterocyclyl, and R6a and R6b, together with the adjacent heteroatom, can form heterocyclyl, wherein, when R6 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with R6c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR6c, OCOR6c, SH, SR6c, SCOR6c, $NO_2$, $NH_2$, NHR6c, NR6cR6d, COR6c, CSR6c, CN, COOH, COOR6c, $CONH_2$, $SO_2R6c$, $SO_3H$, $SO_2NH_2$, CONR6cR6d, $SO_2NR6cR6d$, wherein R6c and R6d are independently selected from $C_{1-6}$ alkyl, substituted $C_{1-6}$ alkyl, $C_{3-8}$ cycloalkyl and heterocyclyl, and R6c and R6d, together with the adjacent heteroatom, can form heterocyclyl, wherein, when the substituent of R6 is $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, heterocyclyl $C_{1-6}$ alkoxy, $C_{3-8}$ cycloalkyl, or is a group containing one or more of these moieties, each of these moieties may optionally be substituted with R6e, $C_{1-6}$ alkyl, OH, OR6e, OCOR6e, SH, SR6e, SCOR6e, $NH_2$, NHR6e, NR6eR6f, COR6e, CSR6e, CN, COOH, COOR6e, $CONH_2$, $SO_2R6e$, $SO_3H$, $SO_2NH_2$, CONR6eR6f, $SO_2NR6eR6f$, wherein R6e and R6f are independently selected from $C_{1-6}$ alkyl, substituted $C_{1-6}$ alkyl, $C_{3-8}$ cycloalkyl and heterocyclyl, and R6e and R6f, together with the adjacent heteroatom, can form heterocyclyl;

Y can be N, CH or C—R7, wherein R7 is selected from $C_{1-6}$ alkyl, aryl, heteroaryl, heterocyclyl, $C_{1-6}$ alkoxy, aryloxy, heteroaryloxy, heterocyclyloxy, R7a, halogen, OH, OR7a, SH, SR7a, OCOR7a, SCOR7a, $NH_2$, NHR7a, NR7aR7b, COR7a, CSR7a, CN, COOH, COOR7a, $CONH_2$, $SO_2R7a$, $SO_3H$, $SO_2NH_2$, CONR7aR7b, $SO_2NR7aR7b$, wherein R7a and R7b are independently selected from $C_{1-6}$ alkyl, substituted $C_{1-6}$ alkyl, $C_{3-8}$ cycloalkyl and heterocyclyl, and R7a and R7b, together with the adjacent heteroatom, can form heterocyclyl, wherein, when R7 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl or is a group containing one or more of these moieties, each of these moieties may optionally be substituted with R7c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, O7c, OCOR7c, SH, SR7c, SCOR7c, $NH_2$, NHR7c, NR7cR7d, COR7c, CSR7c, CN, COOH, COOR7c, $CONH_2$, $SO_2R7c$, $SO_3H$, $SO_2NH_2$, CONR7cR7d, $SO_2NR7cR7d$, wherein R7c and R7d are independently selected from $C_{1-6}$ alkyl, substituted $C_{1-6}$ alkyl, $C_{3-8}$ cycloalkyl and heterocyclyl, and R7c and R7d, together with the adjacent heteroatom, can form heterocyclyl, wherein, when the substituent of R7 is $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with R7e, $C_{1-6}$ alkyl, OH, OR7e, OCOR7e, SH, SR7e, SCOR7e, $NH_2$, NHR7e, NR7eR7f, COR7e, CSR7e, CN, COOH, COOR7e, $CONH_2$, $SO_2R7e$, $SO_3H$, $SO_2NH_2$, CONR7eR7f, $SO_2NR7eR7f$, wherein R7e and R7f are independently selected from $C_{1-6}$ alkyl, substituted $C_{1-6}$ alkyl, $C_{3-8}$ cycloalkyl and heterocyclyl, and R7e and R7f, together with the adjacent heteroatom, can form heterocyclyl;

Z can be N, CH or C—R8, wherein R8 is selected from $C_{1-6}$ alkyl, aryl, heteroaryl, heterocyclyl, $C_{1-6}$ alkoxy, aryloxy, heteroaryloxy, heterocyclyloxy, R8a, halogen, OH, OR8a, SH, SR8a, OCOR8a, SCOR8a, $NH_2$, NHR8a, NR8aR8b, COR8a, CSR8a, CN, COOH, COOR8a, $CONH_2$, $SO_2R8a$, $SO_3H$, $SO_2NH_2$, CONR8aR8b, $SO_2NR8aR8b$, wherein R8a and R8b are independently selected from $C_{1-6}$ alkyl, substituted $C_{1-6}$ alkyl, $C_{3-8}$ cycloalkyl and heterocyclyl, and R8a and R8b, together with the adjacent heteroatom, can form heterocyclyl, wherein, when R8 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with R8c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR8c, OCOR8c, SH, SR8c, SCOR8c, $NH_2$, NHR8c, NR8cR8d, COR8c, CSR8c, CN, COOH, COOR8c, $CONH_2$, $SO_2R8c$, $SO_3H$, $SO_2NH_2$, CONR8cR8d, $SO_2NR8cR8d$, wherein R8c and R8d are independently selected from $C_{1-6}$ alkyl, substituted $C_{1-6}$ alkyl, $C_{3-8}$ cycloalkyl and heterocyclyl, and R8c and R8d, together with the adjacent heteroatom, can form heterocyclyl, wherein, when the substituent of R8 is $C_{1-6}$ alkyl, aryl, heteroaryl, heterocyclyl, alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with R8e, $C_{1-6}$ alkyl, OH, OR8e, OCOR8e, SH, SR8e, SCOR8e, $NH_2$, NHR8e, NR8eR8f, COR8e, CSR8e, CN, COOH, COOR8e, $CONH_2$, $SO_2R8e$, $SO_3H$, $SO_2NH_2$, CONR8eR8f, $SO_2NR8eR8f$, wherein R8e and R8f are independently selected from $C_{1-6}$ alkyl, substituted $C_{1-6}$ alkyl, $C_{3-8}$ cycloalkyl and heterocyclyl, and R8e and R8f, together with the adjacent heteroatom, can form heterocyclyl;

or a pharmaceutically acceptable salt or ester thereof.

In such an embodiment, the compound may be limited by the following exceptions:

provided that when R1 and R2 together form piperidinyl in compounds having Formula I, the piperidinyl is not substituted with methyl, dimethyl, ethyl, isopropyl, tert-butyl, trifluoromethyl, chloro, bromo or benzyl, provided that R1 and R2 together in compounds having Formula I do not form 6,7-dimethoxy-3,4-dihydro-1H-isoquinolin-2-yl, 6-methoxy-3,4-dihydro-1H-isoquinolin-2-yl, 7-methoxy-3,4-dihydro-1H-isoquinolin-2-yl, 7-amino-3,4-dihydro-1H-isoquinolin-2-yl, 7-nitro-3,4-dihydro-1H-isoquinolin-2-yl, 3,4-dihydro-1H-isoquinolin-2-yl, 3,4-dihydro-1H-isoquinolin-1-yl, 3,4-dihydro-2H-quinolin-1-yl, pyrrolidin-1-yl, 3,6-dihydro-2H-pyridin-1-yl, 8-aza-spiro[4.5]dec-8-yl, 1,3-dihydroisoindol-2-yl, octahydroisoindol-2-yl, 1,2,6-triaza-spiro[2.5]oct-1-en-6-yl or azepan-1-yl, and/or provided that Ring A in compounds having Formula I does not form a pyridine, pyrazine, substituted pyridine or substituted pyrazine, when R1 and R2, together with the N to which they are attached, form piperidinyl, piperazinyl, substituted piperidinyl or substituted piperazinyl.

In accordance with a further embodiment of the invention, the process is used for preparing a compound having Formula I or Formula II:

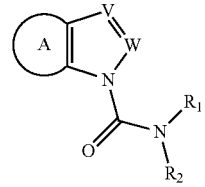

Formula I

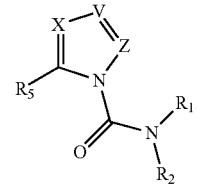

Formula II wherein:

R1 and R2 can each be independently selected from H, $C_{1-20}$ alkyl, $C_{1-6}$ alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, R1a, halogen, OH, OR1a, SH, SR1a, OCOR1a, SCOR1a, $NH_2$, NHR1a, NR1aR1b, COR1a, CSR1a, CN, COOH, COOR1a, $CONH_2$, $SO_2R1a$, $SO_3H$, $SO_2NH_2$, CONR1aR1b, $SO_2NR1aR1b$, wherein R1a and R1b are independently selected from $C_{1-6}$ alkyl, substituted $C_{1-6}$ alkyl, aryl, heteroaryl, $C_{3-8}$ cycloalkyl and heterocyclyl, or R1a and R1b, together with the heteroatom to which they are joined, can form heterocyclyl, wherein, when R1 or R2 is $C_{1-20}$ alkyl (such as $C_{1-6}$ alkyl), alkoxy, aryl, heteroaryl, heterocyclyl, $C_{3-10}$ cycloalkyl (such as $C_{3-8}$ cycloalkyl), aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, or is a group containing one or more of these moieties, each of these moieties may optionally be substituted with one or more groups selected from R1c, halogen, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-10}$ alkyl, OH, OR1c, OCOR1c, SH, SR1c, SCOR1c, $NH_2$, $NO_2$, NHR1c, NR1cR1d, COR1c, CSR1c, CN, COOH, COOR1c, $CONH_2$, $SO_2R1c$, $SO_3H$, $SO_2NH_2$, CONR1cR1d, $SO_2NR1cR1d$, wherein R1c and R1d are independently selected from $C_{1-6}$ alkyl, substituted $C_{1-6}$ alkyl, aryl, heteroaryl, $C_{3-8}$ cycloalkyl and heterocyclyl, or R1c and R1d, together with the heteroatom to which they are joined, can form heterocyclyl, wherein, when the substituent of R1 or R2 is $C_{1-10}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-6}$ alkyl, $C_{3-8}$ cycloalkyl or is a group containing one or more of these moieties, each of these moieties may optionally be substituted with one or more groups selected from R1e, halogen, $C_{1-10}$ alkyl, OH, OR1e, OCOR1e, SH, SR1e, SCOR1e, NH$_2$, NO$_2$, NHR1e, NR1eR1f, COR1e, CSR1e, CN, COOH, COOR1e, CONH$_2$, SO$_2$R1e, SO$_3$H, SO$_2$NH$_2$, CONR1eR1f, SO$_2$NR1eR1f, wherein R1e and R1f are independently selected from $C_{1-6}$ alkyl, substituted $C_{1-6}$ alkyl, aryl, heteroaryl, $C_{3-8}$ cycloalkyl and heterocyclyl, or R1e and R1f, together with the heteroatom to which they are joined, can form heterocyclyl, with the exception that R1 and R2 are not both H, or R1 and R2, together with the N to which they are attached, can form a heteroaryl or heterocyclyl group, each of which may optionally be substituted with one or more oxygen atoms or one or more groups selected from hydroxy, aryl, heteroaryl, partially or fully saturated heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, R2a, halogen, OH, OR2a, SH, SR2a, OCOR2a, SCOR2a, NH$_2$, NO$_2$, NHR2a, NR2aR2b, COR2a, CSR2a, CN, COOH, COOR2a, CONH$_2$, SO$_2$R2a, SO$_3$H, SO$_2$NH$_2$, CONR2aR2b, SO$_2$NR2aR2b, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the substituent of the heteroaryl or heterocyclyl formed by R1 and R2 together is aryl, heteroaryl, heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, or a group containing one or more of these moieties, each of these moieties may optionally be substituted with one or more groups selected from halogen, hydroxyl, $C_{1-6}$ alkyl, aryl, heteroaryl, heterocyclyl, $C_{3-8}$ cycloalkyl, $C_{1-4}$ alkoxy, aryloxy, heteroaryloxy, heterocyclyloxy, $C_{3-8}$ cycloalkyloxy, aryl $C_{1-4}$ alkoxy, heteroaryl $C_{1-6}$ alkoxy, heterocyclyl $C_{1-4}$ alkoxy, $C_{3-8}$ cycloalkyl $C_{1-4}$ alkoxy, R2c, OR2c, SH, SR2c, OCOR2c, SCOR2c, NH$_2$, NO$_2$, NHR2c, NR2cR2d, COR2c, CSR2c, CN, COOH, COOR2c, CONH$_2$, SO$_2$R2c, SO$_3$H, SO$_2$NH$_2$, CONR2cR2d, SO$_2$NR2cR2d, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, wherein, when the substituent of the substituent of the heteroaryl or heterocyclyl formed by R1 and R2 together is $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, or is a group containing one or more of these moieties, each of these moieties may optionally be substituted with one or more groups selected from $C_{1-4}$ alkoxy, R2e, halogen, OH, OR2e, SH, SR2e, OCOR2e, SCOR2e, NH$_2$, NO$_2$, NHR2e, NR2eR2f, NHCOR2e, COR2e, CSR2e, CN, COOH, COOR2e, CONH$_2$, SO$_2$R2e, SO$_3$H, SO$_2$NH$_2$, CONR2eR2f, SO$_2$NR2eR2f, wherein R2e and R2f are independently selected from $C_{1-6}$ alkyl, substituted $C_{1-6}$ alkyl, aryl, heteroaryl, $C_{3-8}$ cycloalkyl and heterocyclyl, or R2e and R2f, together with the heteroatom to which they are joined, can form heterocyclyl;

Ring A is selected from aryl, heteroaryl and heterocyclyl moieties, each of which may optionally be substituted with one or more groups selected from halogen, $C_{1-6}$ alkyl, hydroxyl, aryl, heteroaryl, heterocyclyl, $C_{1-6}$ alkoxy, aryloxy, heteroaryloxy, heterocyclyloxy, Ra, $C_{1-10}$ alkyl, OH, ORa, OCORa, SH, SRa, SCORa, NH$_2$, NO$_2$, NHRa, NRaRb, CORa, CSRa, CN, COOH, COORa, CONH$_2$, CONHOH, CONHORa, SO$_2$Ra, SO$_3$H, SO$_2$NH$_2$, CONRaRb, SO$_2$NRaRb, wherein Ra and Rb are independently selected from $C_{1-6}$ alkyl, substituted $C_{1-6}$ alkyl, aryl, heteroaryl, $C_{3-8}$ cycloalkyl and heterocyclyl, or Ra and Rb, together with the heteroatom to which they are joined, can form heterocyclyl, wherein, when Ring A is substituted with $C_{1-6}$ alkyl, aryl, heteroaryl, heterocyclyl, $C_{1-6}$ alkoxy, aryloxy, heteroaryloxy, heterocyclyloxy, $C_{1-10}$ alkyl, $C_{3-8}$ cycloalkyl or is substituted with a group containing one or more of these moieties, each of these moieties may optionally be substituted with one or more groups selected from halogen, Rc, $C_{1-10}$ alkyl, aryl $C_{1-6}$ alkyl, OH, ORc, OCORc, SH, SRc, SCORc, NH$_2$, NO$_2$, NHRc, NRcRd, CORc, CSRc, CN, COOH, COORc, CONH$_2$, SO$_2$Rc, SO$_3$H, SO$_2$NH$_2$, CONRcRd, SO$_2$NRcRd, wherein Rc and Rd are independently selected from $C_{1-6}$ alkyl, substituted $C_{1-6}$ alkyl, aryl, heteroaryl, $C_{3-8}$ cycloalkyl and heterocyclyl, or Rc and Rd, together with the heteroatom to which they are joined, can form heterocyclyl;

V can be N, CH or C—R3, wherein R3 is halogen, $C_{1-10}$ alkyl, aryl, heteroaryl, heterocyclyl, $C_{3-8}$ cycloalkyl, $C_{1-6}$ alkoxy, aryloxy, heteroaryloxy, heterocyclyloxy, R3a, OH, OR3a, SH, SR3a, OCOR3a, SCOR3a, NH$_2$, NO$_2$, NHR3a, NR3aR3b, COR3a, CSR3a, CN, COOH, COOR3a, CONH$_2$, SO$_2$R3a, SO$_3$H, SO$_2$NH$_2$, CONR3aR3b, SO$_2$NR3aR3b, wherein R3a and R3b are independently selected from $C_{1-6}$ alkyl, substituted $C_{1-6}$ alkyl, aryl, heteroaryl, $C_{3-8}$ cycloalkyl and heterocyclyl, or R3a and R3b, together with the heteroatom to which they are joined, can form heterocyclyl, wherein, when R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R3c, $C_{1-10}$ alkyl, OH, OR3c, OCOR3c, SH, SR3c, SCOR3c, NH$_2$, NO$_2$, NHR3c, NR3cR3d, COR3c, CSR3c, CN, COOH, COOR3c, CONH$_2$, SO$_2$R3c, SO$_3$H, SO$_2$NH$_2$, CONR3cR3d, SO$_2$NR3cR3d, wherein R3c and R3d are independently selected from $C_{1-6}$ alkyl, substituted $C_{1-6}$ alkyl, aryl, heteroaryl, $C_{3-8}$ cycloalkyl and heterocyclyl, or R3c and R3d, together with the heteroatom to which they are joined, can form heterocyclyl, wherein, when the substituent of R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R3e, $C_{1-10}$ alkyl, OH, OR3e, OCOR3e, SH, SR3e, SCOR3e, NH$_2$, NO$_2$, NHR3e, NR3eR3f, COR3e, CSR3e, CN, COOH, COOR3e, CONH$_2$, SO$_2$R3e, SO$_3$H, SO$_2$NH$_2$, CONR3eR3f, SO$_2$NR3eR3f, wherein R3e and R3f are independently selected from $C_{1-6}$ alkyl, substituted $C_{1-6}$ alkyl, aryl, heteroaryl, $C_{3-8}$ cycloalkyl and heterocyclyl, or R3e and R3f, together with the heteroatom to which they are joined, can form heterocyclyl;

W can be N, CH or C—R4, wherein R4 is halogen, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, R4a, OH, OR4a, SH, SR4a, OCOR4a, SCOR4a, $NH_2$, $NO_2$, NHR4a, NR4aR4b, COR4a, CSR4a, CN, COOH, COOR4a, $CONH_2$, $SO_2R4a$, $SO_3H$, $SO_2NH_2$, CONR4aR4b, $SO_2NR4aR4b$, wherein R4a and R4b are independently selected from $C_{1-6}$ alkyl, substituted $C_{1-6}$ alkyl, aryl, heteroaryl, $C_{3-8}$ cycloalkyl and heterocyclyl, or R4a and R4b, together with the heteroatom to which they are joined, can form heterocyclyl, wherein, when R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R4c, $C_{1-10}$ alkyl, OH, OR4c, OCOR4c, SH, SR4c, SCOR4c, $NH_2$, $NO_2$, NHR4c, NR4cR4d, COR4c, CSR4c, CN, COOH, COOR4c, $CONH_2$, $SO_2R4c$, $SO_3H$, $SO_2NH_2$, CONR4cR4d, $SO_2NR4cR4d$, wherein R4c and R4d are independently selected from $C_{1-6}$ alkyl, substituted $C_{1-6}$ alkyl, aryl, heteroaryl, $C_{3-8}$ cycloalkyl and heterocyclyl, or R4c and R4d, together with the heteroatom to which they are joined, can form heterocyclyl, wherein, when the substituent of R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R4e, $C_{1-10}$ alkyl, OH, OR4e, OCOR4e, SH, SR4e, SCOR4e, $NH_2$, $NO_2$, NHR4e, NR4eR4f, COR4e, CSR4e, CN, COOH, COOR4e, $CONH_2$, $SO_2R4e$, $SO_3H$, $SO_2NH_2$, CONR4eR4f, $SO_2NR4eR4f$, wherein R4e and R4f are independently selected from $C_{1-6}$ alkyl, substituted $C_{1-6}$ alkyl, aryl, heteroaryl, $C_{3-8}$ cycloalkyl and heterocyclyl, or R4e and R4f, together with the heteroatom to which they are joined, can form heterocyclyl;

R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, $NO_2$, NHR5c, NR5cR5d, COR5c, CSR5c, CN, COOH, COOR5c, $CONH_2$, $SO_2R5c$, $SO_3H$, $SO_2NH_2$, CONR5cR5d, $SO_2NR5cR5d$, wherein R5c and R5d are independently selected from $C_{1-6}$ alkyl, substituted $C_{1-6}$ alkyl, aryl, heteroaryl, $C_{3-8}$ cycloalkyl and heterocyclyl, or R5c and R5d, together with the heteroatom to which they are joined, can form heterocyclyl, wherein, when the substituent of R5 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R5e, $C_{1-6}$ alkyl, OH, OR5e, OCOR5e, SH, SR5e, SCOR5e, $NH_2$, $NO_2$, NHR5e, NR5eR5f, COR5e, CSR5e, CN, COOH, COOR5e, $CONH_2$, $SO_2R5e$, $SO_3H$, $SO_2NH_2$, CONR5eR5f, $SO_2NR5eR5f$, wherein R5e and R5f are independently selected from $C_{1-6}$ alkyl, substituted $C_{1-6}$ alkyl, aryl, heteroaryl, $C_{3-8}$ cycloalkyl and heterocyclyl, or R5e and R5f, together with the heteroatom to which they are joined, can form heterocyclyl;

X can be N, CH or C—R6, wherein R6 is selected from $C_{1-6}$ alkyl, aryl, heteroaryl, heterocyclyl, $C_{1-6}$ alkoxy, aryloxy, heteroaryloxy, heterocyclyloxy, R6a, halogen, OH, OR6a, SH, SR6a, OCOR6a, SCOR6a, $NH_2$, $NO_2$, NHR6a, NR6aR6b, COR6a, CSR6a, CN, COOH, COOR6a, $CONH_2$, $SO_2R6a$, $SO_3H$, $SO_2NH_2$, CONR6aR6b, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, wherein, when R6 is heteroaryl or heterocyclyl, each of these moieties may optionally be substituted with one or more oxygen atoms, and when R6 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R6c, $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR6c, OCOR6c, SH, SR6c, SCOR6c, $NH_2$, $NO_2$, NHR6c, NR6cR6d, COR6c, CSR6c, CN, COOH, COOR6c, $CONH_2$, CONHOH, $C(NOH)NH_2$, $SO_2R6c$, $SO_3H$, $SO_2NH_2$, CONR6cR6d, $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R6c and R6d, together with the heteroatom to which they are joined, can form heterocyclyl, wherein, when the substituent of R6 is heteroaryl or heterocyclyl, each of these moieties may optionally be substituted with one or more oxygen atoms, or when the substituent of R6 is $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, R6e, $C_{1-6}$ alkyl, $C_{1-4}$ alkoxy, OH, OR6e, OCOR6e, SH, SR6e, SCOR6e, $NH_2$, $NO_2$, NHR6e, NR6eR6f, COR6e, CSR6e, CN, COOH, COOR6e, $CONH_2$, $C(NOH)NH_2$, $SO_2R6e$, $SO_3H$, $SO_2NH_2$, CONR6eR6f, $SO_2NR6eR6f$, wherein R6e and R6f are independently selected from $C_{1-6}$ alkyl, substituted $C_{1-6}$ alkyl, aryl, heteroaryl, $C_{3-8}$ cycloalkyl and heterocyclyl, or R6e and R6f, together with the heteroatom to which they are joined, can form heterocyclyl;

Y can be N, CH or C—R7, wherein R7 is selected from $C_{1-6}$ alkyl, aryl, heteroaryl, heterocyclyl, $C_{1-6}$ alkoxy, aryloxy, heteroaryloxy, heterocyclyloxy, R7a, halogen, OH, OR7a, SH, SR7a, OCOR7a, SCOR7a, $NH_2$, $NO_2$, NHR7a, NR7aR7b, COR7a, CSR7a, CN, COOH, COOR7a, $CONH_2$, $SO_2R7a$, $SO_3H$, $SO_2NH_2$, CONR7aR7b, $SO_2NR7aR7b$, wherein R7a and R7b are independently selected from $C_{1-6}$ alkyl, substituted $C_{1-6}$ alkyl, aryl, heteroaryl, $C_{3-8}$ cycloalkyl and heterocyclyl, or R7a and R7b, together with the heteroatom to which they are joined, can form heterocyclyl, wherein, when R7 is heteroaryl or heterocyclyl, each of these moieties may optionally be substituted with one or more oxygen atoms, and when R7 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl or is a group containing one or more of these moieties, each of these moieties may optionally be substituted with one or more groups selected from halogen, R7c, $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, O7c, OCOR7c, SH, SR7c, SCOR7c, $NH_2$, $NO_2$, NHR7c, NR7cR7d, COR7c, CSR7c, CN, COOH, COOR7c, $CONH_2$, CONHOH, $C(NOH)NH_2$, $SO_2R7c$, $SO_3H$, $SO_2NH_2$, CONR7cR7d, $SO_2NR7cR7d$, wherein R7c and R7d are independently selected from $C_{1-6}$ alkyl, substituted $C_{1-6}$ alkyl, aryl, heteroaryl, $C_{3-8}$ cycloalkyl and heterocyclyl, or R7c and R7d, together with the heteroatom to which they are joined, can form heterocyclyl, wherein, when the substituent of R7 is heteroaryl or heterocyclyl, each of these moieties may optionally be substituted with one or more oxygen atoms, or when the substituent of R7 is $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, aryl, heteroaryl, heterocyclyl, aryl $C_{1-6}$ alkyl, heteroaryl $C_{1-6}$ alkyl, heterocyclyl $C_{1-6}$ alkyl, $C_{1-4}$ alkoxy, R7e, $C_{1-6}$ alkyl, OH, OR7e, OCOR7e, SH, SR7e, SCOR7e, $NH_2$, $NO_2$, NHR7e, NR7eR7f, COR7e, CSR7e, CN, COOH, COOR7e, $CONH_2$, $C(NOH)NH_2$, $SO_2R7e$, $SO_3H$, $SO_2NH_2$, CONR7eR7f, $SO_2NR7eR7f$, wherein R7e and R7f are independently selected from $C_{1-6}$ alkyl, substituted $C_{1-6}$ alkyl, aryl, heteroaryl, $C_{3-8}$ cycloalkyl and heterocyclyl, or R7e and R7f, together with the heteroatom to which they are joined, can form heterocyclyl;

Z can be N, CH or C—R8, wherein R8 is selected from $C_{1-10}$ alkyl, aryl, heteroaryl, heterocyclyl, $C_{1-6}$ alkoxy, aryloxy, heteroaryloxy, heterocyclyloxy, R8a, halogen, OH, OR8a, SH, SR8a, OCOR8a, SCOR8a, $NH_2$, $NO_2$, NHR8a, NR8aR8b, COR8a, CSR8a, CN, COOH, COOR8a, $CONH_2$, $SO_2R8a$, $SO_3H$, $SO_2NH_2$, CONR8aR8b, $SO_2NR8aR8b$, wherein R8a and R8b are independently selected from $C_{1-6}$ alkyl, substituted $C_{1-6}$ alkyl, aryl, heteroaryl, $C_{3-8}$ cycloalkyl and heterocyclyl, or R8a and R8b, together with the heteroatom to which they are joined, can form heterocyclyl, wherein, when R8 is $C_{1-6}$ alkyl, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R8c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR8c, OCOR8c, SH, SR8c, SCOR8c, $NH_2$, $NO_2$, NHR8c, NR8cR8d, COR8c, CSR8c, CN, COOH, COOR8c, $CONH_2$, $SO_2R8c$, $SO_3H$, $SO_2NH_2$, CONR8cR8d, $SO_2NR8cR8d$, wherein R8c and R8d are independently selected from $C_{1-6}$ alkyl, substituted $C_{1-6}$ alkyl, aryl, heteroaryl, $C_{3-8}$ cycloalkyl and heterocyclyl, or R8c and R8d, together with the heteroatom to which they are joined, form heterocyclyl, wherein, when the substituent of R8 is $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, R8e, $C_{1-6}$ alkyl, OH, OR8e, OCOR8e, SH, SR8e, SCOR8e, $NH_2$, $NO_2$, NHR8e, NR8eR8f, COR8e, CSR8e, CN, COOH, COOR8e, $CONH_2$, $SO_2R8e$, $SO_3H$, $SO_2NH_2$, CONR8eR8f, $SO_2NR8eR8f$, wherein R8e and R8f are independently selected from $C_{1-6}$ alkyl, substituted $C_{1-6}$ alkyl, aryl, heteroaryl, $C_{3-8}$ cycloalkyl and heterocyclyl, or R8e and R8f, together with the heteroatom to which they are joined, can form heterocyclyl;

wherein, at most, two of the atoms or groups denoted X, Y and Z can be N;

wherein, when W is N, the CONR1R2 group may be joined to W instead, with the double bonds in Formula I rearranged accordingly;

or a pharmaceutically acceptable salt or ester thereof.

In such an embodiment, the compound may be limited by the following exceptions:

provided that when R1 and R2 together form piperidinyl in compounds having Formula I, the piperidinyl is not substituted with methyl, dimethyl, ethyl, isopropyl, tert-butyl, methoxycarbonyl, trifluoromethyl, chloro, bromo or benzyl, provided that R1 and R2 together in compounds having Formula I do not form 6,7-dimethoxy-3,4-dihydro-1H-isoquinolin-2-yl, 6-methoxy-3,4-dihydro-1H-isoquinolin-2-yl, 7-methoxy-3,4-dihydro-1H-isoquinolin-2-yl, 7-amino-3,4-dihydro-1H-isoquinolin-2-yl, 7-nitro-3,4-dihydro-1H-isoquinolin-2-yl, 3,4-dihydro-1H-isoquinolin-2-yl, 3,4-dihydro-1H-isoquinolin-1-yl, 3,4-dihydro-2H-quinolin-1-yl, pyrrolidin-1-yl, 3,6-dihydro-2H-pyridin-1-yl, 8-aza-spiro[4.5]dec-8-yl, 1,3-dihydroisoindol-2-yl, octahydroisoindol-2-yl, 1,2,6-triaza-spiro[2.5]oct-1-en-6-yl or azepan-1-yl, and/or provided that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl.

In the preceding embodiments, and in those which follow, it will be appreciated that the process used for preparing the specified groups of compounds of Formula II and Formula I employs a carbamate of Formula II' or Formula I' having a corresponding structure in which the —NR1R2 group of Formula II or Formula I is replaced by the —C(O)O-Ph-J group of Formula II' or Formula I'.

Preferably, the compound prepared by the process of the invention has a formula selected from Formula I, Formula IIa, Formula IIb, Formula IIc and Formula IId.

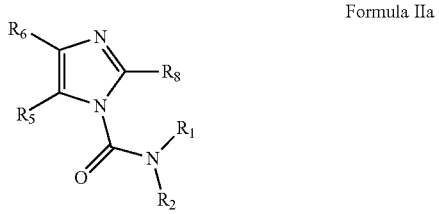

Formula IIa

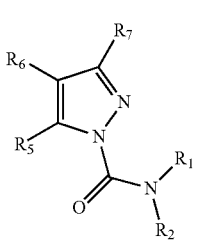

Formula IIb

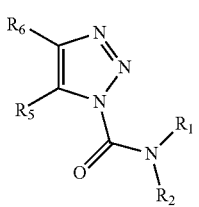

Formula IIc

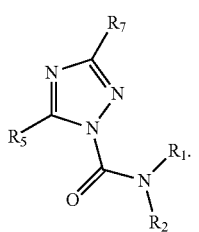

Formula IId

More preferably, the compound of Formula II or Formula I has a formula selected from Formula Ia, Formula IIa, Formula IIb, Formula IIc and Formula IId.

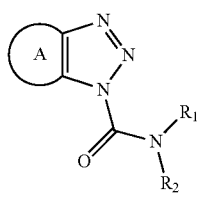

Formula Ia and the carbamate of Formula II' or Formula I' has a corresponding structure in which the —NR1R2 group of Formula IIa-d or Formula Ia is replaced by the —C(O)O-Ph-J group of Formula II' or Formula I'.

In one embodiment of the invention, R1 is preferably selected from H and $C_{1-4}$ alkyl. More preferably, R1 is selected from H and $C_{1-3}$ alkyl, even more preferably, R1 is selected from H, methyl and ethyl and most preferably, R1 is selected from H and methyl.

R2 is preferably selected from $C_{1-4}$ alkyl, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. Preferably, the aryl, heteroaryl, heterocyclyl and $C_{3-10}$ cycloalkyl (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) have a 6 membered monocyclic ring structure. More preferably, the aryl, heteroaryl, heterocyclyl and $C_{3-10}$ cycloalkyl (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) are selected from phenyl, cyclohexyl, phenyl $C_{1-6}$ alkyl and cyclohexyl $C_{1-6}$ alkyl, each of which can be substituted or unsubstituted. Preferably, the $C_{1-6}$ alkyl of each of aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl is a linear alkyl.

Alternatively, R2 can be selected from aryl, heteroaryl, heterocyclyl, aryl $C_{1-6}$ alkyl, heteroaryl $C_{1-6}$ alkyl and heterocyclyl $C_{1-6}$ alkyl, each of which may be substituted or unsubstituted and wherein the aryl, heteroaryl and heterocyclyl (including in aryl $C_{1-6}$ alkyl, heteroaryl $C_{1-6}$ alkyl and heterocyclyl $C_{1-6}$ alkyl) have a bicyclic ring structure, preferably, a 10 membered bicyclic ring structure. More preferably, R2 is selected from naphthalenyl and naphthalenyl $C_{1-6}$ alkyl.

Each of the aryl, heteroaryl, heterocyclyl and $C_{3-10}$ cycloalkyl groups of R2 (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) can be substituted with one or more halogens.

Alternatively, each of the aryl, heteroaryl, heterocyclyl and $C_{3-10}$ cycloalkyl groups (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) can be substituted with $C_{1-4}$ alkoxy or aryloxy. Preferably, the $C_{1-4}$ alkoxy is methoxy or ethoxy. Preferably, the aryloxy is monocyclic aryloxy and, more preferably, phenoxy.

In a preferred embodiment, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from saturated heterocyclyl, and $C_{5-8}$ cycloalkyl each of which are monocyclic and may be substituted or unsubstituted. When R2 is a monocyclic $C_{5-8}$ cycloalkyl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom. Preferably, the heteroatom is a nitrogen or oxygen atom. More preferably, the heterocyclyl is six membered, such as a piperidinyl or tetrahydropyranyl group. If the heteroatom is an oxygen atom, the heterocyclyl is preferably unsubstituted. If the heteroatom is a nitrogen atom, the nitrogen heteroatom may be substituted or unsubstituted. If the nitrogen heteroatom is substituted, it is preferably substituted with a group selected from $C_{1-6}$ alkyl, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, the nitrogen heteroatom is substituted with a group selected from $C_{1-4}$ alkyl, aryl $C_{1-4}$ alkyl, heteroaryl $C_{1-4}$ alkyl, heterocyclyl $C_{1-4}$ alkyl and $C_{5-8}$ cycloalkyl $C_{1-4}$ alkyl. More preferably, the nitrogen heteroatom is substituted with a group selected from aryl $C_{1-4}$ alkyl and heteroaryl $C_{1-4}$ alkyl, wherein the aryl and heteroaryl are monocyclic and, preferably, six membered. Preferably, the nitrogen heteroatom is substituted with a group selected from phenyl $C_{1-2}$ alkyl and pyridyl $C_{1-2}$ alkyl. Preferably, the heteroatom in the said heterocyclyl group is at the 4 position relative to the position of attachment of the heterocyclyl group R2 to the urea nitrogen. When R1 and R2 are as defined in this paragraph, the compound preferably has the formula IIa. Preferably, when R1 and R2 are as defined in this paragraph, R6 is a substituted or unsubstituted aryl or heteroaryl and, preferably, a substituted or unsubstituted monocyclic aryl or heteroaryl. The monocyclic aryl or heteroaryl is preferably six membered. In one embodiment, R6 is a substituted or unsubstituted aryl (such as phenyl) and, preferably, unsubstituted. In another embodiment, R6 is a substituted or unsubstituted heteroaryl and, preferably, substituted or unsubstituted pyridyl. In one embodiment, the heteroaryl is substituted with an oxygen atom. For example, the nitrogen heteroatom of pyridyl may be substituted with an oxygen atom so that it is oxidised, i.e. an N-oxide is formed.

It has been found that compounds with the selection of R1 and R2 in the preceding paragraph show relatively high specificity for FAAH. Further, compounds in which R2 is heterocyclyl, such as piperidinyl or tetrahydropyranyl, have been found to be relatively metabolically stable.

In an alternative embodiment, R2 is preferably $C_{2-20}$ alkyl. More preferably, R2 is $C_{3-16}$ alkyl and, more preferably still, R2 is $C_{4-12}$ alkyl. Preferably, the alkyl in a linear alkyl.

In a preferred embodiment, R1 is selected from H and $C_{1-4}$ alkyl, and R2 is $C_{2-20}$ alkyl.

In various embodiments, when R1 is: H or $C_{1-4}$ alkyl; H or $C_{1-3}$ alkyl; H, methyl or ethyl; H or methyl; or methyl, R2 can be selected from $C_{1-6}$ alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, halogen, OH, OR1a, OCOR1a, SH, SR1a, SCOR1a, $NH_2$, NHR1a, $NHSO_2NH_2$, $NHSO_2R1a$, NR1aCOR1b, NHCOR1a, NR1aR1b, COR1a, CSR1a, CN, COOH, COOR1a, $CONH_2$, CONHOH, CONHR1a, CONHOR1a, $SO_2R1a$, $SO_3H$, $SO_2NH_2$, CONR1aR1b, $SO_2NR1aR1b$, wherein R1a and R1b are independently selected from $C_{1-6}$ alkyl, substituted $C_{1-6}$ alkyl, aryl, heteroaryl, $C_{3-8}$ cycloalkyl and heterocyclyl, or R1a and R1b, together with the heteroatom to which they are joined, can form heterocyclyl, wherein R2 can be substituted or unsubstituted.

Alternatively, in other embodiments, when R1 is: H and $C_{1-4}$ alkyl; H and $C_{1-3}$ alkyl; H, methyl and ethyl; H and methyl; or methyl, R2 can be selected from aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, wherein R2 can be substituted or unsubstituted.

In a preferred embodiment, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl. When R1 and R2 are as defined in this paragraph, the compound preferably has the formula Ia or IIa. Preferably, when R1 and R2 are as defined in this paragraph and the compound has the formula IIa, R6 is a substituted or unsubstituted aryl and, more preferably, phenyl. When R1 and R2 are as defined in this paragraph and the compound has the formula Ia, ring A is preferably an unsubstituted or substituted benzo moiety.

Compounds having R1 and R2 as defined in the preceding paragraph have been found to be relatively potent inhibitors of FAAH. They have also been found to have relatively high specificity for FAAH.

In an alternative embodiment, R1 and R2, together with the N to which they are attached, form a heterocyclyl group which may be substituted or unsubstituted. Preferably, the heterocyclyl is a 5 or 6 membered monocyclic ring and, more preferably, a 6 membered monocyclic ring. Preferably, R1 and R2 together form morpholino, piperazinyl oxazolidinyl, pyrrolidinyl or piperidinyl. More preferably, R1 and R2 together form morpholino or piperazinyl.

Preferably, the heterocyclyl of R1 and R2 together is substituted with $C_{1-4}$ alkyl, aryl, heteroaryl, $C_{3-8}$ cycloalkyl aryl $C_{1-6}$ alkyl, heteroaryl $C_{1-6}$ alkyl, aryloxy, heteroaryloxy, aryl $C_{1-6}$ alkoxy and heteroaryl $C_{1-6}$ alkoxy, each of which may optionally be substituted with one or more halogens or $C_{1-4}$ alkyl groups. Preferably, the substituent aryl, heteroaryl or $C_{3-8}$ cycloalkyl is a 5 or 6 membered monocyclic ring. More preferably, the heterocyclyl of R1 and R2 together is substituted with aryl, aryl $C_{1-6}$ alkyl and aryloxy, each of which may optionally be substituted with one or more halogen. More preferably still, the heterocyclyl of R1 and R2 together is substituted with phenyl, phenyl $C_{1-6}$ alkyl or phenoxy, each of which may optionally be substituted with one or more halogen.

Alternatively, the heterocyclyl of R1 and R2 together may be substituted with a heteroaryl or heteroaryl $C_{1-6}$ alkyl. In one embodiment, the heteroaryl has a bicyclic ring structure, for example, benzodioxolylmethyl. Alternatively, the heteroaryl may be monocyclic, for example, pyridyl.

In another alternative, the heterocyclyl of R1 and R2 together may be substituted with a $C_{3-8}$ cycloalkyl. Preferably, the $C_{3-8}$ cycloalkyl is a monocyclic cycloalkyl such as cyclohexyl.

In one embodiment, the heterocyclyl of R1 and R2 together can be 1,4-dioxa-8-azaspiro[4.5]dec-8-yl, dimethyloxazolidinyl, methylpiperazinyl, benzyloxyphenylpiperazinyl, tolyloxypiperidinyl, pyrrolidinyl $C_{1-4}$ alkyl piperidinyl, pyridylpiperidinyl, pyridyloxadiazol-5-ylpiperidinyl or benzyloxypiperidinyl.

In one embodiment, the heterocyclyl of R1 and R2 together is piperidinyl substituted with phenoxy or phenyl $C_{1-4}$ alkoxy and wherein the phenyl may optionally be substituted with halogen.

In one embodiment of the invention, when V is C—R3, R3 is H or halogen.

In another embodiment of the invention, when W is C—R4, R4 is selected from H and aryl. Preferably, R4 is selected from H and phenyl. More preferably, R4 is H.

In the compound prepared according to the invention, ring A is preferably a substituted or unsubstituted monocyclic aryl or heteroaryl moiety and, more preferably, a monocyclic aryl moiety. Preferably, ring A is a substituted or unsubstituted benzo moiety. When the monocyclic aryl of ring A is substituted, the substituent is one or more of halogen, $C_{1-6}$ alkyl or aryl which can optionally be substituted with one or more of halogen, cyano, carboxylic acid or amide. Preferably, the substituent aryl is monocyclic aryl and, more preferably, phenyl. In a preferred embodiment, the compound, having ring A as defined in this paragraph, has formula Ia.

In one embodiment, ring A is substituted with a moiety selected from $C_{1-6}$ alkoxy, $C_{1-6}$ alkoxy $C_{1-6}$ alkyl, and $C_{0-6}$ alkyl-CO—$C_{0-6}$ alkyl, wherein the $C_{1-6}$ alkoxy, $C_{1-6}$ alkoxy $C_{1-6}$ alkyl, or $C_{0-6}$ alkyl-CO—$C_{0-6}$ alkyl is substituted with a moiety selected from aryl, heteroaryl, heterocyclyl, and $C_{3-10}$ cycloalkyl, wherein each of these moieties may optionally be substituted with aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl, and $C_{3-10}$ cycloalkyl $C_{1-6}$ alkyl. Preferably, ring A is substituted with a $C_{0-6}$ alkyl, wherein the $C_{0-6}$ alkyl-CO—$C_{0-6}$ alkyl is substituted with a moiety selected from aryl, heteroaryl, heterocyclyl, and $C_{3-10}$ cycloalkyl, wherein each of these moieties may optionally be substituted with aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl, and $C_{3-10}$ cycloalkyl $C_{1-6}$ alkyl. Preferably, ring A is substituted with a carbonyl moiety (i.e. $C_o$ alkyl-CO—$C_o$ alkyl). Preferably, the $C_{0-6}$ alkyl-CO—$C_{0-6}$ alkyl is substituted with a heterocyclyl, more preferably, a monocyclic heterocyclyl, more preferably still, a heterocyclyl containing one or two nitrogen heteroatoms, even more preferably, a six membered heterocyclyl, and most preferably, piperazine. Preferably, the $C_{1-6}$ alkoxy, $C_{1-6}$ alkoxy $C_{1-6}$ alkyl, or $C_{0-6}$ alkyl-CO—$C_{0-6}$ alkyl is linear. Preferably, compounds as described in this paragraph are of formula Ia.

In another embodiment, ring A is substituted with one or more groups selected from halogen, $C_{1-6}$ alkyl, $C_{1-6}$ alkoxy, OH, ORa, OCORa, SH, SRa, SCORa, $NH_2$, $NO_2$, NHRa, $NHSO_2NH_2$, $NHSO_2Ra$, NRaCORb, NHCORa, NHC(NH)$NH_2$, NRaRb, CORa, CSRa, CN, COOH, COORa, $CONH_2$, CONHRa, CONHOH, CONHORa, $C(NOH)NH_2$, CONRaRb, $SO_2Ra$, $SO_3H$, $SO_2NH_2$, $SO_2NRaRb$, wherein Ra and Rb are $C_{1-6}$ alkyl. Preferably, ring A is substituted with one or more groups selected from halogen, OH, SH, $NH_2$, $NO_2$, $NHC(NH)NH_2$, CN, COOH, $CONH_2$, CONHOH, $C(NOH)NH_2$, $SO_3H$, and $SO_2NH_2$. More preferably, ring A is substituted with one or more groups selected from halogen, OH, $NH_2$, $NO_2$, $NHC(NH)NH_2$, CN, COOH, $CONH_2$, CONHOH, $C(NOH)NH_2$, $SO_3H$, and $SO_2NH_2$. Preferably, compounds as described in this paragraph are of formula Ia.

Preferably, in the compound prepared according to the invention, R5 is H or halogen, and, more preferably, R5 is H.

In one embodiment, R5 together with the ring carbon to which it is attached, does not form a carbonyl group. The compound is of Formula II as indicated above.

In another embodiment, X is not O. The compound is of Formula II as indicated above.

In compounds having Formula II, when X is C—R6, R6 is preferably a substituted or unsubstituted aryl. Preferably, the aryl R6 is phenyl or naphthalenyl. More preferably, the aryl R6 is phenyl. Preferably, the aryl R6 is substituted with one or more groups selected from halogen, $C_{1-4}$ alkoxy, hydroxyl, amide, nitro, aryl, heterocyclyl, heteroaryl, heterocyclyl, aryloxy, each of which may be substituted or unsubstituted. Preferably, the aryl substituent of R6 is phenyl which may be substituted or unsubstituted. When R6 is defined as in this paragraph, the compound of Formula II is preferably an imidazole (i.e. X is CH or C—R6, Y is N, and Z is CH or C—R8) or a 1,2,3-triazole (i.e. X is CH or C—R6, Y is N, and Z is N). More preferably, the compound has formula IIa.

Alternatively, R6 is preferably H, halogen or aryl and, more preferably, H. When R6 is defined as in this paragraph, the compound of Formula II is preferably a pyrazole (i.e. X is CH or C—R6, Y is CH or C—R7, and Z is N).

In one embodiment of the invention, when Y is C—R7, R7 is selected from aryl or heteroaryl, each of which can be substituted or unsubstituted. Preferably, the aryl and heteroaryl are monocyclic. Preferably, the aryl or heteroaryl is substituted with one or more halogens. In a preferred embodiment of the invention, R7 is substituted or unsubstituted aryl. When R7 is defined as in this paragraph, the compound of Formula II is preferably a pyrazole (i.e. X is CH or C—R6, Y is CH or C—R7, and Z is N) or a 1,2,4-triazole (i.e. X is N, Y is CH or C—R7, and Z is N).

In one embodiment, when Y is C—R7, R7 is H.

In another embodiment of the invention, when Z is C—R8, R8 is selected from H and aryl. Preferably, R8 is selected from H and phenyl. More preferably, R8 is H.

In one embodiment of the invention, R6 is a group selected from aryl, heteroaryl, heterocyclyl, $C_{3-10}$ cycloalkyl, wherein the R6 group is substituted with a group selected from $C_{1-6}$ alkoxy, $C_{1-6}$ alkoxy $C_{1-6}$ alkyl, and $C_{0-6}$ alkyl-CO—$C_{0-6}$ alkyl, wherein the $C_{1-6}$ alkoxy, $C_{1-6}$ alkoxy $C_{1-6}$ alkyl, or $C_{0-6}$ alkyl-CO—$C_{3-6}$ alkyl group is substituted with a group selected from aryl, heteroaryl, heterocyclyl, and $C_{3-10}$ cycloalkyl. Preferably, R6 is a group selected from aryl, heteroaryl, heterocyclyl, $C_{3-10}$ cycloalkyl, wherein the R6 group is substituted with a group selected from $C_{1-6}$ alkoxy and $C_{1-6}$ alkoxy $C_{1-6}$ alkyl, wherein the $C_{1-6}$ alkoxy or $C_{1-6}$ alkoxy $C_{1-6}$ alkyl group is substituted with a group selected from aryl, heteroaryl, heterocyclyl, and $C_{3-10}$ cycloalkyl. Preferably, R6 is a group selected from aryl, heteroaryl, heterocyclyl, $C_{3-10}$ cycloalkyl, wherein the R6 group is substituted with a group selected from $C_{1-6}$ alkoxy and $C_{1-6}$ alkoxy $C_{1-6}$ alkyl, wherein the $C_{1-6}$ alkoxy or $C_{1-6}$ alkoxy $C_{1-6}$ alkyl group is substituted with a heterocyclyl. More preferably, R6 is an aryl which is substituted with a group selected from $C_{1-6}$ alkoxy and $C_{1-6}$ alkoxy $C_{1-6}$ alkyl, wherein the $C_{1-6}$ alkoxy or $C_{1-6}$ alkoxy $C_{1-6}$ alkyl group is substituted with a heterocyclyl. More preferably still, R6 is an aryl which is substituted with $C_{1-6}$ alkoxy, wherein the $C_{1-6}$ alkoxy is substituted with a heterocyclyl.

Preferably, R6 is an aryl. Preferably, R6 has a monocyclic ring structure such as a monocyclic aryl. In one embodiment, R6 has a six membered ring structure such as phenyl.

Preferably, the $C_{1-6}$ alkoxy, $C_{1-6}$ alkoxy $C_{1-6}$ alkyl or $C_{0-6}$ alkyl-CO—$C_{0-6}$ alkyl is linear.

Preferably, the substituent of the $C_{1-6}$ alkoxy or $C_{1-6}$ alkoxy $C_{1-6}$ alkyl is monocyclic. Preferably, the substituent of the $C_{1-6}$ alkoxy or $C_{1-6}$ alkoxy $C_{1-6}$ alkyl is six membered. Preferably, the substituent of the $C_{1-6}$ alkoxy or $C_{1-6}$ alkoxy $C_{1-6}$ alkyl is heterocyclyl. Preferably, the heterocyclyl is fully saturated. Preferably, the heterocyclyl contains one or two heteroatoms such as nitrogen or oxygen. Preferably, the heterocyclyl contains at least one nitrogen heteroatom. In one embodiment, the heterocyclyl is piperidinyl, piperazinyl, or tetrahydropyranyl. In this embodiment, the compound preferably is of formula IIa.

In one embodiment, when W is N, the CONR1R2 group may not be joined to W instead. In this embodiment, the compound is of Formula I as indicated above.

Formula I and Ia

In compounds having formula I and, in particular, compounds having formula Ia, ring A is preferably a substituted or unsubstituted aryl or heteroaryl moiety. More preferably, ring A is a substituted or unsubstituted monocyclic aryl or heteroaryl moiety. More preferably still, ring A is a substituted or unsubstituted six-membered aryl or heteroaryl moiety. Most preferably, ring A is a substituted or unsubstituted monocyclic aryl such as a benzo moiety.

When ring A is substituted, the substituent may be one or more groups selected from halogen, OH, $C_{1-4}$ alkyl, $C_{1-4}$ alkoxy, SH, $NH_2$, $NO_2$, CN, COOH, $CONH_2$, CONHOH, benzoxyaminocarbonyl, $SO_3H$, $SO_2NH_2$, aryl, heteroaryl, heterocyclyl, and $C_{3-8}$ cycloalkyl. When the substituent is $C_{1-4}$ alkyl, aryl, heteroaryl, heterocyclyl, or $C_{3-8}$ cycloalkyl, each of these moieties may optionally be substituted with one or more groups selected from halogen, OH, SH, $NH_2$, $NO_2$, CN, COOH, $CONH_2$, $SO_3H$, $SO_2NH_2$, $C_{1-3}$ alkyl, $C_{1-3}$ alkoxy and benzyl.

Preferably, the substituent of ring A is one or more groups selected from halogen, OH, $C_{1-3}$ alkyl, $C_{1-3}$ alkoxy, $NH_2$, $NO_2$, CN, COOH, $CONH_2$, monocyclic aryl, monocyclic heteroaryl, monocyclic heterocyclyl, and $C_{5-8}$ cycloalkyl. When the substituent is $C_{1-3}$ alkyl, monocyclic aryl, monocyclic heteroaryl, monocyclic heterocyclyl or $C_{5-8}$ cycloalkyl, each of these moieties may optionally be substituted with one or more groups selected from halogen, CN, COOH, $CONH_2$, and $C_{1-3}$ alkoxy.

More preferably, the substituent of ring A is one or more groups selected from halogen, OH, $C_{1-2}$ alkyl, $C_{1-2}$ alkoxy, and phenyl. When the substituent is $C_{1-2}$ alkyl or phenyl, each of these moieties may optionally be substituted with one or more groups selected from halogen, CN, COOH, $CONH_2$, and $C_{1-3}$ alkoxy.

In a preferred embodiment of compounds having formula I and, in particular, compounds having formula Ia, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperidinyl. Where the heterocyclyl is substituted, it is preferably substituted with an aryl or an aryl $C_{1-4}$ alkyl, wherein the aryl is preferably monocyclic and more preferably phenyl. The alkyl is preferably linear. More preferably, the heterocyclyl is substituted with an aryl or an aryl $C_{1-2}$ alkyl, wherein the aryl is preferably monocyclic and more preferably phenyl.

In a preferred embodiment of compounds having formula I and, in particular, compounds having formula Ia, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. In one embodiment, R1 is selected from H, methyl and ethyl, and R2 is selected from aryl, heteroaryl, heterocyclyl, and $C_{5-8}$ cycloalkyl, each of which are monocyclic and may be substituted or unsubstituted. More preferably, R1 is selected from H and methyl. In one embodiment, R1 is methyl. In an alternative embodiment, R1 is H. More preferably, R2 is selected from saturated heterocyclyl, and $C_{5-8}$ cycloalkyl, each of which are monocyclic and may be substituted or unsubstituted. When R2 is a monocyclic $C_{5-8}$ cycloalkyl, it is preferably unsubstituted. Preferably, R2 is a cyclopentyl or cyclohexyl. More preferably, R2 is a cyclohexyl, such as an unsubstituted cyclohexyl. When R2 is a monocyclic saturated heterocyclyl, the heterocyclyl ring preferably contains a single heteroatom. More preferably, the heterocyclyl is six membered, such as a piperidinyl or tetrahydropyranyl group. The nitrogen heteroatom may be substituted or unsubstituted.

In an alternative embodiment, R1 is selected from H, methyl and ethyl, and R2 is selected from aryl $C_{1-6}$ alkyl, heteroaryl $C_{1-6}$ alkyl, heterocyclyl $C_{1-6}$ alkyl, and $C_{5-8}$ cycloalkyl $C_{1-6}$ alkyl, each of which are monocyclic and may be substituted or unsubstituted. More preferably, R2 is aryl $C_{1-6}$ alkyl in which the aryl is monocyclic and may be substituted or unsubstituted. More preferably still, R2 is aryl $C_{1-6}$ alkyl in which the aryl is monocyclic and may be substituted or unsubstituted and the $C_{1-6}$ alkyl is linear. Even more preferably, R2 is phenyl $C_{1-6}$ alkyl which may be substituted or unsubstituted and the $C_{1-6}$ alkyl is linear. In one embodiment, the phenyl is unsubstituted.

In an alternative embodiment, R1 is selected from H, methyl and ethyl, and R2 is $C_{1-4}$ alkyl substituted with a group selected from aryl $C_{1-4}$ alkoxy, heteroaryl $C_{1-4}$ alkoxy, heterocyclyl $C_{1-4}$ alkoxy, and $C_{5-8}$ cycloalkyl $C_{1-4}$ alkoxy, each of which are monocyclic and may be substituted or unsubstituted. Preferably, R2 is substituted $C_{1-3}$ alkyl. In one embodiment, R2 is substituted $C_{1-2}$ alkyl. Preferably, the substituent of R2 is aryl $C_{1-4}$ alkoxy in which the aryl is monocyclic and may be substituted or unsubstituted. More preferably still, the substituent of R2 is aryl $C_{1-4}$ alkoxy in which the aryl is monocyclic and may be substituted or unsubstituted and the $C_{1-4}$ alkoxy is linear. Even more preferably, the substituent of R2 is phenyl $C_{1-4}$ alkoxy which may be substituted or unsubstituted and the $C_{1-4}$ alkoxy is linear. In one embodiment, the substituent of R2 is aryl $C_{1-3}$ alkoxy in which the aryl is monocyclic (e.g. phenyl) and may be substituted or unsubstituted and the $C_{1-3}$ alkoxy is linear. In some embodiments, the phenyl is unsubstituted.

In yet another embodiment of compounds having formula I and, in particular, compounds having formula Ia, R1 is selected from H and $C_{1-4}$ alkyl, and R2 is selected from heterocyclyl which may be substituted or unsubstituted. Preferably, R1 is H, methyl or ethyl, and R2 is a bicyclic heterocyclyl which may be substituted or unsubstituted. More preferably, R1 is H or methyl, and R2 is a bicyclic heterocyclyl which may be substituted or unsubstituted, wherein one of the rings of the heterocyclyl contains two oxygen atoms. In one embodiment, R2 is 3,3-dimethyl-1,5-dioxaspiro[5.5]undec-9-yl.

In an alternative preferred embodiment of compounds having formula I and, in particular, compounds having formula Ia, R1 is selected from H and $C_{1-4}$ alkyl, and R2 is $C_{2-20}$ alkyl. More preferably, R1 is H, methyl or ethyl and more preferably still, R1 is H or methyl. Preferably, R2 is $C_{3-16}$ alkyl, wherein the alkyl is a linear alkyl. More preferably, R2 is $C_{4-14}$ alkyl, wherein the alkyl is a linear alkyl.

Formula IIa

In a preferred embodiment of compounds having Formula IIa, R1 is selected from H and $C_{1-4}$ alkyl, and R2 is selected from $C_{1-6}$ alkyl, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from aryl such as phenyl, saturated heterocyclyl, and $C_{5-8}$ cycloalkyl each of which are monocyclic and may be substituted or unsubstituted. When R2 is a monocyclic $C_{5-8}$ cycloalkyl (i.e. cyclopentyl, cyclohexyl, cycloheptyl or cyclooctyl) or aryl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom, such as nitrogen or oxygen. More preferably, the heterocyclyl is six membered, such as a piperidinyl or tetrahydropyranyl group. In one embodiment, the heteroatom is a nitrogen heteroatom which may be substituted or unsubstituted. Preferably, the heteroatom in the said heterocyclyl group is at the 4-position relative to the position of attachment of the heterocyclyl group R2 to the urea nitrogen. In one embodiment, the nitrogen atom is substituted with monocyclic aryl (preferably phenyl) $C_{1-3}$ alkyl; preferably, the nitrogen atom is substituted with benzyl or phenylethyl; and, more preferably, the nitrogen atom is substituted with benzyl.

In an alternative preferred embodiment of compounds having Formula IIa, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IIa, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogen atoms.

In compounds having formula IIa, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2$R5a, $SO_3H$, $SO_2NH_2$, CONR5aR5b, $SO_2$NR5aR5b, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IIa, R6 is preferably selected from aryl, heteroaryl, heterocyclyl and $C_{3-8}$ cycloalkyl, each of which may be substituted or unsubstituted. More preferably, R6 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring, for example, phenyl or pyridyl. In one embodiment, the heteroaryl contains a nitrogen atom which is substituted with an oxygen atom such as oxidopyridyl. In another embodiment, R6 is unsubstituted monocyclic aryl such as phenyl, or monocyclic aryl such as phenyl substituted with one or more groups selected from halogen, $C_{1-2}$ alkoxy (optionally substituted with one or more halogen atoms), or OH.

In one embodiment, R6 is unsubstituted or substituted 2-oxo-2,3-dihydro-1H-benzo[d]imidazolyl.

When R6 is substituted, the substituent is preferably one or more groups selected from halogen, $C_{1-4}$ alkoxy, aryl, heteroaryl, heterocyclyl, OH, CN, $CONH_2$, $NH_2$, heterocyclyl $C_{1-4}$ alkoxy, aryl $C_{1-4}$ alkoxy, heteroaryl $C_{1-4}$ alkoxy, $NO_2$, $SO_2NH_2$, $SO_3$, $C(NOH)NH_2$, CONHOH, 2H-tetrazol-5-yl, dimethylamino, benzylamino, methylsulfonyl, morpholinosulfonyl and piperidinylsulfonyl. The piperidinylsulfonyl may optionally be substituted with arylmethoxy (preferably benzoxy) or OH. Preferably, the aryl, heteroaryl and heterocyclyl are monocyclic. In one embodiment, the aryl, heteroaryl and heterocyclyl are six-membered monocyclic rings. In a particular embodiment in which R6 is monocyclic aryl, it may optionally be substituted with one or more groups selected from halogen, OH, $C_{1-3}$ alkoxy (preferably $C_{1-2}$ alkoxy), aryl (e.g. a monocyclic aryl such as phenyl), heteroaryl (e.g. monocyclic heteroaryl containing one or two nitrogen atoms, or one oxygen atom), heterocyclyl (e.g. piperazinyl, piperadinyl or morpholino) $C_{1-3}$ alkoxy (preferably $C_{1-2}$ alkoxy), aryl (e.g. monocyclic aryl such as phenyl) $C_{1-3}$ alkoxy (preferably $C_{1-2}$ alkoxy), $CONH_2$, $NH_2$, $NO_2$, $OCHF_2$, $SO_2NH_2$, morpholinosulfonyl and $C(NOH)NH_2$.

In another embodiment in which R6 is monocyclic aryl, it may optionally be substituted with one or more groups selected from halogen, OH, methoxy, phenyl, pyridyl, pyrazinyl, pyranyl, piperazinylmethoxy, piperadinylmethoxy, morpholinomethoxy, benzyloxy, $CONH_2$, $NH_2$, $NO_2$, $OCHF_2$, $SO_2NH_2$, morpholinosulfonyl and $C(NOH)NH_2$.

In one embodiment when R6 is monocyclic aryl such as phenyl, the substituent of R6 is aryl, preferably monocyclic aryl such as phenyl, which may be substituted or unsubstituted. Where it is substituted, preferably it is substituted with $CONH_2$.

When the substituent of R6 is $C_{1-4}$ alkoxy, aryl, heteroaryl, heterocyclyl, heterocyclyl $C_{1-4}$ alkoxy, aryl $C_{1-4}$ alkoxy, heteroaryl $C_{1-4}$ alkoxy or $SO_3$, each of these moieties may optionally be substituted with one or more groups selected from halogen, OH, $C_{1-3}$ alkoxy (which may be substituted with one or more halogen), $CONH_2$, CN, $NCH_3CH_3$, $NHCOCH_3$, methylhydroxybutyl, and methylhydroxybutynyl.

In compounds having formula IIa, R8 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R8a, halogen, OH, OR8a, SH, SR8a, OCOR8a, SCOR8a, $NH_2$, $NO_2$, NHR8a, NR8aR8b, COR8a, CSR8a, CN, COOH, COOR8a, $CONH_2$, $SO_2R8a$, $SO_3H$, $SO_2NH_2$, CONR8aR8b, $SO_2NR8aR8b$, wherein R8a and R8b are independently selected from $C_{1-6}$ alkyl, aryl, heteroaryl, $C_{3-8}$ cycloalkyl and heterocyclyl, and R8a and R8b, together with the heteroatom to which they are joined, can form heterocyclyl. More preferably, R8 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R8 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R8 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R8 is selected from H, $C_{1-2}$ alkyl, halogen and monocyclic aryl such as phenyl. Even more preferably, R8 is selected from H, $C_{1-2}$ alkyl, and halogen such as F, Cl and Br. More preferably still, R8 is selected from H and halogen such as F, Cl and Br. In one embodiment, R8 is H.

In one embodiment of compounds having formula IIa, R1 is selected from H and $C_{1-4}$ alkyl, R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may optionally be substituted with one or more groups selected from R2a, halogen, OH, OR2a, OCOR2a, SH, SR2a, SCOR2a, $NH_2$, NHR2a, $NHSO_2NH_2$, $NHSO_2R2a$, NR2aCOR2b, $NHC(NH)NH_2$, NHCOR2a, NR2aR2b, COR2a, CSR2a, CN, COOH, COOR2a, $CONH_2$, CONHOH, CONHR2a, CONHOR2a, $C(NOH)NH_2$, $SO_2R2a$, $SO_3H$, $SO_2NH_2$, CONR2aR2b, $SO_2NR2aR2b$, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the substituent of R2 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R2c, halogen, OH, OR2c, OCOR2c, SH, SR2c, SCOR2c, $NH_2$, NHR2c, $NHSO_2NH_2$, $NHSO_2R2c$, NR2cCOR2d, $NHC(NH)NH_2$, NHCOR2c, NR2cR2d, COR2c, CSR2c, CN, COOH, COOR2c, $CONH_2$, CONHOH, CONHR2c, CONHOR2c, $C(NOH)NH_2$, $SO_2R2c$, $SO_3H$, $SO_2NH_2$, CONR2cR2d, $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, R5 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, $NHC(NH)NH_2$, NHCOR5a, NR5aR5b, COR5a, CSR5a, CN, COOH, COOR5a, $CONH_2$, CONHOH, CONHR5a, CONHOR5a, $C(NOH)NH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, R6 is selected from aryl, heteroaryl, heterocyclyl, $C_{3-10}$ cycloalkyl, each of which may optionally be substituted with one or more groups selected from R6a, halogen, OH, OR6a, OCOR6a, SH, SR6a, SCOR6a, $NO_2$, $NH_2$, NHR6a, $NHSO_2NH_2$, $NHSO_2R6a$, NR6aCOR6b, $NHC(NH)NH_2$, NHCOR6a, NR6aR6b, COR6a, CSR6a, CN, COOH, COOR6a, $CONH_2$, CONHOH, CONHR6a, CONHOR6a, $C(NOH)NH_2$, $SO_2R6a$, $SO_3H$, $SO_2NH_2$, CONR6aR6b, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, and wherein, when R6 is heteroaryl or heterocyclyl, each of these moieties may optionally be substituted with one or more oxygen atoms, wherein, when the substituent of R6 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R6c, halogen, OH, OR6c, OCOR6c, SH, SR6c, SCOR6c, $NH_2$, NHR6c, $NHSO_2NH_2$, $NHSO_2R6c$, NR6cCOR6d, $NHC(NH)NH_2$, NHCOR6c, NR6cR6d, COR6c, CSR6c, CN, COOH, COOR6c, $CONH_2$, CONHOH, CONHR6c, CONHOR6c, $C(NOH)NH_2$, $SO_2R6c$, $SO_3H$, $SO_2NH_2$, CONR6cR6d, $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, and wherein, when the substituent of R6 is heteroaryl or heterocyclyl, each of these moieties may optionally be substituted with one or more oxygen atoms, and R8 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, $NHC(NH)NH_2$, NHCOR5a, NR5aR5b, COR5a, CSR5a, CN, COOH, COOR5a, $CONH_2$, CONHOH, CONHR5a, CONHOR5a, $C(NOH)NH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl.

In the above embodiment, preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from heterocyclyl, and $C_{5-8}$ cycloalkyl each of which are monocyclic and may be substituted or unsubstituted. Preferably, the heterocyclyl is fully saturated. When R2 is a monocyclic $C_{5-8}$ cycloalkyl (i.e. cyclopentyl, cyclohexyl, cycloheptyl or cyclooctyl), it is preferably unsubstituted. In one embodiment, R2 is a cyclopentyl or a cyclohexyl, such as an unsubstituted cyclopentyl or unsubstituted cyclohexyl. When R2 is a monocyclic saturated heterocyclyl, the heterocyclyl ring preferably contains a single heteroatom, such as nitrogen or oxygen. Preferably, the heterocyclyl is six membered, such as a piperidinyl or tetrahydropyranyl group. Preferably, the heteroatom in the said heterocyclyl group is at the 4-position relative to the position of attachment of the heterocyclyl group R2 to the urea nitrogen. In one embodiment, the heteroatom is a nitrogen heteroatom which may be substituted or unsubstituted.

In a particular embodiment, the nitrogen atom is substituted with a group selected from CN, CONH$_2$, C(NOH)NH$_2$, SO$_2$—C$_{1-4}$ alkyl, SO$_2$-aryl (optionally substituted with a C$_{1-4}$ alkyl or C$_{1-4}$ haloalkyl, such as trifluoromethyl), CO-heteroaryl (optionally substituted with a heteroaryl or halogen), CO—C$_{1-4}$ alkyl, COO—C$_{1-4}$ alkyl, C$_{1-4}$ alkyl (optionally substituted with OH, CN, COOH), aryl C$_{1-3}$ alkyl, heteroaryl C$_{1-3}$ alkyl such as piperidinyl C$_{1-3}$ alkyl (optionally substituted with COO—C$_{1-3}$ alkyl), heterocyclyl C$_{1-3}$ alkyl, aryl, heteroaryl (optionally substituted with one or more halogens such as chlorine), and heterocyclyl. Preferably, the nitrogen atom is substituted with a group selected from CN, CONH$_2$, C(NOH)NH$_2$, SO$_2$—C$_{1-4}$ alkyl, SO$_2$-monocyclic aryl (optionally substituted with a C$_{1-4}$ haloalkyl, such as trifluoromethyl), CO-monocyclic heteroaryl (optionally substituted with a monocyclic heteroaryl or halogen), CO—C$_{1-4}$ alkyl, COO—C$_{1-4}$ alkyl, C$_{1-4}$ alkyl (optionally substituted with OH, CN, COOH), monocyclic aryl C$_{1-3}$ alkyl, monocyclic heteroaryl C$_{1-3}$ alkyl such as piperidinyl C$_{1-3}$ alkyl (optionally substituted with COO—C$_{1-3}$ alkyl), monocyclic heterocyclyl C$_{1-3}$ alkyl, monocyclic aryl, monocyclic heteroaryl (optionally substituted with one or more halogens such as chlorine), and monocyclic heterocyclyl. More preferably, the nitrogen atom is substituted with a group selected from CN, C$_{1-4}$ alkyl (optionally substituted with OH, CN, COOH), monocyclic aryl C$_{1-3}$ alkyl, and monocyclic heteroaryl C$_{1-3}$ alkyl (preferably piperidinyl C$_{1-3}$ alkyl). More preferably still, the nitrogen atom is substituted with a group selected from C$_{1-4}$ alkyl (optionally substituted with OH, CN, COOH), monocyclic aryl C$_{1-3}$ alkyl, and monocyclic heteroaryl C$_{1-3}$ alkyl (preferably piperidinyl C$_{1-3}$ alkyl).

In one embodiment, the nitrogen atom is substituted with monocyclic aryl (preferably phenyl) C$_{1-3}$ alkyl; preferably, the nitrogen atom is substituted with benzyl or phenylethyl; and, more preferably, the nitrogen atom is substituted with benzyl.

In one embodiment R5 is H, halogen, OH or C$_{1-4}$ alkyl. Preferably, R5 is H.

In another embodiment, R6 is selected from aryl, heteroaryl, and heterocyclyl, each of which may be substituted or unsubstituted. Preferably, R6 is selected from monocyclic aryl (such as phenyl), monocyclic heteroaryl (such as pyridyl), and heterocyclyl, each of which may be substituted or unsubstituted. In one embodiment, R6 is an unsubstituted aryl. When R6 is a substituted aryl, it is preferably substituted with one or more groups selected from halogen, R6a, OH, OR6a, NH$_2$, NO$_2$, NHC(NH)NH$_2$, NHR6a, NR6aR6b, C(NOH)NH$_2$, COR6a, COOH, COOR6a, CONH$_2$, CONHOH, SO$_2$R6a, SO$_2$NR6aR6b, wherein R6a and R6b are independently selected from C$_{1-6}$ alkyl, substituted C$_{1-6}$ alkyl, aryl, heteroaryl, C$_{3-8}$ cycloalkyl and heterocyclyl, wherein, when the substituent of R6 is C$_{1-6}$ alkyl, substituted C$_{1-6}$ alkyl, aryl, heteroaryl, C$_{3-8}$ cycloalkyl, heterocyclyl or is a group containing one or more of these moieties, each of these moieties may optionally be substituted with one or more groups selected from OR6c, OH, and CONH$_2$, wherein R6c and R6d are independently selected from C$_{1-6}$ alkyl, substituted C$_{1-6}$ alkyl, aryl, heteroaryl, C$_{3-8}$ cycloalkyl and heterocyclyl, and wherein, when the substituent of R6 is heteroaryl or heterocyclyl, each of these moieties may optionally be substituted with one or more oxygen atoms.

Preferably, when R6 is a substituted aryl, it is substituted with one or more groups selected from halogen, OH, C$_{1-4}$ alkoxy, CONH$_2$, C(NOH)NH$_2$, CONHOH, SO$_2$—C$_{1-4}$ alkyl, heterocyclyl (optionally substituted with an oxygen atom), and aryl (optionally substituted with CONH$_2$). In one embodiment, R6 may be substituted with one or more groups selected from 5-oxo-4,5-dihydro-1,2,4-oxadiazol-3-yl, 3-carbamoylphenyl, 2H-tetrazol-5-yl, C$_{1-4}$ alkoxy, halogen, OH, CONHOH.

When R6 is a heterocyclyl, it is preferably substituted with an oxygen atom. The substituent of R6 may be 2-oxo-2,3-dihydro-1H-benzo[d]imidazol-5-yl or 2-oxo-2,3-dihydrobenzo[d]oxazol-5-yl.

When R6 is a heteroaryl, it is preferably unsubstituted or substituted with an oxygen atom. For example, the heterocyclyl may contain an N-oxide. In one embodiment, R6 is pyridyl or pyridyl oxide.

In another embodiment, R8 is H, halogen, OH or C$_{1-4}$ alkyl. Preferably, R8 is H.

Formula IIb

In a preferred embodiment of compounds having Formula IIb, R1 is selected from H and C$_{1-4}$ alkyl, and R2 is selected from aryl, heteroaryl, heterocyclyl, C$_{3-10}$ cycloalkyl, aryl C$_{1-6}$ alkyl, heteroaryl C$_{1-6}$ alkyl, heterocyclyl C$_{1-6}$ alkyl and C$_{3-10}$ cycloalkyl C$_{1-6}$ alkyl, each of which may be substituted or unsubstituted. More preferably, R1 is selected from H, methyl and ethyl, and R2 is selected from aryl, heteroaryl, heterocyclyl, and C$_{3-10}$ cycloalkyl each of which may be substituted or unsubstituted. More preferably, R1 is methyl. More preferably, R2 is selected from aryl, heteroaryl, heterocyclyl, and C$_{5-8}$ cycloalkyl each of which are monocyclic and may be substituted or unsubstituted. More preferably still, R2 is monocyclic aryl such as phenyl and may be substituted or unsubstituted. When R2 is substituted, the substituent may be aryl, C$_{1-4}$ alkoxy, aryl C$_{1-4}$ alkoxy or aryloxy. Preferably, the substituent of R2 is aryl, C$_{1-3}$ alkoxy, aryl C$_{1-3}$ alkoxy or aryloxy, wherein the aryl is monocyclic and more preferably, phenyl.

When R2 is a monocyclic C$_{5-8}$ cycloalkyl or aryl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom, such as nitrogen or oxygen. More preferably, the heterocyclyl is six membered, such as a piperidinyl or tetrahydropyranyl group. In one embodiment the heteroatom is a nitrogen heteroatom which may be substituted or unsubstituted. Preferably, the heteroatom in the said heterocyclyl group is at the 4 position relative to the position of attachment of the heterocyclyl group R2 to the urea nitrogen. In one embodiment, the nitrogen atom is substituted with monocyclic aryl (preferably phenyl) C$_{1-3}$ alkyl.

In an alternative preferred embodiment of compounds having Formula IIb, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IIb, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogen.

In compounds having formula IIb, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2$R5a, $SO_3H$, $SO_2NH_2$, CONR5aR5b, $SO_2$NR5aR5b, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IIb, R6 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R6a, halogen, OH, OR6a, SH, SR6a, OCOR6a, SCOR6a, $NH_2$, $NO_2$, NHR6a, NR6aR6b, COR6a, CSR6a, CN, COOH, COOR6a, $CONH_2$, $SO_2$R6a, $SO_3H$, $SO_2NH_2$, CONR6aR6b, $SO_2$NR6aR6b, wherein R6a and R6b are independently selected from $C_{1-6}$ alkyl, aryl, heteroaryl, $C_{3-8}$ cycloalkyl and heterocyclyl, and R6a and R6b, together with the heteroatom to which they are joined, can form heterocyclyl. More preferably, R6 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R6 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R6 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R6 is selected from H, $C_{1-2}$ alkyl and halogen. Even more preferably, R6 is selected from H and halogen such as F, Cl and Br. In one embodiment, R6 is H.

In compounds having formula IIb, R7 is preferably selected from aryl, heteroaryl, heterocyclyl and $C_{3-8}$ cycloalkyl each of which may be substituted or unsubstituted. More preferably, R7 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring. In one embodiment, the heteroaryl contains a nitrogen atom which is substituted with an oxygen atom such as oxidopyridyl. In another embodiment, R7 is unsubstituted monocyclic aryl such as phenyl, or monocyclic aryl such as phenyl substituted with one or more groups selected from halogen, $C_{1-2}$ alkoxy (optionally substituted with one or more halogen), or OH. In a particular embodiment, R7 is unsubstituted monocyclic aryl such as phenyl.

When R7 is substituted, the substituent is preferably one or more groups selected from halogen, $C_{1-4}$ alkoxy, aryl, heteroaryl, heterocyclyl, OH, $CONH_2$, $NH_2$, heterocyclyl $C_{1-4}$ alkoxy, aryl $C_{1-4}$ alkoxy, heteroaryl $C_{1-4}$ alkoxy, $NO_2$, $SO_2NH_2$, $SO_3$, $C(NOH)NH_2$ and morpholinosulfonyl. Preferably, the aryl, heteroaryl and heterocyclyl are monocyclic. In one embodiment, the aryl, heteroaryl and heterocyclyl are six membered monocyclic rings. In a particular embodiment in which R7 is monocyclic aryl, it may optionally be substituted with aryl or heteroaryl, each of which are monocyclic.

Formula IIc

In a preferred embodiment of compounds having Formula IIc, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from aryl such as phenyl, saturated heterocyclyl, and $C_{5-8}$ cycloalkyl each of which are monocyclic and may be substituted or unsubstituted. When R2 is a monocyclic $C_{5-8}$ cycloalkyl or aryl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom such as nitrogen or oxygen. More preferably, the heterocyclyl is six membered, such as a piperidinyl or tetrahydropyranyl group. In one embodiment, the heteroatom is a nitrogen heteroatom which may be substituted or unsubstituted. Preferably, the heteroatom in the said heterocyclyl group is at the 4 position relative to the position of attachment of the heterocyclyl group R2 to the urea nitrogen. In one embodiment, the nitrogen atom is substituted with monocyclic aryl (preferably phenyl) $C_{1-3}$ alkyl.

In an alternative preferred embodiment of compounds having Formula IIc, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IIc, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogen.

In compounds having formula IIc, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IIc, R6 is preferably selected from aryl, heteroaryl, heterocyclyl and $C_{3-8}$ cycloalkyl each of which may be substituted or unsubstituted. More preferably, R6 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring. In one embodiment, the heteroaryl contains a nitrogen atom which is substituted with an oxygen atom such as oxidopyridyl. In another embodiment, R6 is unsubstituted monocyclic aryl such as phenyl, or monocyclic aryl such as phenyl substituted with one or more groups selected from halogen, $C_{1-2}$ alkoxy (optionally substituted with one or more halogen), or OH. In a preferred embodiment, R6 is unsubstituted aryl and, preferably, a monocyclic aryl such as phenyl.

When R6 is substituted, the substituent is preferably one or more groups selected from halogen, $C_{1-4}$ alkoxy, aryl, heteroaryl, heterocyclyl, OH, $CONH_2$, $NH_2$, heterocyclyl $C_{1-4}$ alkoxy, aryl $C_{1-4}$ alkoxy, heteroaryl $C_{1-4}$ alkoxy, $NO_2$, $SO_2NH_2$, $SO_3$, $C(NOH)NH_2$ and morpholinosulfonyl. Preferably, the aryl, heteroaryl and heterocyclyl are monocyclic. In one embodiment, the aryl, heteroaryl and heterocyclyl are six membered monocyclic rings. In a particular embodiment in which R6 is monocyclic aryl, it may optionally be substituted with one or more groups selected from halogen, OH, $C_{1-3}$ alkoxy, aryl (e.g. a monocyclic aryl such as phenyl), heteroaryl (e.g. monocyclic heteroaryl containing one or two nitrogen atoms, or one oxygen atom), heterocyclyl (e.g. piperazinyl, piperadinyl or morpholino) $C_{1-3}$ alkoxy, aryl (e.g. monocyclic aryl such as phenyl) $C_{1-3}$ alkoxy, $CONH_2$, $NH_2$, $NO_2$, $OCHF_2$, $SO_2NH_2$, morpholinosulfonyl and $C(NOH)NH_2$.

In one embodiment when R6 is monocyclic aryl such as phenyl, the substituent of R6 is aryl, preferably monocyclic aryl such as phenyl, which may be substituted or unsubstituted. Where it is substituted, preferably it is substituted with $CONH_2$.

When the substituent of R6 is $C_{1-4}$ alkoxy, aryl, heteroaryl, heterocyclyl, heterocyclyl $C_{1-4}$ alkoxy, aryl $C_{1-4}$ alkoxy, heteroaryl $C_{1-4}$ alkoxy or $SO_3$, each of these moieties may optionally be substituted with one or more groups selected from halogen, OH, $C_{1-3}$ alkoxy (which may be substituted with one or more halogen), $CONH_2$, CN, $NCH_3CH_3$, $NHCOCH_3$, methylhydroxybutyl, and methylhydroxybutynyl.

Formula IId

In a preferred embodiment of compounds having Formula IId, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from aryl such as phenyl, saturated heterocyclyl, and $C_{5-8}$ cycloalkyl each of which are monocyclic and may be substituted or unsubstituted. Even more preferably, R2 is aryl, such as phenyl, which is monocyclic and may be substituted or unsubstituted. When R2 is substituted, the substituent is preferably one or more halogen.

In one embodiment, R2 is a cyclohexyl, such as an unsubstituted cyclohexyl. When R2 is a monocyclic saturated heterocyclyl, the heterocyclyl ring preferably contains a single heteroatom such as nitrogen or oxygen. More preferably, the heterocyclyl is six membered, such as a piperidinyl or tetrahydropyranyl group. In one embodiment, the heteroatom is a nitrogen heteroatom which may be substituted or unsubstituted. Preferably, the heteroatom in the said heterocyclyl group is at the 4 position relative to the position of attachment of the heterocyclyl group R2 to the urea nitrogen. In one embodiment, the nitrogen atom is substituted with monocyclic aryl (preferably phenyl) $C_{1-3}$ alkyl.

In an alternative preferred embodiment of compounds having Formula IId, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IId, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogens.

In compounds having formula IId, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, NH$_2$, NO$_2$, NHR5a, NR5aR5b, COR5a, CSR5a, CN, COOH, COOR5a, CONH$_2$, SO$_2$R5a, SO$_3$H, SO$_2$NH$_2$, CONR5aR5b, SO$_2$NR5aR5b, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, NH$_2$, NO$_2$, CN, COOH, CONH$_2$, SO$_3$H, SO$_2$NH$_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, NH$_2$, NO$_2$, CN, COOH, CONH$_2$, SO$_3$H, SO$_2$NH$_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, NH$_2$, COOH and CONH$_2$, wherein the aryl, heteroaryl, heterocyclyl and $C_{5-4}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IId, R7 is preferably selected from aryl, heteroaryl, heterocyclyl and $C_{3-8}$ cycloalkyl each of which may be substituted or unsubstituted. More preferably, R7 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring. In one embodiment, the heteroaryl contains a nitrogen atom which is substituted with an oxygen atom such as oxidopyridyl. In another embodiment, R7 is unsubstituted monocyclic aryl such as phenyl, or monocyclic aryl such as phenyl substituted with one or more groups selected from halogen, $C_{1-2}$ alkoxy (optionally substituted with one or more halogen), or OH.

When R7 is substituted, the substituent is preferably one or more groups selected from halogen, $C_{1-4}$ alkoxy, aryl, heteroaryl, heterocyclyl, OH, CONH$_2$, NH$_2$, heterocyclyl $C_{1-4}$ alkoxy, aryl $C_{1-4}$ alkoxy, heteroaryl $C_{1-4}$ alkoxy, NO$_2$, SO$_2$NH$_2$, SO$_3$, C(NOH)NH$_2$ and morpholinosulfonyl. Preferably, the aryl, heteroaryl and heterocyclyl are monocyclic. In one embodiment, the aryl, heteroaryl and heterocyclyl are six membered monocyclic rings. In a particular embodiment in which R7 is monocyclic aryl, it may optionally be substituted with one or more groups selected from halogen, OH, $C_{1-3}$ alkoxy, aryl (e.g. a monocyclic aryl such as phenyl), heteroaryl (e.g. monocyclic heteroaryl containing one or two nitrogen atoms, or one oxygen atom), heterocyclyl (e.g. piperazinyl, piperadinyl or morpholino) $C_{1-3}$ alkoxy, aryl (e.g. monocyclic aryl such as phenyl) $C_{1-3}$ alkoxy, CONH$_2$, NH$_2$, NO$_2$, OCHF$_2$, SO$_2$NH$_2$, morpholinosulfonyl and C(NOH)NH$_2$. In one embodiment when R7 is monocyclic aryl such as phenyl, the substituent of R7 is aryl (e.g. monocyclic aryl such as phenyl) $C_{1-3}$ alkoxy.

When the substituent of R7 is $C_{1-4}$ alkoxy, aryl, heteroaryl, heterocyclyl, heterocyclyl $C_{1-4}$ alkoxy, aryl $C_{1-4}$ alkoxy, heteroaryl $C_{1-4}$ alkoxy or SO$_3$, each of these moieties may optionally be substituted with one or more groups selected from halogen, OH, $C_{1-3}$ alkoxy (which may be substituted with one or more halogen), CONH$_2$, CN, NCH$_3$CH$_3$, NHCOCH$_3$, methylhydroxybutyl, and methylhydroxybutynyl In an alternative embodiment of the process of the invention, a compound is prepared having Formula I or Formula II:

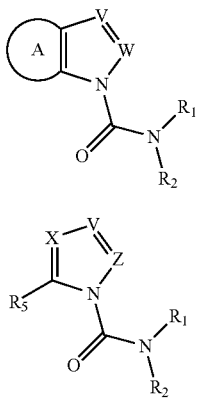

Formula I

Formula II wherein R1, R2, R5, ring A, V, W, X, Y and Z are as defined above;

or a pharmaceutically acceptable salt or ester thereof;

provided that Ring A in compounds having Formula I does not form pyridine, pyrimidine, substituted pyridine or substituted pyrimidine, when 121 and R2, together with the N to which they are attached, form piperidinyl, piperazinyl, substituted piperidinyl or substituted piperazinyl, provided that Ring A is not unsubstituted benzo, hydroxybenzo, phenoxybenzo, fluorochlorobenzo, chlorobenzo, bromobenzo, nitrobenzo, aminobenzo, cyanobenzo, methylbenzo, trifluoromethylbenzo, trifluoromethylchlorobenzo, phenylketobenzo, phenylhydroxymethylbenzo, cyclohexylthiobenzo, methoxycarbonylbenzo or methoxybenzo, provided that when R1 or R2 is methyl, the other of 121 or R2 is not 4-chlorobutyl, 4-azidobutyl, or 4-isothiocyanatobutyl, and/or provided that the compound is not (4-phenyl-1H-imidazol-1-yl)(4-(quinolin-2-ylmethyl)piperazin-1-yl)methanone.

In a particularly preferred embodiment, the compound has the Formula IIa, and the carbamate of Formula II' has a corresponding structure in which the —NR1R2 group of Formula IIa is replaced by the —C(O)O-Ph-J group of Formula II'.

In such an embodiment, the compound may, for example, be of Formula IIa, wherein:

R1 is selected from H and $C_{1-4}$ alkyl,

R2 is selected from $C_{1-6}$ alkyl, aryl, heteroaryl, heterocyclyl, $C_{3413}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may optionally be substituted with one or more groups selected from R2a, halogen, OH, OR2a, OCOR2a, SH, SR2a, SCOR2a, $NH_2$, NHR2a, $NHSO_2NH_2$, $NHSO_2R2a$, NR2aCOR2b, $NHC(NH)NH_2$, NHCOR2a, NR2aR2b, COR2a, CSR2a, CN, COOH, COOR2a, $CONH_2$, CONHOH, CONHR2a, CONHOR2a, $C(NOH)NH_2$, $SO_2R2a$, $SO_3H$, $SO_2NH_2$, CONR2aR2b, $SO_2NR2aR2b$, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the substituent of R2 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R2c, halogen, OH, OR2c, OCOR2c, SH, SR2c, SCOR2c, $NH_2$, NHR2c, $NHSO_2NH_2$, $NHSO_2R2c$, NR2cCOR2d, $NHC(NH)NH_2$, NHCOR2c, NR2cR2d, COR2c, CSR2c, CN, COOH, COOR2c, $CONH_2$, CONHOH, CONHR2c, CONHOR2c, $C(NOH)NH_2$, $SO_2R2c$, $SO_3H$, $SO_2NH_2$, CONR2cR2d, $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, R5 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, $NHC(NH)NH_2$, NHCOR5a, NR5aR5b, COR5a, CSR5a, CN, COOH, COOR5a, $CONH_2$, CONHOH, CONHR5a, CONHOR5a, $C(NOH)NH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, R6 is selected from aryl, heteroaryl, heterocyclyl, $C_{3-10}$ cycloalkyl, each of which may optionally be substituted with one or more groups selected from R6a, halogen, OH, OR6a, OCOR6a, SH, SR6a, SCOR6a, $NO_2$, $NH_2$, NHR6a, $NHSO_2NH_2$, $NHSO_2R6a$, NR6aCOR6b, $NHC(NH)NH_2$, NHCOR6a, NR6aR6b, COR6a, CSR6a, CN, COOH, COOR6a, $CONH_2$, CONHOH, CONHR6a, CONHOR6a, $C(NOH)NH_2$, $SO_2R6a$, $SO_3H$, $SO_2NH_2$, CONR6aR6b, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, and wherein, when R6 is heteroaryl or heterocyclyl, each of these moieties may optionally be substituted with one or more oxygen atoms, wherein, when the substituent of R6 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R6c, halogen, OH, OR6c, OCOR6c, SH, SR6c, SCOR6c, $NH_2$, NHR6c, $NHSO_2NH_2$, $NHSO_2R6c$, NR6cCOR6d, $NHC(NH)NH_2$, NHCOR6c, NR6cR6d, COR6c, CSR6c, CN, COOH, COOR6c, $CONH_2$, CONHOH, CONHR6c, CONHOR6c, $C(NOH)NH_2$, $SO_2R6c$, $SO_3H$, $SO_2NH_2$, CONR6cR6d, $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, and wherein, when the substituent of R6 is heteroaryl or heterocyclyl, each of these moieties may optionally be substituted with one or more oxygen atoms, and R8 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, $NHC(NH)NH_2$, NHCOR5a, NR5aR5b, COR5a, CSR5a, CN, COOH, COOR5a, $CONH_2$, CONHOH, CONHR5a, CONHOR5a, $C(NOH)NH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl.

In particular instances of this preferred embodiment, R1 may be selected from H, methyl and ethyl, and R2 may be selected from aryl, heteroaryl, heterocyclyl, and $C_{3-10}$ cycloalkyl, each of which may be substituted or unsubstituted. R2 may, for example, be selected from fully saturated heterocyclyl, and $C_{5-8}$ cycloalkyl, each of which are monocyclic and may be substituted or unsubstituted. By way of further example, R2 may be an unsubstituted cyclopentyl or unsubstituted cyclohexyl. As an alternative example, R2 may be a fully saturated heterocyclyl, wherein the heterocyclyl ring contains a single heteroatom, such as nitrogen or oxygen. In such embodiments, the heterocyclyl R2 may be six membered and the heteroatom in the said heterocyclyl group may be at the 4-position relative to the position of attachment of the heterocyclyl group R2 to the urea nitrogen. In particular embodiments, the heteroatom in heterocyclyl R2 may be a nitrogen heteroatom, which may be substituted with a group selected from CN, $CONH_2$, $C(NOH)NH_2$, $SO_2$—$C_{1-4}$ alkyl, $SO_2$-aryl, CO-heteroaryl, CO—$C_{1-4}$ alkyl, COO—$C_{1-4}$ alkyl, COO-aryl, $C_{1-4}$ alkyl, aryl $C_{1-3}$ alkyl, heteroaryl $C_{1-3}$ alkyl, heterocyclyl $C_{1-3}$ alkyl, aryl, heteroaryl, and heterocyclyl, wherein the $C_{1-4}$ alkyl may optionally be substituted with OH, CN, COOH, the $SO_2$-aryl may optionally be substituted with a $C_{1-4}$ alkyl or $C_{1-4}$ haloalkyl, the CO-heteroaryl may optionally be substituted with a heteroaryl or halogen, the heteroaryl $C_{1-3}$ alkyl may optionally be substituted with COO—$C_{1-3}$ alkyl, and the heteroaryl may optionally be substituted with one or more halogens. For example, the nitrogen heteroatom in heterocyclyl R2 may be substituted with phenyl $C_{1-3}$ alkyl.

In particular embodiments of the process of the invention, R6 may be selected from monocyclic aryl, monocyclic heteroaryl, and heterocyclyl, each of which may be substituted or unsubstituted. For example, R6 may be a substituted aryl, wherein said aryl may be substituted with one or more groups selected from halogen, R6a, OH, OR6a, $NH_2$, $NO_2$, $NHC(NH)NH_2$, NHR6a, NR6aR6b, $C(NOH)NH_2$, COR6a, COOH, COOR6a, $CONH_2$, CONHOH, $SO_2$R6a, $SO_2$NR6aR6b, wherein R6a and R6b are independently selected from $C_{1-6}$ alkyl, substituted $C_{1-6}$ alkyl, aryl, heteroaryl, $C_{3-8}$ cycloalkyl and heterocyclyl, wherein, when the substituent of R6 is $C_{1-6}$ alkyl, substituted $C_{1-6}$ alkyl, aryl, heteroaryl, $C_{3-8}$ cycloalkyl, heterocyclyl or is a group containing one or more of these moieties, each of these moieties may optionally be substituted with one or more groups selected from OR6c, OH, and $CONH_2$, wherein R6c is selected from $C_{1-6}$ alkyl, substituted $C_{1-6}$ alkyl, aryl, heteroaryl, $C_{3-8}$ cycloalkyl and heterocyclyl, and wherein, when the substituent of R6 is heteroaryl or heterocyclyl, each of these moieties may optionally be substituted with one or more oxygen atoms.

In certain embodiments wherein R6 is a substituted aryl, R6 may be substituted with one or more groups selected from halogen, OH, $NO_2$, $C_{1-4}$ alkoxy, $CONH_2$, C(NOH)$NH_2$, CONHOH, $SO_2$—$C_{1-4}$ alkyl, heterocyclyl, and aryl, wherein the heterocyclyl substituent on R6 may optionally be substituted with an oxygen atom and the aryl substituent on R6 may optionally be substituted with $CONH_2$.

In certain embodiments wherein R6 is a heterocyclyl, R6 is optionally substituted with an oxygen atom. Similarly, in certain embodiments wherein R6 is a monocyclic heteroaryl, R6 is optionally substituted with an oxygen atom.

In particular embodiments of the process of the invention, R8 is H. In certain embodiments, R5 is H. In certain examples of the process of the invention, R5 and R8 are both H.

In preferred embodiments, J is a nitro group, and is attached at any available position on the phenyl ring. It may be preferred for the nitro group J to be at the 3- or 4-position (particularly the 4-position) on the phenyl ring, relative to the position of attachment of the phenyl ring to the carbamate oxygen.

It has been found that, surprisingly, processes of the invention employing a carbamate of Formula II' (or potentially Formula I') in which J is a nitro group result in a further significant improvement in the yield of compounds of Formula II (or Formula I) compared to processes in which J is H. For example, when the process of the invention is used to produce N-cyclohexyl-N-methyl-4-(pyridin-3-yl)-1H-imidazole-1-carboxamide (i.e. the non-N-oxidised precursor to compound A), the yield of this compound is around 49% when J is H, but is improved substantially to around 80% when J is a nitro group, in particular a 4-nitro group. Similar improvements in yield may be observed in the production of other compounds of Formula II (especially Formula IIa) and, to a varying extent, in the production of other compounds of Formula II or potentially Formula I.

In a particular group of embodiments, the present invention provides a process for preparing a substituted urea of Formula IIa, or a pharmaceutically acceptable salt or ester thereof, as described above, the process comprising the reaction of an imidazolyl carbamate of Formula II' having a structure corresponding with Formula IIa in which the —NR1R2 group of Formula IIa is replaced by the —C(O)O-Ph-J group of Formula II', with a primary or secondary amine of the formula: R1R2NH, wherein J is H;

R8 is H;

R1 and R2 can each be independently selected from H, $C_{1-20}$ alkyl, $C_{1-6}$ alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl-$C_{1-6}$ alkyl, each of which may be optionally substituted, or R1 and R2, together with the N to which they are attached, can form a heteroaryl or heterocyclyl group, each of which may optionally be substituted, or R1 and R2 can each be independently selected from R1a, halogen, OH, OR1a, OCOR1a, SH, SR1a, SCOR1a, $NH_2$, NHR1a, $NHSO_2NH_2$, $NHSO_2$R1a, NR1aCOR1b, NHCOR1a, NR1aR1b, COR1a, CSR1a, CN, COOH, COOR1a, $CONH_2$, CONHOH, CONHR1a, CONHOR1a, $SO_2$R1a, $SO_3$H, $SO_2NH_2$, CONR1aR1b, $SO_2$NR1aR1b, wherein R1a and R1b are independently selected from optionally substituted $C_{1-6}$ alkyl, aryl, heteroaryl, $C_{3-8}$ cycloalkyl and heterocyclyl, or R1a and R1b, together with the heteroatom to which they are joined, can form heterocyclyl, with the exception that R1 and R2 are not both H;

R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, $NHSO_2NH_2$, $NHSO_2$R5a, NR5aCOR5b, NHCOR5a, $NHC(NH)NH_2$, NR5aR5b, COR5a, CSR5a, CN, COOH, COOR5a, $CONH_2$, CONHOH, CONHR5a, CONHOR5a, $C(NOH)NH_2$, CONR5aR5b, $SO_2$R5a, $SO_3$H, $SO_2NH_2$, $SO_2$NR5aR5b, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, $NO_2$, NHR5c, $NHSO_2NH_2$, $NHSO_2$R5c, NR5cCOR5d, NHCOR5c, NHC(NH)$NH_2$, NR5cR5d, COR5c, CSR5c, CN, COOH, COOR5c, $CONH_2$, CONHOH, CONHR5c, CONHOR5c, C(NOH)NH$_2$, CONR5cR5d, SO$_2$R5c, SO$_3$H, SO$_2$NH$_2$, SO$_2$NR5cR5d, wherein R5c and R5d are independently selected from C$_{1-6}$ alkyl, substituted C$_{1-6}$ alkyl, aryl, heteroaryl, C$_{3-8}$ cycloalkyl and heterocyclyl, or R5c and R5d, together with the heteroatom to which they are joined, can form heterocyclyl, wherein, when the substituent of R5 is C$_{1-6}$ alkyl, aryl, heteroaryl, heterocyclyl, C$_{1-6}$ alkoxy, aryloxy, heteroaryloxy, heterocyclyloxy, C$_{3-8}$ cycloalkyl, or is a group containing one or more of these moieties, each of these moieties may optionally be substituted with one or more groups selected from halogen, R5e, C$_{1-6}$ alkyl, OH, OR5e, OCOR5e, SH, SR5e, SCOR5e, NH$_2$, NO$_2$, NHR5e, NHSO$_2$NH$_2$, NHSO$_2$R5e, NR5eCOR5f, NHCOR5e, NHC(NH)NH$_2$, NR5eR5f, COR5e, CSR5e, CN, COOH, COOR5e, CONH$_2$, CONHOH, CONHR5e, CONHOR5e, C(NOH)NH$_2$, CONR5eR5f, SO$_2$R5e, SO$_3$H, SO$_2$NH$_2$, SO$_2$NR5eR5f, wherein R5e and R5f are independently selected from C$_{1-6}$ alkyl, substituted C$_{1-6}$ alkyl, aryl, heteroaryl, C$_{3-8}$ cycloalkyl and heterocyclyl, or R5e and R5f, together with the heteroatom to which they are joined, can form heterocyclyl;

R6 is selected from C$_{1-6}$ alkyl, aryl, heteroaryl, heterocyclyl, C$_{1-6}$ alkoxy, aryloxy, heteroaryloxy, heterocyclyloxy, R6a, halogen, OH, OR6a, SH, SR6a, OCOR6a, SCOR6a, NH$_2$, NO$_2$, NHR6a, NHSO$_2$NH$_2$, NHSO$_2$R6a, NR6aCOR6b, NHCOR6a, NHC(NH)NH$_2$, NR6aR6b, COR6a, CSR6a, CN, COOH, COOR6a, CONH$_2$, CONHOH, CONHR6a, CONHOR6a, C(NOH)NH$_2$, CONR6aR6b, SO$_2$R6a, SO$_3$H, SO$_2$NH$_2$, SO$_2$NR6aR6b, wherein R6a and R6b are independently selected from C$_{1-6}$ alkyl, substituted C$_{1-6}$ alkyl, aryl, heteroaryl, C$_{3-8}$ cycloalkyl and heterocyclyl, or R6a and R6b, together with the heteroatom to which they are joined, can form heterocyclyl, wherein, when R6 is heteroaryl or heterocyclyl, each of these moieties may optionally be substituted with one or more oxygen atoms, and when R6 is C$_{1-6}$ alkyl, aryl, heteroaryl, heterocyclyl, C$_{1-6}$ alkoxy, aryloxy, heteroaryloxy, heterocyclyloxy, C$_{3-8}$ cycloalkyl, or is a group containing one or more of these moieties, each of these moieties may optionally be substituted with one or more groups selected from halogen, R6c, C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, OH, OR6c, OCOR6c, SH, SR6c, SCOR6c, NH$_2$, NO$_2$, NHR6c, NHSO$_2$NH$_2$, NHC(NH)NH$_2$, NHSO$_2$R6c, NR6cCOR6d, NHCOR6c, NR6cR6d, COR6c, CSR6c, CN, COOH, COOR6c, CONH$_2$, CONHR6c, CONHOR6c, CONHOH, C(NOH)NH$_2$, CONR6cR6d, SO$_2$R6c, SO$_3$H, SO$_2$NH$_2$, SO$_2$NR6cR6d, wherein R6c and R6d are independently selected from C$_{1-6}$ alkyl, substituted C$_{1-6}$ alkyl, aryl, heteroaryl, C$_{3-8}$ cycloalkyl and heterocyclyl, or R6c and R6d, together with the heteroatom to which they are joined, can form heterocyclyl, wherein, when the substituent of R6 is heteroaryl or heterocyclyl, each of these moieties may optionally be substituted with one or more oxygen atoms, or when the substituent of R6 is C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, cycloalkyl, or is a group containing one or more of these moieties, each of these moieties may optionally be substituted with one or more groups selected from halogen, R6e, C$_{1-6}$ alkyl, C$_{1-4}$ alkoxy, OH, OR6e, OCOR6e, SH, SR6e, SCOR6e, NH$_2$, NO$_2$, NHR6e, NHSO$_2$NH$_2$, NHC(NH)NH$_2$, NHSO$_2$R6e, NR6eCOR6f, NHCOR6e, NR6eR6f, COR6e, CSR6e, CN, COOH, COOR6e, CONH$_2$, CONHOH, CONHR6e, CONHOR6e, C(NOH)NH$_2$, CONR6eR6f, SO$_2$R6e, SO$_3$H, SO$_2$NH$_2$, SO$_2$NR6eR6f, wherein R6e and R6f are independently selected from C$_{1-6}$ alkyl, substituted C$_{1-6}$ alkyl, aryl, heteroaryl, cycloalkyl and heterocyclyl, or R6e and R6f, together with the heteroatom to which they are joined, can form heterocyclyl.

In certain embodiments of the process of the invention, for example in the particular group of embodiments mentioned immediately above for the preparation of compounds of Formula IIa, R1 and R2 are not both methyl. In particular embodiments, when R1 or R2 is methyl, the other of R1 or R2 is not 4-chlorobutyl, 4-azidobutyl, or 4-isothiocyanatobutyl. In an embodiment, the substituted urea is not (4-phenyl-1H-imidazol-1-yl)(4-(quinolin-2-ylmethyl)piperazin-1-yl)methanone.

R1 and R2 may, especially in the particular group of embodiments mentioned immediately above for the preparation of compounds of Formula IIa, optionally be substituted in the manner set out in claim 1 of WO 2010/074588 A2. In particular, in preferred embodiments, when R1 or R2 is C$_{1-20}$ alkyl, alkoxy, aryl, heteroaryl, heterocyclyl, C$_{3-10}$ cycloalkyl, aryl C$_{1-6}$ alkyl, heteroaryl C$_{1-6}$ alkyl, heterocyclyl C$_{1-6}$ alkyl, C$_{3-10}$ cycloalkyl C$_{1-6}$ alkyl, C$_{1-6}$ alkyl, C$_{3-8}$ cycloalkyl or is a group containing one or more of these moieties, each of these moieties may optionally be substituted with one or more groups selected from R1c, halogen, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-10}$ alkyl, OH, OR1c, OCOR1c, SH, SR1c, SCOR1c, NH$_2$, NO$_2$, NHR1c, NHSO$_2$NH$_2$, NHSO$_2$R1c, NR1cCOR1d, NHC(NH)NH$_2$, NHCOR1c, NR1cR1d, COR1c, CSR1c, CN, COOH, COOR1c, CONH$_2$, CONHOH, CONHR1c, CONHOR1c, C(NOH)NH$_2$, CONR1cR1d, SO$_2$R1c, SO$_3$H, SO$_2$NH$_2$, SO$_2$NR1cR1d, wherein R1c and R1d are independently selected from C$_{1-6}$ alkyl, substituted C$_{1-6}$ alkyl, aryl, heteroaryl, C$_{3-8}$ cycloalkyl and heterocyclyl, or R1c and R1d, together with the heteroatom to which they are joined, can form heterocyclyl, wherein, when the substituent of R1 or R2 is C$_{1-10}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-6}$ alkyl, C$_{3-8}$ cycloalkyl or is a group containing one or more of these moieties, each of these moieties may optionally be substituted with one or more groups selected from R1e, halogen, C$_{1-10}$ alkyl, OH, OR1e, OCOR1e, SH, SR1e, SCOR1e, NH$_2$, NO$_2$, NHR1e, NHSO$_2$NH$_2$, NHSO$_2$R1e, NR1eCOR1f, NHC(NH)NH$_2$, NHCOR1e, NR1eR1f, COR1e, CSR1e, CN, COOH, COOR1e, CONH$_2$, CONHOH, CONHR1e, CONHOR1e, C(NOH)NH$_2$, CONR1eR1f, SO$_2$R1e, SO$_3$H, SO$_2$NH$_2$, SO$_2$NR1eR1f, wherein R1e and R1f are independently selected from C$_{1-6}$ alkyl, substituted C$_{1-6}$ alkyl, aryl, heteroaryl, C$_{3-8}$ cycloalkyl and heterocyclyl, or R1e and R1f, together with the heteroatom to which they are joined, can form heterocyclyl, or R1 and R2, together with the N to which they are attached, can form a heteroaryl or heterocyclyl group, each of which may optionally be substituted with one or more oxygen atoms or one or more groups selected from aryl, heteroaryl, partially or fully saturated heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, R2a, halogen, OH, OR2a, OCOR2a, SH, SR2a, SCOR2a, $NH_2$, $NO_2$, NHR2a, $NHSO_2NH_2$, $NHSO_2R2a$, NR2aCOR2b, $NHC(NH)NH_2$, NHCOR2a, NR2aR2b, COR2a, CSR2a, CN, COOH, COOR2a, $CONH_2$, CONHOH, CONHR2a, CONHOR2a, $C(NOH)NH_2$, CONR2aR2b, $SO_2R2a$, $SO_3H$, $SO_2NH_2$, $SO_2NR2aR2b$, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the substituent of the heteroaryl or heterocyclyl formed by R1 and R2 together is aryl, heteroaryl, heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, or a group containing one or more of these moieties, each of these moieties may optionally be substituted with one or more groups selected from halogen, hydroxyl, $C_{1-6}$ alkyl, aryl, heteroaryl, heterocyclyl, $C_{3-8}$ cycloalkyl, $C_{1-4}$ alkoxy, aryloxy, heteroaryloxy, heterocyclyloxy, $C_{3-8}$ cycloalkyloxy, aryl $C_{1-4}$ alkoxy, heteroaryl $C_{1-6}$ alkoxy, heterocyclyl $C_{1-4}$ alkoxy, $C_{3-8}$ cycloalkyl $C_{1-4}$ alkoxy, R2c, OR2c, OCOR2c, SH, SR2c, SCOR2c, $NH_2$, $NO_2$, NHR2c, $NHSO_2NH_2$, $NHSO_2R2c$, NR2cCOR2d, $NHC(NH)NH_2$, NHCOR2c, NR2cR2d, COR2c, CSR2c, CN, COOH, COOR2c, $CONH_2$, CONHOH, CONHR2c, CONHOR2c, $C(NOH)NH_2$, CONR2cR2d, $SO_2R2c$, $SO_3H$, $SO_2NH_2$, $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, wherein, when the substituent of the substituent of the heteroaryl or heterocyclyl formed by R1 and R2 together is $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, or is a group containing one or more of these moieties, each of these moieties may optionally be substituted with one or more groups selected from $C_{1-4}$ alkoxy, R2e, halogen, OH, OR2e, OCOR2e, SH, SR2e, SCOR2e, $NH_2$, $NO_2$, NHR2e, $NHSO_2NH_2$, $NHSO_2R2e$, NR2eCOR2f, $NHC(NH)NH_2$, NR2eR2f, NHCOR2e, COR2e, CSR2e, CN, COOH, COOR2e, $CONH_2$, CONHOH, CONHR2e, CONHOR2e, $C(NOH)NH_2$, CONR2eR2f, $SO_2R2e$, $SO_3H$, $SO_2NH_2$, $SO_2NR2eR2f$, wherein R2e and R2f are independently selected from $C_{1-6}$ alkyl, substituted $C_{1-6}$ alkyl, aryl, heteroaryl, $C_{3-8}$ cycloalkyl and heterocyclyl, or R2e and R2f, together with the heteroatom to which they are joined, can form heterocyclyl.

In certain embodiments of the process of the invention for the preparation of compounds of Formula II, and especially in the particular group of embodiments mentioned immediately above for the preparation of compounds of Formula IIa, the urea compound of Formula II has the following features:

R1 is selected from H and $C_{1-4}$ alkyl,

R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may optionally be substituted with one or more groups selected from R2a, halogen, OH, OR2a, OCOR2a, SH, SR2a, SCOR2a, $NH_2$, NHR2a, $NHSO_2NH_2$, $NHSO_2R2a$, NR2aCOR2b, $NHC(NH)NH_2$, NHCOR2a, NR2aR2b, COR2a, CSR2a, CN, COOH, COOR2a, $CONH_2$, CONHOH, CONHR2a, CONHOR2a, $C(NOH)NH_2$, $SO_2R2a$, $SO_3H$, $SO_2NH_2$, CONR2aR2b, $SO_2NR2aR2b$, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the substituent of R2 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R2c, halogen, OH, OR2c, OCOR2c, SH, SR2c, SCOR2c, $NH_2$, NHR2c, $NHSO_2NH_2$, $NHSO_2R2c$, NR2cCOR2d, $NHC(NH)NH_2$, NHCOR2c, NR2cR2d, COR2c, CSR2c, CN, COOH, COOR2c, $CONH_2$, CONHOH, CONHR2c, CONHOR2c, $C(NOH)NH_2$, $SO_2R2c$, $SO_3H$, $SO_2NH_2$, CONR2cR2d, $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, R5 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, $NHC(NH)NH_2$, NHCOR5a, NR5aR5b, COR5a, CSR5a, CN, COOH, COOR5a, $CONH_2$, CONHOH, CONHR5a, CONHOR5a, $C(NOH)NH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, R6 is selected from aryl, heteroaryl, heterocyclyl, $C_{3-10}$ cycloalkyl, each of which may optionally be substituted with one or more groups selected from R6a, halogen, OH, OR6a, OCOR6a, SH, SR6a, SCOR6a, $NH_2$, NHR6a, $NHSO_2NH_2$, $NHSO_2R6a$, NR6aCOR6b, $NHC(NH)NH_2$, NHCOR6a, NR6aR6b, COR6a, CSR6a, CN, COOH, COOR6a, $CONH_2$, CONHOH, CONHR6a, CONHOR6a, $C(NOH)NH_2$, $SO_2R6a$, $SO_3H$, $SO_2NH_2$, CONR6aR6b, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, and wherein, when R6 is heteroaryl or heterocyclyl, each of these moieties may optionally be substituted with one or more oxygen atoms, and wherein, when the substituent of R6 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R6c, halogen, OH, OR6c, OCOR6c, SH, SR6c, SCOR6c, $NH_2$, NHR6c, $NHSO_2NH_2$, $NHSO_2R6c$, NR6cCOR6d, $NHC(NH)NH_2$, NHCOR6c, NR6cR6d, COR6c, CSR6c, CN, COOH, COOR6c, $CONH_2$, CONHOH, CONHR6c, CONHOR6c, $C(NOH)NH_2$, $SO_2R6c$, $SO_3H$, $SO_2NH_2$, CONR6cR6d, $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, and wherein, when the substituent of R6 is heteroaryl or heterocyclyl, each of these moieties may optionally be substituted with one or more oxygen atoms.

In such embodiments, R1 may be selected from H, methyl and ethyl, with R2 selected from aryl, heteroaryl, heterocyclyl, and $C_{3-10}$ cycloalkyl, each of which may be substituted or unsubstituted.

In particular, R2 may be selected from fully saturated heterocyclyl and $C_{5-4}$ cycloalkyl, each of which are monocyclic and may be substituted or unsubstituted. Preferably, R2 is an unsubstituted cyclopentyl or unsubstituted cyclohexyl.

Alternatively in such embodiments, R2 may be a fully saturated heterocyclyl, wherein the heterocyclyl ring contains a single heteroatom, such as nitrogen or oxygen. Such heterocyclyl may be six membered, the heteroatom in the said heterocyclyl group preferably being at the 4-position relative to the position of attachment of the heterocyclyl group R2 to the urea nitrogen. The said heteroatom at the 4-position may be a nitrogen heteroatom which is substituted with a group selected from CN, $CONH_2$, C(NOH)$NH_2$, $SO_2$—$C_{1-4}$ alkyl, $SO_2$-aryl, CO-heteroaryl, CO—$C_{1-4}$ alkyl, COO—$C_{1-4}$ alkyl, $C_{1-4}$ alkyl, aryl $C_{1-3}$ alkyl, heteroaryl $C_{1-3}$ alkyl, heterocyclyl $C_{1-3}$ alkyl, aryl, heteroaryl, and heterocyclyl, wherein the $C_{1-4}$ alkyl may optionally be substituted with OH, CN, COOH, the $SO_2$-aryl may optionally be substituted with a $C_{1-4}$ alkyl or $C_{1-4}$ haloalkyl, the CO-heteroaryl may optionally be substituted with a heteroaryl or halogen, the heteroaryl $C_{1-3}$ alkyl may optionally be substituted with COO—$C_{1-3}$ alkyl, and the heteroaryl may optionally be substituted with one or more halogens. In certain such embodiments, the said nitrogen heteroatom is substituted with phenyl $C_{1-3}$ alkyl.

In particular embodiments, and especially in the particular group of embodiments mentioned immediately above for the preparation of compounds of Formula IIa, R6 is selected from monocyclic aryl, monocyclic heteroaryl, and heterocyclyl, each of which may be substituted or unsubstituted. In such embodiments, R6 may be a substituted aryl, wherein said aryl is substituted with one or more groups selected from halogen, R6a, OH, OR6a, $NH_2$, $NO_2$, NHC(NH)$NH_2$, NHR6a, NR6aR6b, C(NOH)$NH_2$, COR6a, COOH, COOR6a, $CONH_2$, CONHOH, $SO_2$R6a, $SO_2$NR6aR6b, wherein R6a and R6b are independently selected from $C_{1-6}$ alkyl, substituted $C_{1-6}$ alkyl, aryl, heteroaryl, $C_{3-8}$ cycloalkyl and heterocyclyl, wherein, when the substituent of R6 is $C_{1-6}$ alkyl, substituted $C_{1-6}$ alkyl, aryl, heteroaryl, $C_{3-8}$ cycloalkyl, heterocyclyl or is a group containing one or more of these moieties, each of these moieties may optionally be substituted with one or more groups selected from OR6c, OH, and $CONH_2$, wherein R6c is selected from $C_{1-6}$ alkyl, substituted $C_{1-6}$ alkyl, aryl, heteroaryl, $C_{3-8}$ cycloalkyl and heterocyclyl, and wherein, when the substituent of R6 is heteroaryl or heterocyclyl, each of these moieties may optionally be substituted with one or more oxygen atoms. In particular, R6 may be a substituted aryl which is substituted with one or more groups selected from halogen, OH, $C_{1-4}$ alkoxy, $CONH_2$, C(NOH)$NH_2$, CONHOH, $SO_2$—$C_{1-4}$ alkyl, heterocyclyl, and aryl, wherein the heterocyclyl may optionally be substituted with an oxygen atom and the aryl may optionally be substituted with $CONH_2$.

In alternative embodiments, R6 is a heterocyclyl which is substituted with an oxygen atom. In yet further embodiments, R6 is a monocyclic heteroaryl which is substituted with an oxygen atom.

In preferred embodiments of the process of the invention, R1R2NH is a secondary amine.

In particular embodiments, including in the particular group of embodiments mentioned immediately above for the preparation of compounds of Formula IIa, R1 is $C_{1-20}$ alkyl, preferably $C_{1-10}$ alkyl, more preferably $C_{1-6}$ alkyl, such as methyl. In particular embodiments, the said alkyl is unsubstituted.

In certain embodiments, including in the particular group of embodiments mentioned immediately above for the preparation of compounds of Formula IIa, R2 is $C_{3-10}$ cycloalkyl, preferably $C_{3-8}$ cycloalkyl, such as cyclohexyl. In particular embodiments, the said cycloalkyl is unsubstituted.

In particular embodiments, including in the particular group of embodiments mentioned immediately above for the preparation of compounds of Formula IIa, R5 is H. In certain embodiments, including in the particular group of embodiments mentioned immediately above for the preparation of compounds of Formula IIa, R6 is heteroaryl. Said heteroaryl R6 may be six-membered. For example, R6 may be pyridyl, such as 2-pyridyl, 3-pyridyl or 4-pyridyl (and particularly 3-pyridyl). In such embodiments, the urea of Formula II may be subjected to a further step of N-oxidation of the pyridine (or other heteroaryl) R6. In particular, the N-oxidation may be conducted using a peroxyacid, such as peracetic acid.

In a preferred embodiment of the present invention, the process of the invention is used for the preparation of 3-(1-(cyclohexyl(methyl)carbamoyl-1H-imidazol-4-yl)pyridine 1-oxide (compound A). In another embodiment, the process of the invention is used for the preparation of N-cyclohexyl-N-methyl-4-(pyridin-3-yl)-1H-imidazole-1-carboxamide. In a further embodiment, the process of the invention is used for the preparation of a compound selected from those described in the Examples hereinbelow.

In certain embodiments, the reaction between the carbamate of Formula II' or Formula I' and the amine R1R2NH is conducted in tetrahydrofuran.

In particular embodiments of the process of the invention, including in the particular group of embodiments mentioned immediately above for the preparation of compounds of Formula IIa, the carbamate of Formula II' or Formula I' is prepared by reacting a heteroaryl intermediate having a structure corresponding with Formula II' or Formula I' in which the —C(O)O-Ph-J group is replaced with H, with phenyl chloroformate, the phenyl group of which bears J as a substituent, wherein R5 and R6 are as defined above.

In such embodiments, the heteroaryl intermediate having a structure corresponding with Formula II' or Formula I' in which the —C(O)O-Ph-J group is replaced with H (for example, in the case of a process of the invention for the preparation of a compound of Formula IIa, an imidazole derivative of Formula III):

Formula III may be reacted with the phenyl chloroformate in a suitable solvent such as tetrahydrofuran (or, for example, dichloromethane or 2-methyltetrahydrofuran), and preferably in the presence of an organic base, such as pyridine or triethylamine. The carbamate of Formula II' or Formula I' may, optionally, be used directly without isolation before addition of the amine R1R2NH. Thus, in potentially preferred embodiments, and particularly those embodiments in which J is a nitro group, and/or particularly in those embodiments in which a compound of Formula IIa is prepared, the phenyl carbamate of Formula II' or Formula I' is not isolated, but is instead used directly in the next step (i.e. reaction with the secondary amine R1R2NH) in a telescoped, one-pot process.

In such potentially preferred embodiments, the process is made more straightforward, with potential improvements in yield and speed, since the phenyl carbamate intermediate does not require isolation.

In another aspect the present invention provides a substituted urea of Formula II or Formula I as defined above, or a pharmaceutically acceptable salt or ester thereof, obtained or obtainable by the process of the invention as defined above.

In a further aspect, the present invention provides an intermediate compound of Formula II' or Formula I':

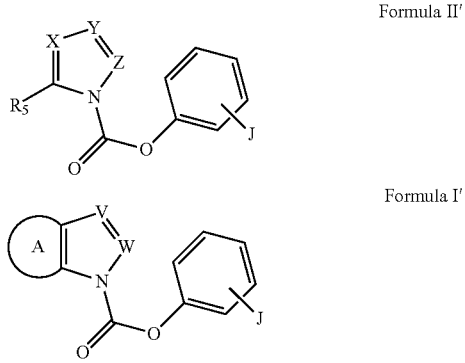

Formula II'

Formula I' wherein J is a nitro group, and is attached at any available position on the phenyl ring, wherein ring A, and V, W, X, Y, Z and R5 are as defined above.

Crystal Form A of compound A is a crystalline, essentially non-hygroscopic anhydrate form having a melting point of 228-232 deg C. It may be obtained by crystallisation of compound A from a variety of solvents, and isopropanol (IPA) may in particular be mentioned (as in the Examples; other suitable solvents for crystallisation include acetic acid, acetone, dichloromethane (DCM), acetonitrile, DCM:IPA (in all proportions), dimethylacetamide, dimethylformamide, dimethylsulfoxide, dioxane, dioxane:water, ethyl acetate, methanol, methanol:water, nitromethane, pyridine, toluene, trifluoroethanol, trifluoroethanol:water, tetrahydrofuran, water, and combinations thereof). Another crystal form, Form B, may be obtained by crystallisation of compound A from hexafluoroisopropanol (HFIPA). Form B is a solvate, and is usually unstable, converting to Form A, e.g. under ambient conditions or by vacuum drying.

In a further aspect, the invention provides 3-(1-(cyclohexyl(methypcarbamoyl-1H-imidazol-4-yl)pyridine 1-oxide (compound A), wherein the compound A is in a crystalline form having the characteristics of Form A as described herein. In another aspect, Form B of compound A is also provided.

Figure 2:
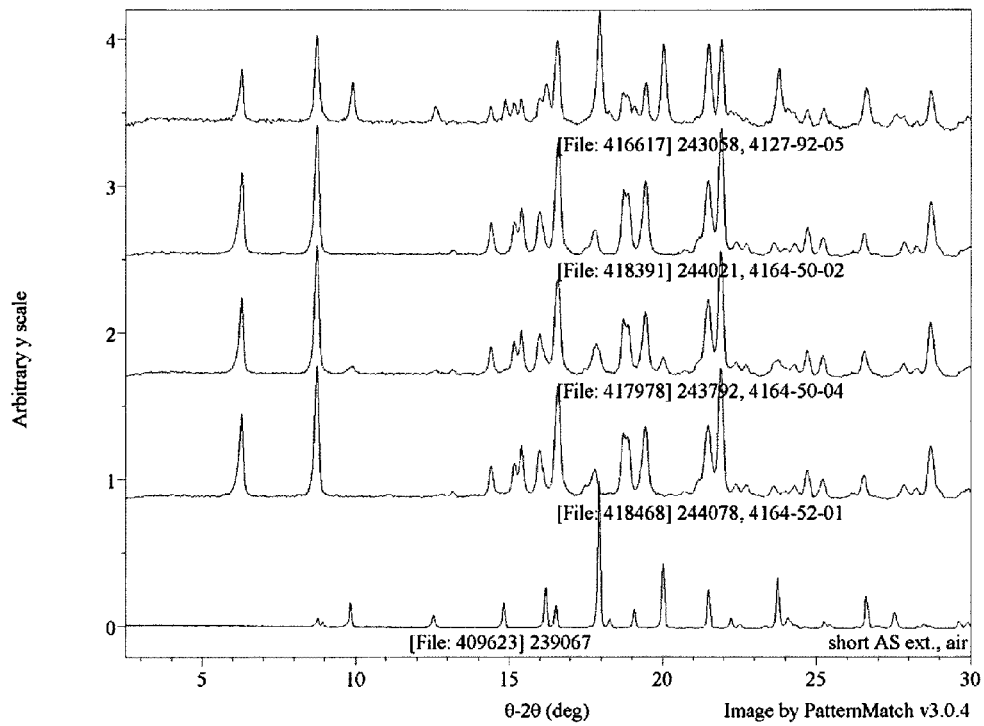

The present invention will now be described in more detail by way of example only, with reference to the appended Figures, as follows:

FIG. 1, which shows X-ray powder diffractograms for a number of samples of crystal Form A of compound A; and FIG. 2, which shows X-ray powder diffractograms for a number of samples of compound A containing crystal Form B.

EXAMPLE 1

Preparation of N-cyclohexyl-N-methyl-4-(pyridin-3-yl)-1H-imidazole-1-carboxamide

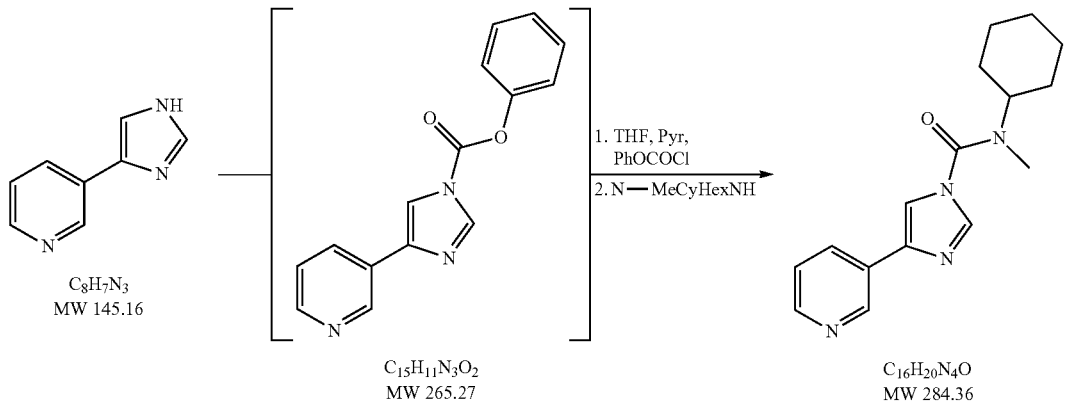

In preferred embodiments of this aspect of the invention, J is at the 2- or 4-position (preferably the 4-position) of the phenyl ring, relative to the position of attachment of the phenyl ring to the carbamate oxygen.

In a preferred embodiment of the present invention, the process of the invention is used for the preparation of 3-(1-(cyclohexyl(methyl)carbamoyl-1H-imidazol-4-yl)pyridine 1-oxide (compound A), wherein the compound A is obtained in a crystalline form having the characteristics of Form A as described herein.

To a suspension of 3-(1H-imidazol-4-yl)pyridine in tetrahydrofuran (THF) containing pyridine at 25° C. was slowly added a solution of phenyl chloroformate in THF over 60 to 90 min. The resulting fine white suspension was then maintained at 25° C. for at least 60 min. before the addition of N-methyl-N-cyclohexylamine in a single portion, causing the suspension to thin and become yellow in colour. The reaction mixture was then stirred for 90 min. before filtering and washing the filter cake with additional THF. The mother liquors were then maintained at 25° C. for at least 18 h, whereupon 65% of the volume of THF was distilled off under atmospheric pressure. The resulting solution was then diluted with 2-propanol and maintained at >50° C. for 10 min. prior to cooling down to 20° C. The resulting suspension was aged at 20° C. for 15 min. prior to cooling to 0° C. and aging for a further 60 min. The reaction mixture was then filtered and the product was washed with additional 2-propanol, before drying at 50° C. under vacuum to afford the title compound as an off-white crystalline solid.

The purity of the product was ascertained by HPLC, with identity confirmable by NMR. The yield was consistently around 50% in several production runs.

EXAMPLE 2

3-(1-(cyclohexyl(methyl)carbamoyl-1H-imidazol-4-yl)pyridine 1-oxide (compound A)

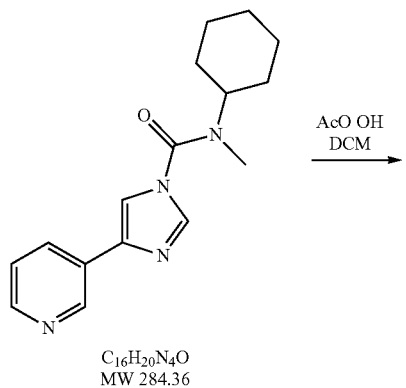

To a solution of N-cyclohexyl-N-methyl-4-(pyridin-3-yl)-1H-imidazole-1-carboxamide in dichloromethane at 25° C. was added peracetic acid (38%; the concentration is not critical, and may be varied) in a single portion. The reaction mixture was then maintained at 25° C. for at least 20 h, whereupon the reaction was washed four times with water. The dichloromethane solution was then filtered prior to diluting with 2-propanol. Dichloromethane (50%) was then distilled off under atmospheric pressure, whereupon, 2-propanol was charged at the same rate as the distillate was collected. The distillation was continued until >90% of the dichloromethane was collected. The resulting suspension was then cooled to 20° C. and aged for at least 30 min. prior to cooling to 0° C. and aging for a further 60 min. The reaction mixture was then filtered and the product washed with additional 2-propanol, before drying at 50° C. under vacuum to afford the title compound as an off-white crystalline solid.

The purity of the product was ascertained by HPLC, with identity confirmable by NMR. The yield was consistently >80% in several production runs. It will be appreciated that this gives an overall yield of compound A many times greater than that achieved in the prior art.

In a further run of this synthesis, in a 2 L reactor to a mixture of N-cyclohexyl-N-methyl-4-(pyridin-3-yl)-1H-imidazole-1-carboxamide (90 g, 317 mmol) and dichloromethane (1350 ml) was added peracetic acid (84 ml, 475 mmol). The reaction mixture was stirred at 25° C. Completion of the reaction was monitored by HPLC for the disappearance of N-cyclohexyl-N-methyl-4-(pyridin-3-yl)-1H-imidazole-1-carboxamide. After reaction completion a solution of sodium metabisulfite (60.2 g, 317 mmol) in water (270 ml) was added to the reaction mixture maintaining the temperature below 30° C. After phase separation the organic phase was washed with water. After phase separation the organic phase was concentrated at atmospheric pressure until 5 vol. Then solvent was swapped to isopropanol (1350 ml) and the suspension was cooled to 0° C. during 4 hours and stirred at that temperature for 1 hour. The resulting solid was collected by filtration and was rinsed with water (270 ml) and isopropanol (270 ml) to afford a white crystalline solid in 84.8 g (89%).

EXAMPLE 3

Preparation of 4-nitrophenyl 4-(pyridin-3-yl)-1H-imidazole-1-carboxylate

This example illustrates the synthesis of the nitrophenyl carbamate intermediate for preparing urea compounds by the process of the invention (i.e. intermediates in which J of Formula I' or II' is nitro).

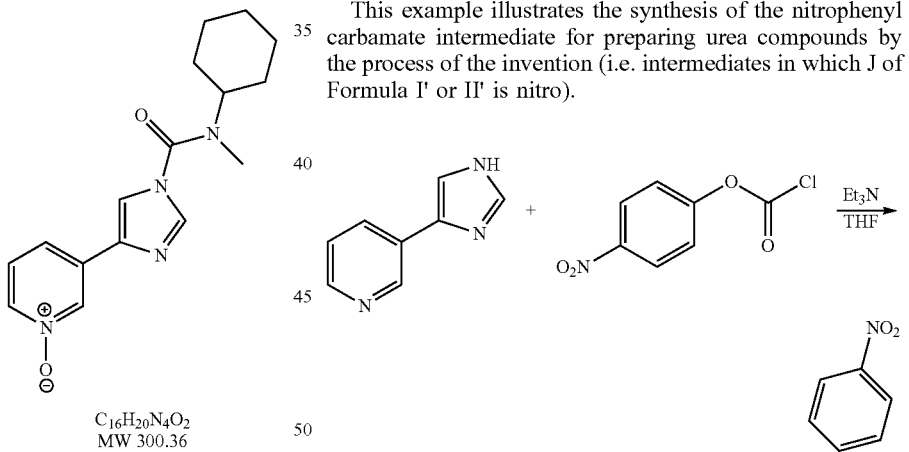

In a 250 ml reactor to a mixture of 3-(1H-imidazol-4-yl)pyridine (5 g, 34.4 mmol) and tetrahydrofuran (100 ml) was charged triethylamine (5.76 ml, 41.3 mmol) and then a solution of 4-nitrophenyl chloroformate (7.29 g, 36.2 mmol) in tetrahydrofuran (25 ml) maintaining the temperature below 30° C. After the addition finished, the reaction mixture was left stirring for 4 hours. The suspension was filtered and washed with water (V=150 ml) and THF (25 ml) to afford a light yellow solid 8.0 g (61%).

NMR spectra of this nitrophenyl carbamate intermediate were recorded at 20° C., on a Bruker 400 MHz DPX spectrometer with solvent used as internal standard. Data are reported in the following order: approximate chemical shift (ppm), number of protons, multiplicity (d, doublet; d d, doublet of doublet; d d d, doublet of doublet of doublet; t d, triplet of doublet; m d, multiplet of doublet) and coupling constant (Hz)

$^1$H NMR (400 MHz, DMSO, 20° C.) δ: 9.18 (1H, d, J=2.3 Hz), 8.67 (1H, d, J=2.3 Hz), 8.57 (1H, d, J=1.3 Hz), 8.55 (1H, dd, J=1.6, 5.0 Hz), 8.42 (2H, m d, J=9.3 Hz), 8.36 (1H, t d, J=1.8, 8.0 Hz), 7.79 (2H, m d, J=9.3 Hz), 7.53 (1H, d d d, J=0.8, 4.9, 8.0 Hz).

$^{13}$C NMR (100 MHz, DMSO, 20° C.) δ: 154.3, 147.9, 146.1, 145.8, 145.7, 139.2, 139.0, 133.1, 128.7, 125.6, 124.2, 123.2, 114.8

Mp (° C.): 202-204

EXAMPLE 4

N-Cyclohexyl-N-methyl-4-(pyridin-3-yl)-1H-imidazole-1-carboxamide

This example illustrates the synthesis of the compound of Example 1 via a nitrophenyl carbamate intermediate. The said intermediate is not isolated.

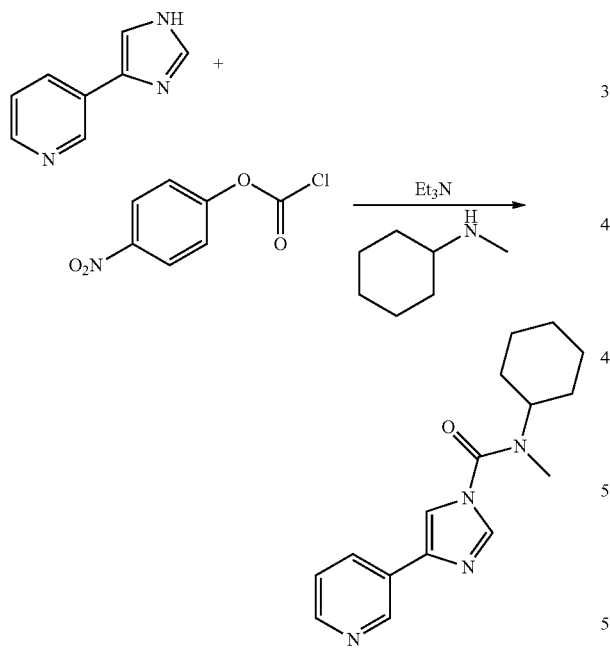

In a 1 L reactor a mixture of 3-(1H-imidazol-4-yl)pyridine (60 g, 413 mmol) in tetrahydrofuran (360 ml) was cooled to 15° C. To this slurry was added triethylamine (69.1 ml, 496 mmol) and then a solution of 4-nitrophenyl chloroformate (96 g, 475 mmol) in tetrahydrofuran (240 ml) maintaining the temperature below 30° C. After the addition finished, the reaction mixture was left stirring for 4 hours. The reaction mixture was then cooled to 20° C. and N-methyl-N-cyclohexylamine (82 ml, 620 mmol) was added to the slurry. Completion of the reaction was monitored by HPLC for the disappearance of 4-nitrophenyl 4-(pyridin-3-yl)-1H-imidazole-1-carboxylate. ⅔ of the solvent were removed from the reaction mixture under vacuum and then the mixture was cooled to 20° C. and stirred for 1 hour. The resulting solid was collected by filtration and was rinsed with cold tetrahydrofuran (180 ml), water (1200 ml) and cold isopropanol (180 ml) to afford a light yellow solid in 93.7 g (80%).

From a comparison of Examples 1 and 4, it can be seen that the use of the nitrophenyl carbamate route leads to a significant improvement in yield (i.e. increased from 50% to 80%).

EXAMPLE 5

Synthesis of other Compounds of Formula I or II by Means of the Process of the Invention The general applicability of the process of the invention to the preparation of the compounds of Formula I and Formula II is illustrated by the following specific compounds and reaction schemes, each of which was performed using methods of the invention analogous to those described above. NMR data was obtained in each case as described above.

EXAMPLE 5.1

Structure

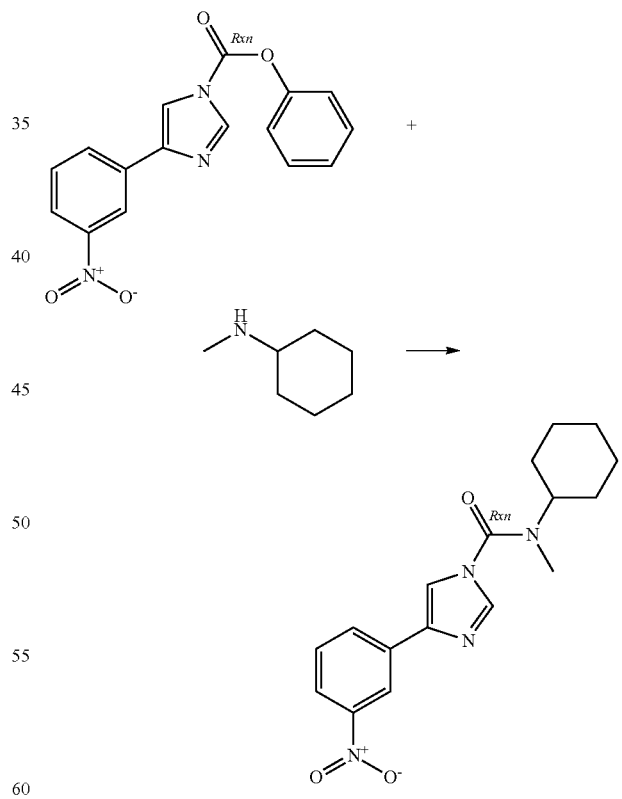

Yield (%) [43.6%]

Product Name N-cyclohexyl-N-methyl-4-(3-nitrophenyl)-1H-imidazole-1-carboxamide

NMR Solvent CDCl3

13C 150.9, 148.6, 140, 137.3, 134.9, 130.9, 129.7, 122, 119.9, 114.6, 57.6, 31.4, 29.9, 25.4, 25.2

1H 8.61 (1H, t, J=2 Hz), 8.14 (2H, m), 7.94 (1H, d, J=1.3 Hz), 7.64 (1H, d, J=1.3 Hz), 7.57 (1H, t, J=8.0 Hz), 3.96 (1H, m, J=12.0 Hz), 3.02 (3H, s), 1.88 (4H, m), 1.72 (1H, m), 1.60 (2H, d q, J=3.5, 12.5 Hz), 1.39 (2H, t q, J=3.0, 13.0 Hz), 1.4 (1H, t q, J=3.5, 13.0 Hz)

Mp (° C.) 160-162

EXAMPLE 5.2

Structure

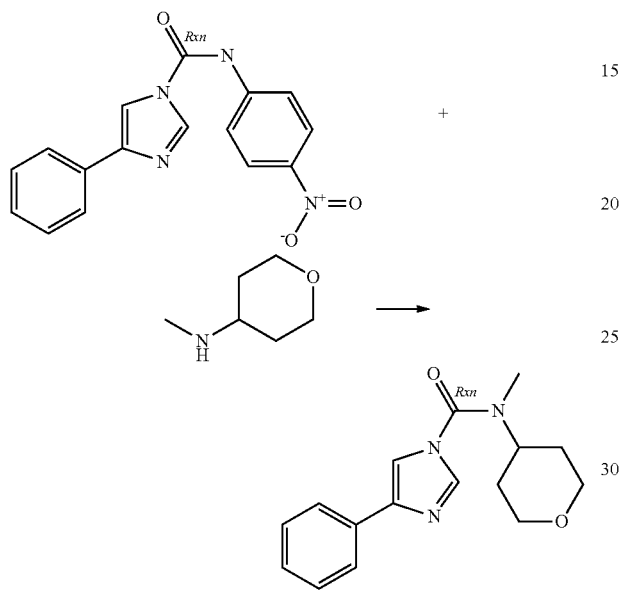

Yield (%) [72.1%]
Product Name N-methyl-4-phenyl-N-(tetrahydro-2H-pyran-4-yl)-1H-imidazole-1-carboxamide
NMR Solvent CDCl3
13C 151.5, 142.3, 136.9, 132.8, 128.7, 127.6, 125.1, 113.1, 67, 54.4, 31.8, 29.5
1H 7.94 (1H, s), 7.80 (2H, d, J=7.6 Hz), 7.51 (1H, s), 7.41 (2H, t, J=7.6 Hz), 7.30 (1H, t, J=7.3 Hz), 4.28 (1H, m), 4.09 (2H, dd, J=4.0, 11.5 Hz), 3.50 (2H, t, J=11.5 Hz), 3.04 (3H, s), 1.94 (2H, d q, J=4.5, 12.3 Hz), 1.77 (2H, d br, J=12.0H)
Mp (° C.) 160

EXAMPLE 5.3

Structure

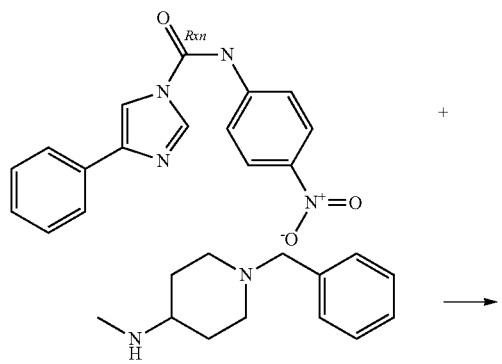

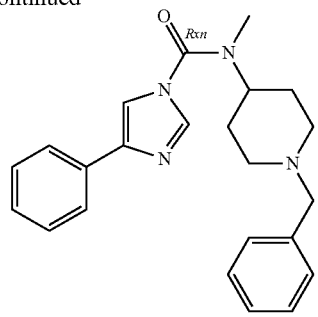

Yield (%) [77%]
Product Name N-(1-benzylpiperidin-4-yl)-N-methyl-4-phenyl-1H-imidazole-1-carboxamide
NMR Solvent CDCl3
13C 151.5, 142.2, 138.1, 137, 132.9, 129.1, 128.7, 128.3, 127.6, 127.2, 125.1, 113.1, 62.8, 55.8, 52.5, 31.6, 28.9
1H 7.92 (1H, d, J=1.3 Hz), 7.80 (2H, m, J=8.0 Hz), 7.50 (1H, d, J=1.3 Hz), 7.41 (2H, t, J=7.6 Hz), 7.37-7.25 (6H, m), 4.03 (1H, m), 3.53 (2H, s), 3.03 (3H, s), 3.01 (2H, m), 2.11 (2H, t br, J=11.2 Hz), 1.90 (2H, q br, J=12.0 Hz), 1.79 (2H, d br, =12.0 Hz)
Mp (° C.) 189-191

EXAMPLE 5.9

Structure

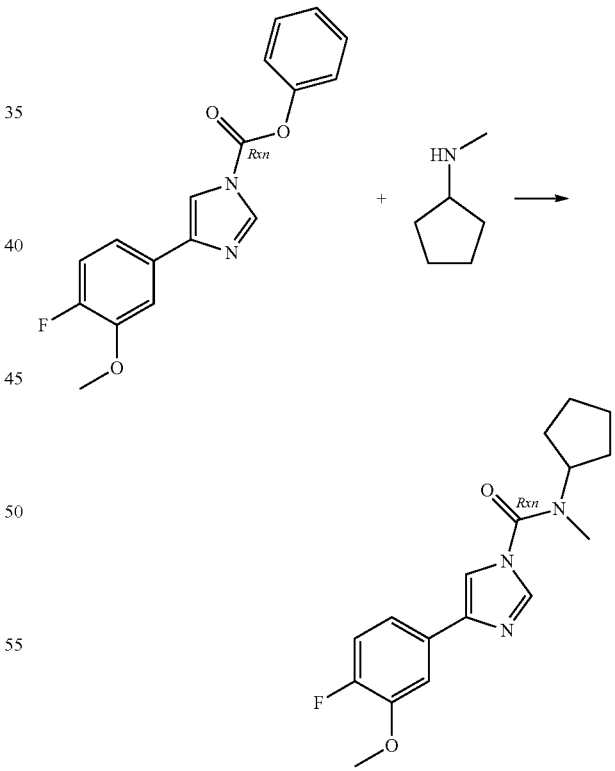

Yield (%) [60.8%]
Product Name N-cyclopentyl-4-(4-fluoro-3-methoxyphenyl)-N-methyl-1H-imidazole-1-carboxamide
NMR Solvent CDCl3
13C 151.9 (d, J=246.0 Hz), 151.5, 147.8 (d, J=11.0 Hz), 141.3, 136.8, 129.5 (d, J=3.5 Hz), 117.3 (d, J=7.0 Hz), 116.2 (d, J=19.0 Hz), 113.2, 110.3, 59.3, 56.2, 31.2, 28.9, 24.3

1H 7.94 (1H, d, J=1.0 Hz), 7.50 (1H, dd, J=2.0, 7.50 Hz), 7.47 (1H, d, J=1.0 Hz), 7.24 (1H, d d d, J=2.0, 4.3, 8.3 Hz), 7.09 (1H, dd, J=8.3, 11.0 Hz), 4.44 (1H, qt, J=8.0 Hz), 3.97 (3H, s), 3.0 (3H, s), 1.96 (2H, m), 1.75 (4H, m), 1.63 (2H, m)

Mp (° C.) 100-103

EXAMPLE 5.5

Structure

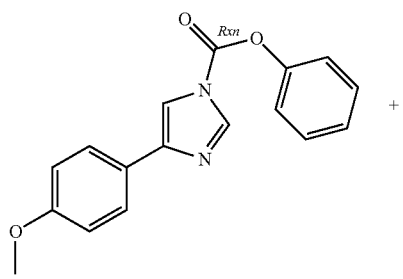

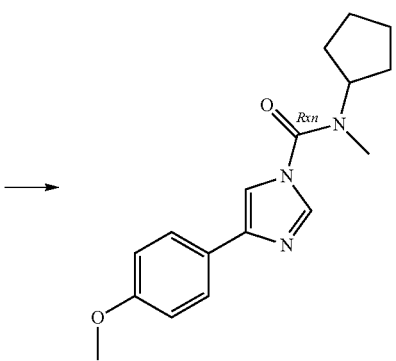

Yield (%) [49.5%]
Product Name N-cyclopentyl-4-(4-methoxyphenyl)-N-methyl-1H-imidazole-1-carboxamide
NMR Solvent CDCl3
13C 159.1, 151.8, 142, 136.8, 126.4, 125.8, 114, 112.1, 59.3, 55.3, 31.1, 28.8, 24.3
1H 7.91 (1H, d, J=1.2 Hz), 7.73 (2H, d, J=8.8 Hz), 7.41 (1H, d, J=1.2 Hz), 6.95 (2H, d, J=8.8 Hz), 4.45 (1H, qt, J=8.0 Hz), 3.85 (3H, s), 3.0 (3H, s), 1.95 (2H, m), 1.76 (2H, m), 1.67 (2H, m), 1.63 (2H, m)
Mp (° C.) 105-107

EXAMPLE 5.6

Structure

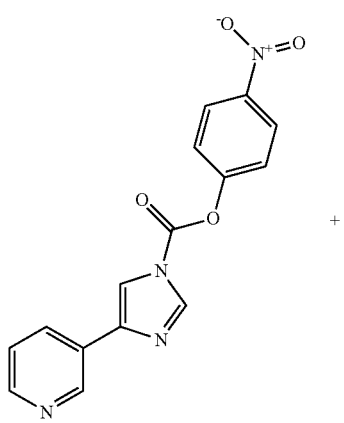

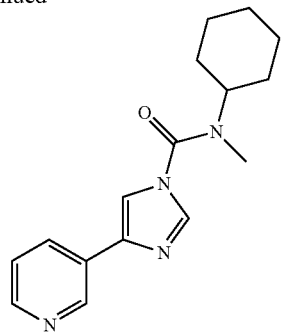

Yield (%) [85%]
Product Name N-cyclohexyl-N-methyl-4-(pyridin-3-yl)-1H-imidazole-1-carboxamide
NMR Solvent CDCl3
13C 151, 148.5, 146.7, 139.2, 137.3, 132.4, 129, 123.6, 114, 57.6, 31.4, 30, 25.4, 25.2
1H 9.01 (1H, dd, J=0.8, 2.3 Hz), 8.53 (1H, dd, J=1.7, 4.8 Hz), 8.12 (1H, d d d, J=1.8, 2.2, 8.0 Hz), 7.94 (1H, d, J=1.3 Hz), 7.58 (1H, d, J=1.3 Hz), 7.34 (1H, d d d, J=0.8, 4.9, 8.0 Hz), 3.95 (1H, m), 3.01 (3H, s), 1.87 (4H, m), 1.71 (1H, d br, J=13.5 Hz), 1.59 (2H, d q, J=3.5, 12.5 Hz), 1.38 (2H, t q, J=3.5, 13.0 Hz), 1.13 (1H, t q, J=3.5, 13.5 Hz)
Mp (° C.) 161-163

EXAMPLE 5.7

Structure

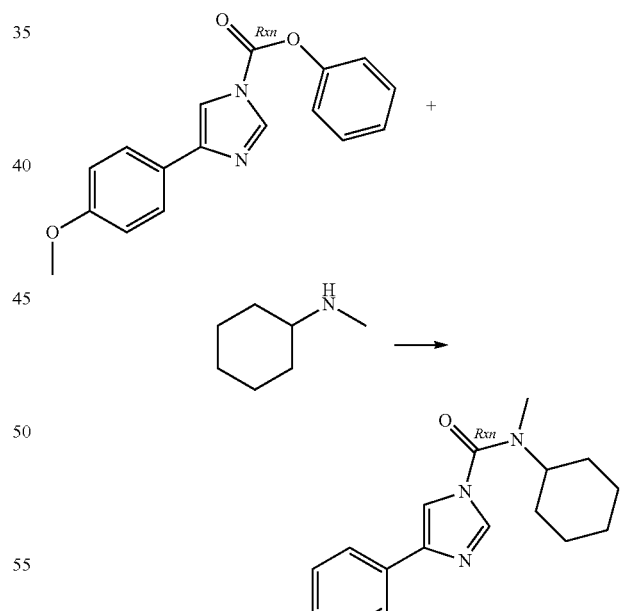

Yield (%) [86%]
Product Name N-cyclohexyl-4-(4-methoxyphenyl)-N-methyl-1H-imidazole-1-carboxamide
NMR Solvent CDCl3
13C 159.1, 151.4, 142, 136.8, 126.4, 125.8, 114, 112.1, 57.5, 55.3, 31.3, 30, 25.4, 25.2
1H 7.89 (1H, d, J=1.3 Hz), 7.40 (1H, d, J=1.3 Hz), 7.33 (2H, m d, J=9.0 Hz), 6.95 (2H, m d, J=9.0 Hz), 3.95 (1H, m), 3.84 (3H, s), 2.99 (3H, s), 1.86 (4H, m), 1.70 (1H, d br, J=13.0 Hz), 1.58 (2H, d q, J=3.5, 12.5 Hz), 1.37 (2H, t q, J=3.2, 13. Hz), 1.12 (1H, t q, J=3.5, 13.0 Hz)

Mp (° C.) 164-165

EXAMPLE 5.8

Structure

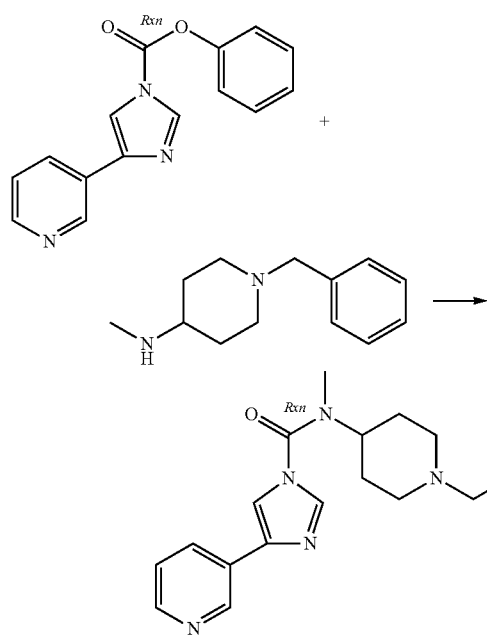

Yield (%) [49.7%]
Product Name N-(1-benzylpiperidin-4-yl)-N-methyl-4-(pyridin-3-yl)-1H-imidazole-1-carboxamide
NMR Solvent CDCl3

13C 151.2, 148.6, 146.7, 139.3, 138, 137.3, 132.4, 129.1, 129, 128.3, 127.2, 123.6, 113.9, 62.8, 55.9, 52.5, 31.7, 28.9

1H 9.0 (1H, dd, J=0.7, 2.2 Hz), 8.53 (1H, dd, J=1.7, 4.9 Hz), 8.12 (1H, d t, J=1.7, 7.9 Hz), 7.94 (1H, d, J=1.3 Hz), 7.58 (1H, d, J=1.3 Hz), 7.35 (1H, m), 7.34-7.24 (5H, m), 4.02 (1H, m), 3.52 (2H, s), 3.03 (3H, s), 3.0 (2H, m), 2.11 (2H, t br, J=12.0 Hz), 1.94 (2H, d q, J=3.5, 12.0 Hz), 1.79 (2H, d br, J=12.0 Hz)

Mp (° C.) 176-177

EXAMPLE 5.9

Structure

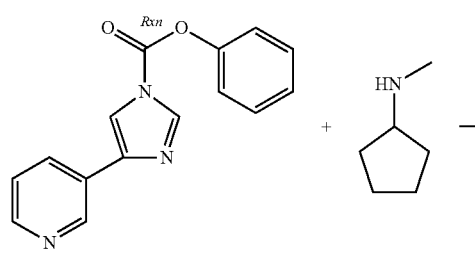

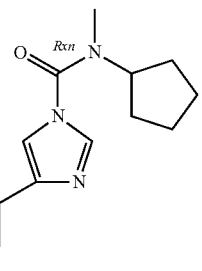

Yield (%) [43.9%]
Product Name N-cyclopentyl-N-methyl-4-(pyridin-3-yl)-1H-imidazole-1-carboxamide
NMR Solvent CDCl3

13C 151.4, 148.5, 146.6, 139.2, 137.3, 132.4, 129, 123.6, 114, 59.4, 31.2, 28.9, 24.3

1H 9.01 (1H, d, J=1.7 Hz), 8.53 (1H, dd, J=1.5, 4.8 Hz), 8.12 (1H, t d, J=2.0, 7.9 Hz), 7.96 (1H, d, J=1.3 Hz), 7.59 (1H, d, J=1.3 Hz), 7.34 (1H, dd, J=4.8, 7.9 Hz), 4.44 (1H, qt, J=8.2 Hz), 3.0 (3H, s), 1.96 (2H, m), 1.77 (2H, m), 1.70 (2H), 1.63 (2H, m)

Mp (° C.) 112-113

EXAMPLE 5.10

Structure

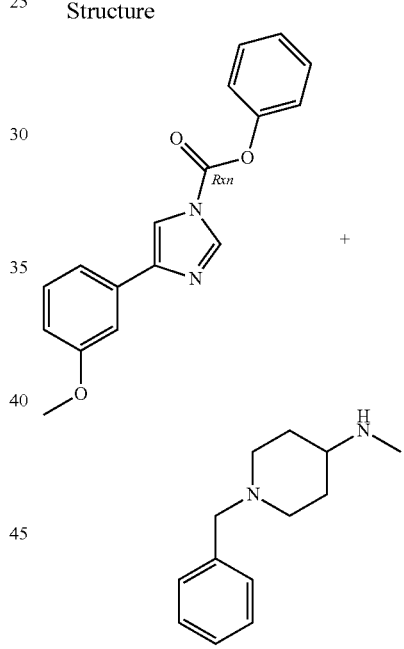

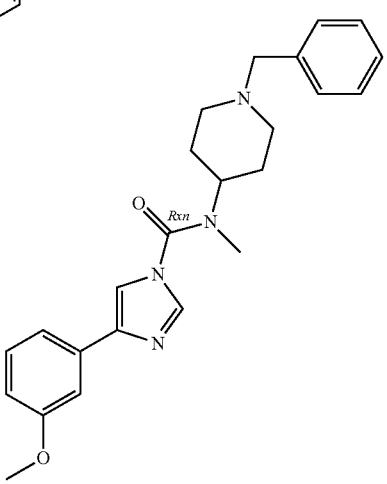

Yield (%) [61.0%]

Product Name N-(1-benzylpiperidin-4-yl)-4-(3-methoxyphenyl)-N-methyl-1H-imidazole-1-carboxamide NMR Solvent CDCl3

13C 159.9, 151.5, 142.1, 138, 136.9, 134.3, 129.7, 129.1, 128.3, 127.2, 117.5, 113.7, 113.4, 110.1, 62.8, 55.8, 55.3, 52.5, 31.6, 28.9

1H 7.92 (1H, d, J=1.3 Hz), 7.49 (1H, d, J=1.3 Hz), 7.40 (1H, dd, J=1.4, 2.4 Hz), 7.38-7.24 (6H, m), 7.31 (1H, t, J=7.6 Hz), 6.86 (1H, d d d, J=1.2, 2.5, 7.9 Hz), 4.02 (1H, m), 3.88 (3H, s), 3.52 (2H, s), 3.02 (3H, s), 3.0 (2H, m), 2.10 (2H, t br, =11.5 Hz), 1.94 (2H, d q, J=3.3, 12.0 Hz), 1.79 (2H, d br, J=12.0 Hz)

Mp (° C.) 138-140

EXAMPLE 5.11

Structure

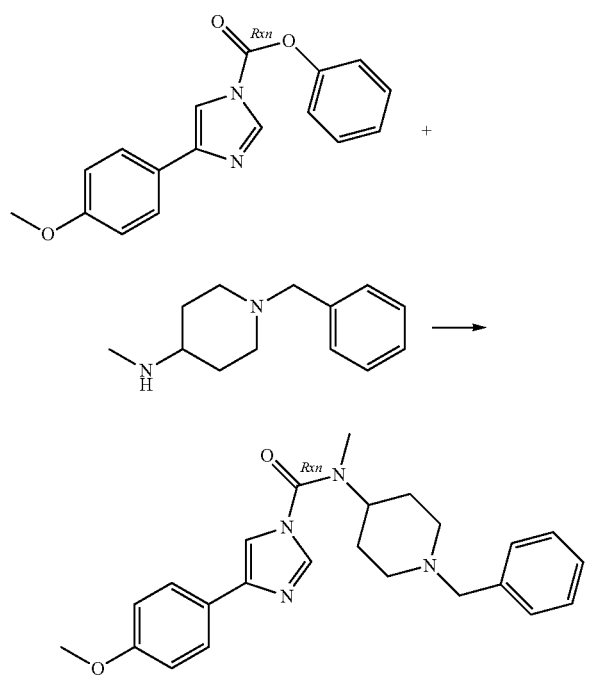

Yield (%) [64%]

Product Name N-(1-benzylpiperidin-4-yl)-4-(4-methoxyphenyl)-N-methyl-1H-imidazole-1-carboxamide NMR Solvent CDCl3

13C 159.2, 151.6, 142.1, 138, 136.8, 129.1, 128.3, 127.2, 126.4, 125.8, 114.1, 112, 62.8, 55.8, 55.3, 52.5, 31.6, 28.9

1H 7.90 (1H, d, J=1.3 Hz), 7.73 (2H, m d, J=9.0 Hz), 7.39 (1H, d, J=1.3 Hz), 7.37-7.23 (5H, m), 6.85 (2H, m d, J=9.0 Hz), 4.03 (1H, m), 3.84 (3H, s), 3.52 (2H, s), 3.02 (3H, s), 3.0 (2H, m), 2.10 (2H, t br, J=12.0 Hz), 1.93 (2H, d q, J=3.6, 12.0 z), 1.78 (2H, d br, J=13.0 Hz)

Mp (° C.) 190-191

EXAMPLE 5.12

Structure

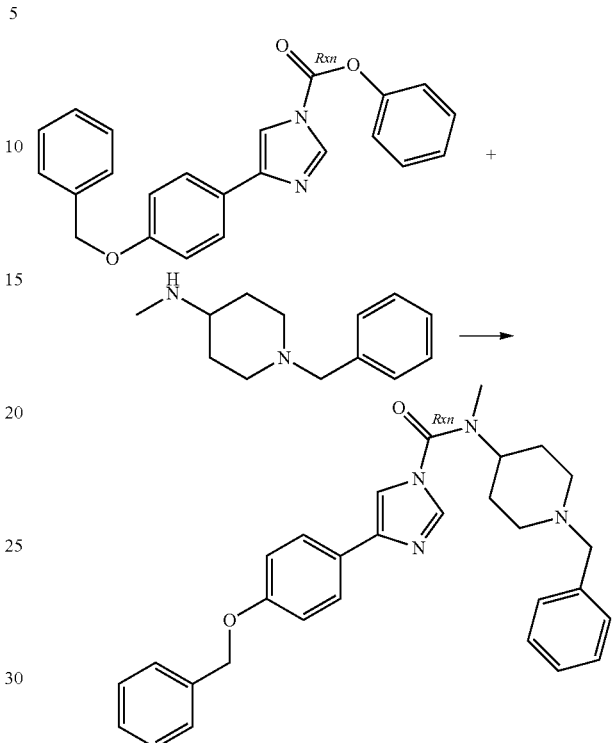

Yield (%) [59.0%]

Product Name 4-(4-(benzyloxy)phenyl)-N-(1-benzylpiperidin-4-yl)-N-methyl-1H-imidazole-1-carboxamide NMR Solvent CDCl3

13C 158.4, 151.6, 142.1, 138, 136.9, 136.8, 129.1, 128.6, 128.3, 128, 127.5, 127.2, 126.4, 126, 115, 112.1, 70, 62.8, 55.8, 52.5, 31.6, 28.9

1H 7.89 (1H, s), 7.72 (2H, m d, J=8.6 Hz), 7.45 (2H, d, J=7.5 Hz), 7.40 (2H, m), 7.38 (1H, s), 7.37-7.23 (6H, m), 7.02 (2H, m d, J=8.6 Hz), 5.10 (2H, s), 4.01 (1H, m), 3.52 (2H, s), 3.01 (3H, s), 2.99 (2H, m), 2.09 (2H, t br, J=10.7 Hz), 1.93 (2H, q r, J=12.5 Hz), 1.78 (2H, d br, J=12.5 Hz)

Mp (° C.) 190-191

EXAMPLE 5.13

Structure

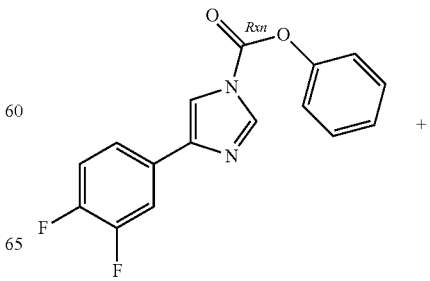

-continued

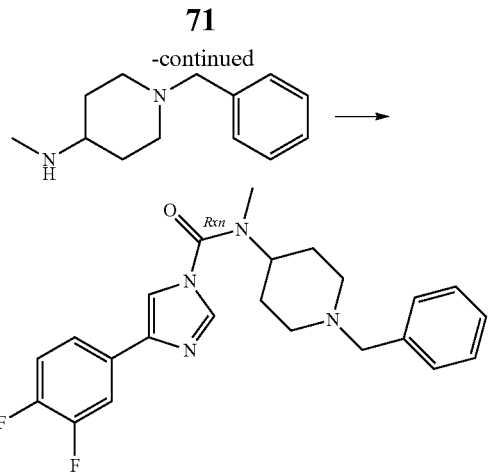

Yield (%) [35%]
Product Name N-(1-benzylpiperidin-4-yl)-4-(3,4-difluorophenyl)-N-methyl-1H-imidazole-1-carboxamide
NMR Solvent CDCl3
13C 150.6 (d d, J=13.0, 247.5 Hz), 151.2, 149.8 (d d, J=12.0, 248.0 Hz), 140.4, 138, 137, 130.2 (d d, J=4.0, 6.5 Hz), 129.1, 128.3, 127.2, 121.0 (d d, J=3.5, 6.2 Hz), 117.5 (d, J=17.5 Hz), 114.2 (d, J=19.0 Hz), 113.5, 62.8, 55.9, 52.5, 31.7, 28.9
1H 7.89 (1H, d, J=1.3 Hz), 7.61 (1H, d d d, J=2.2, 7.2, 11.5 Hz), 7.50 (1H, m), 7.46 (1H, d, J=1.3 Hz), 7.37-7.25 (5H, m), 7.18 (1H, d t, J=8.4, 10.2 Hz), 4.02 (1H, m), 3.53 (2H, s), 3.03 (3H, s), 3.01 (2H, m), 2.11 (2H, t br, J=12.0 Hz), 1.93 (2H d q, J=3.5, 12.0 Hz), 1.78 (2H, d br, J=12.0 Hz)
Mp (° C.) 204-205

EXAMPLE 5.14

Structure

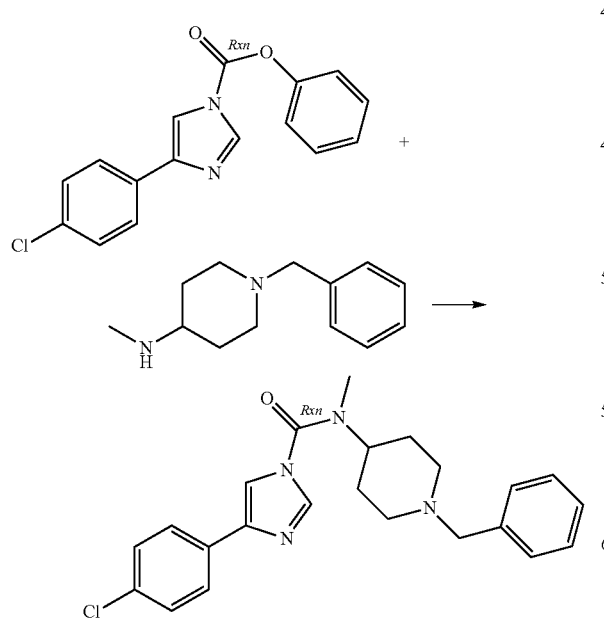

Yield (%) [41.6%]
Product Name N-(1-benzylpiperidin-4-yl)-4-(4-chlorophenyl)-N-methyl-1H-imidazole-1-carboxamide
NMR Solvent CDCl3
13C 151.3, 141.2, 138, 137, 133.1, 131.5, 129.1, 128.8, 128.3, 127.2, 126.4, 113.4, 62.8, 55.8, 52.5, 31.6, 28.9
1H 7.91 (1H, d, J=1.3 Hz), 7.49 (1H, d, J=1.3 Hz), 7.73 (2H, m d, J=8.5 Hz), 7.37 (2H, m d, J=8.5 Hz), 7.35-7.25 (5H, m), 4.02 (1H, m), 3.52 (2H, s), 3.02 (3H, s), 3.0 (2H, m), 2.10 (2H, t br, J=11.5 Hz), 1.93 (2H, J=3.5, 12.0 Hz), 1.78 (2H, d br J=12.0 Hz)
Mp (° C.) 222-223

EXAMPLE 5.15

Structure

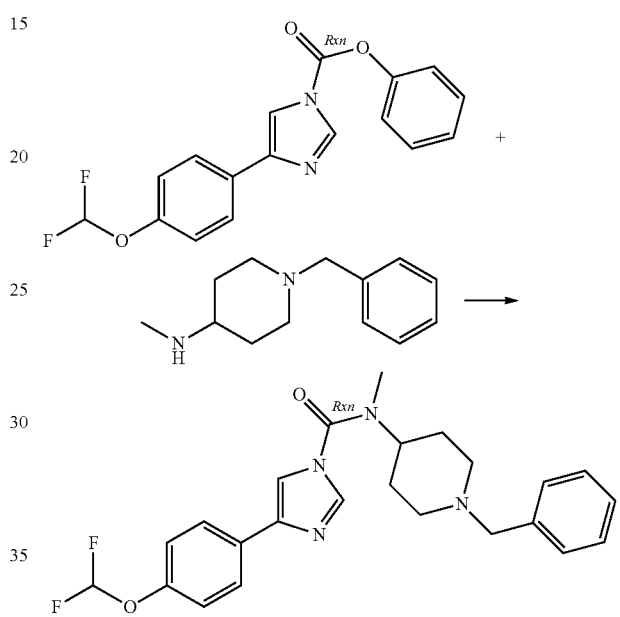

Yield (%) [62%]
Product Name N-(1-benzylpiperidin-4-yl)-4-(4-(difluoromethoxy)phenyl)-N-methyl-1H-imidazole-1-carboxamide
NMR Solvent CDCl3
13C 151.4, 150.5, 141.2, 138, 137, 130.4, 129.1, 128.3, 127.2, 126.6, 119.7, 115.9, 113.2, 62.8, 55.9, 52.5, 31.6, 28.9
1H 7.91 (1H, d, J=1.3 Hz), 7.79 (2H, m d, J=8.8 Hz), 7.47 (1H, d, J=1.3 Hz), 7.37-7.25 (5H, m), 7.16 (2H, m d, J=8.8 Hz), 6.54 (1H, t, J=74.0 Hz), 4.03 (1H, m), 3.53 (2H, s), 3.03 (3H, s), 3.01 (2H, m), 2.11 (2H, t br, J=12.0 Hz), 1.93 (2H, d q, =3.5, 12.0 Hz), 1.79 (2H, d br, J=12.5 Hz)
Mp (° C.) 203-204

EXAMPLE 5.16

Structure

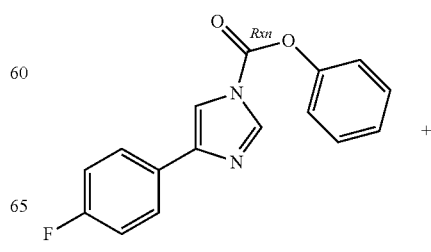

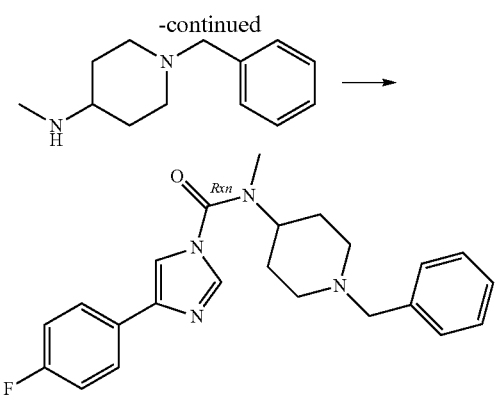

Yield (%) [49.4%]
Product Name N-(1-benzylpiperidin-4-yl)-4-(4-fluorophenyl)-N-methyl-1H-imidazole-1-carboxamide
NMR Solvent CDCl3
13C 162.3 (d, J=247.0 Hz), 151.4, 141.4, 138, 136.9, 129.2 (d, J=3.5 Hz), 129.1, 128.3, 127.2, 126.8 (d, J=8.0 Hz), 115.6 (d, J=21.5 Hz), 112.9, 62.8, 55.8, 52.5, 31.6, 28.9
1H 7.90 (1H, d, J=1.3 Hz), 7.76 (2H, m, J=5.3, 8.8 Hz), 7.45 (1H, d, J=1.3 Hz), 7.37-7.25 (5H, m), 7.10 (2H, m t, J=8.9 Hz), 4.03 (1H, m), 3.52 (2H, s), 3.02 (3H, s), 3.0 (2H, m), 2.10 (2H, t br, J=12.0 Hz), 1.93 (2H, d q, J=3.5, 12.0 Hz), 1.78 (H, d br, J=10.5 Hz)
Mp (° C.) 211-212

EXAMPLE 5.17

Structure

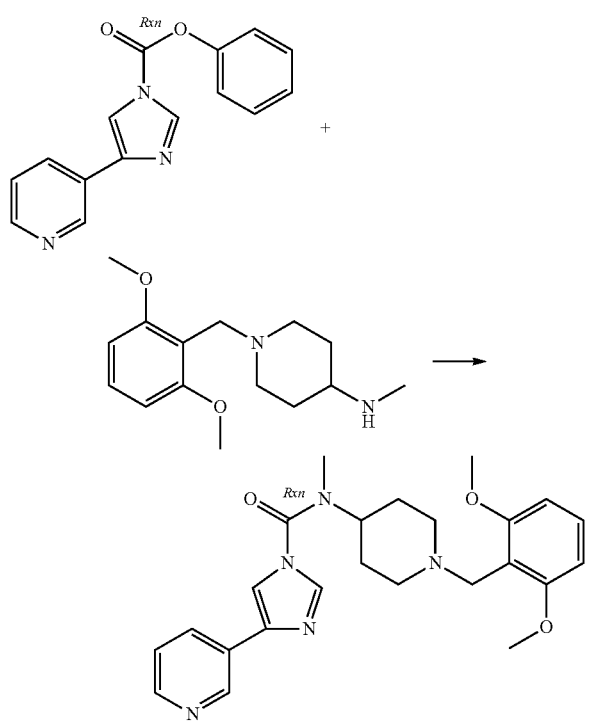

Yield (%) [33.6%]
Product Name N-(1-(2,6-dimethoxybenzyl)piperidin-4-yl)-N-methyl-4-(pyridin-3-yl)-1H-imidazole-1-carboxamide NMR Solvent CDCl3
13C 159.3, 151.2, 148.5, 146.7, 139.2, 137.2, 132.4, 129, 128.7, 123.6, 114, 113.7, 103.8, 56.2, 55.8, 52.1, 48.9, 31.5, 29.1
1H 9.0 (1H, d, J=1.8 Hz), 8.53 (1H, dd, J=1.5, 4.8 Hz), 8.11 (1H, t d, J=1.8, 7.9 Hz), 7.92 (1H, d, J=1.0 Hz), 7.57 (1H, d, J=1.0 Hz), 7.34 (1H, dd, J=4.8, 7.9 Hz), 7.22 (1H, t, J=8.3 Hz), 6.57 (2H, d, J=8.3 Hz), 3.91 (1H, m), 3.81 (6H, s), 3.71 (2H, s), 3.09 (2H, d br, J=12.0 Hz), 3.0 (3H, s), 2.20 (2H, t br, J=11.6 Hz), 1.94 (2H, d q, J=3.2, 12.0 Hz), 1.72 (2H, d br, J=12.0 Hz)
Mp (° C.) 190-191

EXAMPLE 5.18

Structure

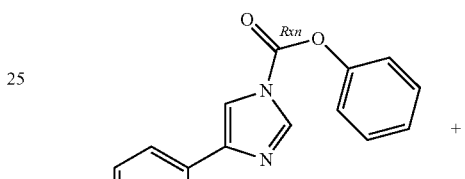

Yield (%) [53%]
Product Name N-(1-benzylpiperidin-4-yl)-4-(3,4-dimethoxyphenyl)-N-methyl-1H-imidazole-1-carboxamide
NMR Solvent CDCl3
13C 151.6, 149.1, 148.6, 142.1, 138, 136.7, 129.1, 128.3, 127.2, 126.1, 117.4, 112.3, 111.3, 108.4, 62.8, 55.9, 55.9, 55.8, 52.5, 31.6, 28.9
1H 7.90 (1H, d, J=1.3 Hz), 7.42 (1H, d, J=1.3 Hz), 7.40 (1H, d, J=1.9 Hz), 7.37-7.24 (5H, m), 7.30 (1H, dd, J=1.9, 8.3 Hz), 6.91 (1H, d, J=8.3 Hz), 4.03 (1H, m), 3.97 (3H, s), 3.92 (3H, s), 3.53 (2H, s), 3.03 (3H, s), 3.01 (2H, m), 2.11 (2H, t br, J=11.5 Hz), 1.94 (2H, d q, J=3.2, 11.8 Hz), 1.79 (2H, d br, J=11.8 Hz)
Mp (° C.) 161-162

EXAMPLE 5.19

Structure

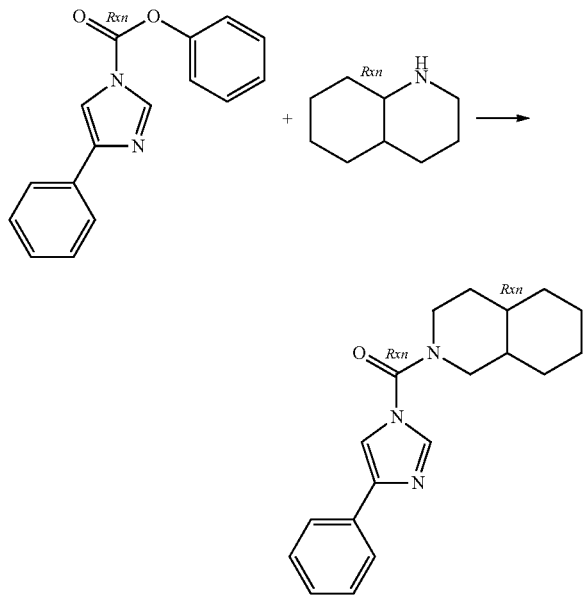

Yield (%) [41.4%]

Product Name (octahydroisoquinolin-2(1H)-yl)(4-phenyl-1H-imidazol-1-yl)methanone NMR Solvent CDCl3

13C 150.7, 142.2, 136.8, 133, 128.7, 127.5, 125.1, 113.1, 56.2, 42.2, 35.3, 31, 25.9, 25.4, 24.4, 23.7, 19.9

1H 7.88 (1H, s), 7.81 (2H, d, J=7.8 Hz), 7.46 (1H, s), 7.41 (2H, t, J=7.7 Hz), 7.30 (1H, t, J=7.4 Hz), 4.19 (1H, s br), 3.91 (1H, s br), 3.14 (1H, t, J=12.7 Hz), 2.10-1.20 (13H, m)

Mp (° C.) 126-128

EXAMPLE 5.20

Structure

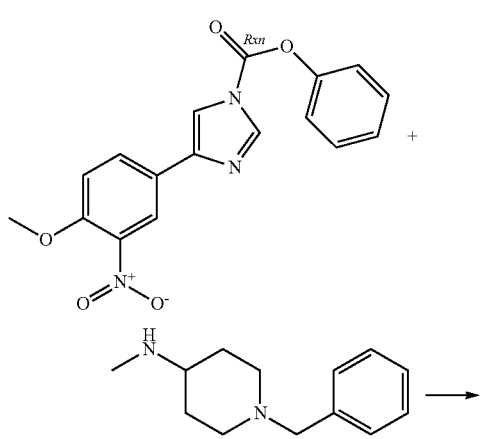

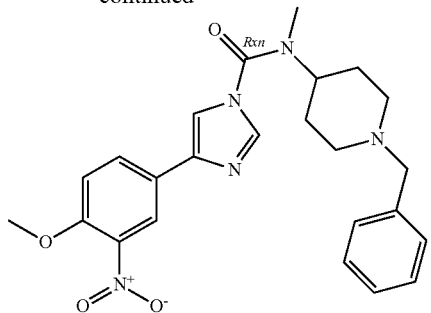

Yield (%) [50.0%]

Product Name N-(1-benzylpiperidin-4-yl)-4-(4-methoxy-3-nitrophenyl)-N-methyl-1H-imidazole-1-carboxamide NMR Solvent CDCl3

13C 152.2, 151.2, 139.9, 139.6, 138, 137.2, 130.7, 129.1, 128.3, 127.2, 126, 122.3, 113.8, 113.3, 62.8, 56.6, 55.9, 52.5, 31.7, 28.8

1H 8.24 (1H, d, J=2.2 Hz), 8.0 (1H, dd, J=2.2, 8.8 Hz), 7.91 (1H, d, J=1.3 Hz), 7.49 (1H, d, J=1.3 Hz), 7.37-7.25 (5H, m), 7.13 (1H, d, J=8.8 Hz), 4.03 (1H, m), 4.0 (3H, s), 3.53 (2H, s), 3.03 (3H, s), 3.01 (2H, m), 2.11 (2H, t br, J=11.5 Hz), 193 (2H, d q, J=3.5, 12.0 Hz), 1.79 (2H, d br, J=12.0 Hz)

Mp (° C.) 169-170

EXAMPLE 5.21

Structure

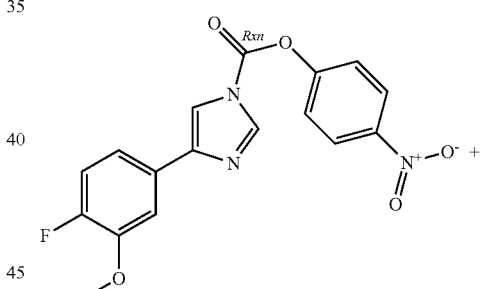

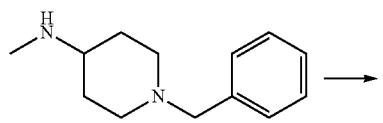

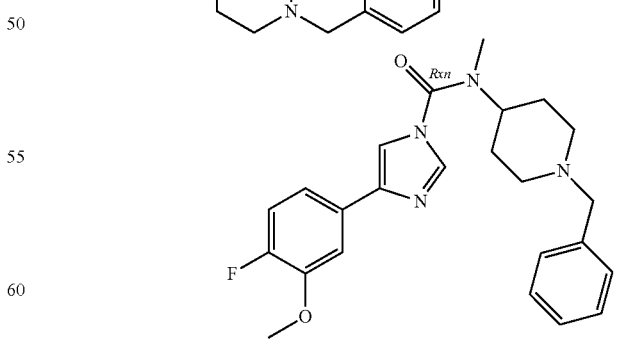

Yield (%) [57.4%]

Product Name N-(1-benzylpiperidin-4-yl)-4-(4-fluoro-3-methoxyphenyl)-N-methyl-1H-imidazole-1-carboxamide NMR Solvent CDCl3

13C 151.9 (d, J=246.0 Hz), 151.4, 147.8 (d, J=11.2 Hz), 141.5, 138, 136.8, 129.6 (d, J=4.0 Hz), 129.1, 128.3, 127.2, 117.3 (d, J=7.0 Hz), 116.2 (d, J=18.5 Hz), 113.1, 110.4 (d, J=1.7 Hz), 62.8, 56.2, 55.9, 52.5, 31.7, 28.9

1H 7.90 (1H, d, J=1.3 Hz), 7.50 (1H, dd, J=1.8, 8.3 Hz), 7.46 (1H, d, J=1.3 Hz), 7.37-7.27 (5H, m), 7.24 (1H, m), 7.09 (1H, dd, J=8.5, 11.0 Hz), 4.03 (1H, m), 3.97 (3H, s), 3.53 (2H, s), 3.03 (3H, s), 3.01 (2H, m), 2.10 (2H, t br, J=11.8 Hz), 1.9 (2H, d q, J=3.0, 12.0 Hz), 1.79 (2H, d br, J=11.5 Hz)

Mp (° C.) 162

EXAMPLE 5.22

Structure

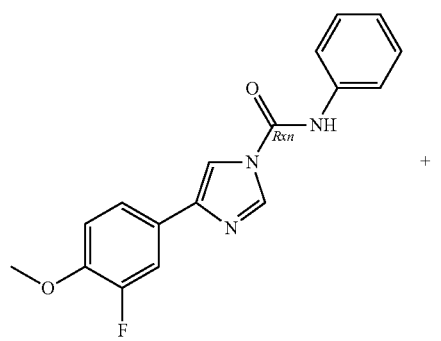

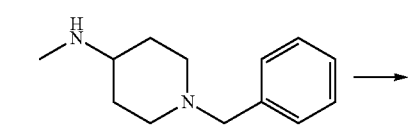

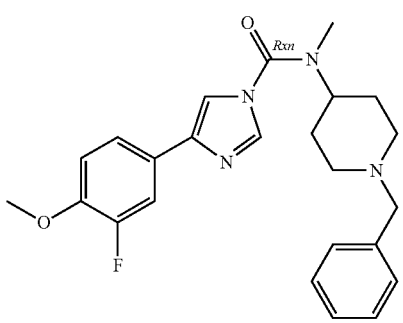

Yield (%) [60%]

Product Name N-(1-benzylpiperidin-4-yl)-4-(3-fluoro-4-methoxyphenyl)-N-methyl-1H-imidazole-1-carboxamide NMR Solvent CDCl3

13C 152.5 (d, J=245.0 Hz), 151.4, 147.1 (d, J=11.0 Hz), 141.1 (d, J=2.5 Hz), 138, 136.9, 129.1, 128.3, 127.2, 126.5 (d, J=7.2 Hz), 120.9 (d, J=3.5 Hz), 113.5 (d, J=2.5 Hz), 113.1 (d, J=19.7 Hz), 112.6, 62.8, 56.3, 55.8, 52.5, 31.6, 28.9

1H 7.89 (1H, d, J=1.3 Hz), 7.53 (1H, m), 7.50 (1H, dd, J=2.5, 8.5 Hz), 7.40 (1H, d, J=1.3 Hz), 7.37-7.23 (5H, m), 6.99 (1H, t, J=8.4 Hz), 4.02 (1H, m), 3.92 (3H, s), 3.52 (2H, s), 3.02 (3H, s), 3.0 (2H, m), 2.10 (2H, t br, J=11.8 Hz), 1.93 (2H, d, J=3.5, 12.0 Hz), 1.78 (2H, m)

Mp (° C.) 188-189

EXAMPLE 5.23

Structure

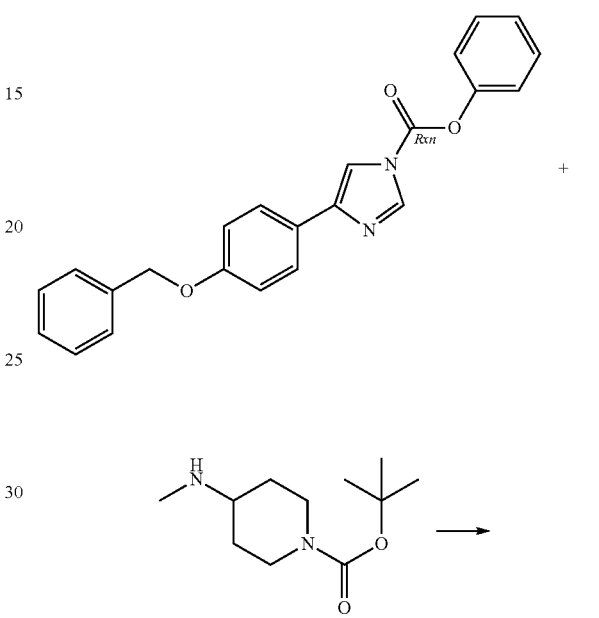

Yield (%) [61.9%]

Product Name tert-butyl 4-(4-(4-(benzyloxy)phenyl)-N-methyl-1H-imidazole-1-carboxamido)piperidine-1-carboxylate NMR Solvent DMSO 13C 157.6, 153.8, 151.1, 140.6, 137.5, 137.1, 128.5, 127.9, 127.8, 126.3, 126.1, 114.9, 113.2, 78.8, 69.2, 55.1, 43, 42.2, 31.7, 28.1 (2 sig.)

1H 8.09 (1H, d, J=1.3 Hz), 7.88 (1H, d, J=1.3 Hz), 7.77 (2H, m d, J=8.7 Hz), 7.46 (2H, d, J=8.4 Hz), 7.40 (2H, t, J=7.4 Hz), 7.33 (1H, t, J=7.3 Hz), 7.03 (2H, m d, J=8.7 Hz), 5.12 (2H, s), 4.03 (3H, m), 2.92 (3H, s), 2.79 (2H, br), 1.76 (2H, d r, J=11.5 Hz), 1.66 (2H, d q, J=4.3, 12.1 Hz), 1.41 (9H, s)

Mp (° C.) 168

EXAMPLE 5.24

Structure

Yield (%) [60.5%]
Product Name 4-(3-cyano-4-methoxyphenyl)-N-cyclohexyl-N-methyl-1H-imidazole-1-carboxamide
NMR Solvent CDCl3
13C 160.4, 151.1, 140, 137.1, 131.1, 130.3, 126.5, 116.3, 113, 111.6, 102, 57.6, 56.2, 31.4, 30, 25.4, 25.2
1H 7.98 (1H, dd, J=2.2, 8.5 Hz), 7.97 (1H, d, J=2.2 Hz), 7.89 (1H, d, J=1.3 Hz), 7.44 (1H, d, J=1.3 Hz), 7.02 (1H, d, J=8.5 Hz), 3.96 (3H, s), 3.95 (1H, m), 3.0 (3H, s), 1.87 (4H, m), 1.71 (1H, m), 1.58 (2H, d q, J=3.5, 12.5 Hz), 1.38 (2H, t q, =3.0, 13.0 Hz), 1.13 (1H, t q, J=3.5, 13 Hz)
Mp (° C.) 170-171

EXAMPLE 5.25

Structure

Yield (%) [51.0%]
Product Name N-(1-benzylpiperidin-4-yl)-4-(3-cyano-4-methoxyphenyl)-N-methyl-1H-imidazole-1-carboxamide
NMR Solvent CDCl3
13C 160.5, 151.2, 140.1, 138, 137.1, 131.1, 130.3, 129.1, 128.3, 127.2, 126.4, 116.3, 112.9, 111.6, 102, 62.8, 56.2, 55.9, 52.5, 31.7, 28.9
1H 7.98 (1H, dd, J=2.2, 8.5 Hz), 7.97 (1H, d, J=2.2 Hz), 7.90 (1H, d, J=1.3 Hz), 7.44 (1H, d, J=1.3 Hz), 7.37-7.23 (5H, m), 7.01 (1H, d, J=8.5 Hz), 4.01 (1H, m), 3.96 (3H, s), 3.53 (2H, s), 3.03 (3H, s), 3.01 (2H, m), 2.10 (2H, t br, J=12.0 Hz), 1.94 (2H, d q, J=3.5, 12.0 Hz), 1.79 (2H, d br, J=12.0 Hz)
Mp (° C.) 176-177

EXAMPLE 5.26

Structure

-continued

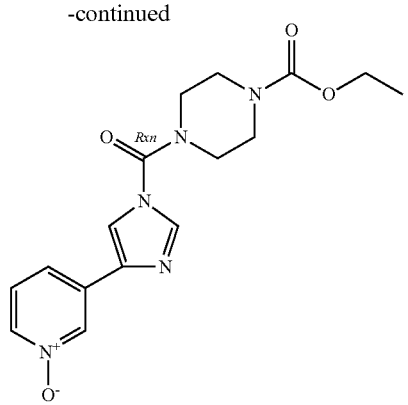

Yield (%) [7.22%]
Product Name 3-(1-(4-(ethoxycarbonyl)piperazine-1-carbonyl)-1H-imidazol-4-yl)pyridine 1-oxide
NMR Solvent CDCl3
13C 155.1, 150.2, 137.9, 137.6, 137.5, 136.2, 132.5, 126, 122.7, 115, 62.1, 46.4, 43.3, 14.6
1H 8.68 (1H, s br), 8.15 (1H, d, J=6.3 Hz), 7.94 (1H, d, J=1.3 Hz), 7.71 (1H, d, J=8.0 Hz), 7.57 (1H, d, J=1.3 Hz), 7.33 (1H, dd, J=6.3, 8.0 Hz), 4.20 (2H, q, J=7.2 Hz), 3.64 (8H, m), 1.30 (3H, t, J=7.2 Hz)
Mp (° C.) 180-182

EXAMPLE 5.27

Structure

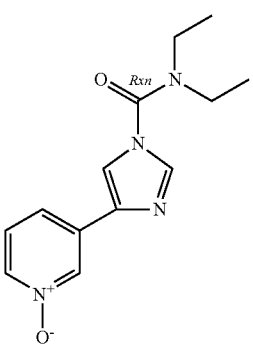

Yield (%) [16.23%]
Product Name 3-(1-(butyl(methyl)carbamoyl)-1H-imidazol-4-yl)pyridine 1-oxide
NMR Solvent CDCl3
13C 150.8, 137.6, 137.6, 136.9, 136, 132.7, 125.9, 122.7, 115.3, 50.6, 36.4, 29.3, 19.8, 13.7
1H 8.67 (1H, t, J=1.5 Hz), 8.14 (1H, d d d, J=1.0, 1.6, 6.4 Hz), 7.94 (1H, d, J=1.3 Hz), 7.71 (1H, t d, J=1.3, 8.1 Hz), 7.58 (1H, d, J=1.3 Hz), 7.32 (1H, dd, J=6.4, 8.1 Hz), 3.46 (2H, t, J=7.6 Hz), 3.13 (3H, s), 1.68 (2H, m), 1.37 (2H, m), 0.97 (3H, t, J=7.4 Hz)
Mp (° C.) 110-112

EXAMPLE 5.28

Structure

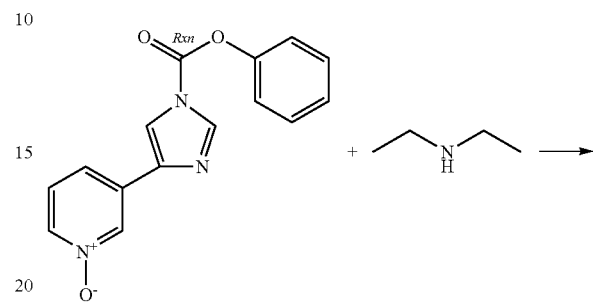

Yield (%) [30.8%]
Product Name 3-(1-(diethylcarbamoyl)-1H-imidazol-4-yl)pyridine 1-oxide
NMR Solvent CDCl3
13C 150.3, 137.6, 137.3, 136.9, 136, 132.7, 125.9, 122.8, 115.1, 42.8, 13.2
1H 8.67 (1H, t br, J=1.3 Hz), 8.14 (1H, d, J=6.4 Hz), 7.93 (1H, d, J=1.3 Hz), 7.72 (1H, d, J=8.0 Hz), 7.57 (1H, d, J=1.3 Hz), 7.32 (1H, dd, J=6.4, 8.0 Hz), 3.49 (4H, q, J=7.2 Hz), 1.31 (6H, t, J=7.2 Hz)
Mp (° C.) 74-76

EXAMPLE 5.29

Structure

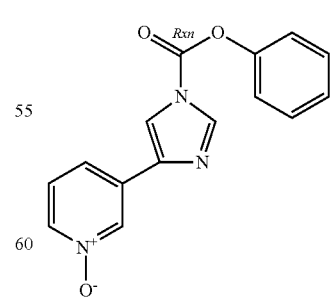

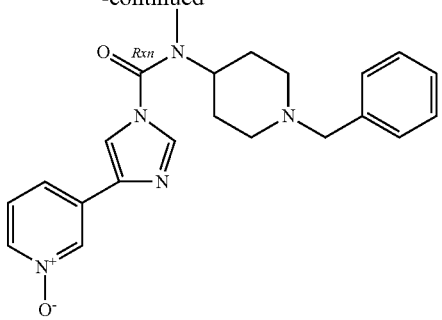

Yield (%) [16.84%]
Product Name 3-(1-((1-benzylpiperidin-4-yl)(methyl)carbamoyl)-1H-imidazol-4-yl)pyridine 1-oxide
NMR Solvent CDCl3
13C 150.8, 137.9, 137.6, 137.6, 136.9, 136, 132.7, 129.1, 128.3, 127.2, 125.9, 122.6, 115.3, 62.8, 56, 52.4, 31.7, 28.9
1H 8.66 (1H, s br), 8.13 (1H, d, J=6.3 Hz), 7.93 (1H, s br), 7.70 (1H, d, J=8.1 Hz), 7.58 (1H, s br), 7.30 (6H, m), 3.99 (1H, m), 3.52 (2H, s), 3.02 (3H, s), 3.01 (2H, m), 2.10 (2H, t br, J=10.9 Hz), 1.93 (2H, m), 1.78 (2H, d br, J=10.9 Hz)
Mp (° C.) 199-201

EXAMPLE 5.30

Structure

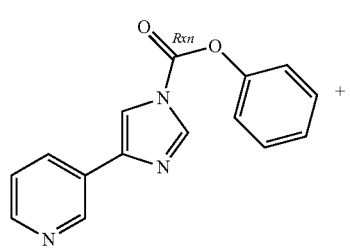

Yield (%) [42.9%]
Product Name N-methyl-4-(pyridin-3-yl)-N-(tetrahydro-2H-pyran-4-yl)-1H-imidazole-1-carboxamide
NMR Solvent CDCl3
13C 151.2, 148.6, 146.7, 139.4, 137.3, 132.5, 128.9, 123.6, 113.9, 66.9, 54.5, 31.8, 29.5
1H 9.00 (1H, dd, J=1.0, 2.2 Hz), 8.53 (1H, dd, J=1.7, 4.8 Hz), 8.11 (1H, d d d, J=1.8, 2.3, 7.9 Hz), 7.96 (1H, d, J=1.3 Hz), 7.59 (1H, d, J=1.3 Hz), 7.34 (1H, d d d, J=1.0, 4.8, 7.9 Hz), 4.29 (1H, m), 4.09 (2H, dd, J=4.6, 11.5 Hz), 3.50 (2H, d t, J=2.2, 12.0 Hz), 3.04 (3H, s), 1.95 (2H, m), 1.78 (2H, m)
My (° C.) 181-183

EXAMPLE 5.31

Structure

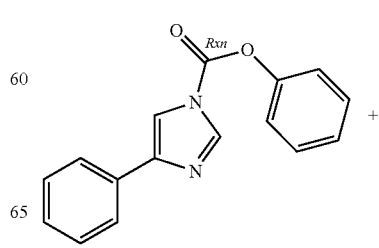

Yield (%) [49.4%]
Product Name 4-(3-fluoro-4-methoxyphenyl)-N-methyl-N-(tetrahydro-2H-pyran-4-yl)-1H-imidazole-1-carboxamide
NMR Solvent DMSO
13C 151.7 (d, J=242.5 Hz), 151.0, 146.2 (d, J=10.8 Hz), 139.6 (d, J=2.5 Hz), 137.7, 126.7 (d, J=7.5 Hz), 120.9 (d, J=3.5 Hz), 114.1 (2 sig.), 112.3 (d, J=19.7 Hz), 66.3, 56.0, 54.2, 31.6, 29.1
1H 8.11 (1H, d, J=1.3 Hz), 7.98 (1H, d, J=1.3 Hz), 7.66 (1H, m), 7.63 (1H, m), 7.19 (1H, t, J=8.7 Hz), 4.09 (1H, m), 3.93 (2H, dd, J=4.5, 12.3 Hz), 3.85 (3H, s), 3.38 (2H, m), 2.94 (3H, s), 1.85 (2H, d q, J=4.5, 12.3 Hz), 1.69 (2H, d br, J=12.3 z)
Mp (° C.) 221-222

EXAMPLE 5.32

Structure

-continued

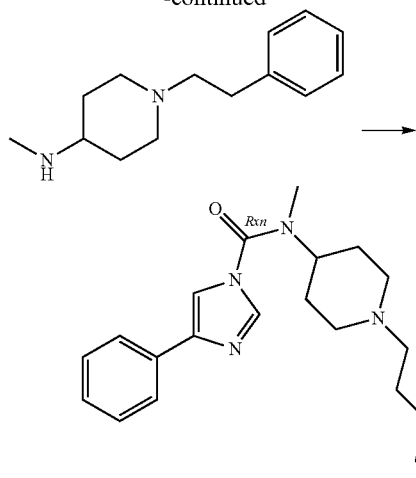

Yield (%) [35.7%]
Product Name N-methyl-N-(1-phenethylpiperidin-4-yl)-4-phenyl-1H-imidazole-1-carboxamide
NMR Solvent CDCl3
13C 151.5, 142.3, 140, 137, 132.9, 128.7, 128.6, 128.4, 127.6, 126.1, 125.1, 113.1, 60.2, 55.7, 52.6, 33.8, 31.6, 28.9
1H 7.93 (1H, d, J=1.3 Hz), 7.81 (2H, m d, J=8.2 Hz), 7.51 (1H, d, J=1.3 Hz), 7.41 (2H, t, J=7.9 Hz), 7.30 (3H, t, J=7.4 Hz), 7.22 (1H, m), 7.21 (2H, d, J=7.4 Hz), 4.06 (1H, m), 3.13 (2H, d br, J=11.8 Hz), 3.04 (3H, s), 2.82 (2H, m), 2.63 (2H, m, 2.17 (2H, d t, J=2.4, 12.0 Hz), 1.96 (2H, d q, J=3.6, 12.1 Hz), 1.85 (2H, d br, J=12.0 Hz)
Mp (° C.) 177

EXAMPLE 5.33

Structure

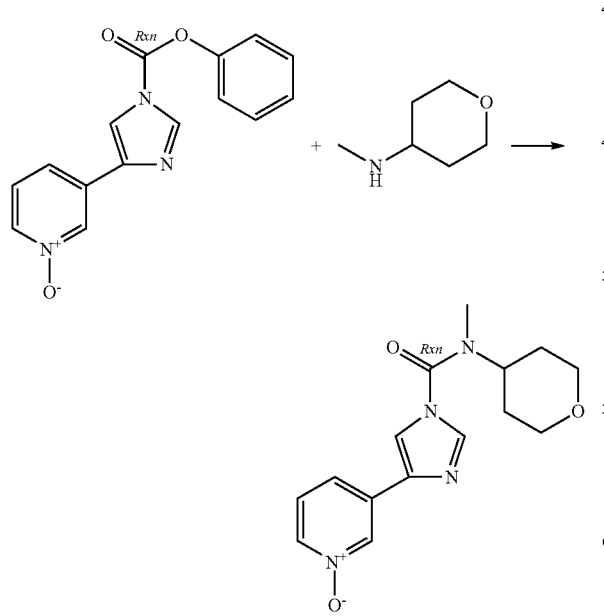

Yield (%) [12.18%]
Product Name 3-(1-(methyl(tetrahydro-2H-pyran-4-yl)carbamoyl)-1H-imidazol-4-yl)pyridine 1-oxide
NMR Solvent CDCl3

13C 150.8, 137.7, 137.6, 137, 136.1, 132.7, 126, 122.8, 115.3, 66.9, 54.6, 31.9, 29.5
1H 8.68 (1H, t, J=1.3 Hz), 8.15 (1H, d d d, J=1.0, 1.6, 6.4 Hz), 7.95 (1H, d, J=1.3 Hz), 7.73 (1H, t d, J=1.2, 8.1 Hz), 7.60 (1H, d, J=1.3 Hz), 7.33 (1H, dd, J=6.4, 8.1 Hz), 4.28 (1H, m), 4.10 (2H, dd, J=4.5, 11.6 Hz), 3.51 (2H, d t, J=1.8, 12.0 Hz), 3.04 (3H, s), 1.96 (2H, d q, J=4.4, 12.2 Hz), 1.79 (2H, m)
Mp (° C.) 217 (dec.)

EXAMPLE 5.34

Structure

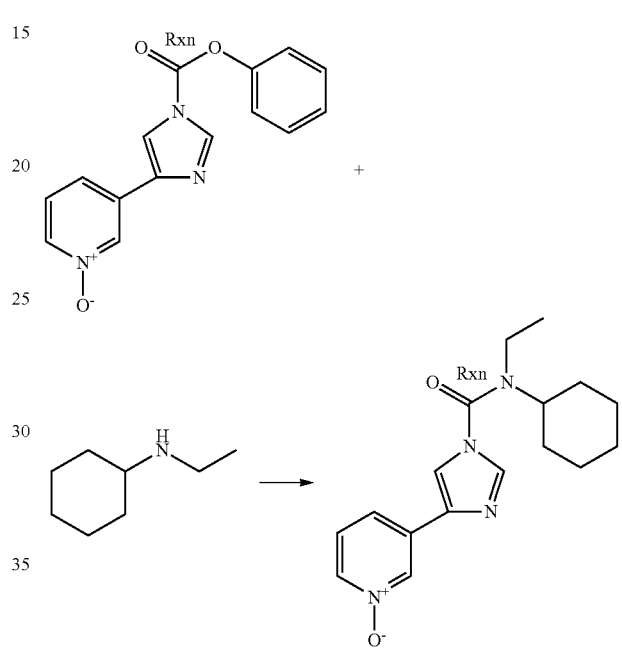

Yield (%) [66.1%]
Product Name 3-(1-(cyclohexyl(ethyl)carbamoyl)-1H-imidazol-4-yl)pyridine 1-oxide
NMR Solvent CDCl3
13C 150.1, 137.6, 137.2, 136.9, 136, 132.8, 125.9, 122.8, 115.1, 59.1, 39.6, 31.3, 25.5, 25, 14.9
1H 8.67 (1H, t, J=1.6 Hz), 8.14 (1H, d d d, J=1.0, 1.6, 6.4 Hz), 7.89 (1H, d, J=1.3 Hz), 7.72 (1H, t d, J=1.3, 8.1 Hz), 7.55 (1H, d, J=1.3 Hz), 7.31 (1H, dd, J=6.4, 8.1 Hz), 3.69 (1H, m), 3.42 (2H, q, J=7.0 Hz), 1.84 (4H, m), 1.68 (3H, m), 1.2 (2H, m, J=13.0 Hz), 1.25 (3H, t, J=7.0 Hz), 1.12 (1H, m, J=12.8 Hz)
Mp (° C.) 205-207

EXAMPLE 5.35

Structure

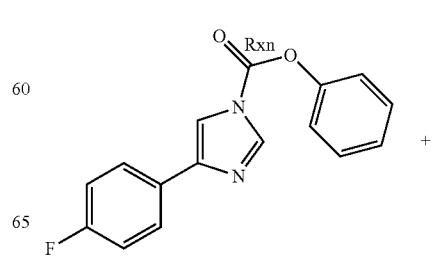 +

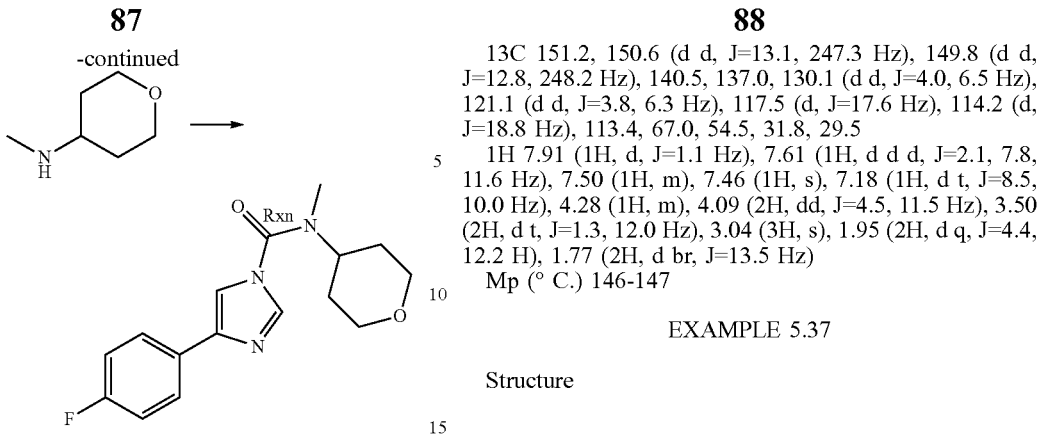

Yield (%) [48.9%]
Product Name 4-(4-fluorophenyl)-N-methyl-N-(tetrahydro-2H-pyran-4-yl)-1H-imidazole-1-carboxamide
NMR Solvent CDCl3
13C 162.3 (d, J=246.7 Hz), 151.4, 141.5, 136.9, 129.1 (d, J=3.6 Hz), 126.8 (d, J=8.5 Hz), 115.6 (d, J=21.7 Hz), 112.8, 67, 54.4, 31.8, 29.5
1H 7.91 (1H, d, J=1.3 Hz), 7.76 (2H, m, J=5.5, 8.9 Hz), 7.46 (1H, d, J=1.3 Hz), 7.10 (2H, m t, J=8.8 Hz), 4.28 (1H, m), 4.09 (2H, dd, J=4.6, 11.6 Hz), 3.50 (2H, d t, J=1.7, 11.9 Hz), 3.04 (3H, s), 1.95 (2H, d q, J=4.6, 12.3 Hz), 1.77 (2H, d br J=11.0 Hz)
Mp (° C.) 153-154

EXAMPLE 5.36

Structure

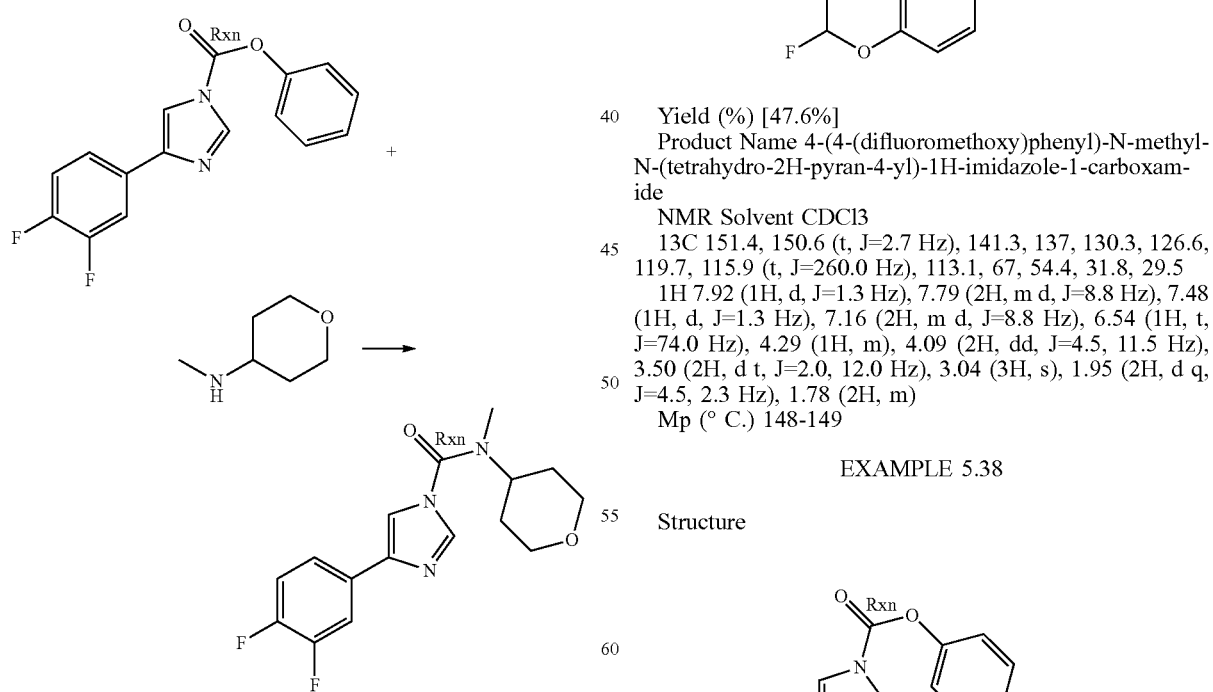

Yield (%) [29.0%]
Product Name 4-(3,4-difluorophenyl)-N-methyl-N-(tetrahydro-2H-pyran-4-yl)-1H-imidazole-1-carboxamide
NMR Solvent CDCl3
13C 151.2, 150.6 (d d, J=13.1, 247.3 Hz), 149.8 (d d, J=12.8, 248.2 Hz), 140.5, 137.0, 130.1 (d d, J=4.0, 6.5 Hz), 121.1 (d d, J=3.8, 6.3 Hz), 117.5 (d, J=17.6 Hz), 114.2 (d, J=18.8 Hz), 113.4, 67.0, 54.5, 31.8, 29.5
1H 7.91 (1H, d, J=1.1 Hz), 7.61 (1H, d d d, J=2.1, 7.8, 11.6 Hz), 7.50 (1H, m), 7.46 (1H, s), 7.18 (1H, d t, J=8.5, 10.0 Hz), 4.28 (1H, m), 4.09 (2H, dd, J=4.5, 11.5 Hz), 3.50 (2H, d t, J=1.3, 12.0 Hz), 3.04 (3H, s), 1.95 (2H, d q, J=4.4, 12.2 H), 1.77 (2H, d br, J=13.5 Hz)
Mp (° C.) 146-147

EXAMPLE 5.37

Structure

Yield (%) [47.6%]
Product Name 4-(4-(difluoromethoxy)phenyl)-N-methyl-N-(tetrahydro-2H-pyran-4-yl)-1H-imidazole-1-carboxamide
NMR Solvent CDCl3
13C 151.4, 150.6 (t, J=2.7 Hz), 141.3, 137, 130.3, 126.6, 119.7, 115.9 (t, J=260.0 Hz), 113.1, 67, 54.4, 31.8, 29.5
1H 7.92 (1H, d, J=1.3 Hz), 7.79 (2H, m d, J=8.8 Hz), 7.48 (1H, d, J=1.3 Hz), 7.16 (2H, m d, J=8.8 Hz), 6.54 (1H, t, J=74.0 Hz), 4.29 (1H, m), 4.09 (2H, dd, J=4.5, 11.5 Hz), 3.50 (2H, d t, J=2.0, 12.0 Hz), 3.04 (3H, s), 1.95 (2H, d q, J=4.5, 2.3 Hz), 1.78 (2H, m)
Mp (° C.) 148-149

EXAMPLE 5.38

Structure

-continued

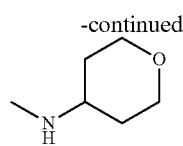
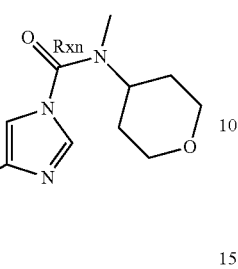

Yield (%) [36.9%]
Product Name 4-(4-methoxyphenyl)-N-methyl-N-(tetrahydro-2H-pyran-4-yl)-1H-imidazole-1-carboxamide
NMR Solvent CDCl3
13C 159.2, 151.6, 142.2, 136.8, 126.4, 125.6, 114.1, 112, 67, 55.3, 54.3, 31.8, 29.5
1H 7.91 (1H, d, J=1.3 Hz), 7.72 (2H, m d, J=8.9 Hz), 7.40 (1H, d, J=1.3 Hz), 6.94 (2H, m d, J=8.9 Hz), 4.28 (1H, m), 4.08 (2H, dd, J=4.4, 11.5 Hz), 3.84 (3H, s), 3.50 (2H, d t, J=1.9, 11.8 Hz), 3.03 (3H, s), 1.94 (2H, d q, J=4.5, 12.2 Hz), 1.7 (2H, m d, J=12.3 Hz)
Mp (° C.) 183-184

EXAMPLE 5.39

Structure

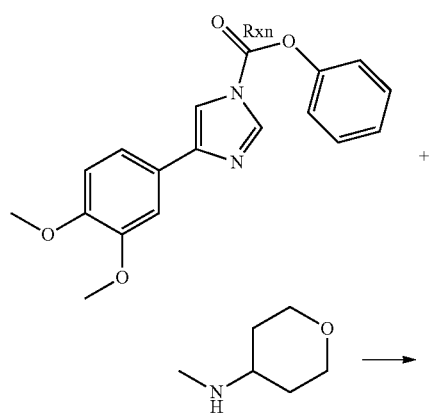

Yield (%) [36.1%]
Product Name 4-(3,4-dimethoxyphenyl)-N-methyl-N-(tetrahydro-2H-pyran-4-yl)-1H-imidazole-1-carboxamide
NMR Solvent CDCl3

13C 151.5, 149.1, 148.6, 142.2, 136.7, 125.9, 117.4, 112.3, 111.2, 108.4, 67, 55.9, 55.9, 54.4, 31.8, 29.5
1H 7.91 (1H, d, J=1.3 Hz), 7.43 (1H, d, J=1.3 Hz), 7.39 (1H, d, J=2.0 Hz), 7.30 (1H, dd, J=2.0, 8.3 Hz), 6.90 (1H, d, J=8.3 Hz), 4.29 (1H, m), 4.09 (2H, dd, J=4.3, 11.6 Hz), 3.96 (3H, s), 3.92 (3H, s), 3.50 (2H, d t, J=1.7, 12.0 Hz), 3.04 (3H s), 1.95 (2H, d q, J=4.5, 12.4 Hz), 1.77 (2H, d br, J=12.3 Hz)
Mp (° C.) 130

EXAMPLE 5.40

Structure

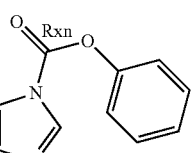

Yield (%) [41.4%]
Product Name 4-(4-chlorophenyl)-N-methyl-N-(tetrahydro-2H-pyran-4-yl)-1H-imidazole-1-carboxamide
NMR Solvent CDCl3
13C 151.3, 141.3, 137, 133.2, 131.4, 128.9, 126.4, 113.3, 67, 54.4, 31.8, 29.5
1H 7.92 (1H, s), 7.73 (2H, d, J=8.5 Hz), 7.50 (1H, s), 7.37 (2H, d, J=8.5 Hz), 4.28 (1H, m), 4.09 (2H, dd, J=4.5, 11.5 Hz), 3.50 (2H, t. J=11.5 Hz), 3.03 (3H, s), 1.95 (2H, d q, J=4.5, 12.2 Hz), 1.77 (2H, d br, J=12.5 Hz)
Mp (° C.) 174-176

EXAMPLE 5.41

Structure

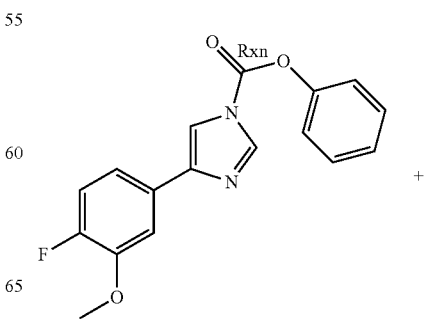

-continued

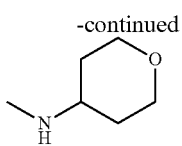

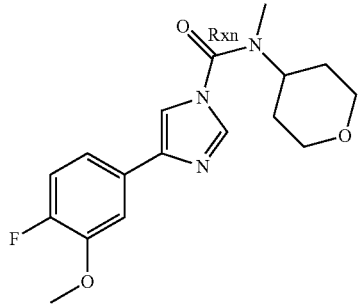

Yield (%) [43.2%]
Product Name 4-(4-fluoro-3-methoxyphenyl)-N-methyl-N-(tetrahydro-2H-pyran-4-yl)-1H-imidazole-1-carboxamide
NMR Solvent CDCl3
13C 151.9 (d, J=246.5 Hz), 151.4, 147.8 (d, J=11.2 Hz), 141.5, 136.8, 129.5 (d, J=3.8 Hz), 117.3 (d, J=6.9 Hz), 116.2 (d, J=18.7 Hz), 113, 110.3 (d, J=2.0 Hz), 67, 56.2, 54.4, 31.8, 29.5
1H 7.92 (1H, d, J=1.3 Hz), 7.50 (1H, dd, J=2.0, 8.3 Hz), 7.47 (1H, d, J=1.3 Hz), 7.24 (1H, m), 7.09 (1H, dd, J=8.3, 11.0 Hz), 4.29 (1H, m), 4.10 (2H, dd, J=4.5, 11.5 Hz), 3.96 (3H, s), 3.50 (2H, d t, J=1.8, 12.0 Hz), 3.04 (3H, s), 1.95 (2H, d, J=4.6, 12.4 Hz), 1.78 (2H, d br, J=12.5 Hz)
Mp (° C.) 119-120

EXAMPLE 5.42

Structure

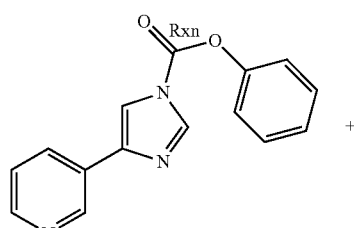

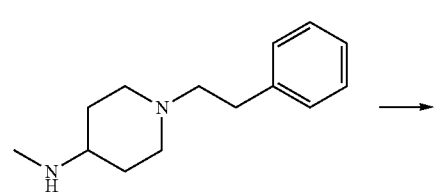

Yield (%) [23.70%]
Product Name N-methyl-N-(1-phenethylpiperidin-4-yl)-4-(pyridin-3-yl)-1H-imidazole-1-carboxamide
NMR Solvent CDCl3
13C 151.2, 148.6, 146.7, 140, 139.3, 137.3, 132.4, 128.9, 128.6, 128.4, 126.1, 123.6, 113.9, 60.2, 55.8, 52.6, 33.8, 31.7, 28.8
1H 9.01 (1H, dd, J=0.7, 2.2 Hz), 8.53 (1H, dd, J=1.6, 4.8 Hz), 8.12 (1H, d d d, J=1.7, 2.6, 8.0 Hz), 7.96 (1H, d, J=1.3 Hz), 7.59 (1H, d, J=1.3 Hz), 7.34 (1H, d d d, J=1.0, 4.8, 8.0 Hz), 7.30 (2H, m, J=7.5 Hz), 7.21 (1H, m), 7.20 (2H, m, J=0.1 Hz), 4.05 (1H, m), 3.14 (2H, d br, J=12.0 Hz), 3.05 (3H, s), 2.81 (2H, m), 2.63 (2H, m), 2.17 (2H, d t, J=2.0, 11.6 Hz), 1.97 (2H, d q, J=3.7, 12.0 Hz), 1.85 (2H, d br, J=12.0 Hz)
Mp (° C.) 175

EXAMPLE 5.43

Structure

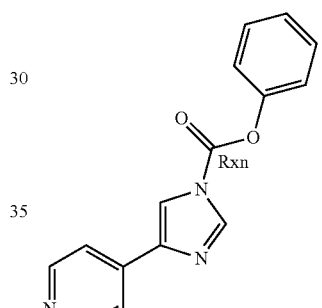

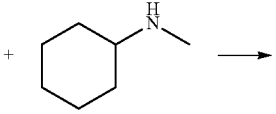

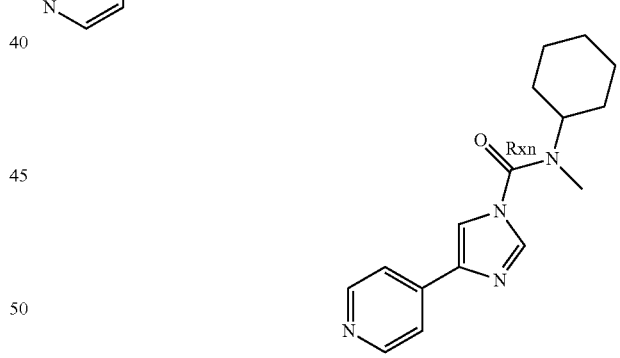

Yield (%) [52.6%]
Product Name N-cyclohexyl-N-methyl-4-(pyridin-4-yl)-1H-imidazole-1-carboxamide
NMR Solvent CDCl3
13C 150.8, 150.2, 140.4, 139.6, 137.3, 119.4, 115.7, 57.7, 31.4, 30, 25.4, 25.2
1H 8.62 (2H, m), 7.93 (1H, d, J=1.3 Hz), 7.68 (1H, d, J=1.3 Hz), 7.67 (2H, m), 3.94 (1H, m), 3.0 (3H, s), 1.86 (4H, m), 1.71 (1H, d br, J=13.0 Hz), 1.59 (2H, d q, J=3.4, 12.3 Hz), 1.38 (2H, m q, J=13.0 Hz), 1.13 (1H, t q, J=3.4, 13.0 Hz)
Mp (° e) 140

EXAMPLE 5.44

Structure

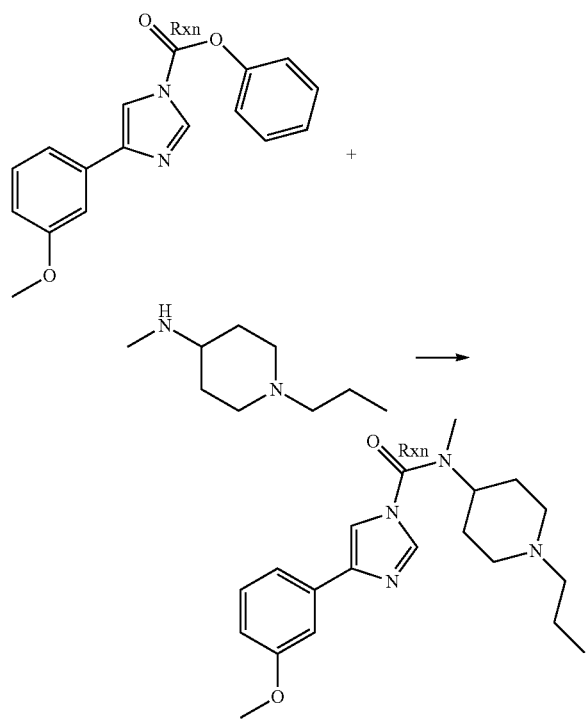

Yield (%) [19.35%]
Product Name 4-(3-methoxyphenyl)-N-methyl-N-(1-propylpiperidin-4-yl)-1H-imidazole-1-carboxamide
NMR Solvent CDCl3
13C 159.6, 151.1, 141.7, 136.5, 133.9, 129.4, 117.2, 113.3, 113, 109.8, 60, 55.4, 54.9, 52.3, 31.2, 28.4, 19.8, 11.6
1H 7.92 (1H, d, J=1.3 Hz), 7.49 (1H, d, J=1.3 Hz), 7.39 (1H, dd, J=1.4, 2.6 Hz), 7.35 (1H, d t, J=1.4, 7.7 Hz), 7.31 (1H, t, J=7.7 Hz), 6.85 (1H, d d d, J=1.4, 2.6, 8.0 Hz), 4.02 (1H, m), 3.87 (3H, s), 3.06 (2H, d br, J=11.7 Hz), 3.02 (3H, s), 2.32 (2H, m), 2.06 (2H, t br, J=11.5 Hz), 1.95 (2H, d q, J=3.4, 12.2 Hz), 1.80 (2H, d br, J=12.0 Hz), 1.52 (2H, m), 0.91 (3H, t, J=7.4 Hz)
Mp (° C.) 109-110

EXAMPLE 5.45

Structure

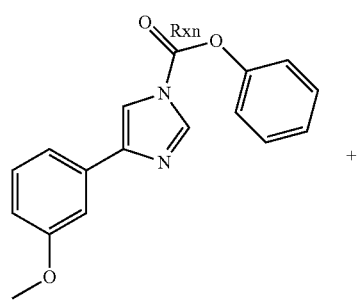

-continued

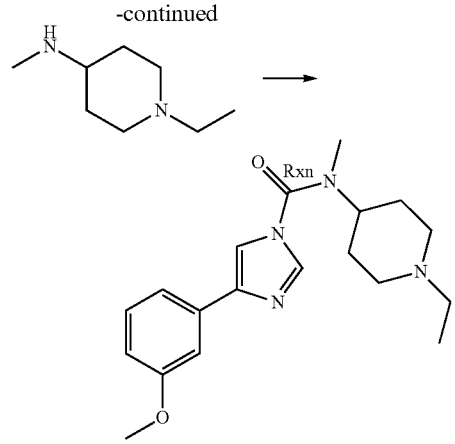

Yield (%) [26.6%]
Product Name N-(1-ethylpiperidin-4-yl)-4-(3-methoxyphenyl)-N-methyl-1H-imidazole-1-carboxamide
NMR Solvent CDCl3
13C 159.9, 151.5, 142.1, 136.9, 134.3, 129.7, 117.5, 113.7, 113.4, 110.2, 55.7, 55.3, 52.2, 52.1, 31.6, 28.8, 12.1
1H 7.92 (1H, s), 7.49 (1H, s), 7.39 (1H, t br), 7.36 (1H, d, J=7.6 Hz), 7.30 (1H, t, J=7.9 Hz), 6.85 (1H, d br, J=8.1 Hz), 4.03 (1H, m), 3.87 (3H, s), 3.08 (2H, d br, J=11.0 Hz), 3.02 (3H, s), 2.45 (2H, q, J=7.3 Hz), 2.05 (2H, t br, J=11.4 Hz), 196 (2H, d q, J=2.5, 11.8 Hz), 1.85 (2H, d br, J=11.0 Hz), 1.11 (3H, t, J=7.3 Hz)
Mp (° e) 120-121

EXAMPLE 5.46

Structure

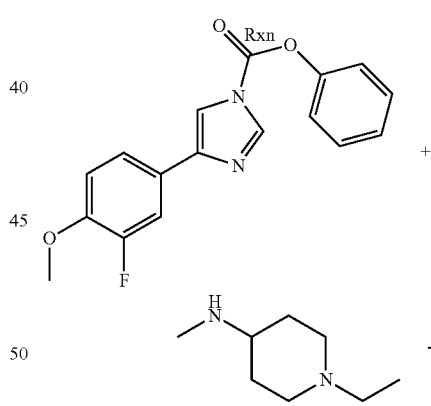

Yield (%) [29.3%]
Product Name N-(1-ethylpiperidin-4-yl)-4-(3-fluoro-4-methoxyphenyl)-N-methyl-1H-imidazole-1-carboxamide NMR Solvent CDCl3

13C 152.5 (d, J=245.0 Hz), 151.4, 147.1 (d, J=11.0 Hz), 141.1 (d, J=2.5 Hz), 136.9, 126.4 (d, J=7.0 Hz), 120.9 (d, J=3.6 Hz), 113.5 (d, J=2.5 Hz), 113.0 (d, J=20.0 Hz), 112.6, 56.3, 55.7, 52.2, 52.1, 31.6, 28.7, 12.1

1H 7.88 (1H, d, J=1.3 Hz), 7.50 (2H, m), 7.40 (1H, d, J=1.3 Hz), 6.99 (1H, t, J=8.3 Hz), 4.03 (1H, m), 3.91 (3H, s), 3.09 (2H, d br, J=11.5 Hz), 3.02 (3H, s), 2.45 (2H, q, J=7.3 Hz), 2.06 (2H, t, J=12.0 Hz), 1.96 (2H, d q, J=3.5, 12.0 Hz), 1.83 (2H, d br, J=12.0 Hz), 1.11 (3H, t, J=7.3 Hz)

Mp (° C.) 158-159

EXAMPLE 5.47

Structure

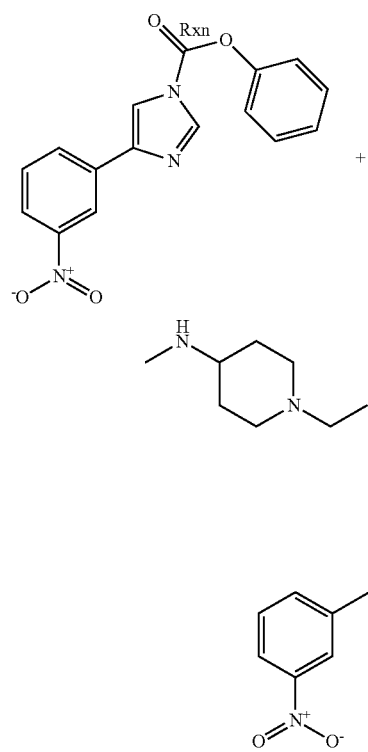

Yield (%) [23.57%]

Product Name N-(1-ethylpiperidin-4-yl)-N-methyl-4-(3-nitrophenyl)-1H-imidazole-1-carboxamide NMR Solvent DMSO 13C 150.7, 148.4, 138.5, 138.2, 135.2, 131, 130.3, 121.6, 118.9, 116.3, 55.6, 51.9, 51.4, 31.5, 28.1, 12.2

1H 8.66 (1H, t, J=1.8 Hz), 8.31 (1H, s), 8.29 (1H, d t, J=1.8, 8.0 Hz), 8.20 (1H, d, J=1.3 Hz), 8.10 (1H, d br, J=8.0 Hz), 7.69 (1H, t, J=8.0 Hz), 3.83 (1H, m), 2.96 (2H, m), 2.95 (3H, s), 2.32 (2H, q, J=7.1 Hz), 1.93 (2H, t br, J=10.5 Hz), 1.8 (2H, d q, J=3.0, 12.0 Hz), 1.73 (2H, d br, J=12.0 Hz), 0.99 (3H, t, J=7.1 Hz)

Mp (° C.) 137-139 (dec.)

EXAMPLE 5.48

Structure

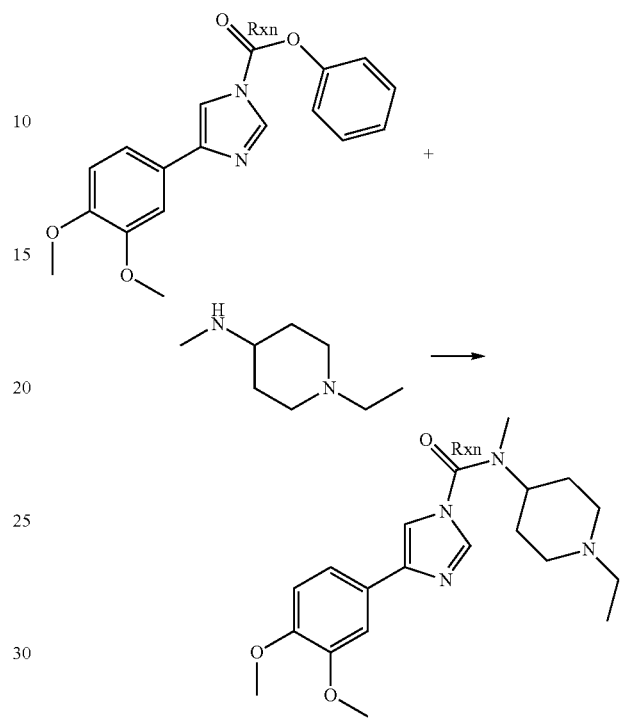

Yield (%) [33%]

Product Name 4-(3,4-dimethoxyphenyl)-N-(1-ethylpiperidin-4-yl)-N-methyl-1H-imidazole-1-carboxamide NMR Solvent CDCl3

13C 151.5, 149.1, 148.6, 142.1, 136.7, 126, 117.4, 112.3, 111.2, 108.4, 55.9, 55.9, 55.6, 52.2, 52.1, 31.6, 28.7, 12.1

1H 7.89 (1H, d, J=1.3 Hz), 7.42 (1H, d, J=1.3 Hz), 7.39 (1H, d, J=2.0 Hz), 7.30 (1H, dd, J=2.0, 8.4 Hz), 6.90 (1H, d, J=8.4 Hz), 4.04 (1H, m), 3.96 (3H, s), 3.91 (3H, s), 3.08 (2H, d br, J=11.5 Hz), 3.02 (3H, s), 2.44 (2H, q, J=7.4 Hz), 2.05 (H, t br, J=11.5 Hz), 1.96 (2H, d q, J=3.0, 11.8 Hz), 1.82 (2H, d br, J=11.8 Hz), 1.10 (3H, t, J=7.4 Hz)

Mp (° C.) 133-134

EXAMPLE 5.49

Structure

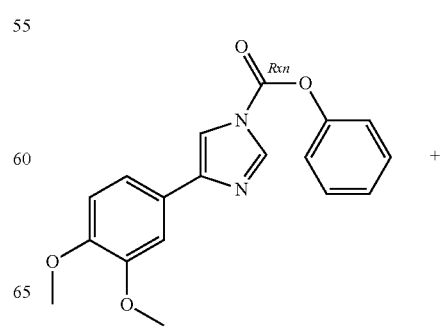

-continued

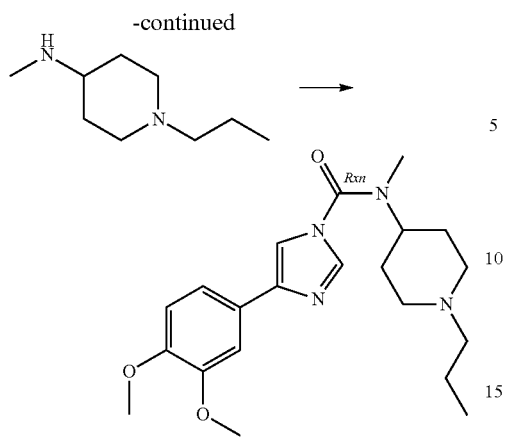

Yield (%) [41.7%]
Product Name 4-(3,4-dimethoxyphenyl)-N-methyl-N-(1-propylpiperidin-4-yl)-1H-imidazole-1-carboxamide
NMR Solvent CDCl3
13C 151.5, 149.1, 148.6, 142.1, 136.7, 126.1, 117.4, 112.3, 111.3, 108.4, 60.4, 55.9, 55.9, 55.8, 52.6, 31.6, 28.9, 20.3, 11.9
1H 7.89 (1H, d, J=1.3 Hz), 7.42 (1H, d, J=1.3 Hz), 7.40 (1H, d, J=2.0 Hz), 7.30 (1H, dd, J=2.0, 8.3 Hz), 6.90 (1H, d, J=8.3 Hz), 4.02 (1H, m), 3.96 (3H, s), 3.91 (3H, s), 3.04 (2H, d, J=11.0 Hz), 3.02 (3H, s), 2.31 (2H, m), 2.05 (2H, d t, J=1, 11.8 Hz), 1.93 (2H, d q, J=3.7, 12.0 Hz), 1.80 (2H, d br, J=12.0 Hz), 1.51 (2H, m), 0.9 (3H, t, J=7.3 Hz)
MP (° C.) 153-154

EXAMPLE 5.50

Structure

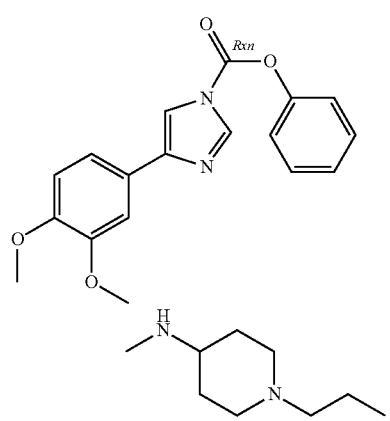

Yield (%) [48.9%]
Product Name 4-(3-fluoro-4-methoxyphenyl)-N-methyl-N-(1-propylpiperidin-4-yl)-1H-imidazole-1-carboxamide
NMR Solvent CDCl3
13C 152.5 (d, J=245.0 Hz), 151.4, 147.0 (d, J=11.0 Hz), 141.1 (d, J=2.6 Hz), 136.9, 126.4 (d, J=7.3 Hz), 120.9 (d, J=3.5 Hz), 113.4 (d, J=2.0 Hz), 113.0 (d, J=20.0 Hz), 112.6, 60.4, 56.2, 55.8, 52.6, 31.6, 28.9, 20.3, 11.9
1H 7.88 (1H, d, J=1.3 Hz), 7.50 (2H, m), 7.40 (1H, d, J=1.3 Hz), 6.99 (1H, t, J=8.4 Hz), 4.0 (1H, m), 3.91 (3H, s), 3.04 (2H, d br, J=11.7 Hz), 3.01 (3H, s), 2.31 (2H, m), 2.05 (2H, d t, J=2.0, 12.0 Hz), 1.93 (2H, d q, J=3.5, 12.0 Hz), 1.80 (2H, br, J=12.0 Hz), 1.51 (2H, m), 0.9 (3H, t, J=7.5 Hz)
Mp (° C.) 185-186

EXAMPLE 5.51

Structure

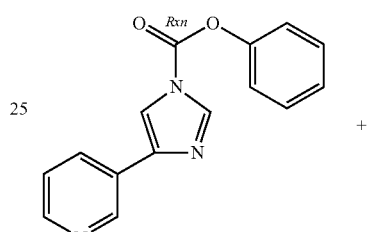

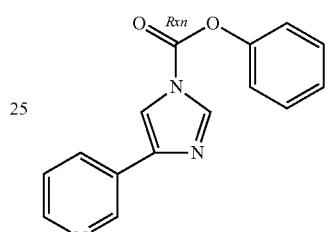

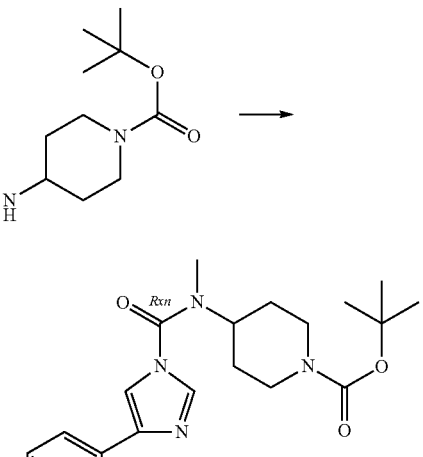

Yield (%) [72%]
Product Name tert-butyl 4-(N-methyl-4-(pyridin-3-yl)-1H-imidazole-1-carboxamido)piperidine-1-carboxylate
NMR Solvent CDCl3
13C 154.5, 151.2, 148.6, 146.7, 139.4, 137.4, 132.5, 128.9, 123.6, 113.9, 80, 55.7, 42.9, 31.9, 28.7, 28.4
1H 9.01 (1H, d, J=2.2 Hz), 8.54 (1H, d d, J=1.7, 4.8 Hz), 8.12 (1H, d d d, J=1.7, 2.2, 8.0 Hz), 7.96 (1H, d, J=1.3 Hz), 7.59 (1H, d, J=1.3 Hz), 7.35 (1H, d d d, J=0.9, 4.8, 8.0 Hz), 4.28 (2H, br), 4.20 (1H, m), 3.02 (3H, s), 2.81 (2H, br), 1.88-0.69 (4H, m), 1.48 (9H, s)
Mp (° C.) 171-172

EXAMPLE 5.52

Structure

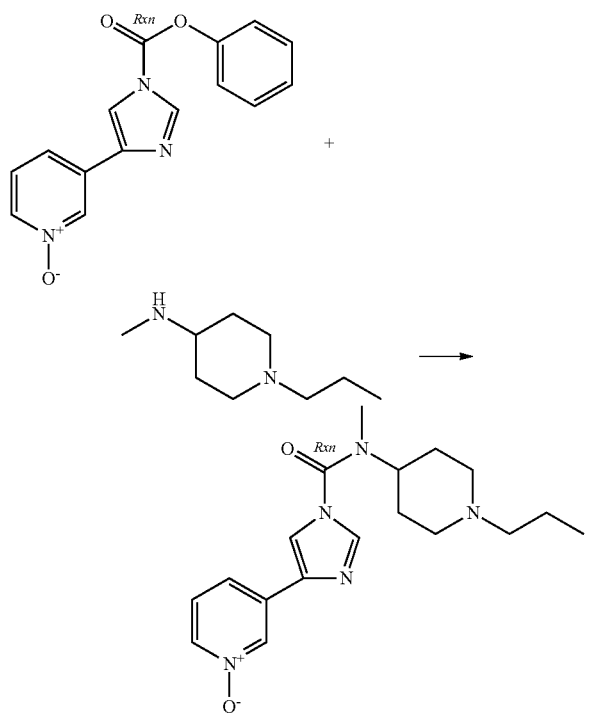

Yield (%) [24.12%]
Product Name 3-(1-(methyl(1-propylpiperidin-4-yl)carbamoyl)-1H-imidazol-4-yl)pyridine 1-oxide
NMR Solvent CDCl3
13C 150.8, 137.6, 137.6, 136.9, 136, 132.7, 125.9, 122.8, 115.3, 60.4, 56, 52.6, 31.7, 28.8, 20.2, 11.9

1H 8.66 (1H, t, J=1.6 Hz), 8.13 (1H, d d d, J=1.0, 1.7, 6.4 Hz), 7.93 (1H, d, J=1.3 Hz), 7.71 (1H, t d, J=1.2, 7.9 Hz), 7.59 (1H, d, J=1.3 Hz), 7.31 (1H, dd, J=6.4, 7.9 Hz), 3.98 (1H, m), 3.04 (2H, m d, J=12.0 Hz), 3.01 (3H, s), 2.30 (2H, m), 0.04 (2H, d t, J=2.0, 12.0 Hz), 1.93 (2H, d q, J=3.5, 12.0 Hz), 1.80 (2H, d br, J=11.5 Hz), 1.50 (2H, m), 0.9 (3H, t, J=7.4 Hz)
Mp (° C.) 158-159

EXAMPLE 5.53

Structure

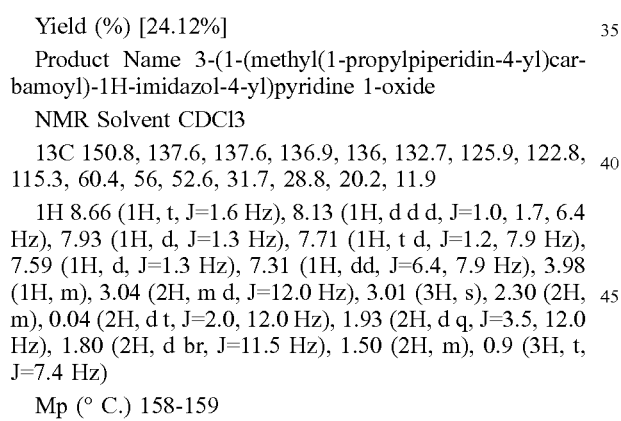

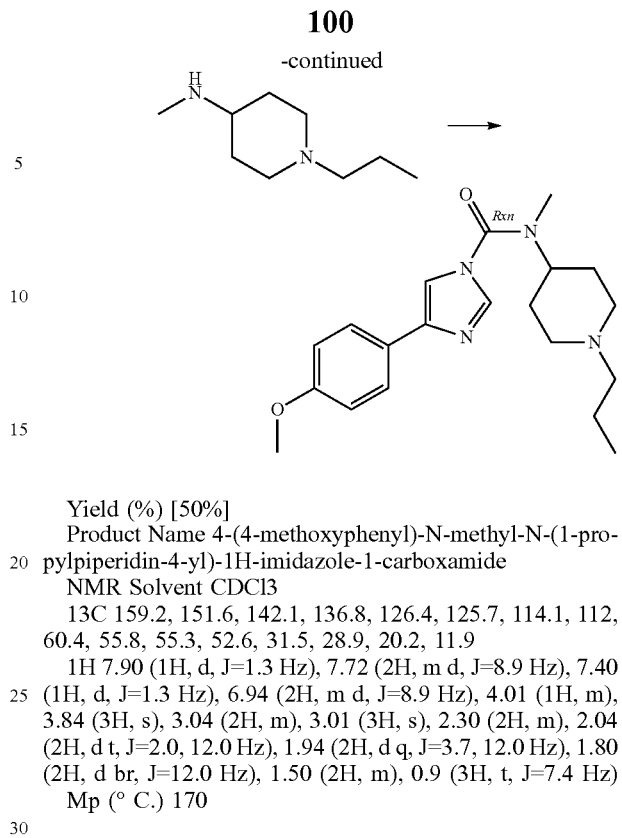

Yield (%) [50%]
Product Name 4-(4-methoxyphenyl)-N-methyl-N-(1-propylpiperidin-4-yl)-1H-imidazole-1-carboxamide
NMR Solvent CDCl3
13C 159.2, 151.6, 142.1, 136.8, 126.4, 125.7, 114.1, 112, 60.4, 55.8, 55.3, 52.6, 31.5, 28.9, 20.2, 11.9

1H 7.90 (1H, d, J=1.3 Hz), 7.72 (2H, m d, J=8.9 Hz), 7.40 (1H, d, J=1.3 Hz), 6.94 (2H, m d, J=8.9 Hz), 4.01 (1H, m), 3.84 (3H, s), 3.04 (2H, m), 3.01 (3H, s), 2.30 (2H, m), 2.04 (2H, d t, J=2.0, 12.0 Hz), 1.94 (2H, d q, J=3.7, 12.0 Hz), 1.80 (2H, d br, J=12.0 Hz), 1.50 (2H, m), 0.9 (3H, t, J=7.4 Hz)
Mp (° C.) 170

EXAMPLE 5.54

Structure

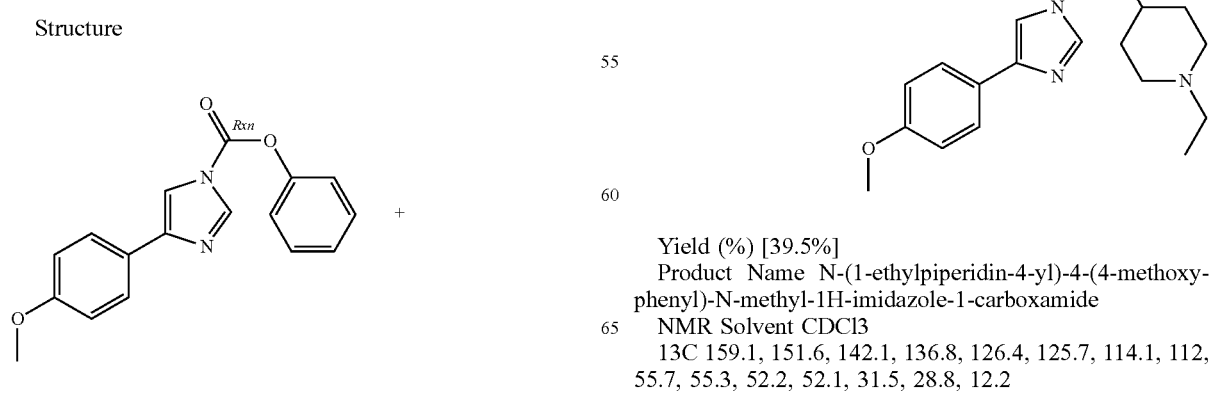

Yield (%) [39.5%]
Product Name N-(1-ethylpiperidin-4-yl)-4-(4-methoxyphenyl)-N-methyl-1H-imidazole-1-carboxamide
NMR Solvent CDCl3
13C 159.1, 151.6, 142.1, 136.8, 126.4, 125.7, 114.1, 112, 55.7, 55.3, 52.2, 52.1, 31.5, 28.8, 12.2

1H 7.89 (1H, d, J=1.3 Hz), 7.72 (2H, m d, J=8.9 Hz), 7.39 (1H, d, J=1.3 Hz), 6.94 (2H, m d, J=8.9 Hz), 4.02 (1H, m), 3.84 (3H, s), 3.07 (2H, m d, J=11.7 Hz), 3.01 (3H, s), 2.43 (2H, q, J=7.3 Hz), 2.03 (2H, d t, J=2.0, 12.0 Hz), 1.93 (2H, d q, J=3.5, 12.0 Hz), 1.82 (2H, d br, J=12.0 Hz), 1.09 (3H, t, J=7.2 Hz)

Mp (° C.) 163-164

EXAMPLE 5.55

Structure

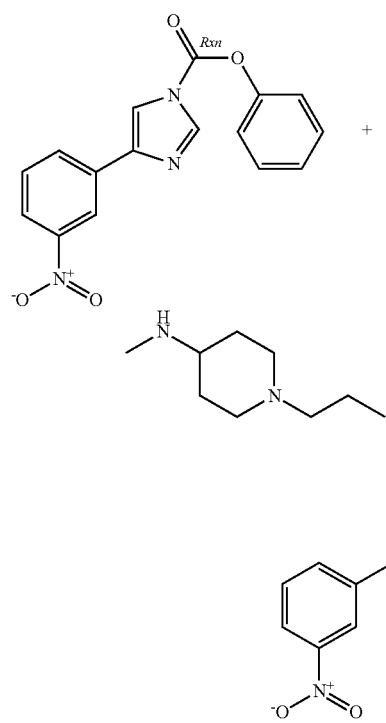

Yield (%) [35.6%]
Product Name N-methyl-4-(3-nitrophenyl)-N-(1-propylpiperidin-4-yl)-1H-imidazole-1-carboxamide
NMR Solvent DMSO 13C 150.7, 148.4, 138.5, 138.2, 135.2, 131, 130.3, 121.6, 118.9, 116.4, 59.6, 55.6, 52.4, 31.6, 28.2, 19.8, 11.9
1H 8.66 (1H, t, J=1.8 Hz), 8.32 (1H, s), 8.30 (1H, d br, J=7.9 Hz), 8.20 (1H, s), 8.11 (1H, dd, J=2.2, 8.1 Hz), 7.69 (1H, t, J=8.1 Hz), 3.82 (1H, m), 2.95 (3H, s), 2.93 (2H, m), 2.21 (2H, t br, J=7.5 Hz), 1.91 (2H, t br, J=11.2 Hz), 1.81 (2H, d, J=3.0, 11.7 Hz), 1.72 (2H, d br, J=12.0 Hz), 1.41 (2H, m), 0.84 (3H, t, J=7.5 Hz)

Mp (° C.) 127

EXAMPLE 5.56

Structure

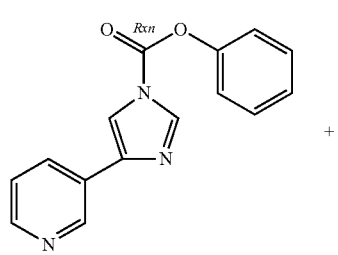

-continued

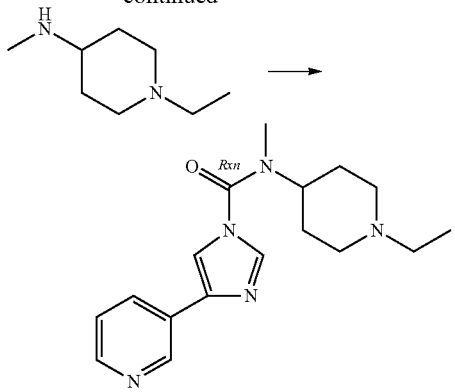

Yield (%) [27.3%]
Product Name N-(1-ethylpiperidin-4-yl)-N-methyl-4-(pyridin-3-yl)-1H-imidazole-1-carboxamide
NMR Solvent CDCl3
13C 151.2, 148.6, 146.7, 139.3, 137.3, 132.4, 128.9, 123.6, 113.9, 55.9, 52.2, 52.1, 31.6, 28.8, 12.2
1H 9.0 (1H, dd, J=1.0, 2.3 Hz), 8.52 (1H, dd, J=1.7, 4.9 Hz), 8.11 (1H, d d d, J=1.7, 2.2, 7.9 Hz), 7.94 (1H, d, J=1.3 Hz), 7.58 (1H, d, J=1.3 Hz), 7.34 (1H, d d d, J=1.0, 4.9, 8.0 Hz), 4.03 (1H, m), 3.07 (2H, m d, J=11.5 Hz), 3.03 (3H, s), 243 (2H, q, J=7.3 Hz), 2.03 (2H, d t, J=2.0, 11.7 Hz), 1.94 (2H, d q, J=3.5, 12.0 Hz), 1.83 (2H, d br, J=12.0 Hz), 1.09 (3H, t, J=7.3 Hz)

Mp (° C.) 167-168

EXAMPLE 5.57

Structure

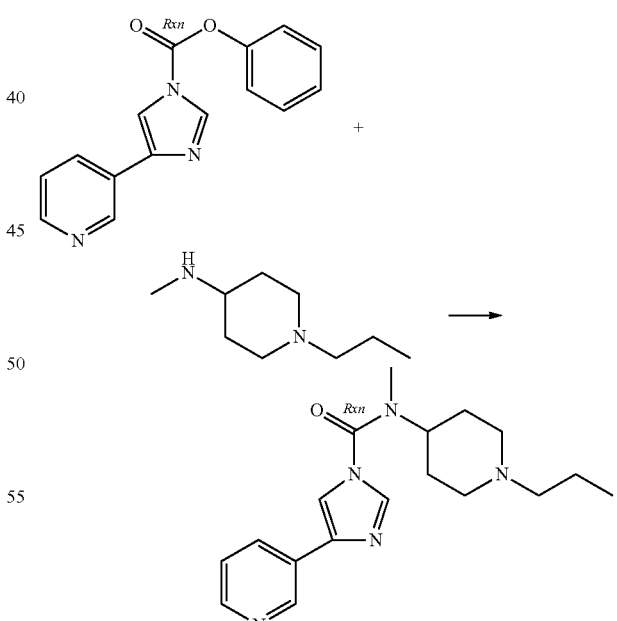

Yield (%) [30%]
Product Name N-methyl-N-(1-propylpiperidin-4-yl)-4-(pyridin-3-yl)-1H-imidazole-1-carboxamide
NMR Solvent CDCl3
13C 151.2, 148.6, 146.7, 139.3, 137.3, 132.4, 128.9, 123.6, 113.9, 60.4, 55.9, 52.6, 31.6, 28.9, 20.3, 11.9

1H 9.0 (1H, d, J=2.0 Hz), 8.52 (1H, dd, J=1.6, 4.8 Hz), 8.11 (1H, t d, J=2.0, 8.1 Hz), 7.94 (1H, d, J=1.3 Hz), 7.57 (1H, d, J=1.3 Hz), 7.33 (1H, dd, J=4.8, 8.1 Hz), 4.01 (1H, m), 3.05 (2H, m), 3.02 (3H, s), 2.30 (2H, m), 2.04 (2H, t br, J=11. Hz), 1.93 (2H, d q, J=3.1, 12.0 Hz), 1.81 (2H, d br, J=11.2 Hz), 1.50 (2H, m), 0.9 (3H, t, J=7.4 Hz)

Mp (° C.) 154-155

EXAMPLE 5.58

Structure

Yield (%) [63%]
Product Name N-methyl-N-(1-(methylsulfonyl)piperidin-4-yl)-4-(pyridin-3-yl)-1H-imidazole-1-carboxamide
NMR Solvent DMSO
13C 150.9, 148.1, 146.2, 138.2, 137.8, 131.9, 129.1, 123.8, 115.5, 54.5, 44.9, 34.4, 31.7, 27.7

1H 9.07 (1H, s), 8.46 (1H, s), 8.19 (3H, m), 7.42 (1H, s br), 3.98 (1H, m br), 3.66 (2H, m d, J=10.0 Hz), 2.96 (3H, s), 2.88 (3H, s), 2.85 (2H, m br), 1.88 (4H, m br)

Mp (° C.) 259-260

EXAMPLE 5.59

Structure

Yield (%) [63.1%]
Product Name N-(1-ethylpiperidin-4-yl)-4-(4-fluoro-3-methoxyphenyl)-N-methyl-1H-imidazole-1-carboxamide
NMR Solvent CDCl3
13C 151.9 (d, J=246.2 Hz), 151.4, 147.8 (d, J=11.0 Hz), 141.5, 136.8, 129.6 (d, J=3.8 Hz), 117.3 (d, J=6.8 Hz), 116.1 (d, J=19.0 Hz), 113.1, 110.3 (d, J=1.5 Hz), 56.2, 55.8, 52.2, 52.1, 31.6, 28.8, 12.2

1H 7.90 (1H, s), 7.49 (1H, dd, J=1.7, 8.5 Hz), 7.45 (1H, s), 7.24 (1H, m), 7.08 (1H, dd, J=8.6, 11.1 Hz), 4.03 (1H, m), 3.96 (3H, s), 3.08 (2H, d br, J=11.2 Hz), 3.02 (3H, s), 2.44 (2H, q, J=7.4 Hz), 2.05 (2H, t br, J=11.0 Hz), 1.95 (2H, d q, J=2.6, 11.9 Hz), 1.83 (2H, d br, J=10.5 Hz), 1.10 (3H, t, J=7.4 Hz)

Mp (° C.) 144-146

EXAMPLE 5.60

Structure

Yield (%) [42.0%]
Product Name N-methyl-4-(pyridin-4-yl)-N-(tetrahydro-2H-pyran-4-yl)-1H-imidazole-1-carboxamide NMR Solvent CDCl3

13C 151, 150.3, 140.2, 139.8, 137.3, 119.4, 115.6, 66.9, 54.5, 31.9, 29.5

1H 8.63 (2H, m d, J=4.6 Hz), 7.95 (1H, d, J=1.3 Hz), 7.69 (1H, d, J=1.3 Hz), 7.67 (2H, m d, J=4.6 Hz), 4.28 (1H, m), 4.09 (2H, dd, J=4.7, 11.5 Hz), 3.50 (2H, d t, J=2.1, 12.0 Hz), 3.04 (3H, s), 1.95 (2H, d q, J=4.9, 12.5 Hz), 1.78 (2H, m d, J=12.3 Hz)

Mp (° C.) 175

EXAMPLE 5.61

Structure

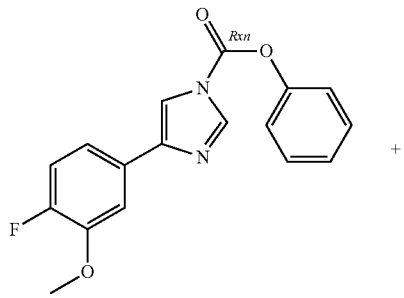

+

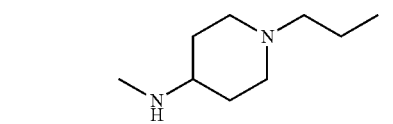

→

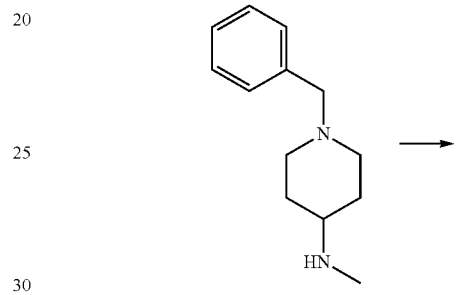

Yield (%) [53.2%]

Product Name 4-(4-fluoro-3-methoxyphenyl)-N-methyl-N-(1-propylpiperidin-4-yl)-1H-imidazole-1-carboxamide NMR Solvent CDCl3

13C 151.9 (d, J=246.5 Hz), 151.4, 147.8 (d, J=11.0 Hz), 141.4, 136.8, 129.6 (d, J=4.0 Hz), 117.3 (d, J=7.0 Hz), 116.1 (d, J=18.8 Hz), 113.1, 110.3 (d, J=2.0 Hz), 60.4, 56.2, 55.8, 52.6, 31.6, 28.8, 20.2, 11.9

1H 7.89 (1H, d, J=1.3 Hz), 7.49 (1H, dd, J=2.0, 8.2 Hz), 7.45 (1H, d, J=1.3 Hz), 7.24 (1H, m), 7.09 (1H, dd, J=8.3, 11.0 Hz), 4.02 (1H, m), 3.96 (3H, s), 3.05 (2H, d br, J=12.0 Hz), 3.02 (3H, s), 2.31 (2H, m), 2.05 (2H, d t, J=2.0, 12.0 Hz), 1.4 (2H, d q, J=3.5, 12.0 Hz), 1.80 (2H, d br, J=12.0 Hz), 1.51 (2H, m), 0.91 (3H, t, J=7.5 Hz)

Mp (° C.) 127-128

EXAMPLE 5.62

Structure

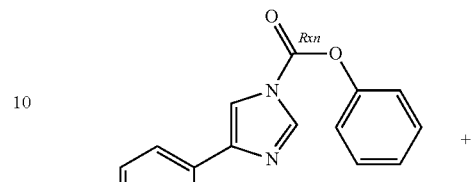

+

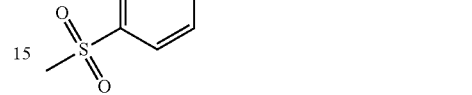

→

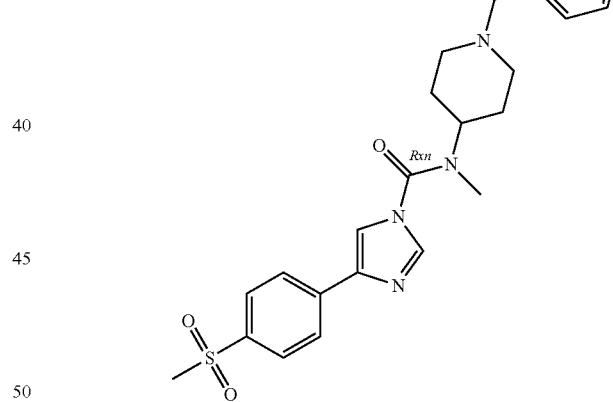

Yield (%) [18.51%]

Product Name N-(1-benzylpiperidin-4-yl)-N-methyl-4-(4-(methylsulfonyl)phenyl)-1H-imidazole-1-carboxamide NMR Solvent DMSO 13C 150.7, 139, 138.8, 138.5, 138.4, 138.3, 128.8, 128.2, 127.6, 127, 125.2, 116.8, 61.9, 55.6, 52.2, 43.7, 31.6, 28.2

1H 8.25 (1H, d, J=1.1 Hz), 8.20 (1H, d, J=1.1 Hz), 8.10 (2H, m d, J=8.7 Hz), 7.93 (2H, m d, J=8.7 Hz), 7.36-7.20 (5H, m), 3.83 (1H, m), 3.46 (2H, s), 3.22 (3H, s), 2.95 (3H, s), 2.90 (2H, m d, J=11.0 Hz), 2.0 (2H, t br, J=11.0 Hz), 1.83 (2H, d q, J=3.5, 12.0 Hz), 1.72 (2H, d br, J=12.0 Hz)

Mp (° C.) 219-220

EXAMPLE 5.63

Structure

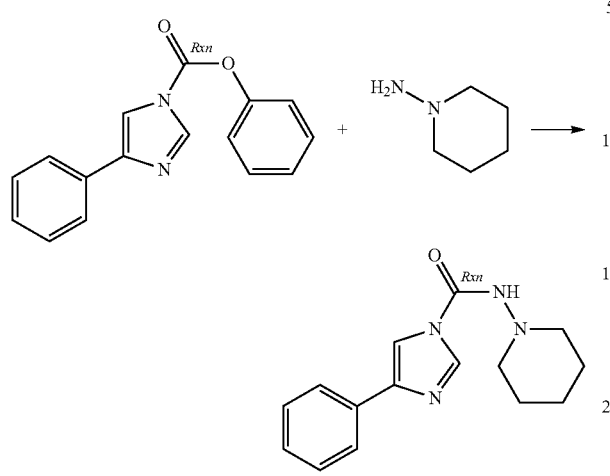

Yield (%) [77%]
Product Name 4-phenyl-N-(piperidin-1-yl)-1H-imidazole-1-carboxamide
NMR Solvent CDCl3
13C 150.8, 142.3, 136.9, 133, 128.7, 127.5, 125.1, 113.1, 47.6, 25.8, 24.2
1H 7.91 (1H, d, J=1.3 Hz), 7.80 (2H, d, J=8.2 Hz), 7.47 (1H, d, J=1.3 Hz), 7.41 (2H, t, J=7.8 Hz), 7.30 (1H, t, J=7.3 Hz), 3.59 (4H, m), 1.73 (2H, m), 1.70 (4H, m)
Mp (° C.) 113

EXAMPLE 5.64

Structure

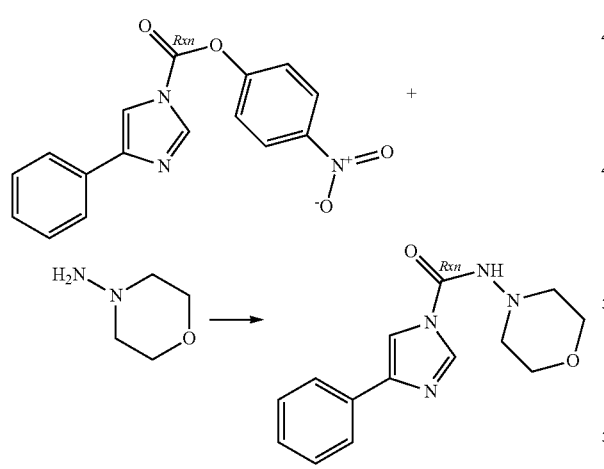

Yield (%) [4.21%]
Product Name N-morpholino-4-phenyl-1H-imidazole-1-carboxamide
NMR Solvent CDCl3
13C 150.8, 142.7, 137.0, 132.7, 128.7, 127.7, 125.2, 112.8, 65.5, 46.8
1H 7.93 (1H, d, J=1.3 Hz), 7.80 (2H, m d, J=8.2 Hz), 7.47 (1H, d, J=1.3 Hz), 7.42 (2H, m t, J=7.4 Hz), 7.31 (1H, m t, J=7.4 Hz), 3.80 (4H, m), 3.70 (4H, m)
Mp (° C.) 98

EXAMPLE 5.65

Structure

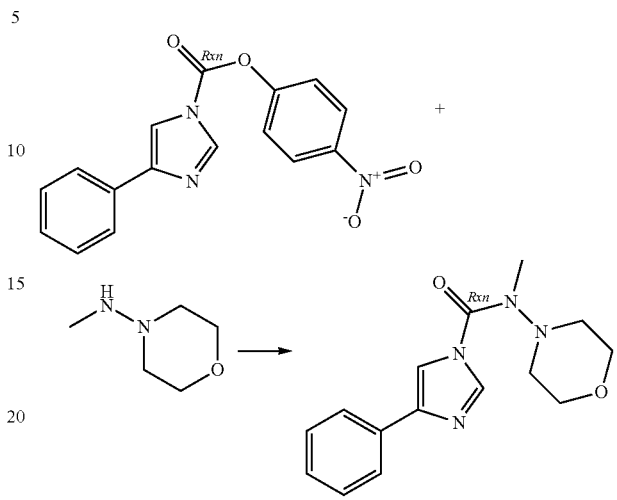

Yield (%) [10.88%]
Product Name N-methyl-N-morpholino-4-phenyl-1H-imidazole-1-carboxamide
NMR Solvent CDCl3
13C 149.9, 140.4, 138.2, 132.4, 128.7, 127.7, 125.1, 114.8, 66.1, 51.4, 26.5
1H 8.61 (1H, d, J=1.0 Hz), 7.95 (1H, d, J=1.0 Hz), 7.82 (2H, d, J=8.6 Hz), 7.42 (2H, t, J=8.0 Hz), 7.31 (1H, t, J=7.0 Hz), 3.86 (4H, br), 2.98 (4H, br)
Mp (° C.) 133

EXAMPLE 5.66

Structure

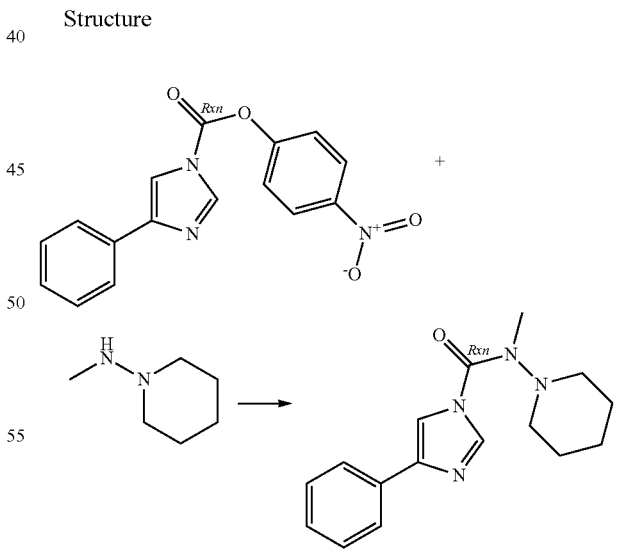

Yield (%) [2.53%]
Product Name N-methyl-4-phenyl-N-(piperidin-1-yl)-1H-imidazole-1-carboxamide
NMR Solvent CDCl3
13C 149.8, 140.2, 138.6, 132.7, 128.7, 127.5, 125, 115, 52.5, 26.2, 25.4, 22.9

1H 8.64 (1H, d, J=1.0 Hz), 7.99 (1H, d, J=1.0 Hz), 7.82 (2H, d, J=8.4 Hz), 7.41 (2H, t, J=7.7 Hz), 7.30 (1H, t, J=7.5 Hz), 3.13 (3H, s), 2.88 (4H, br), 1.78 (5H, m), 1.16 (1H, br)

Mp (° C.) 85

EXAMPLE 5.67

Structure

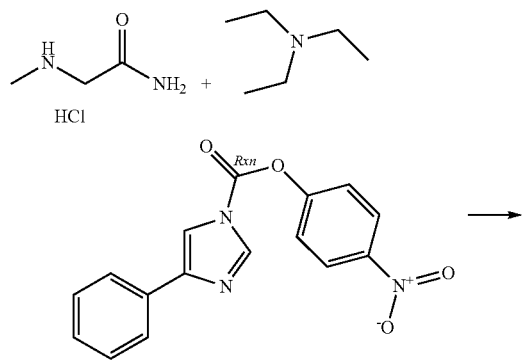

Yield (%) [35.8%]

Product Name N-(2-amino-2-oxoethyl)-N-methyl-4-phenyl-1H-imidazole-1-carboxamide NMR Solvent DMSO 13C 169.3, 151.7, 140.7, 137.6, 133.3, 128.7, 127.1, 124.8, 114.4, 52.9, 38.1

1H 8.12 (1H, sbr), 8.0 (1H, sbr), 7.84 (2H, d, J=8.0 Hz), 7.61 (1H, sbr), 7.39 (2H, t, J=8.0 Hz), 7.30 (1H, sbr), 7.26 (1H, mt, J=7.5 Hz), 4.0 (2H, s), 3.07 (3H, s)

Mp (° C.) 185 (dec)

EXAMPLE 5.68

Structure

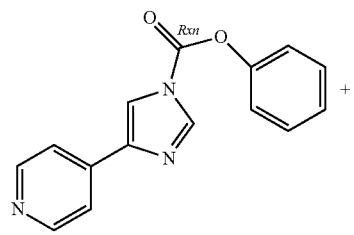

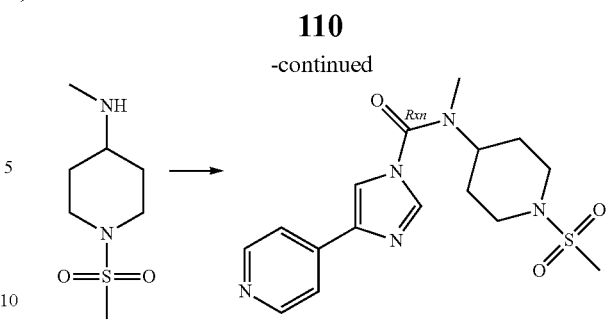

Yield (%) [43.5%]

Product Name N-methyl-N-(1-(methylsulfonyl)piperidin-4-yl)-4-(pyridin-4-yl)-1H-imidazole-1-carboxamide NMR Solvent DMSO 13C 150.8, 150, 140.5, 138.3, 138.2, 119.1, 117.5, 54.5, 44.9, 34.3, 31.7, 27.6

1H 8.56 (2H, md, J=4.9 Hz), 8.31 (1H, s), 8.23 (1H, s), 7.80 (2H, md, J=4.9 Hz), 3.98 (1H, sbr), 3.66 (2H, dbr, J=12.0 Hz), 2.96 (3H, s), 2.89 (3H, s), 2.85 (2H, mbr), 1.88 (4H, m)

Mp (° C.) ND

EXAMPLE 5.69

Structure

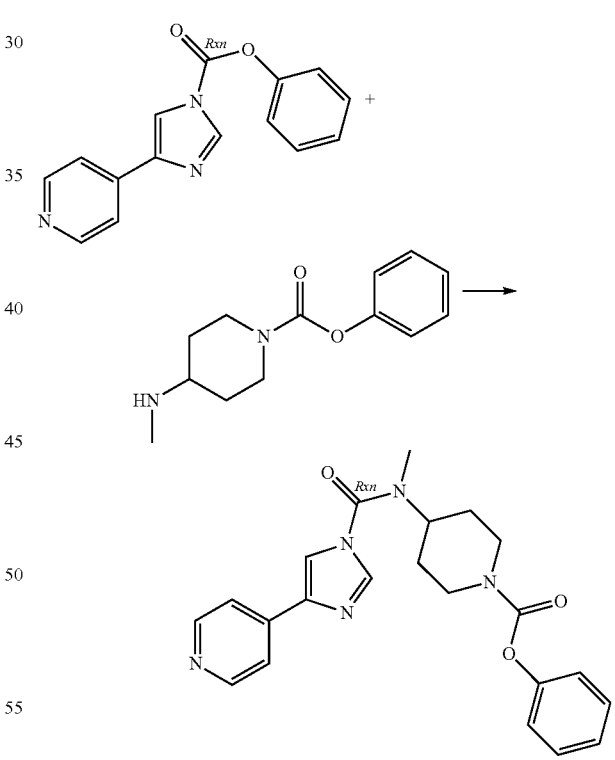

Yield (%) [24.21%]

Product Name phenyl 4-(N-methyl-4-(pyridin-4-yl)-1H-imidazole-1-carboxamido)piperidine-1-carboxylate NMR Solvent CDCl3

13C 153.5, 151.2, 151.1, 150.3, 140.2, 139.9, 137.4, 129.3, 125.5, 121.6, 119.5, 115.6, 55.4, 43.7, 43.4, 32.1, 28.7, 28.4

1H 8.63 (2H, md, J=4.9 Hz), 7.98 (1H, d, J=1.3 Hz), 7.71 (1H, d, J=1.3 Hz), 7.69 (2H, md, J=4.9 Hz), 7.38 (2H, mt,

J=7.8 Hz), 7.22 (1H, mt, J=7.6 Hz), 7.12 (2H, md, J=8.5 Hz), 4.49 (2H, m), 4.30 (1H, m), 3.12 (1H, m), 3.06 (3H, s), 2.95 (1H, m), 1.94 (2H, m), 1.90 (2H, m)

Mp (° C.) 210-211

EXAMPLE 5.70

Structure

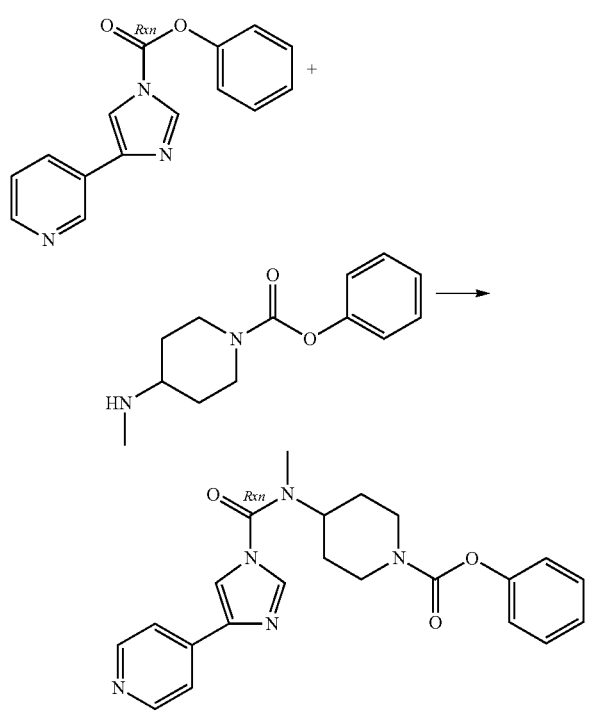

Yield (%) [27.8%]

Product Name phenyl 4-(N-methyl-4-(pyridin-3-yl)-1H-imidazole-1-carboxamido)piperidine-1-carboxylate NMR Solvent CDCl3

13C 153.5, 151.3, 151.2, 148.7, 146.7, 139.5, 137.4, 132.5, 129.3, 128.9, 125.4, 123.6, 121.6, 113.8, 55.4, 43.7, 43.4, 32.1, 28.8, 28.4

1H 9.03 (1H, dd, J=0.9, 2.3 Hz), 8.55 (1H, dd, J=1.6, 4.7 Hz), 8.13 (1H, ddd, J=1.7, 2.2, 7.8 Hz), 7.99 (1H, d, J=1.3 Hz), 7.61 (1H, d, J=1.3 Hz), 7.38 (2H, mt, J=8.0 Hz), 7.36 (1H, ddd, J=0.8, 4.5, 7.8 Hz), 7.23 (1H, mt, J=7.5 Hz), 7.13 (2H, md, J=8.5 Hz), 4.50 (2H, m), 4.31 (1H, m), 3.12 (1H, m), 3.07 (3H, s), 2.97 (1H, m), 1.95 (2H, m), 1.90 (2H, m)

Mp (° C.) 199

EXAMPLE 6

Synthesis of further compounds of Formula I or II, or intermediates useful in the synthesis thereof, by means of the process of the invention The general applicability of the process of the invention to the preparation of the compounds of Formula I and Formula II, and intermediates useful in the preparation thereof, is illustrated by the following specific compounds and reaction schemes, each of which was performed using methods of the invention analogous to those described above. NMR data was obtained in each case as described above.

EXAMPLE 6.1

Structure

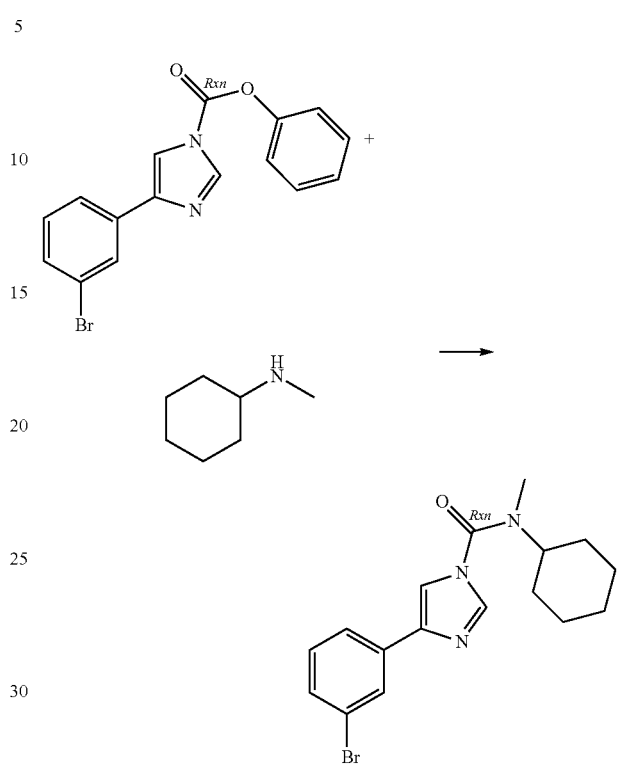

Yield (%) [41.9%]

Product Name 4-(3-bromophenyl)-N-cyclohexyl-N-methyl-1H-imidazole-1-carboxamide

NMR Solvent CDCl3

13C 151.1, 140.7, 137, 135.1, 130.3, 130.2, 128.1, 123.6, 122.9, 113.8, 57.6, 31.4, 30, 25.4, 25.2

Mp ND

EXAMPLE 6.2

Structure

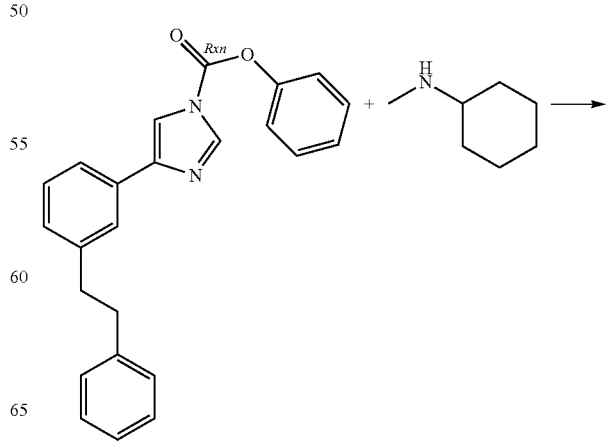

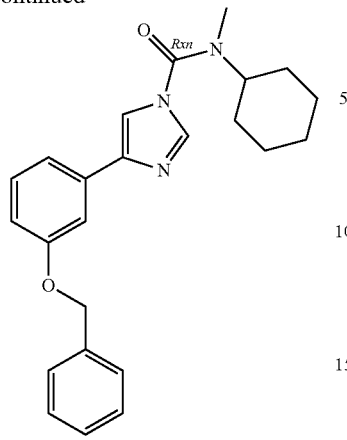

Yield (%) [52.2%]
Product Name 4-(3-(benzyloxy)phenyl)-N-cyclohexyl-N-methyl-1H-imidazole-1-carboxamide
NMR Solvent CDCl3
13C 159.2, 151.3, 141.9, 137, 136.9, 134.4, 129.7, 128.5, 127.9, 127.5, 117.8, 114.4, 113.4, 111.2, 70, 57.5, 31.3, 30, 25.4, 25.2
1H NA
Mp ND

EXAMPLE 6.3

Structure

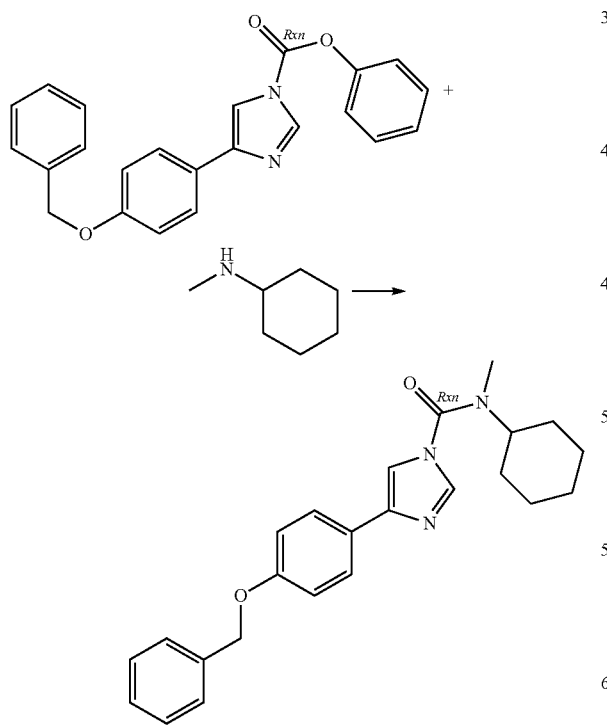

Yield (%) [66.9%]
Product Name 4-(4-(benzyloxy)phenyl)-N-cyclohexyl-N-methyl-1H-imidazole-1-carboxamide
NMR Solvent CDCl3
13C 158.4, 151.4, 141.9, 136.9, 136.8, 128.6, 128, 127.5, 126.4, 125.9, 115.1, 112.2, 70, 57.5, 31.3, 30, 25.4, 25.2
1H NA
Mp ND

EXAMPLE 6.4

Structure

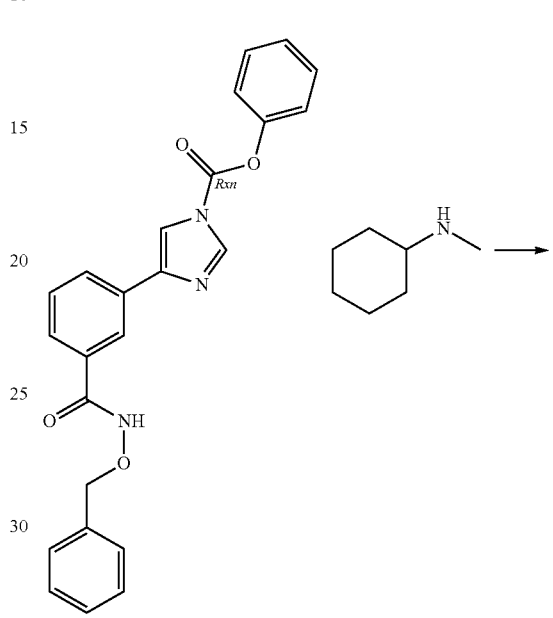

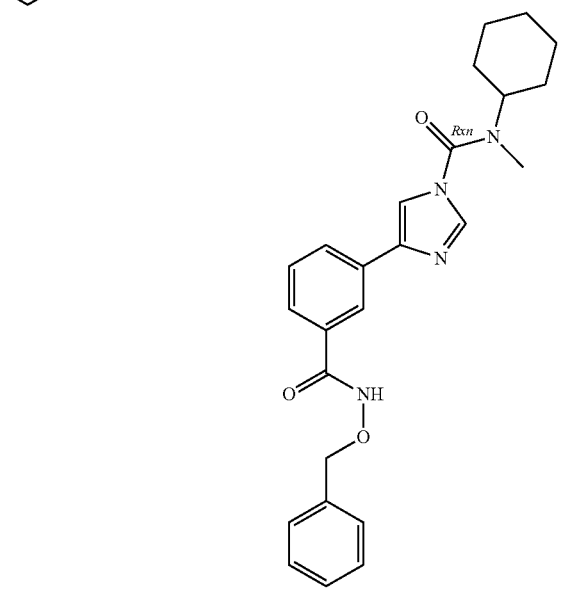

Yield (%) [51%]
Product Name 4-(3-(benzyloxycarbamoyl)phenyl)-N-cyclohexyl-N-methyl-1H-imidazole-1-carboxamide
NMR Solvent CDCl3
13C 166.2, 151.1, 140.9, 137.2, 135.2, 133.5, 132.4, 129.4, 129.2, 128.8, 128.6, 128.6, 126.2, 123.5, 113.9, 78.4, 57.6, 31.4, 29.9, 25.4, 25.2
1H NA
Mp ND

EXAMPLE 6.5
Structure
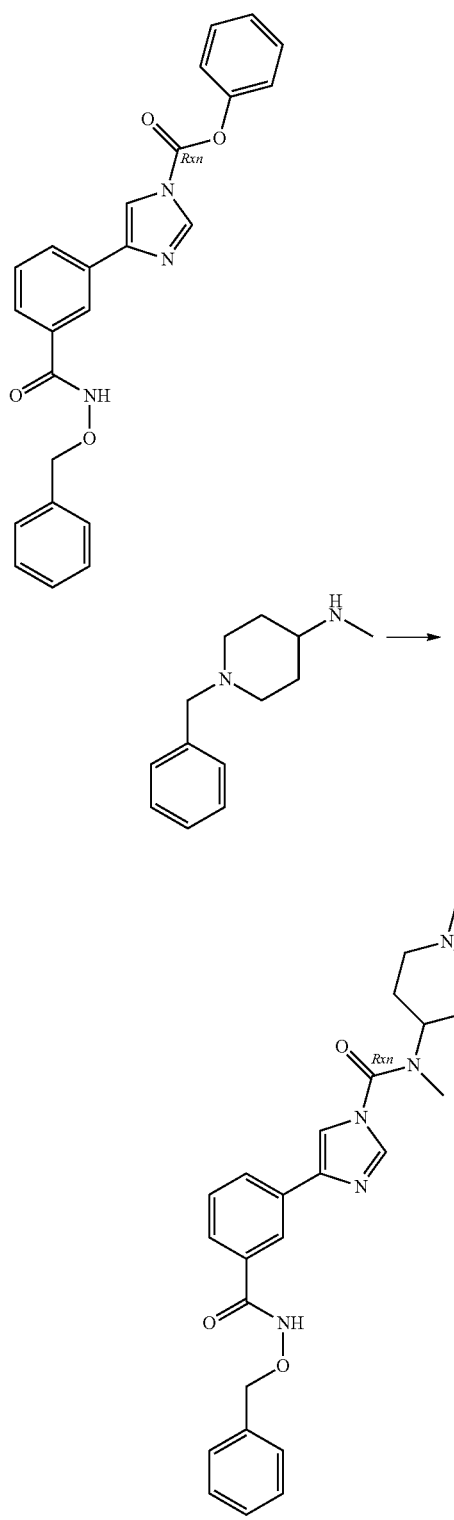
Yield (%) [51.9%]
Product Name 4-(3-(benzyloxycarbamoyl)phenyl)-N-(1-benzylpiperidin-4-yl)-N-methyl-1H-imidazole-1-carboxamide
NMR Solvent CDCl3
13C 166.3, 151.3, 141.1, 137.9, 137.2, 135.3, 133.5, 132.4, 129.4, 129.2, 129.1, 128.8, 128.6, 128.6, 128.3, 127.2, 126.2, 123.6, 113.9, 78.4, 62.8, 55.8, 52.5, 31.7, 28.8
1H NA
Mp ND
EXAMPLE 6.6
Structure
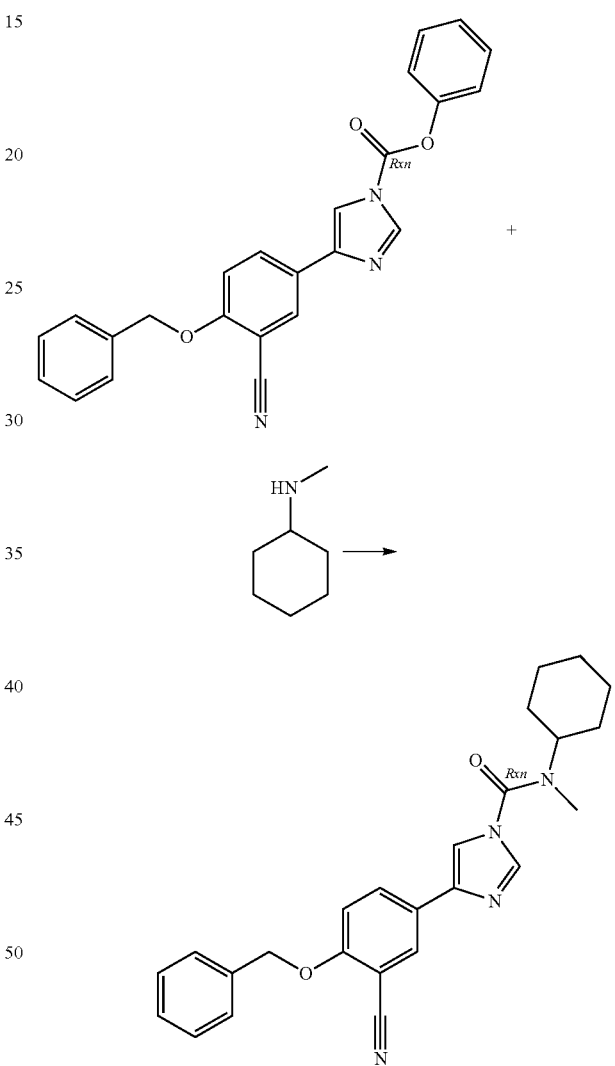
Yield (%) [43.6%]
Product Name 4-(4-(benzyloxy)-3-cyanophenyl)-N-cyclohexyl-N-methyl-1H-imidazole-1-carboxamide
NMR Solvent CDCl3
13C 159.4, 151.1, 140, 137.1, 135.6, 130.9, 130.4, 128.7, 128.2, 127, 126.8, 116.3, 113.2, 113.1, 102.7, 70.7, 57.6, 31.4, 30, 25.4, 25.2
1H NA
Mp ND

EXAMPLE 6.7
Structure
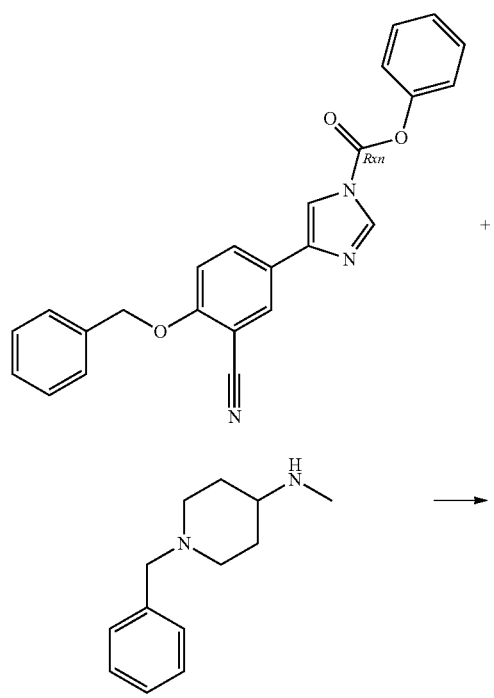
Yield (%) [47.8%]
Product Name 4-(4-(benzyloxy)-3-cyanophenyl)-N-(1-benzylpiperidin-4-yl)-N-methyl-1H-imidazole-1-carboxamide
NMR Solvent CDCl3
13C 159.5, 151.2, 140.1, 138, 137.1, 135.6, 130.9, 130.4, 129.1, 128.7, 128.3, 128.2, 127.2, 127, 126.7, 116.3, 113.2, 113, 102.7, 70.7, 62.8, 55.9, 52.5, 31.7, 28.9
1H NA
Mp ND
EXAMPLE 6.8
Structure
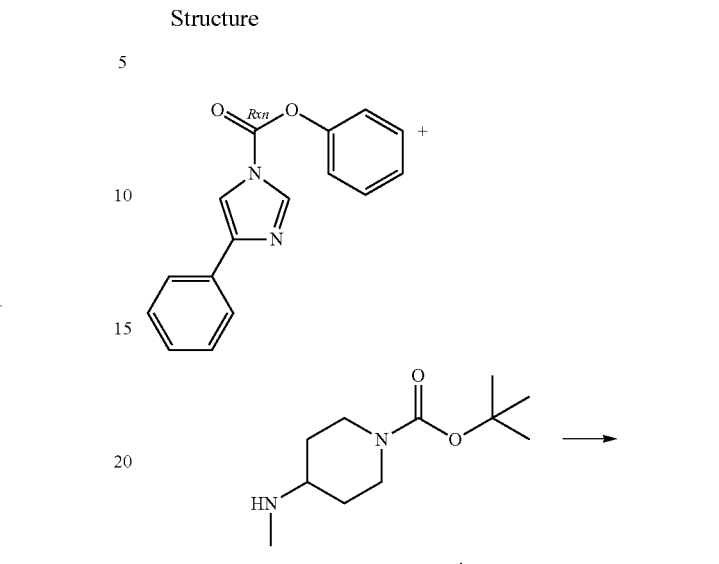
Yield (%) [52.8%]
Product Name tert-butyl 4-(N-methyl-4-phenyl-1H-imidazole-1-carboxamido)piperidine-1-carboxylate
NMR Solvent CDCl3
13C 154.5, 151.5, 142.3, 137, 132.8, 128.7, 127.6, 125.2, 113.1, 80, 55.6, 42.9, 31.9, 28.7, 28.4
1H NA
Mp ND
EXAMPLE 6.9
Structure
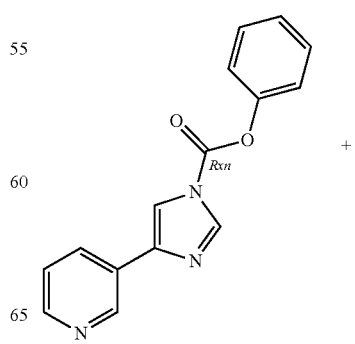

119
-continued

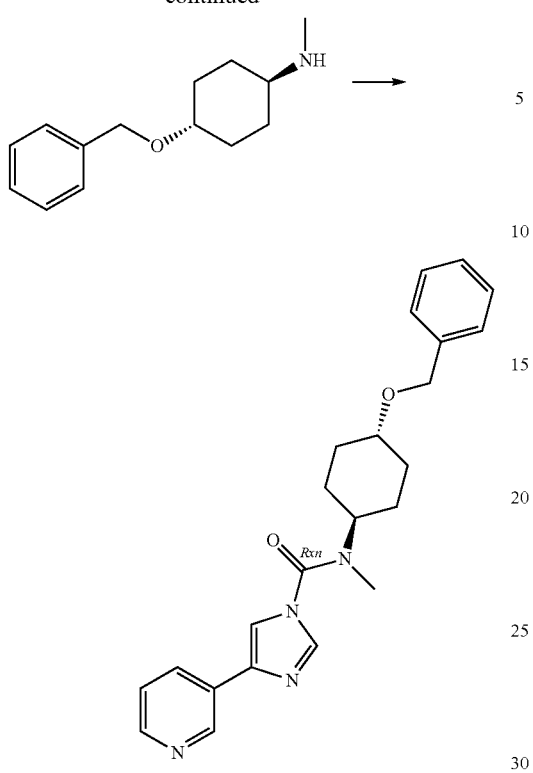

Yield (%) [28.0%]

Product Name N-((1r,4r)-4-(benzyloxy)cyclohexyl)-N-methyl-4-(pyridin-3-yl)-1H-imidazole-1-carboxamide NMR Solvent CDCl3

13C 151.1, 148.6, 146.7, 139.3, 138.6, 137.3, 132.5, 129, 128.4, 127.6, 127.5, 123.6, 113.9, 75.9, 70.1, 56.7, 31.7, 30.9, 27.4

1H NA

Mp ND

EXAMPLE 6.10

Structure

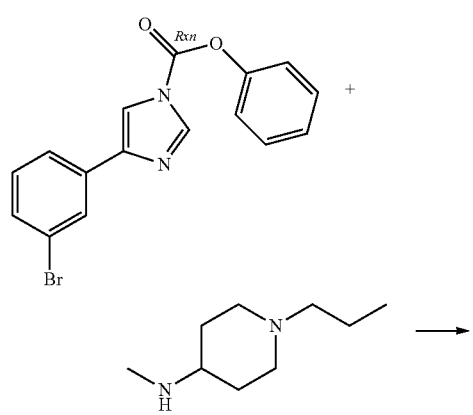

120
-continued

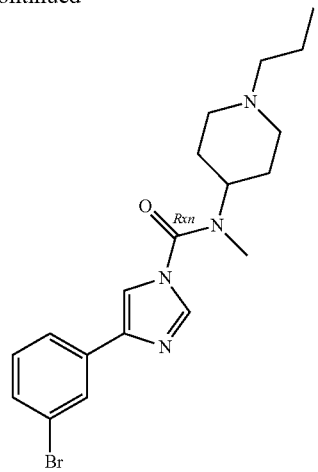

Yield (%) [36.4%]
Product Name 4-(3-bromophenyl)-N-methyl-N-(1-propylpiperidin-4-yl)-1H-imidazole-1-carboxamide
NMR Solvent CDCl3
13C 151.3, 140.8, 137.1, 135, 130.4, 130.2, 128.1, 123.6, 122.9, 113.8, 60.4, 55.9, 52.6, 31.6, 28.8, 20.3, 11.9
1H NA
Mp ND

EXAMPLE 6.11

Structure

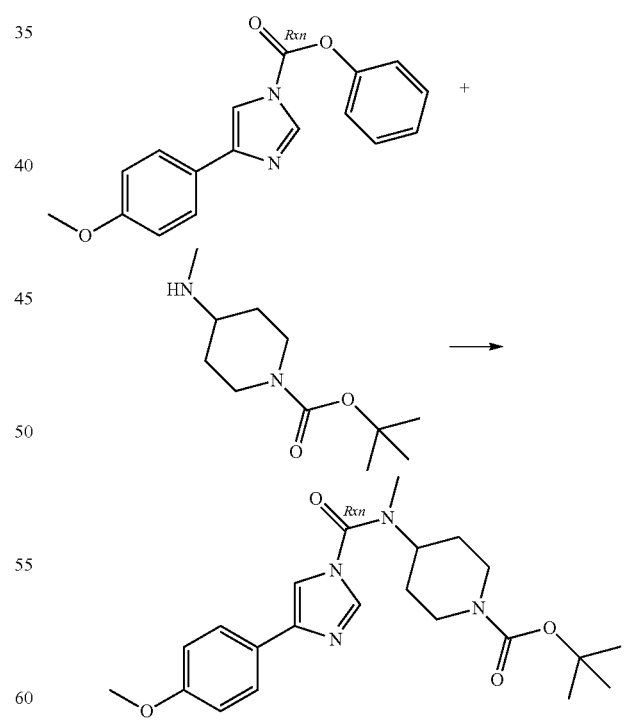

Yield (%) [59.1%]
Product Name tert-butyl 4-(4-(4-methoxyphenyl)-N-methyl-1H-imidazole-1-carboxamido)piperidine-1-carboxylate
NMR Solvent CDCl3

13C 159.2, 154.5, 151.6, 142.2, 136.9, 126.4, 125.6, 114.1, 112, 80, 55.5, 55.3, 42.9, 31.8, 28.7, 28.4
1H NA
Mp ND

EXAMPLE 6.12

Structure

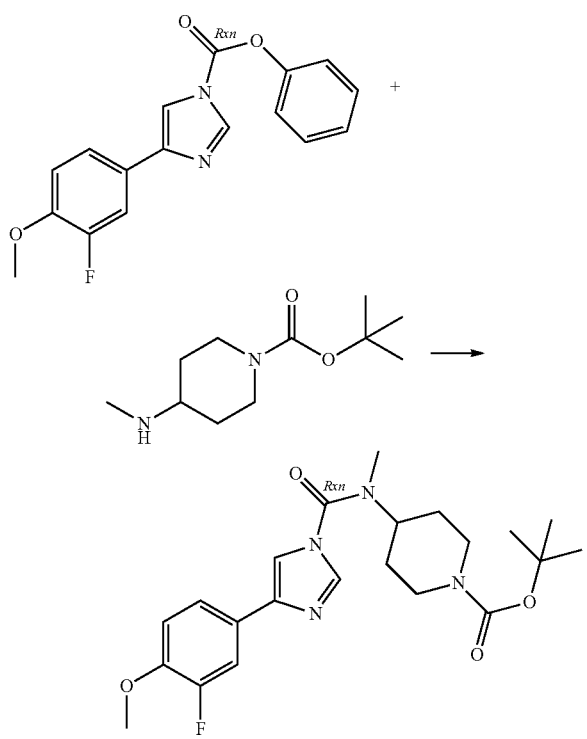

Yield (%) [55%]
Product Name tert-butyl 4-(4-(3-fluoro-4-methoxyphenyl)-N-methyl-1H-imidazole-1-carboxamido)piperidine-1-carboxylate
NMR Solvent DMSO
13C 153.8, 151.6 (d, J=243 Hz), 150.1, 146.8 (d, J=11 Hz), 137.6, 137.3, 124.5, 121.4, 114.7, 114.2, 112.6 (d, J=20 Hz), 78.9, 56.1, 55.3, 43, 42.2, 31.8, 28.1, 28
1H NA
Mp ND

EXAMPLE 6.13

Structure

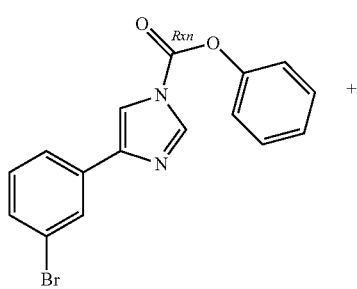

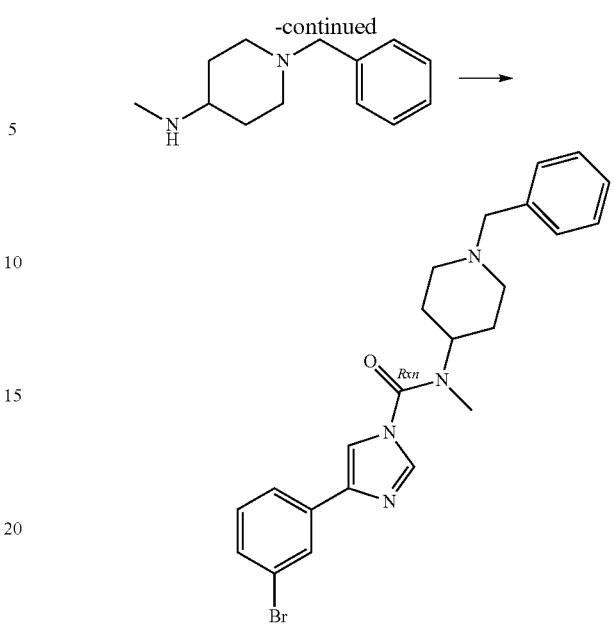

Yield (%) [44%]
Product Name N-(1-benzylpiperidin-4-yl)-4-(3-bromophenyl)-N-methyl-1H-imidazole-1-carboxamide
NMR Solvent CDCl3
13C 151.3, 140.8, 138, 137.1, 135.1, 130.4, 130.2, 129.1, 128.3, 128.1, 127.2, 123.6, 122.9, 113.8, 62.8, 55.9, 52.5, 31.7, 28.9
1H NA
Mp ND

EXAMPLE 6.14

Structure

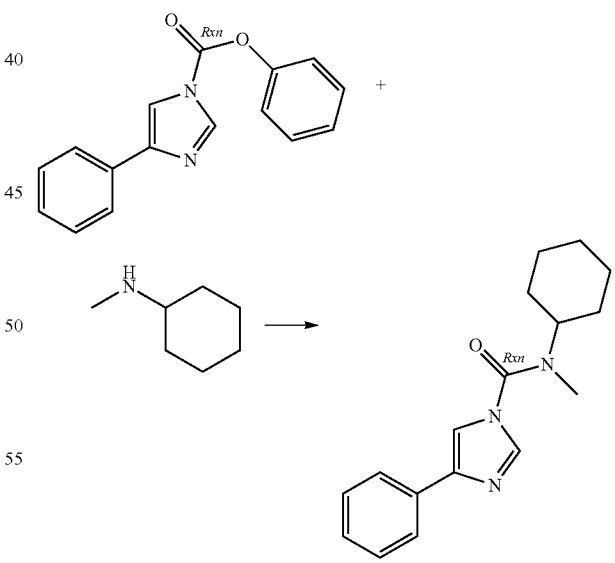

Yield (%) [56%]
Product Name N-cyclohexyl-N-methyl-4-phenyl-1H-imidazole-1-carboxamide
NMR Solvent CDCl3
13C 151.3, 142.1, 136.9, 133, 128.7, 127.5, 125.1, 113.2, 57.5, 31.3, 30, 25.4, 25.2
1H NA
Mp ND

EXAMPLE 6.15

Structure

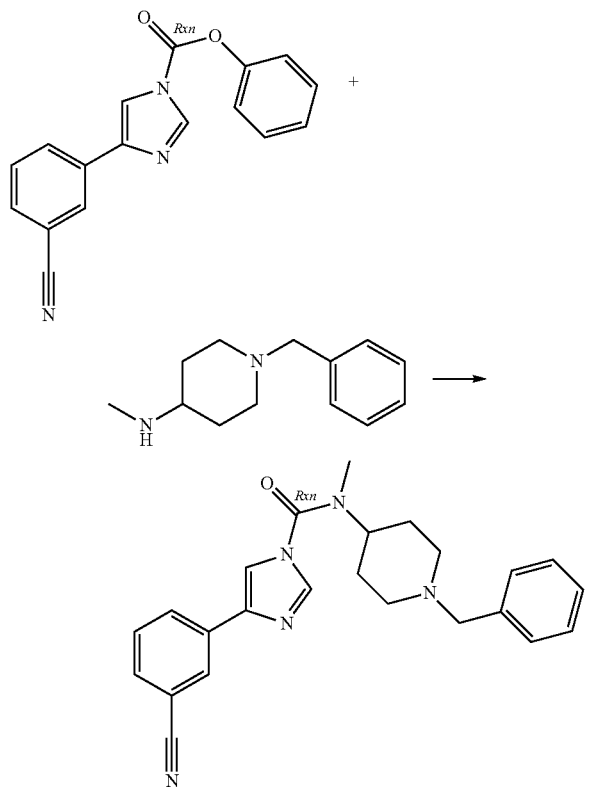

Yield (%) [45%]
Product Name N-(1-benzylpiperidin-4-yl)-4-(3-cyanophenyl)-N-methyl-1H-imidazole-1-carboxamide
NMR Solvent CDCl3
13C 151.2, 140.2, 137.3, 137.3, 134.2, 130.8, 129.8, 129.5, 129.3, 128.7, 128.7, 128.2, 118.8, 114.2, 112.8, 62.2, 54.7, 52.1, 32, 27.6
1H NA
Mp ND

EXAMPLE 6.16

Structure

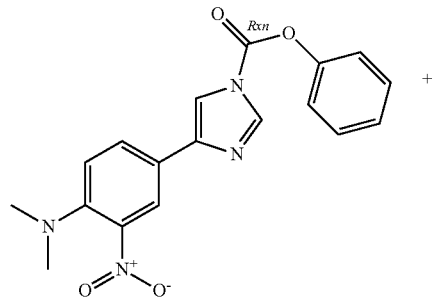

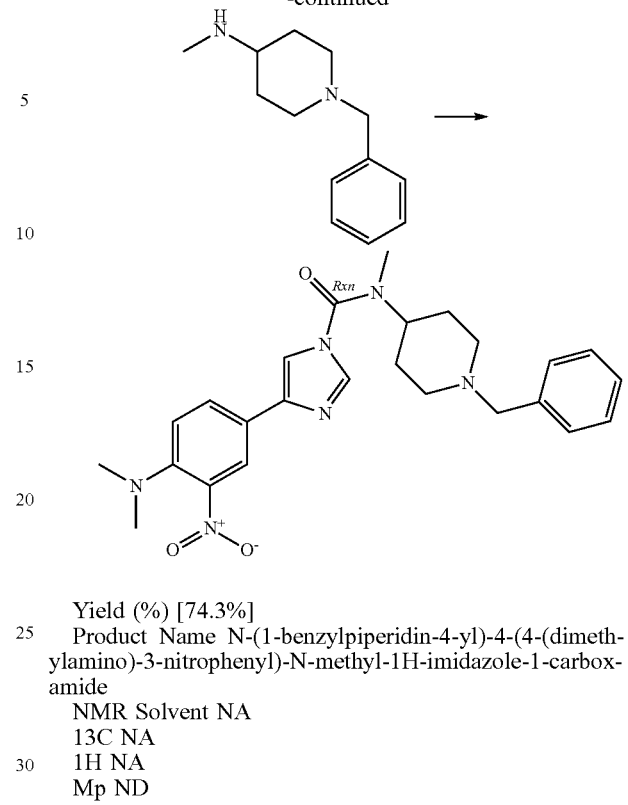

Yield (%) [74.3%]
Product Name N-(1-benzylpiperidin-4-yl)-4-(4-(dimethylamino)-3-nitrophenyl)-N-methyl-1H-imidazole-1-carboxamide
NMR Solvent NA
13C NA
1H NA
Mp ND

EXAMPLE 6.17

Structure

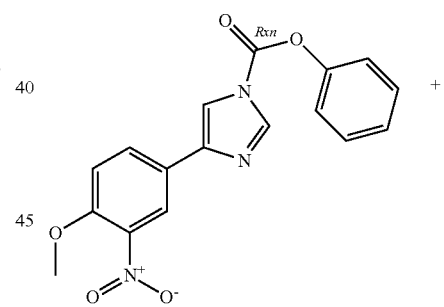

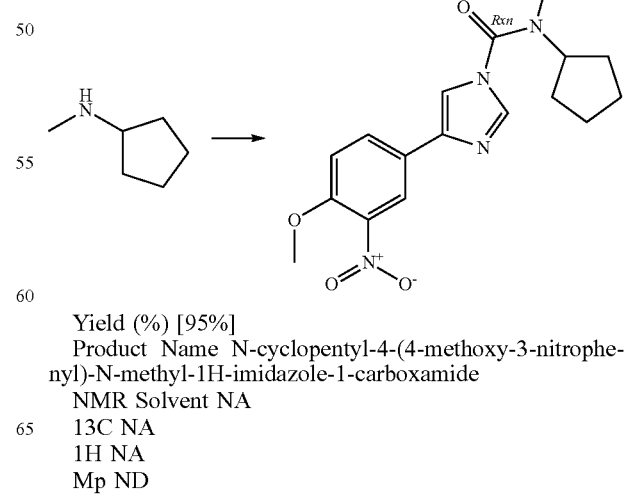

Yield (%) [95%]
Product Name N-cyclopentyl-4-(4-methoxy-3-nitrophenyl)-N-methyl-1H-imidazole-1-carboxamide
NMR Solvent NA
13C NA
1H NA
Mp ND

EXAMPLE 6.18
Structure
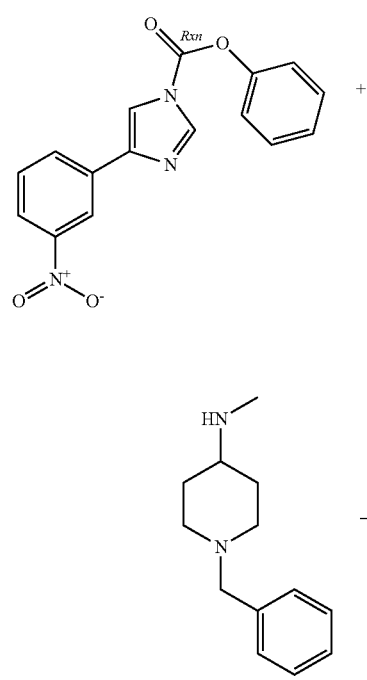
Yield (%) [40.6%]
Product Name N-(1-benzylpiperidin-4-yl)-N-methyl-4-(3-nitrophenyl)-1H-imidazole-1-carboxamide
NMR Solvent CDCl3
13C 151.1, 148.6, 140.1, 138, 137.3, 134.8, 130.9, 129.7, 129.1, 128.3, 127.2, 122.1, 119.9, 114.6, 62.8, 55.9, 52.5, 31.7, 28.9
1H NA
Mp ND
EXAMPLE 6.19
Structure
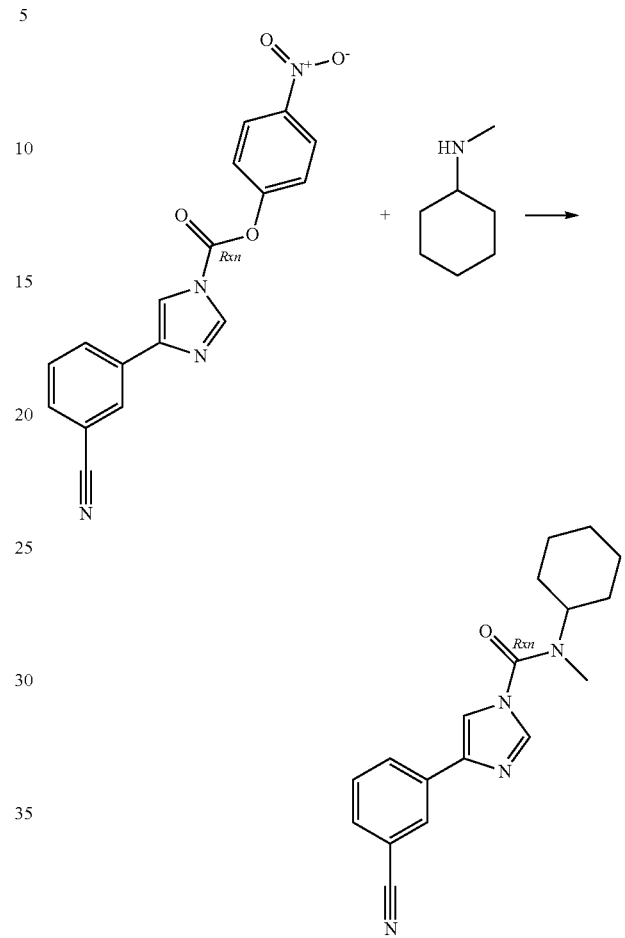
Yield (%) [72.1%]
Product Name 4-(3-cyanophenyl)-N-cyclohexyl-N-methyl-1H-imidazole-1-carboxamide
NMR Solvent CDCl3
13C 150.9, 140.1, 137.3, 134.4, 130.7, 129.5, 129.2, 128.6, 118.8, 114.3, 112.8, 57.7, 31.4, 30, 25.4, 25.2
1H NA
Mp ND
EXAMPLE 6.20
Structure
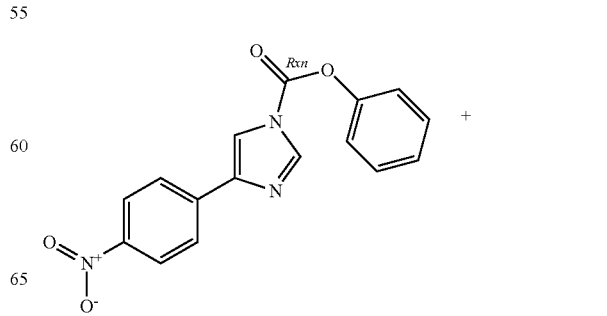

127

-continued

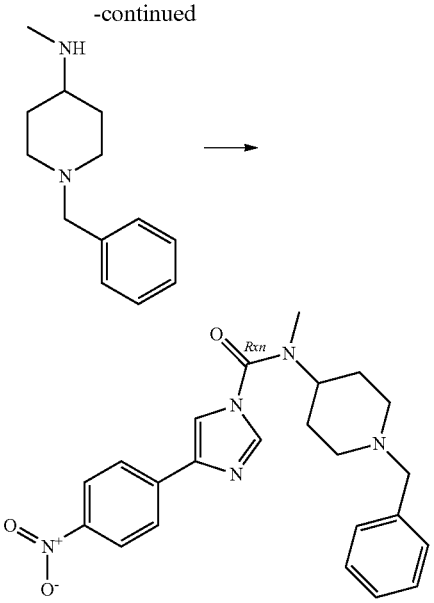

Yield (%) [32.5%]
Product Name N-(1-benzylpiperidin-4-yl)-N-methyl-4-(4-nitrophenyl)-1H-imidazole-1-carboxamide
NMR Solvent NA
13C NA
1H NA
Mp ND

EXAMPLE 6.21

Structure

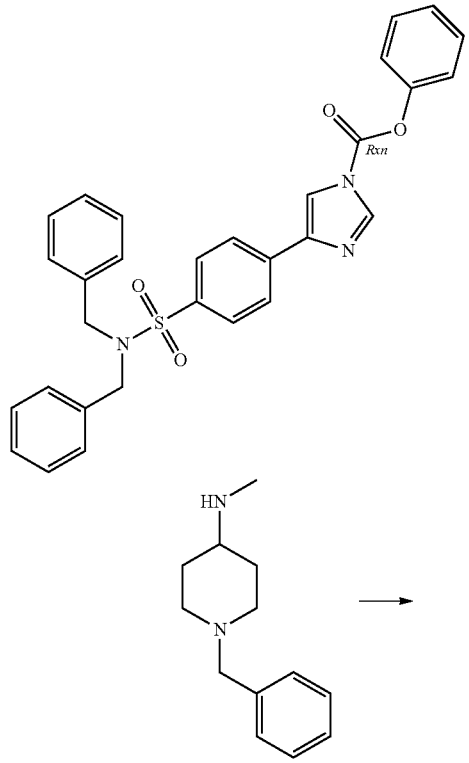

128

-continued

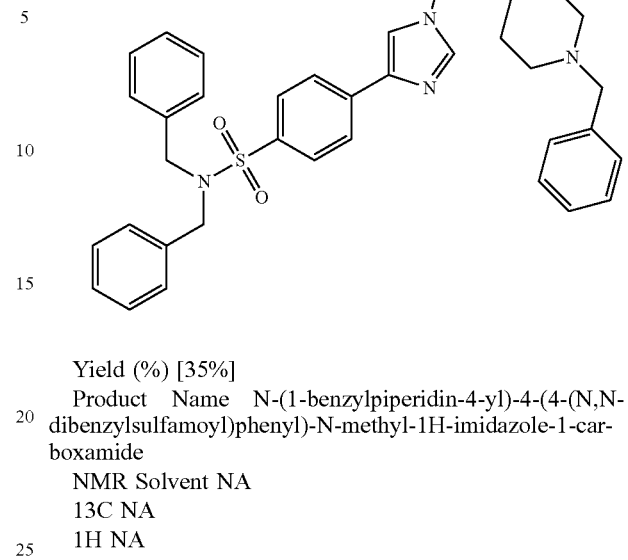

Yield (%) [35%]
Product Name N-(1-benzylpiperidin-4-yl)-4-(4-(N,N-dibenzylsulfamoyl)phenyl)-N-methyl-1H-imidazole-1-carboxamide
NMR Solvent NA
13C NA
1H NA
Mp ND

EXAMPLE 6.22

Structure

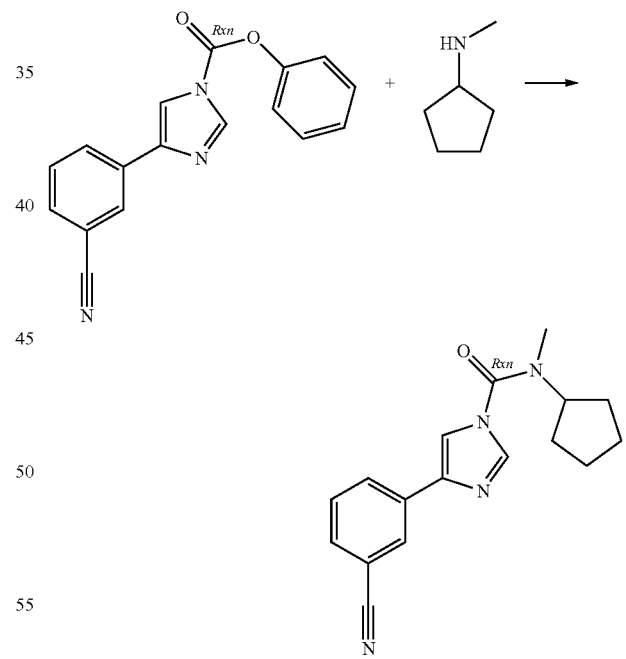

Yield (%) [40.1%]
Product Name 4-(3-cyanophenyl)-N-cyclopentyl-N-methyl-1H-imidazole-1-carboxamide
NMR Solvent CDCl3
13C 151.3, 140.1, 137.3, 134.4, 130.7, 129.5, 129.2, 128.6, 118.8, 114.3, 112.8, 59.4, 31.3, 28.9, 24.4
1H NA
Mp ND

EXAMPLE 6.23
Structure
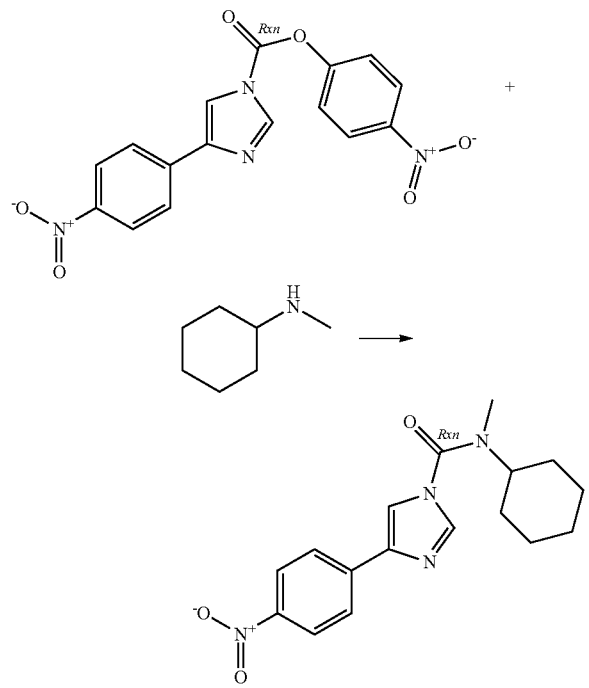
Yield (%) [86%]
Product Name N-cyclohexyl-N-methyl-4-(4-nitrophenyl)-1H-imidazole-1-carboxamide
NMR Solvent NA
13C NA
1H NA
Mp ND
EXAMPLE 6.24
Structure
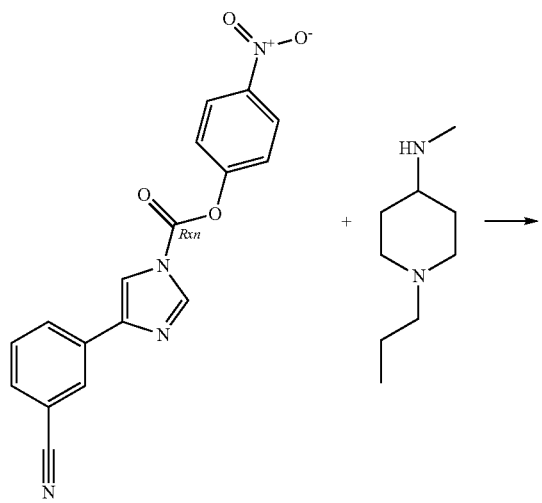
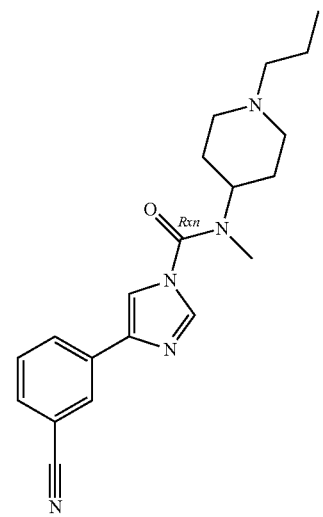
Yield (%) [72.3%]
Product Name 4-(3-cyanophenyl)-N-methyl-N-(1-propylpiperidin-4-yl)-1H-imidazole-1-carboxamide
NMR Solvent CDCl3
13C 151.1, 140.1, 137.3, 134.3, 130.8, 129.5, 129.2, 128.6, 118.8, 114.3, 112.8, 60.4, 56, 52.6, 31.6, 28.9, 20.3, 11.9
1H NA
Mp ND
EXAMPLE 6.25
Structure
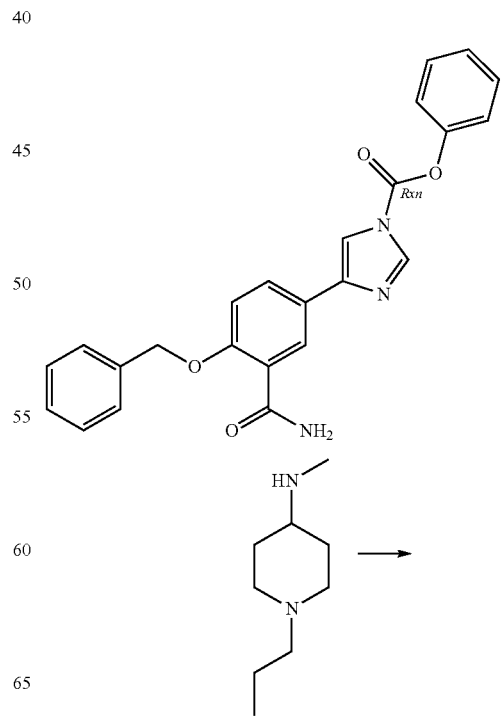

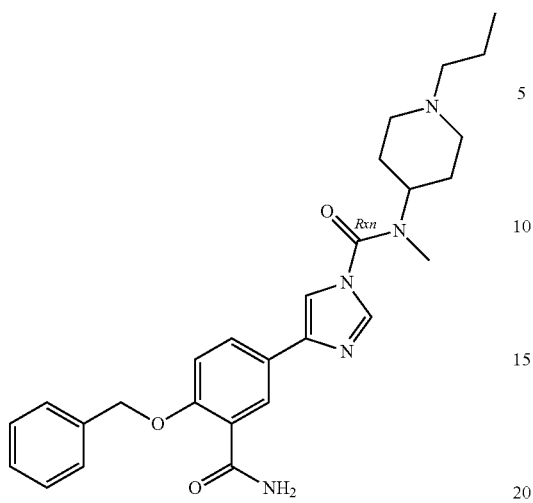
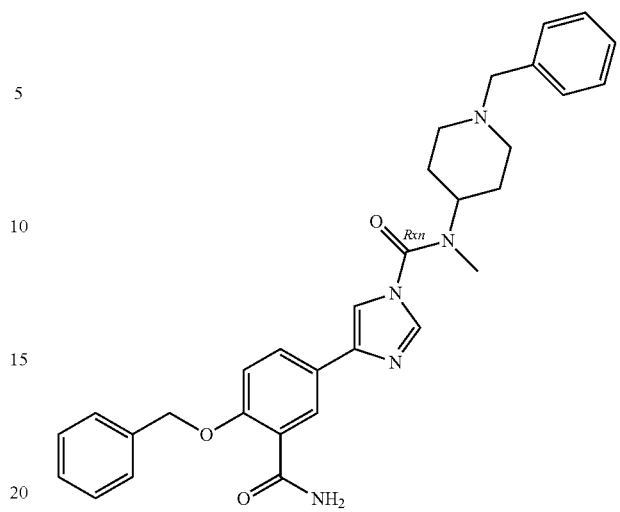
Yield (%) [24.0%]
Product Name 4-(4-(benzyloxy)-3-carbamoylphenyl)-N-methyl-N-(1-propylpiperidin-4-yl)-1H-imidazole-1-carboxamide
NMR Solvent DMSO
13C 166.6, 155.2, 151, 140, 137.7, 136.6, 128.6, 128.4, 128.1, 127.9, 127, 126.2, 123.8, 113.7, 113.7, 70.1, 59.7, 55.6, 52.4, 31.5, 28.3, 19.9, 11.9
1H NA
Mp ND
Yield (%) [36.9%]
Product Name 4-(4-(benzyloxy)-3-carbamoylphenyl)-N-(1-benzylpiperidin-4-yl)-N-methyl-1H-imidazole-1-carboxamide
NMR Solvent DMSO
13C 166.6, 155.2, 151, 140, 138.5, 137.7, 136.6, 128.8, 128.6, 128.4, 128.2, 128.1, 127.8, 127, 127, 126.2, 123.8, 113.7, 113.7, 70.1, 61.9, 55.4, 52.2, 31.5, 28.2
1H NA
Mp ND
EXAMPLE 6.26
Structure
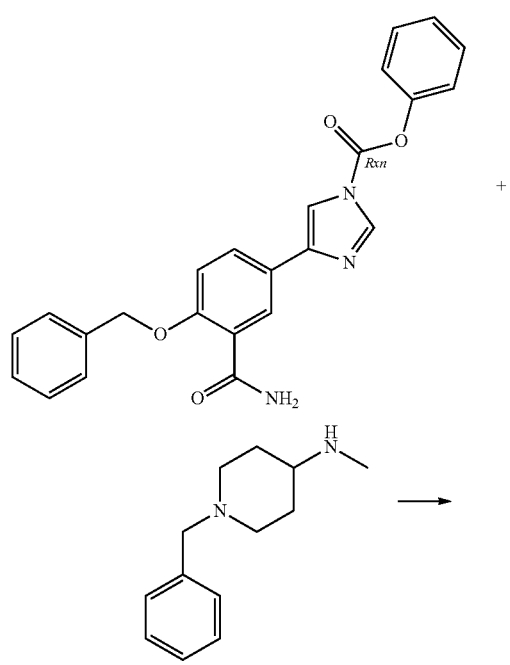
EXAMPLE 6.27
Structure
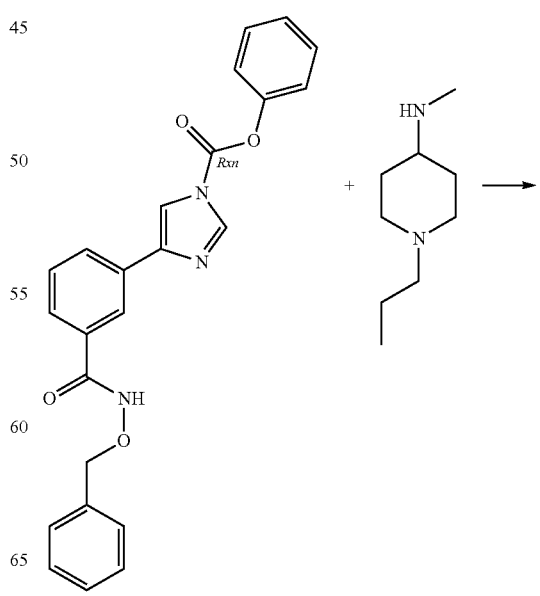

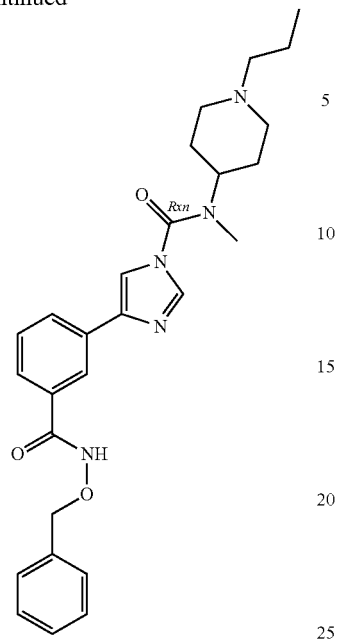
Yield (%) [44.1%]
Product Name 4-(3-(benzyloxycarbamoyl)phenyl)-N-methyl-N-(1-propylpiperidin-4-yl)-1H-imidazole-1-carboxamide
NMR Solvent CDCl3
13C 151.3, 141.1, 137.2, 133.5, 129.4, 129.2, 128.8, 128.7, 128.6, 126.1, 123.5, 113.9, 78.3, 60.4, 55.8, 52.6, 31.7, 28.8, 20.2, 11.9
1H NA
Mp ND
EXAMPLE 6.28
Structure
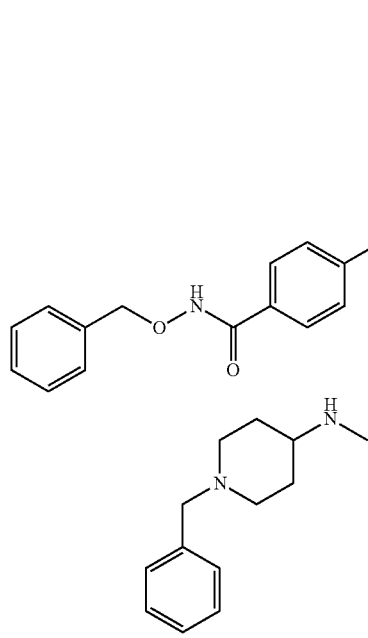
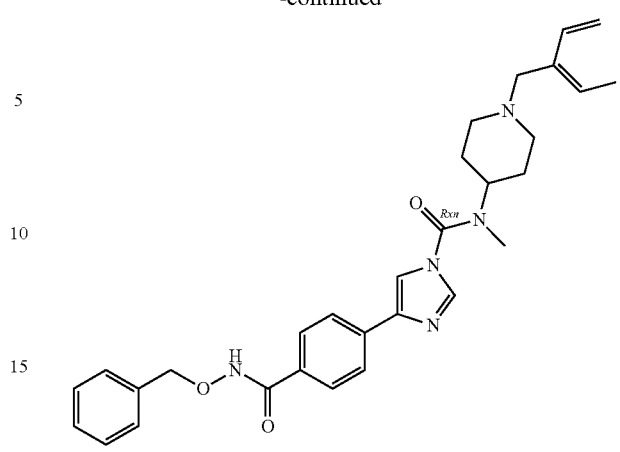
Yield (%) [33.8%]
Product Name 4-(4-(benzyloxycarbamoyl)phenyl)-N-(1-benzylpiperidin-4-yl)-N-methyl-1H-imidazole-1-carboxamide
NMR Solvent DMSO
13C 164.2, 150.9, 139.7, 138.5, 138, 136.5, 136, 130.5, 129, 128.9, 128.4, 128.4, 128.2, 127.6, 127, 124.5, 115.8, 77, 61.9, 55.5, 52.2, 31.6, 28.2
1H NA
Mp ND
EXAMPLE 6.29
Structure
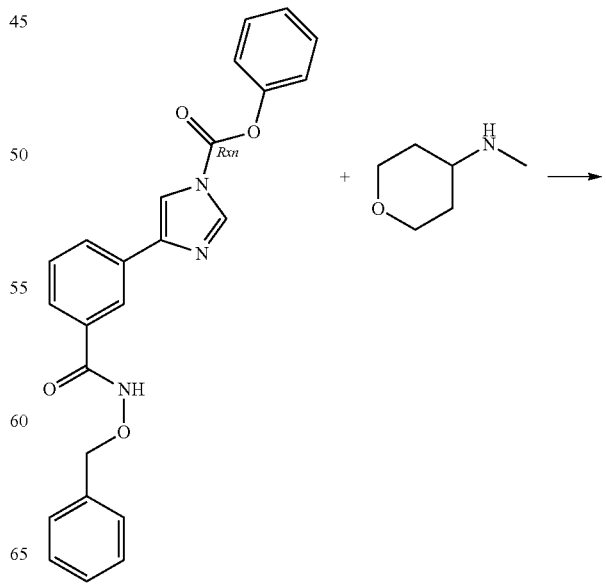

135
-continued
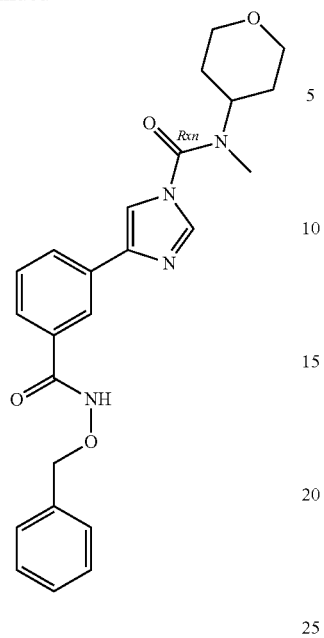
Yield (%) [40.5%]
Product Name 4-(3-(benzyloxycarbamoyl)phenyl)-N-methyl-N-(tetrahydro-2H-pyran-4-yl)-1H-imidazole-1-carboxamide
NMR Solvent CDCl3
13C 166.1, 151.3, 141.2, 137.2, 135.2, 133.4, 132.4, 129.4, 129.2, 128.8, 128.6, 128.6, 126.2, 123.7, 113.8, 78.4, 67, 54.4, 31.9, 29.4
1H NA
Mp ND
EXAMPLE 6.30
Structure
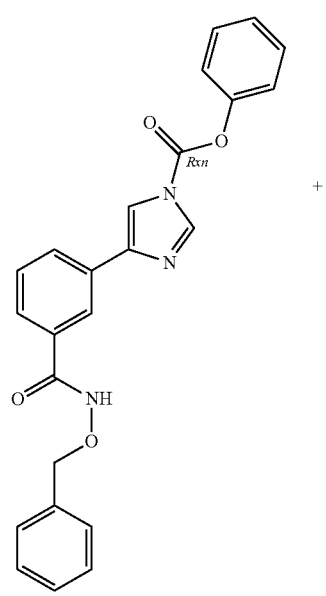
136
-continued
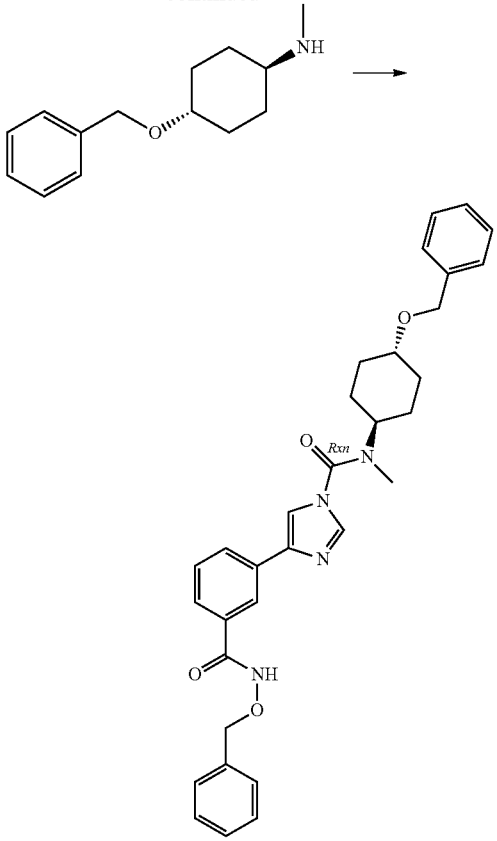
Yield (%) [52.5%]
Product Name N-((1r,4r)-4-(benzyloxy)cyclohexyl)-4-(3-(benzyloxycarbamoyl)phenyl)-N-methyl-1H-imidazole-1-carboxamide
NMR Solvent NA
13C NA
1H NA
Mp ND
EXAMPLE 6.31
Structure
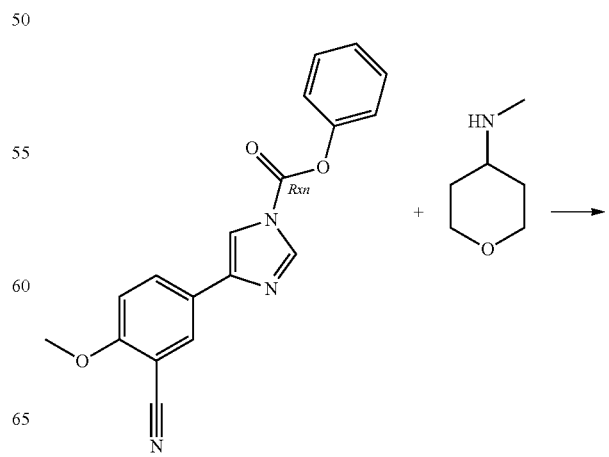

137
-continued
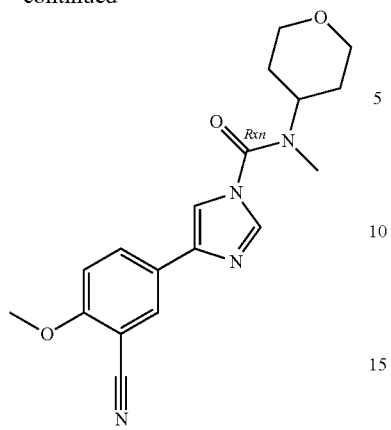
Yield (%) [31.4%]
Product Name 4-(3-cyano-4-methoxyphenyl)-N-methyl-N-(tetrahydro-2H-pyran-4-yl)-1H-imidazole-1-carboxamide
NMR Solvent CDCl3
13C 160.5, 151.3, 140.3, 137.1, 131.1, 130.3, 126.3, 116.3, 112.9, 111.6, 102.1, 67, 56.2, 54.5, 31.9, 29.5
1H NA
Mp ND
EXAMPLE 6.32
Structure
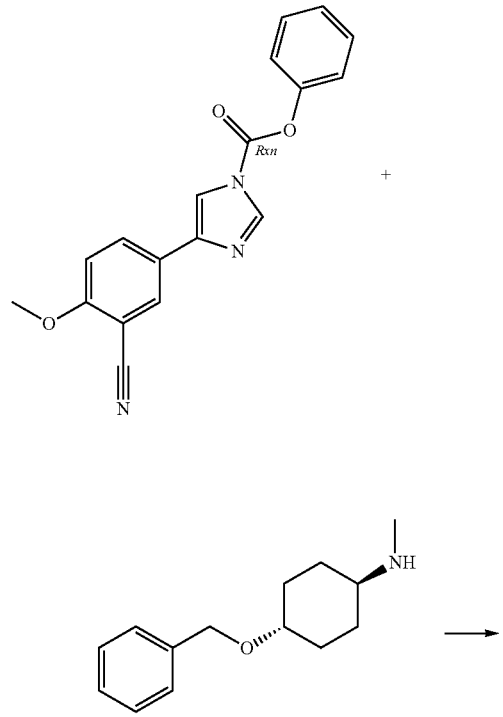
138
-continued
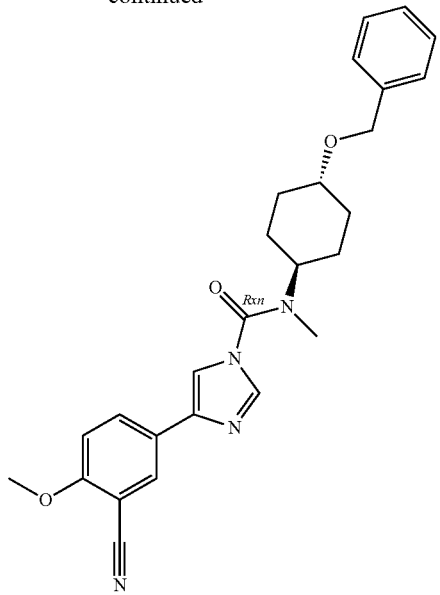
Yield (%) [11.2%]
Product Name N-((1r,4r)-4-(benzyloxy)cyclohexyl)-4-(3-cyano-4-methoxyphenyl)-N-methyl-1H-imidazole-1-carboxamide
NMR Solvent CDCl3
13C 160.5, 151.2, 140.2, 138.6, 137.1, 131.1, 130.3, 128.4, 127.6, 127.5, 126.4, 116.4, 112.9, 111.6, 102.1, 75.9, 70.1, 56.7, 56.2, 31.7, 30.9, 27.4
1H NA
Mp ND
EXAMPLE 6.33
Structure
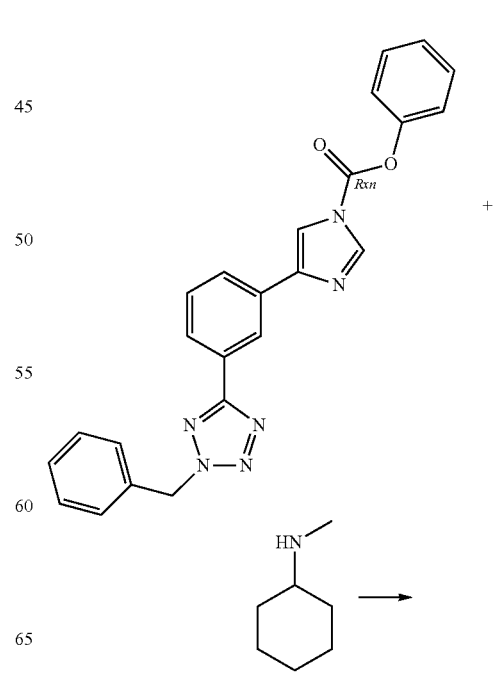

139

-continued

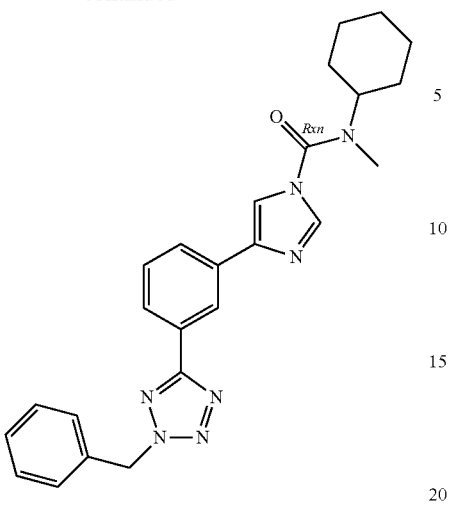

Yield (%) [46.1%]

Product Name 4-(3-(2-benzyl-2H-tetrazol-5-yl)phenyl)-N-cyclohexyl-N-methyl-1H-imidazole-1-carboxamide NMR Solvent CDCl3

13C 165.3, 151.2, 141.4, 137.2, 133.6, 133.3, 129.4, 129, 128.9, 128.4, 127.6, 127.1, 125.9, 123.5, 115.3, 57.5, 56.8, 31.4, 29.9, 25.4, 25.2

1H NA

Mp ND

EXAMPLE 6.34

Structure

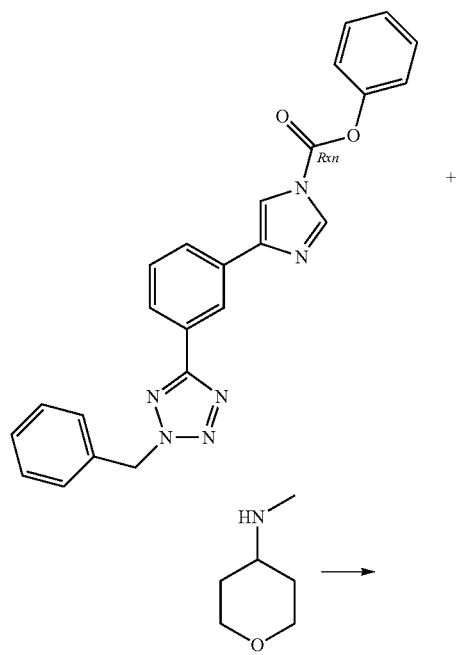

140

-continued

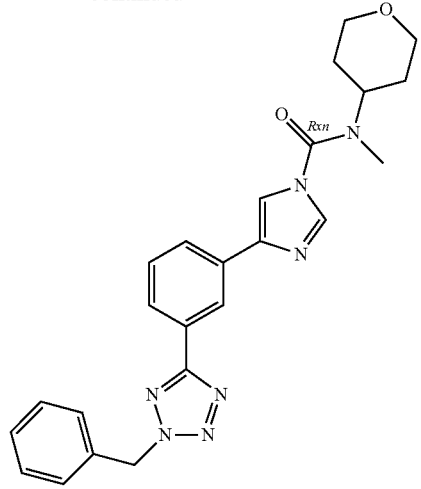

Yield (%) [51.8%]

Product Name 4-(3-(2-benzyl-2H-tetrazol-5-yl)phenyl)-N-methyl-N-(tetrahydro-2H-pyran-4-yl)-1H-imidazole-1-carboxamide NMR Solvent NA

13C NA

1H NA

Mp ND

EXAMPLE 6.35

Structure

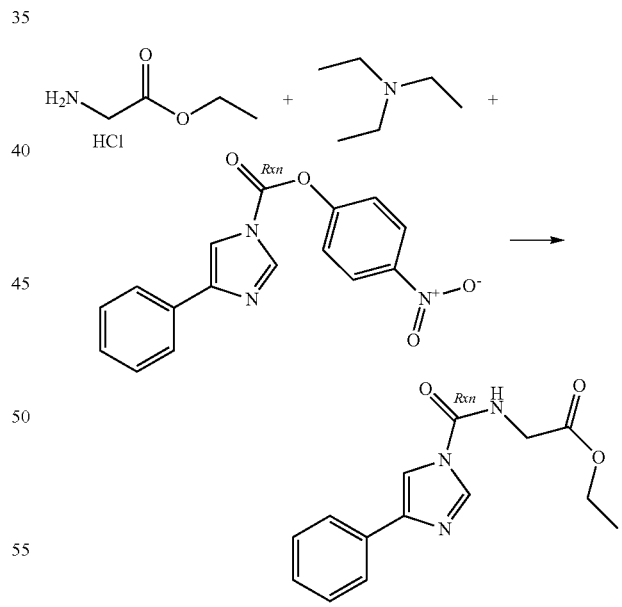

Yield (%) [22.6%]

Product Name ethyl 2(4-phenyl-1H-imidazole-1-carboxamido)acetate

NMR Solvent CDCl3

13C 169.4, 148.8, 143.3, 136.1, 132.5, 128.7, 127.8, 125.2, 110.9, 62.1, 42.3, 14.1

1H NA

Mp ND

EXAMPLE 6.36

Structure

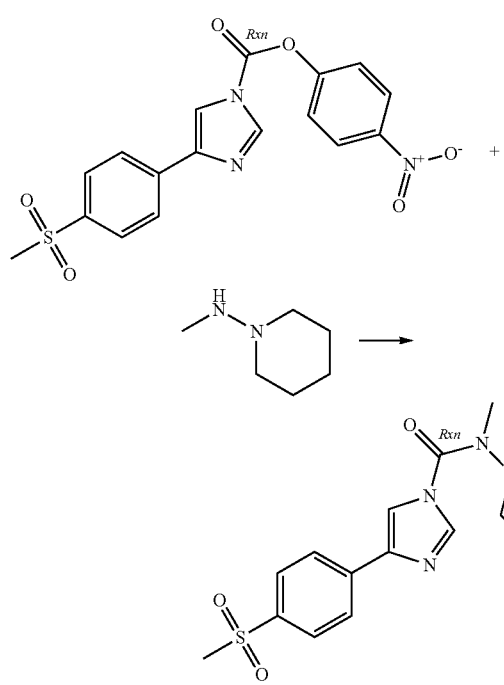

Yield (%) [10.1%]
Product Name N-methyl-4-(4-(methylsulfonyl)phenyl)-N-(piperidin-1-yl)-1H-imidazole-1-carboxamide
NMR Solvent NA
13C NA
1H NA
Mp ND

EXAMPLE 6.37

Structure

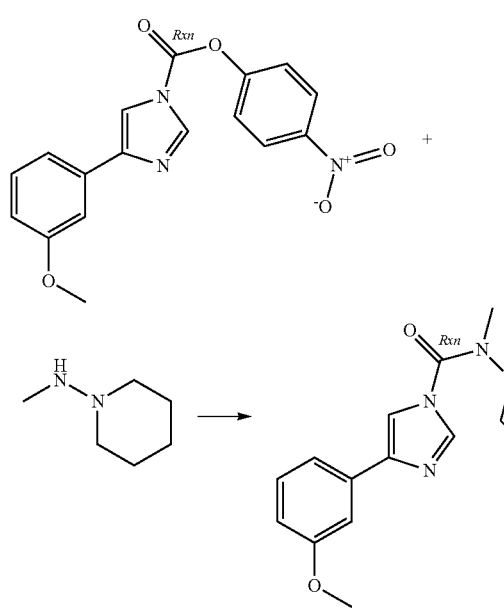

Yield (%) [36%]
Product Name 4-(3-methoxyphenyl)-N-methyl-N-(piperidin-1-yl)-1H-imidazole-1-carboxamide
NMR Solvent NA
13C NA
1H NA
Mp ND

EXAMPLE 6.38

Structure

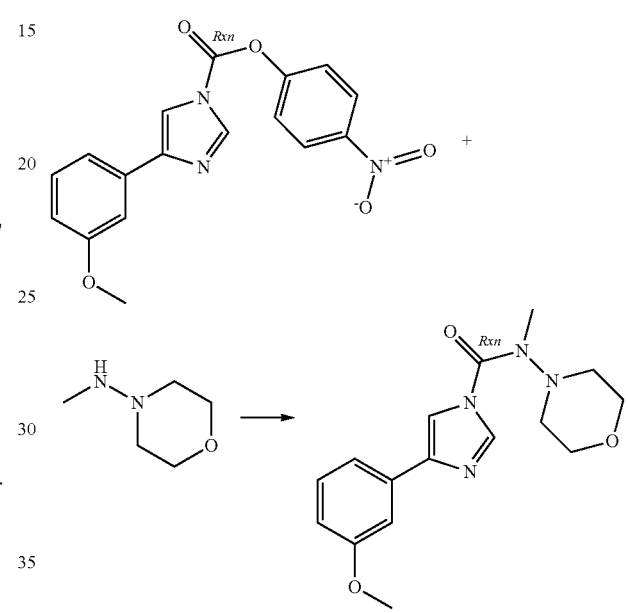

Yield (%) [25.2%]
Product Name 4-(3-methoxyphenyl)-N-methyl-N-morpholino-1H-imidazole-1-carboxamide
NMR Solvent NA
13C NA
1H NA
Mp ND

EXAMPLE 6.39

Structure

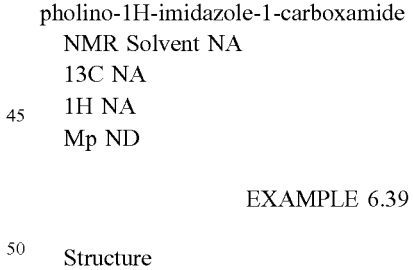

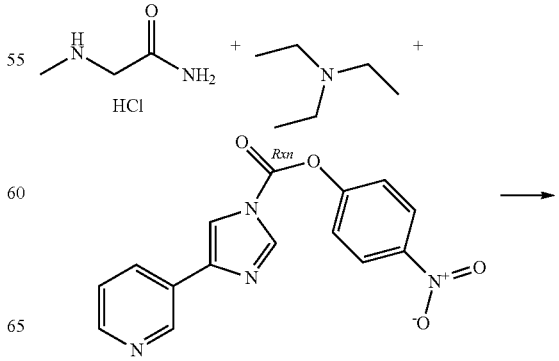

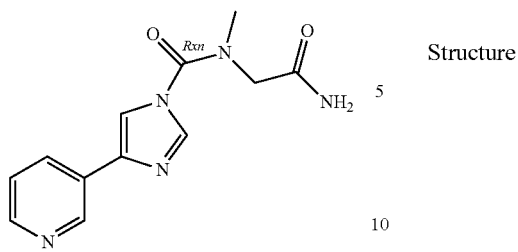

Yield (%) [32.9%]

Product Name N-(2-amino-2-oxoethyl)-N-methyl-4-(pyridin-3-yl)-1H-imidazole-1-carboxamide NMR Solvent NA

13C NA

1H NA

Mp ND

EXAMPLE 6.40

Structure

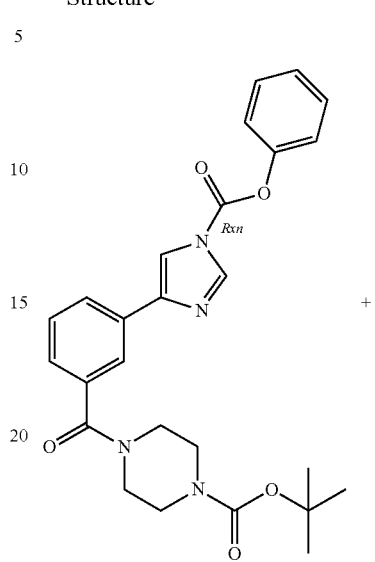

Yield (%) [34.8%]

Product Name N-benzyl-N-methyl-4-(pyridin-3-yl)-1H-imidazole-1-carboxamide

NMR Solvent CDCl3

13C 151.6, 148.5, 146.6, 139.4, 137.5, 135.1, 132.5, 129.2, 128.9, 128.3, 127.4, 123.6, 113.9, 54.2, 36.5

1H NA

Mp ND

EXAMPLE 6.41

Structure

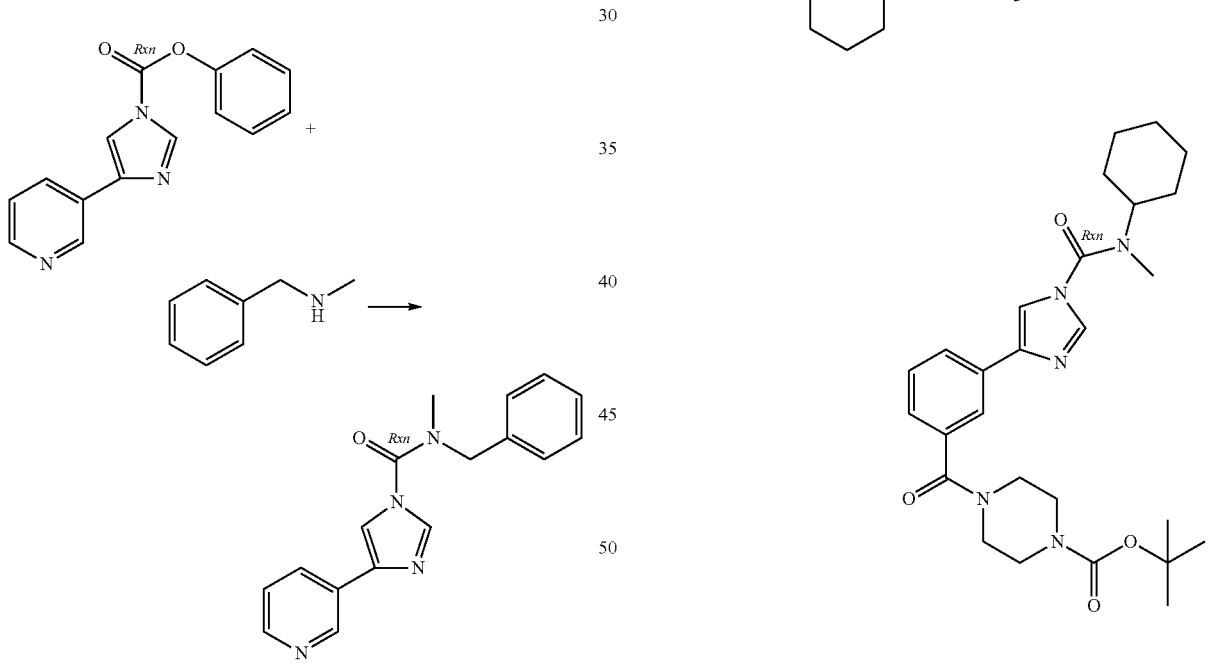

Yield (%) [55.4%]

Product Name tert-butyl 4-(3-(1-(cyclohexyl(methyl)carbamoyl)-1H-imidazol-4-yl)benzoyl)piperazine-1-carboxylate NMR Solvent CDCl3

13C 170.5, 154.6, 151.2, 141.2, 137.1, 135.9, 133.6, 129, 126.5, 125.9, 123.7, 113.8, 80.3, 57.6, 47.6, 43.7, 42.1, 31.4, 30, 28.3, 25.4, 25.2

1H NA

Mp ND

145

EXAMPLE 6.42

Structure

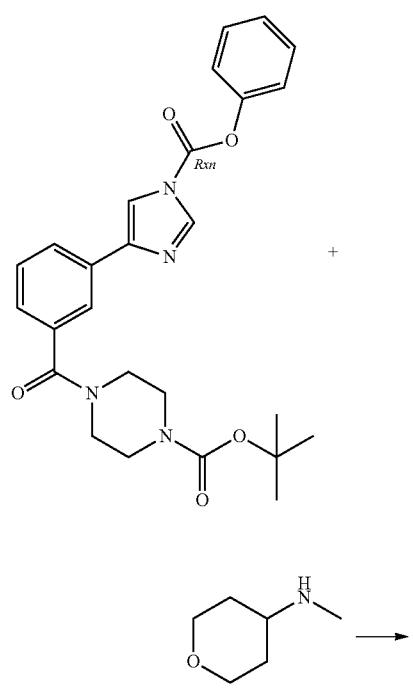

Yield (%) [23.8%]

Product Name tert-butyl 4-(3-(1-(methyl(tetrahydro-2H-pyran-4-yl)carbamoyl)-1H-imidazol-4-yl)benzoyl)piperazine-1-carboxylate NMR Solvent CDCl3

13C 170.4, 154.6, 151.4, 141.5, 137.2, 135.9, 133.5, 129.1, 126.6, 126, 123.8, 113.7, 80.4, 67, 54.5, 47.6, 44.4, 43.4, 42, 31.9, 29.5, 28.4

1H NA

Mp ND

146

EXAMPLE 6.43

Structure

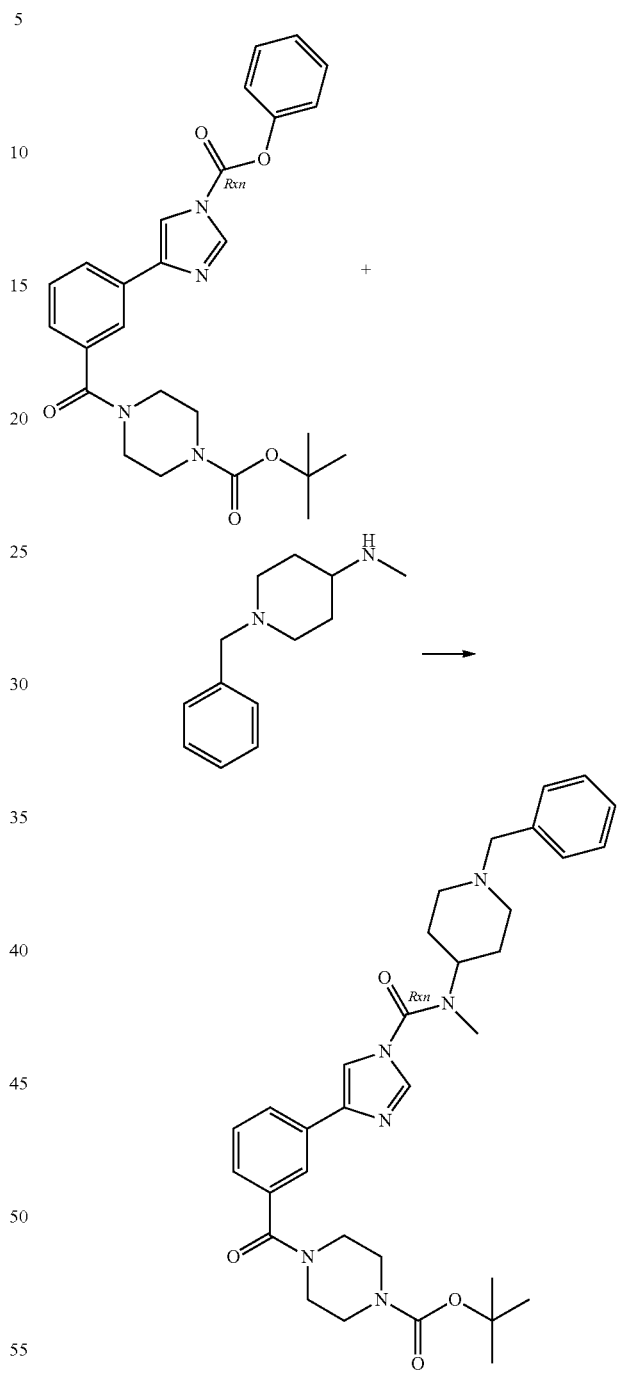

Yield (%) [40.1%]

Product Name tert-butyl 4-(3-(1-(1-benzylpiperidin-4-yl)(methypcarbamoyl)-1H-imidazol-4-yl)benzoyl)piperazine-1-carboxylate NMR Solvent CDCl3

13C NA 1H 7.92 (1H, d, J=1.3 Hz), 7.87 (1H, ddd, J=1.3, 1.7, 7.9 Hz), 7.83 (1H, t br, J=1.5 Hz), 7.52 (1H, d, J=1.3 Hz), 7.46 (1H, t, J=7.7 Hz), 7.37-7.28 (6H, m), 4.03 (1H, m br), 3.77 (2H, m br), 3.53 (3H, s), 3.44 (5H, br), 3.03 (3H, s), 3.01

(2H, d br), 2.11 (2H, t br, J=11.5 Hz), 1.93 (2H, dq, J=3.5, 12.0 Hz), 1.79 (2H, d br, J=11.5 Hz), 1.48 (9H, s)
Mp ND
EXAMPLE 6.44
Structure
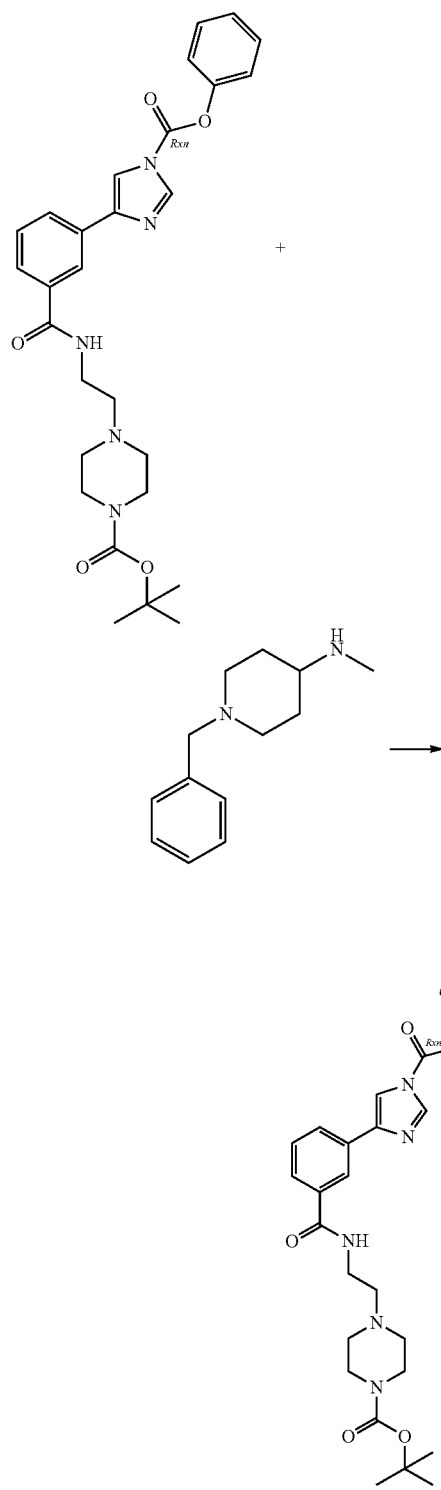
Yield (%) [53.0%]
Product Name tert-butyl 4-(2-(3-(1-((1-benzylpiperidin-4-yl)(methyl)carbamoyl)-1H-imidazol-4-yl)benzamido)ethyl)piperazine-1-carboxylate
NMR Solvent NA
13C NA
1H NA
Mp ND
EXAMPLE 6.45
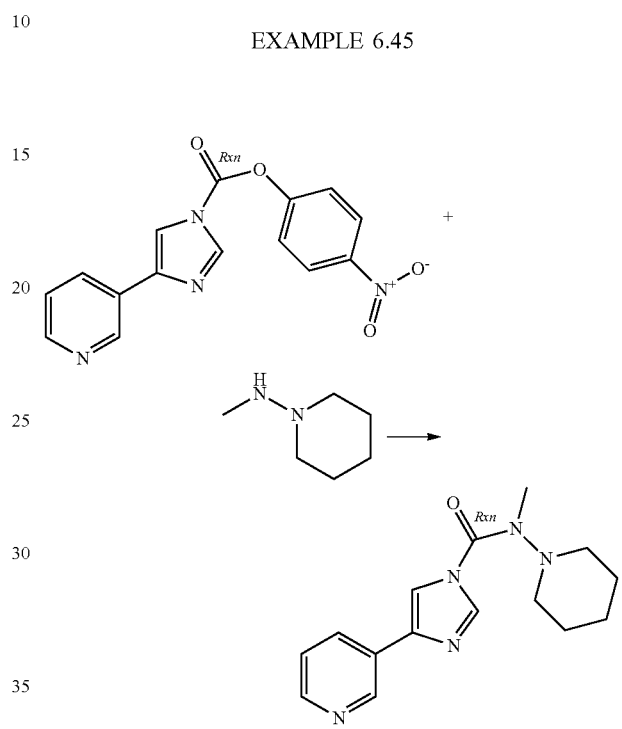
Structure
Yield (%) [4.80%]
Product Name N-methyl-N-(piperidin-1-yl)-4-(pyridin-3-yl)-1H-imidazole-1-carboxamide
NMR Solvent NA
13C NA
1H NA
Mp ND
EXAMPLE 6.46
Structure
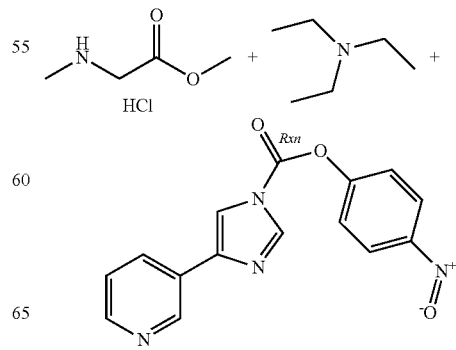

-continued

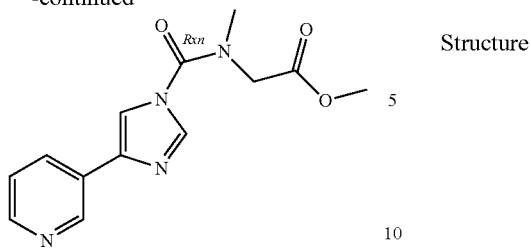

Yield (%) [95%]
Product Name methyl 2-(N-methyl-4-(pyridin-3-yl)-1H-imidazole-1-carboxamido)acetate
NMR Solvent NA
13C NA
1H NA
Mp ND

EXAMPLE 6.47

Structure

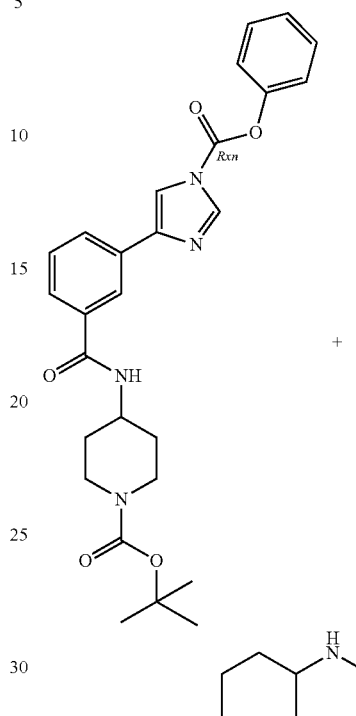

Yield (%) [23.2%]
Product Name ethyl 2-(3-(1-((1-benzylpiperidin-4-yl)(methyl)carbamoyl)-1H-imidazol-4-yl)phenoxy)acetate
NMR Solvent CDCl3
13C 168.9, 158.2, 151.5, 141.8, 138.1, 137, 134.5, 129.9, 129.1, 128.3, 127.2, 118.6, 114.1, 113.5, 111.3, 65.4, 62.8, 61.4, 55.9, 52.5, 31.6, 28.9, 14.2
1H NA
Mp ND

EXAMPLE 6.48

Structure

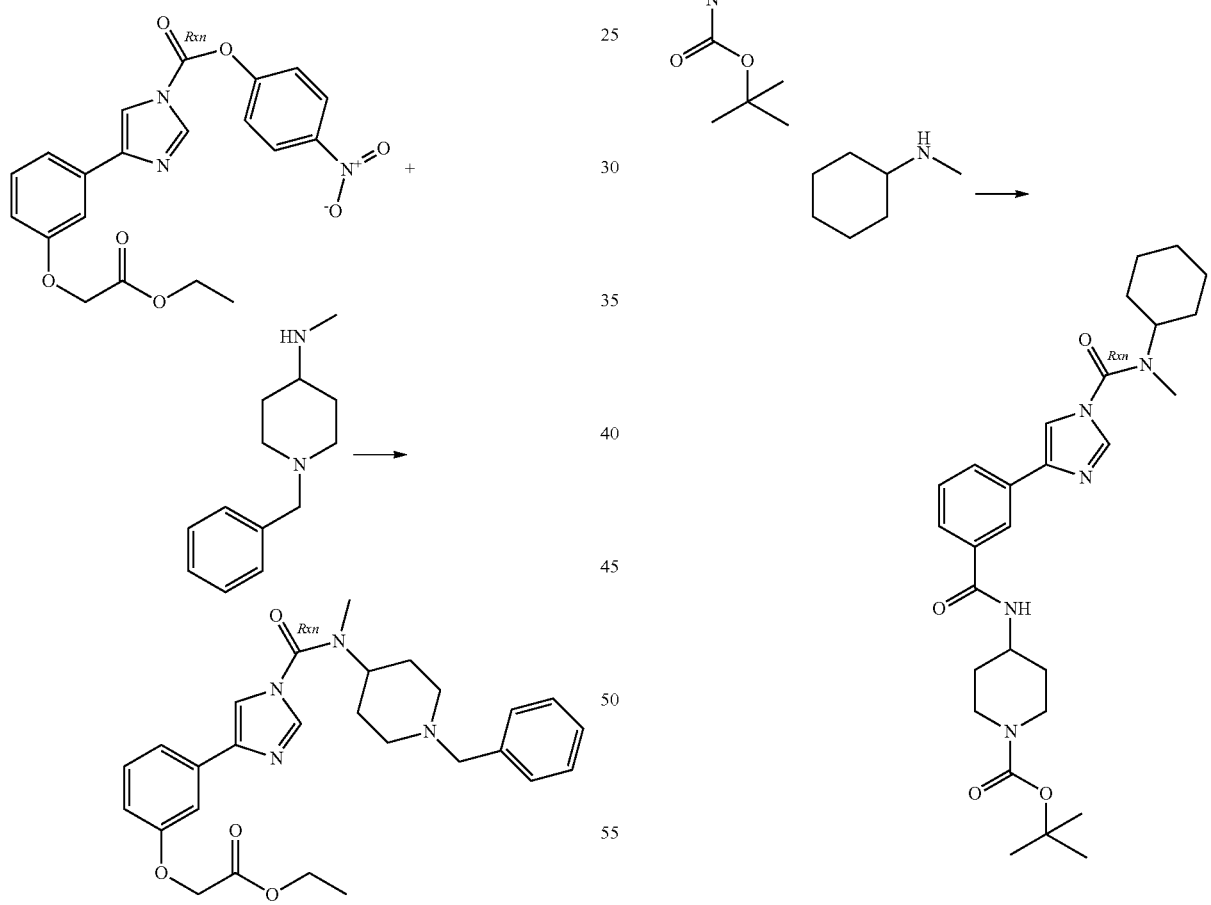

Yield (%) [60.0%]
Product Name tert-butyl 4-(3-(1-(cyclohexyl(methyl)carbamoyl)-1H-imidazol-4-yl)benzamido)piperidine-1-carboxylate
NMR Solvent CDCl3
13C NA
1H 8.16 (1H, t, J=1.5 Hz), 7.94 (1H, d, J=1.3 Hz), 7.90 (1H, ddd, J=1.2, 1.7, 7.7 Hz), 7.74 (1H, ddd, J=1.2, 1.6, 7.8 Hz), 7.57 (1H, d, J=1.3 Hz), 7.48 (1H, t, J=7.7 Hz), 6.17 (1H, d, J=7.8 Hz), 4.16 (3H, m), 3.96 (1H, m), 3.01 (3H, s), 2.92

(1H, mt), 12.04 (2H, d br, J=12.5 Hz), 1.87 (4H, m), 1.72 (2H, d br, J=12.5 Hz), 1.59 (2H, dq, J=3.5, 12.0 Hz), 1.48 (9H, s), 1.40 (4H, m), 1.14 (1H, tq, J=3.5, 12.5 Hz)
Mp ND

EXAMPLE 6.49

Structure

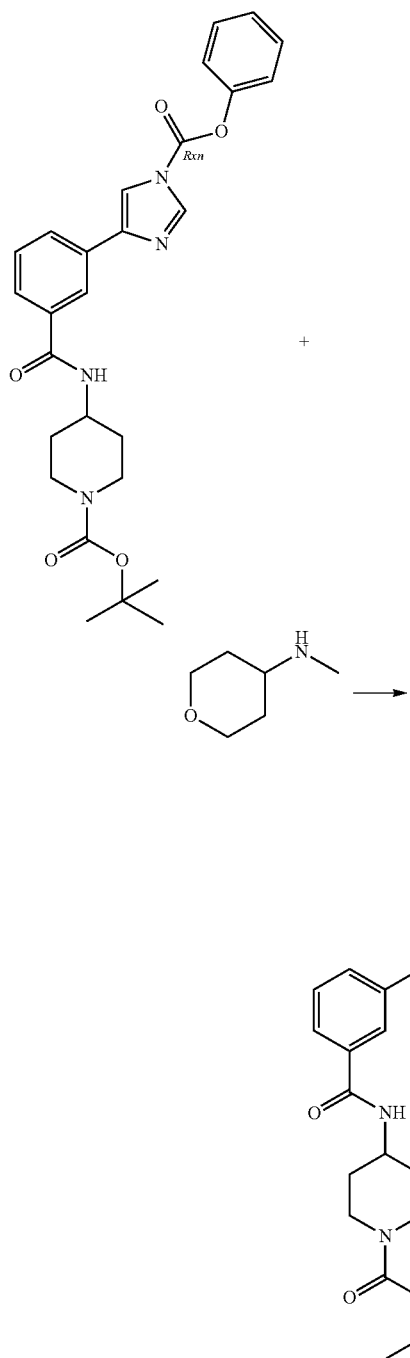

Yield (%) [48.8%]
Product Name tert-butyl 4-(3-(1-(methyl(tetrahydro-2H-pyran-4-yl)carbamoyl)-1H-imidazol-4-yl)benzamido)piperidine-1-carboxylate
NMR Solvent CDCl3

13C NA
1H 8.15 (1H, t, J=1.6 Hz), 7.96 (1H, d, J=1.3 Hz), 7.92 (1H, dt, J=1.2, 7.7 Hz), 7.73 (1H, ddd, J=1.0, 1.6, 7.8 Hz), 7.59 (1H, d, J=1.3 Hz), 7.49 (1H, t, J=7.8 Hz), 6.11 (1H, d, J=7.9 Hz), 4.30 (1H, m), 4.23-4.02 (5H, m), 3.52 (2H, dt, J=2.0, 12.0 Hz), 3.06 (3H, s), 2.92 (2H, t br, J=12.5 Hz), 2.10-1.89 (4H, m), 1.80 (2H, d br, J=12.0 Hz), 1.48 (9H, s), 1.44 (2H, m)
Mp ND

EXAMPLE 6.50

Structure

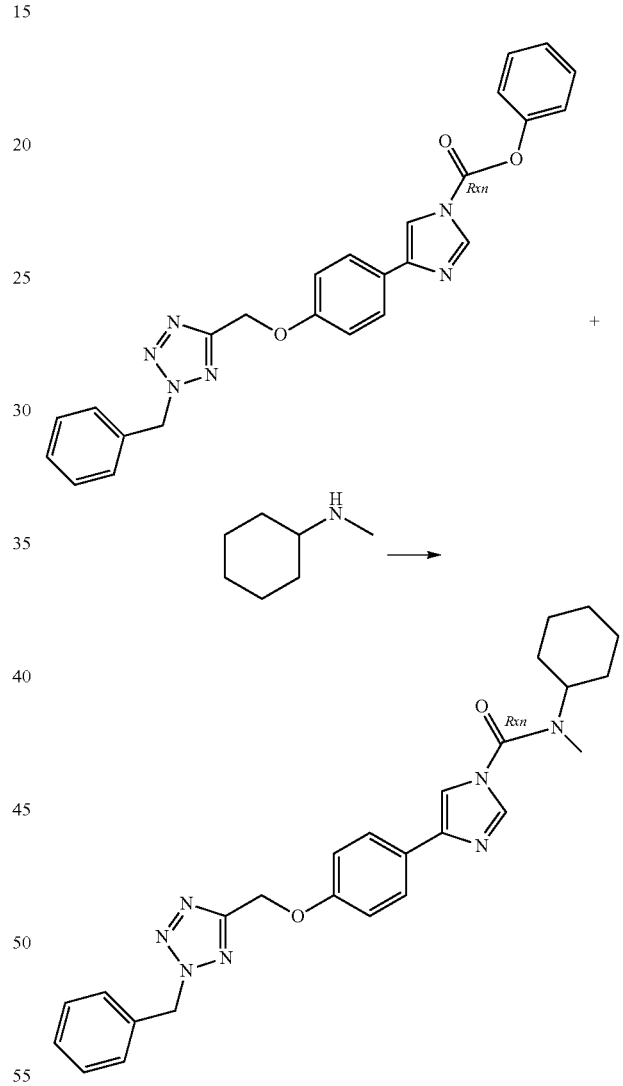

Yield (%) [56.2%]
Product Name 4-(4-(2-benzyl-2H-tetrazol-5-yl)methoxy)phenyl)-N-cyclohexyl-N-methyl-1H-imidazole-1-carboxamide
NMR Solvent CDCl3
13C 162.8, 157.5, 151.4, 141.8, 136.8, 132.9, 129.1, 129, 128.5, 126.8, 126.4, 115.1, 112.3, 60.8, 57.5, 56.9, 31.3, 30, 25.4, 25.2
1H NA
Mp ND

EXAMPLE 6.51

Structure

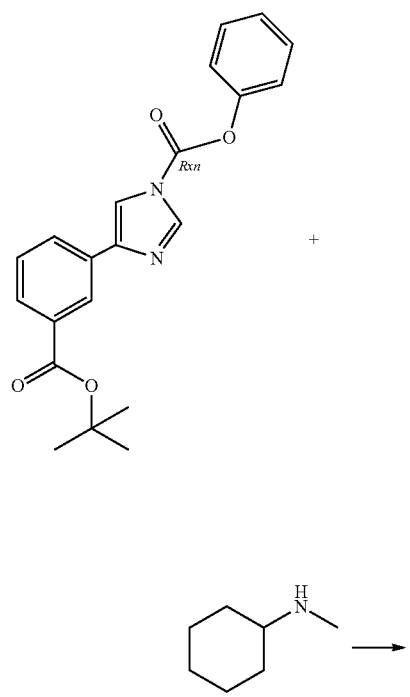

Yield (%) [49.9%]

Product Name tert-butyl 3-(1-(cyclohexyl(methypcarbamoyl)-1H-imidazol-4-yl)benzoate NMR Solvent CDCl3

13C NA 1H 8.34 (1H, dt, J=0.4, 1.7 Hz), 8.02 (1H, ddd, J=0.4, 1.9, 7.8 Hz), 7.94 (1H, d, J=1.3 Hz), 7.92 (1H, ddd, J=1.2, 1.7, 7.8 Hz), 7.56 (1H, d, J=1.3 Hz), 7.47 (1H, dt, J=0.5, 7.7 Hz), 3.97 (1H, m), 3.0 (3H, s), 1.87 (4H, m), 1.71 (1H, d br, J=12.0 Hz), 1.62 (9H, s), 1.59 (2H, dq, J=3.5, 12.5 Hz), 1.39 (2H, tq, J=3.5, 13.0 Hz), 1.14 (1H, tq, J=3.5, 13.0 Hz)

Mp ND

EXAMPLE 6.52

Structure

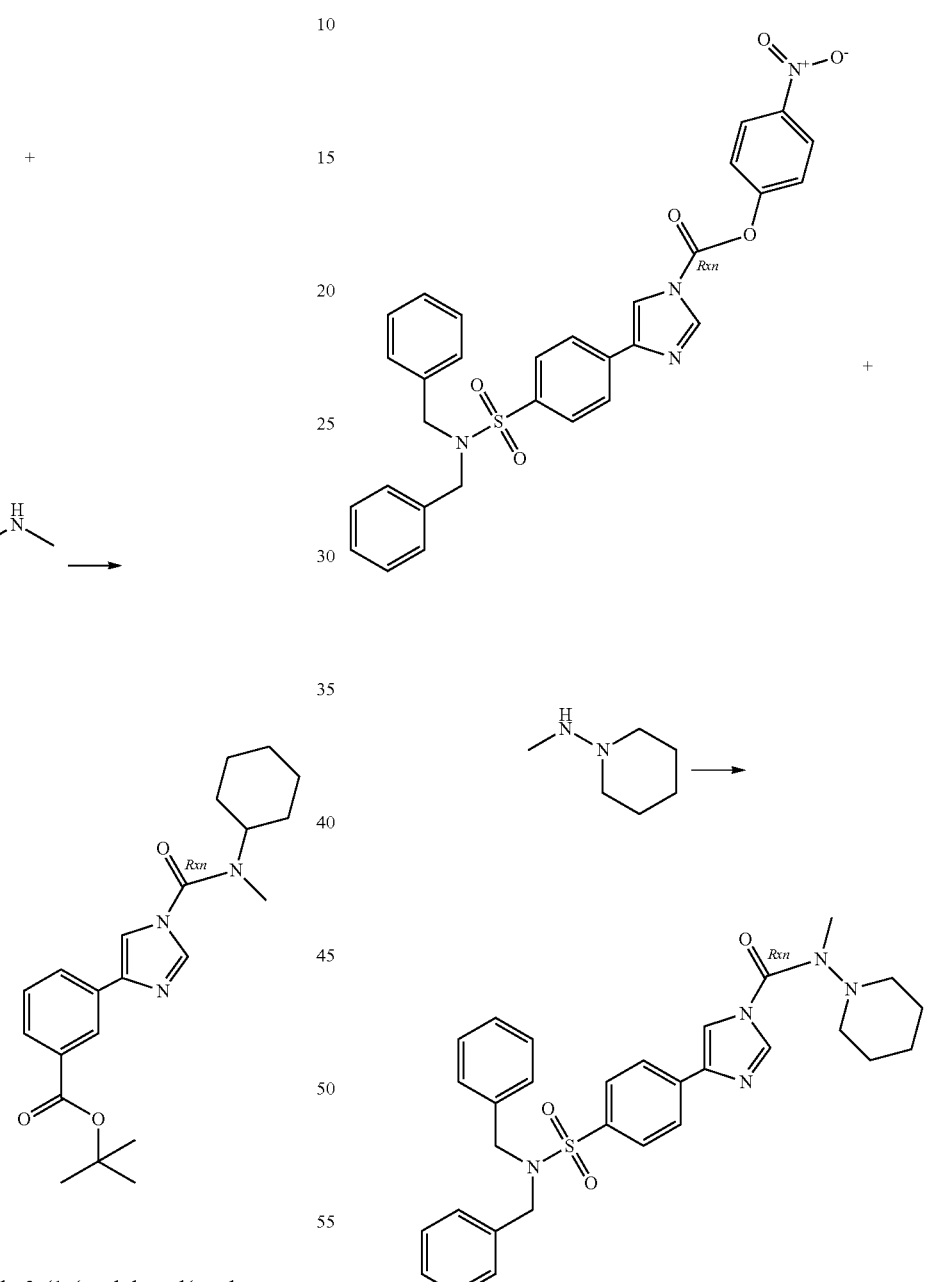

Yield (%) [14.9%]

Product Name 4-(4-(N,N-dibenzylsulfamoyl)phenyl)-N-methyl-N-(piperidin-1-yl)-1H-imidazole-1-carboxamide NMR Solvent NA

13C NA

1H NA

Mp ND

EXAMPLE 6.53
Structure
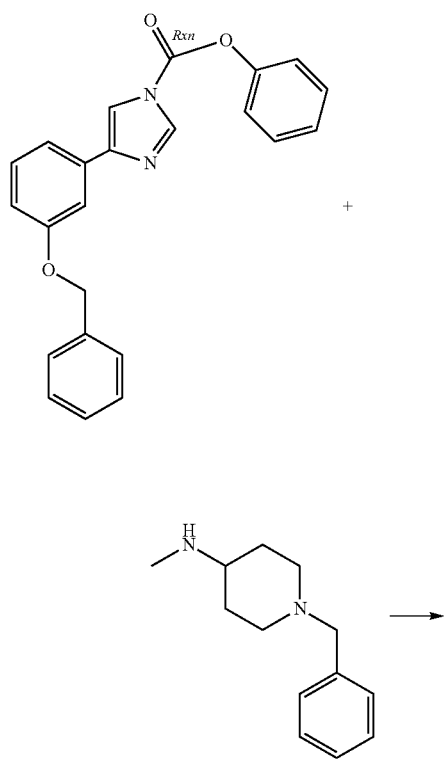
Yield (%) [41.8%]
Product Name 4-(3-(benzyloxy)phenyl)-N-(1-benzylpiperidin-4-yl)-N-methyl-1H-imidazole-1-carboxamide
NMR Solvent NA
13C NA
1H NA
Mp ND
EXAMPLE 6.54
Structure
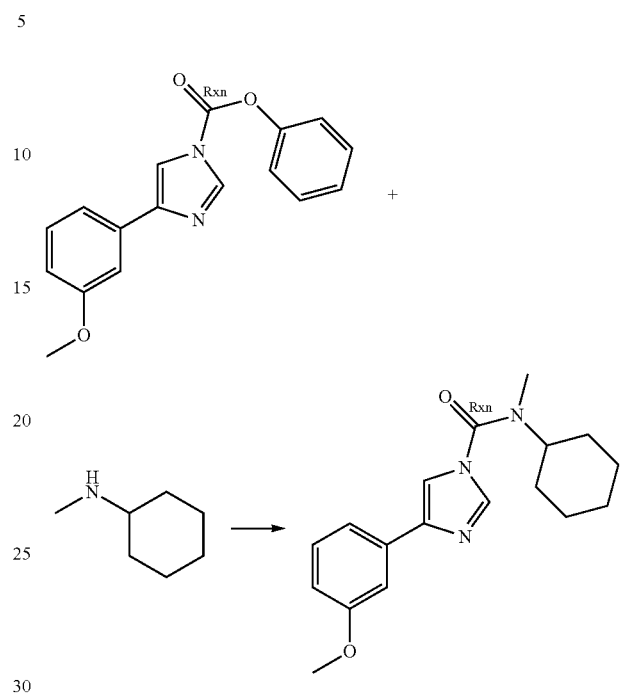
Yield (%) [60.9%]
Product Name N-cyclohexyl-4-(3-methoxyphenyl)-N-methyl-1H-imidazole-1-carboxamide
NMR Solvent CDCl3
13C 159.9, 151.3, 141.9, 136.8, 134.3, 129.7, 117.5, 113.6, 113.4, 110.1, 57.5, 55.3, 31.3, 30, 25.4, 25.2
1H NA
Mp ND
EXAMPLE 6.55
Structure
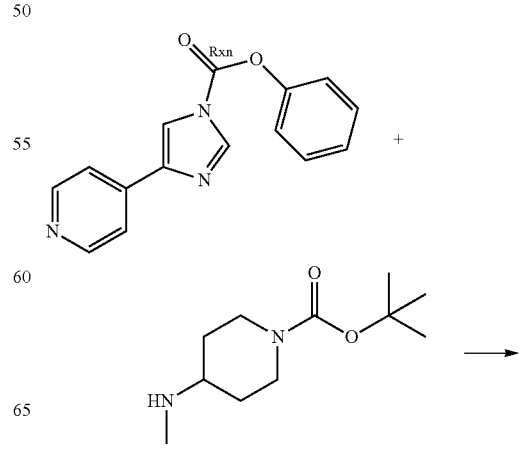

-continued

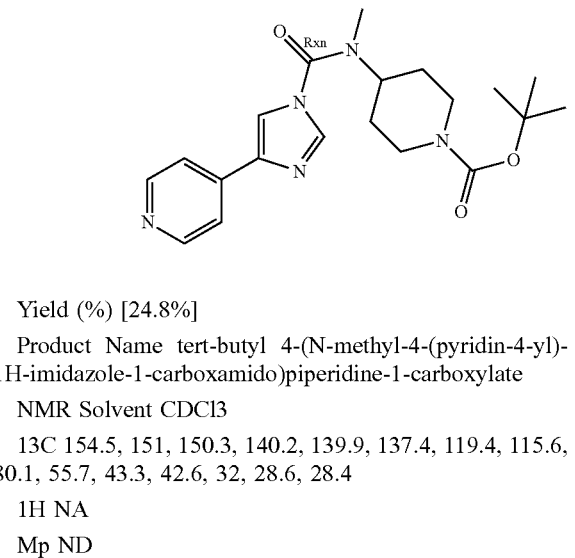

Yield (%) [24.8%]

Product Name tert-butyl 4-(N-methyl-4-(pyridin-4-yl)-1H-imidazole-1-carboxamido)piperidine-1-carboxylate NMR Solvent CDCl3

13C 154.5, 151, 150.3, 140.2, 139.9, 137.4, 119.4, 115.6, 80.1, 55.7, 43.3, 42.6, 32, 28.6, 28.4

1H NA

Mp ND

EXAMPLE 6.56

Structure

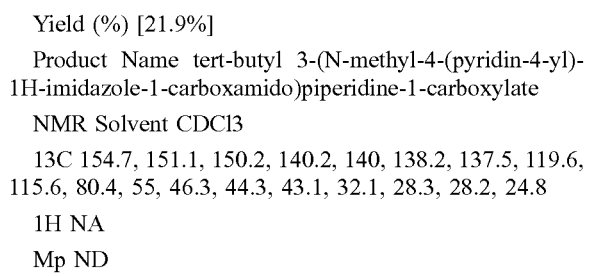

Yield (%) [21.9%]

Product Name tert-butyl 3-(N-methyl-4-(pyridin-4-yl)-1H-imidazole-1-carboxamido)piperidine-1-carboxylate NMR Solvent CDCl3

13C 154.7, 151.1, 150.2, 140.2, 140, 138.2, 137.5, 119.6, 115.6, 80.4, 55, 46.3, 44.3, 43.1, 32.1, 28.3, 28.2, 24.8

1H NA

Mp ND

EXAMPLE 6.57

Structure

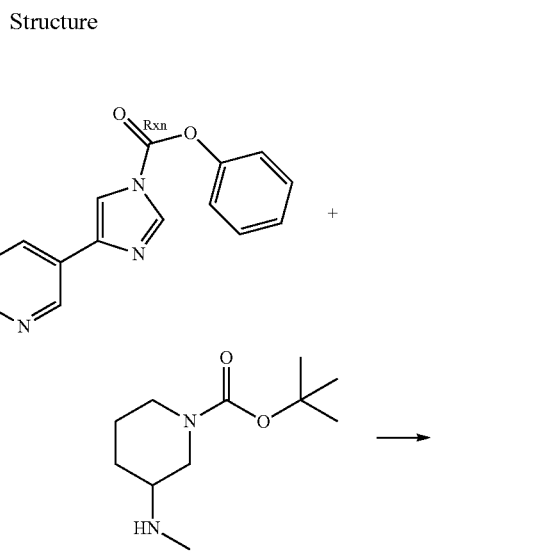

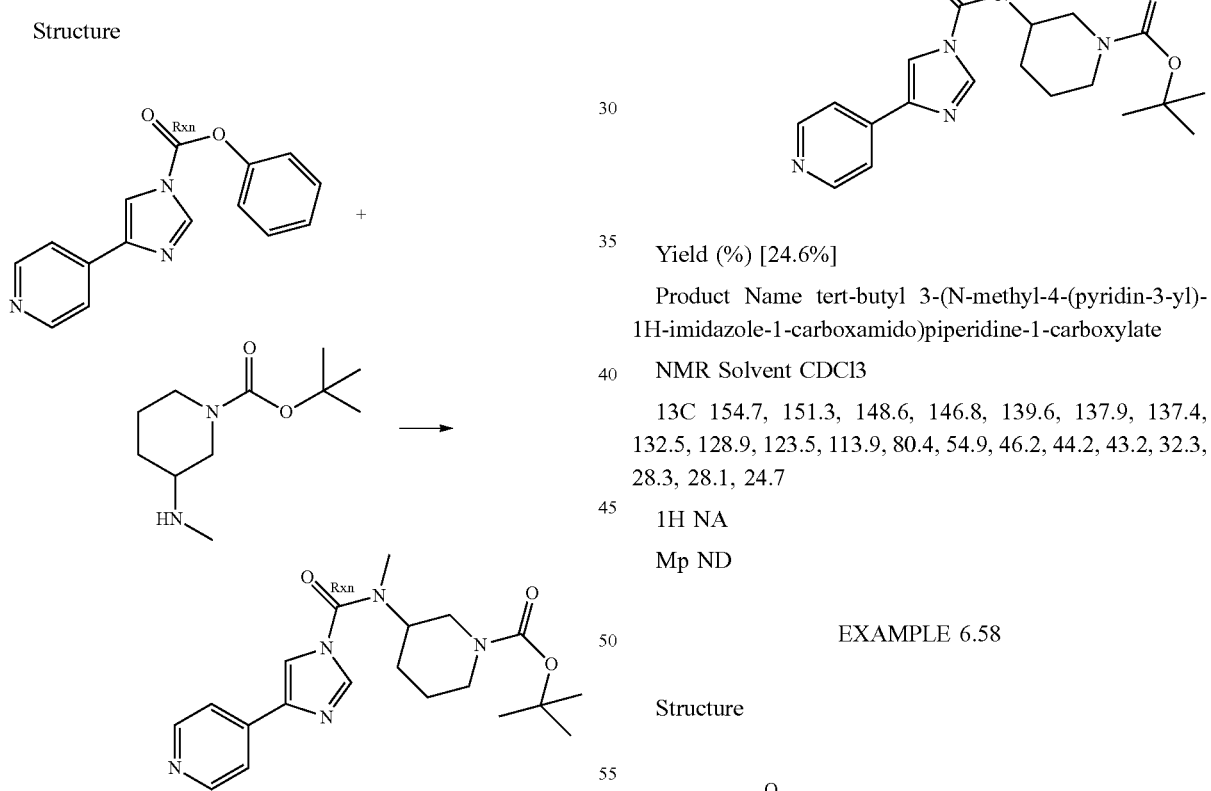

Yield (%) [24.6%]

Product Name tert-butyl 3-(N-methyl-4-(pyridin-3-yl)-1H-imidazole-1-carboxamido)piperidine-1-carboxylate NMR Solvent CDCl3

13C 154.7, 151.3, 148.6, 146.8, 139.6, 137.9, 137.4, 132.5, 128.9, 123.5, 113.9, 80.4, 54.9, 46.2, 44.2, 43.2, 32.3, 28.3, 28.1, 24.7

1H NA

Mp ND

EXAMPLE 6.58

Structure

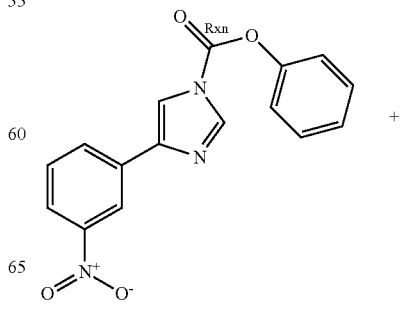

-continued

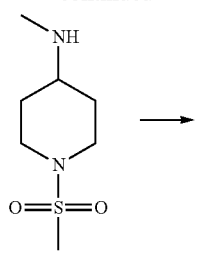

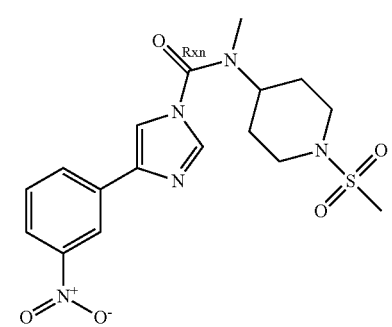

Yield (%) [39.4%]

Product Name N-methyl-N-(1-(methylsulfonyl)piperidin-4-yl)-4-(3-nitrophenyl)-1H-imidazole-1-carboxamide NMR Solvent DMSO 13C 150.9, 148.4, 138.6, 138.3, 135.2, 131, 130.3, 121.6, 118.9, 116.4, 54.5, 44.9, 34.4, 31.7, 27.6

1H NA

Mp ND

EXAMPLE 6.59

Structure

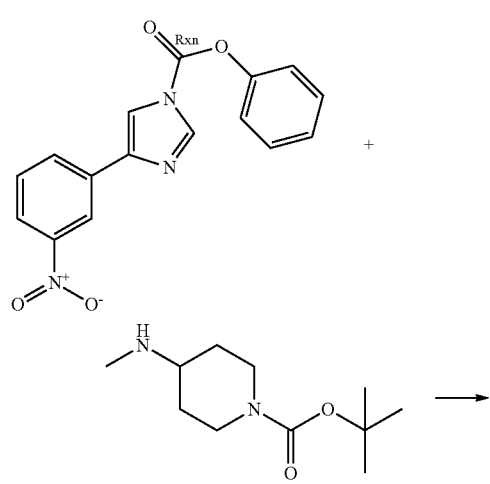

-continued

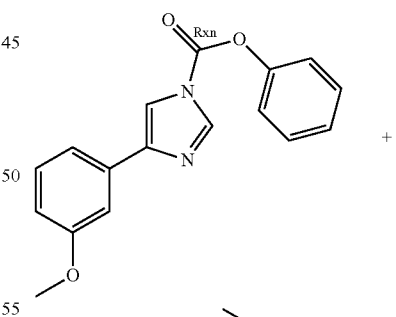

Yield (%) [21%]

Product Name tert-butyl 4-(N-methyl-4-(3-nitrophenyl)-1H-imidazole-1-carboxamido)piperidine-1-carboxylate NMR Solvent DMSO

13C NA 1H 8.66 (1H, t, J=2.0 Hz), 8.33 (1H, s), 8.30 (1H, ddd, J=1.0, 1.5, 7.7 Hz), 8.22 (1H, d, J=1.2 Hz), 8.11 (1H, ddd, J=1.0, 2.5, 8.2 Hz), 7.70 (1H, t, J=8.0 Hz), 4.05 (3H, m), 2.93 (3H, s), 2.80 (2H, m br), 1.77 (2H, d br, J=12.0 Hz), 1.68 (2H, dq, J=4.5, 12.5 Hz), 1.41 (9H, s)

Mp ND

EXAMPLE 6.60

Structure

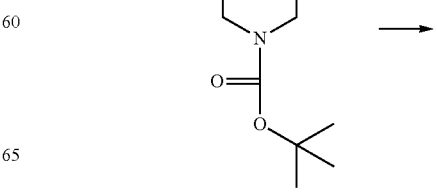

-continued

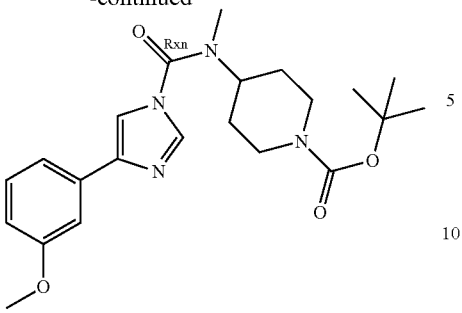

Yield (%) [19.8%]
Product Name tert-butyl 4-(4-(3-methoxyphenyl)-N-methyl-1H-imidazole-1-carboxamido)piperidine-1-carboxylate
NMR Solvent CDCl3
13C NA
1H 7.93 (1H, d, J=1.3 Hz), 7.50 (1H, d, J=1.3 Hz), 7.39 (1H, dd, J=1.5, 2.4 Hz), 7.36 (1H, md, J=7.7 Hz), 7.32 (1H, t, J=7.7 Hz), 6.86 (1H, ddd, J=1.0, 2.6, 8.0 Hz), 4.28 (2H, s br), 4.19 (1H, m), 3.88 (3H, s), 3.01 (3H, s), 2.81 (2H, s br), 1.83 (2H, d br, J=12.0 Hz), 1.75 (2H, m), 1.48 (9H, s)
Mp ND

EXAMPLE 6.61

Structure

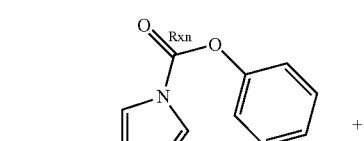

+

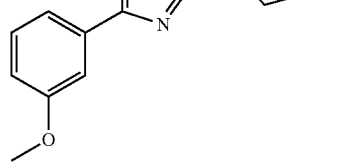

→

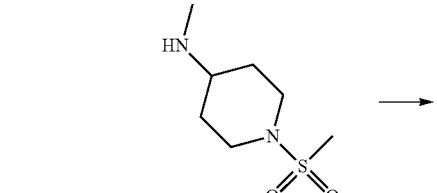

Yield (%) [21%]
Product Name 4-(3-methoxyphenyl)-N-methyl-N-(1-(methylsulfonyl)piperidin-4-yl)-1H-imidazole-1-carboxamide
NMR Solvent NA
13C NA
1H NA
Mp ND

EXAMPLE 6.62

Structure

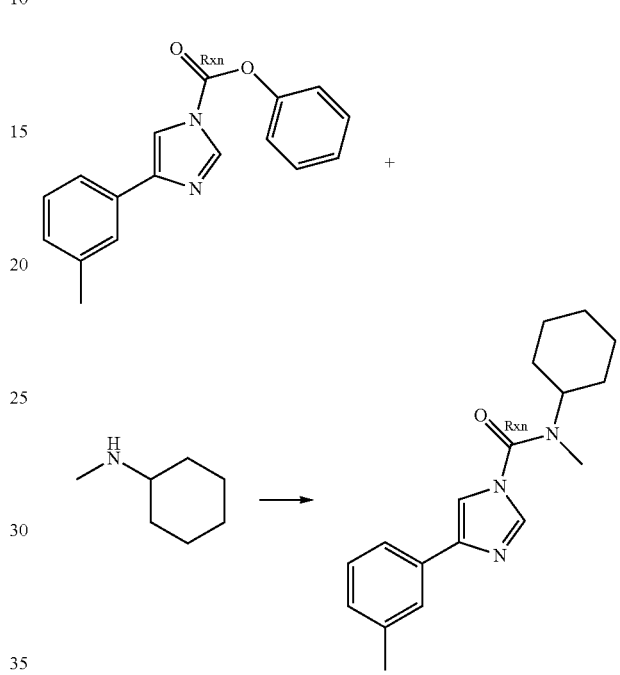

Yield (%) [45.5%]
Product Name N-cyclohexyl-N-methyl-4-m-tolyl-1H-imidazole-1-carboxamide
NMR Solvent CDCl3
13C 151.4, 142.2, 138.3, 136.9, 132.9, 128.6, 128.3, 125.8, 122.2, 113.1, 57.5, 31.3, 30, 25.4, 25.2, 21.4
1H NA
Mp ND

EXAMPLE 6.63

Structure

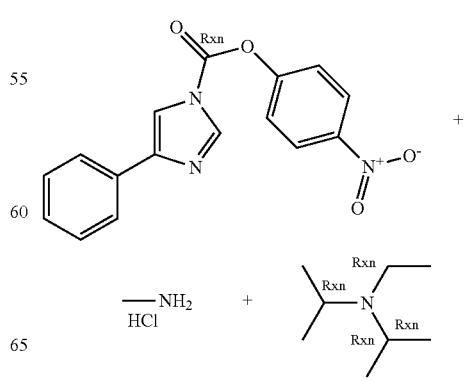

-continued

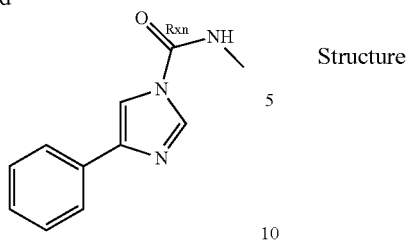

Yield (%) [12.1%]
Product Name N-methyl-4-phenyl-1H-imidazole-1-carboxamide
NMR Solvent DMSO
13C 147.7, 136.4, 136.3, 129.2, 129, 128.8, 125.2, 113.8, 27.1
1H NA
Mp ND

EXAMPLE 6.64

Structure

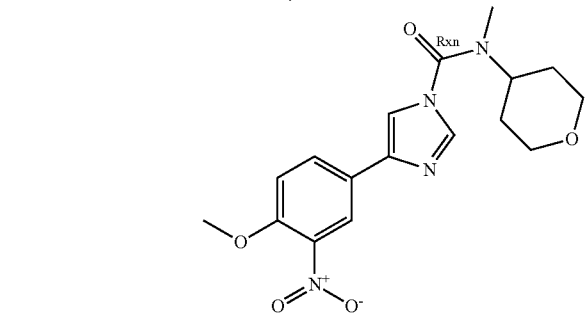

Yield (%) [48.4%]
Product Name 4-(4-methoxy-3-nitrophenyl)-N-methyl-N-(tetrahydro-2H-pyran-4-yl)-1H-imidazole-1-carboxamide
NMR Solvent CDCl3
13C 152.2, 151.2, 140, 139.7, 137.2, 130.8, 126, 122.3, 113.8, 113.2, 67, 56.6, 54.5, 31.9, 29.5
1H NA
Mp ND

EXAMPLE 6.65

Structure

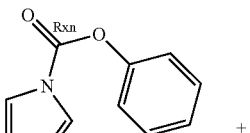

+

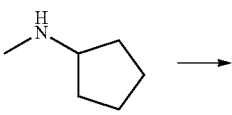

→

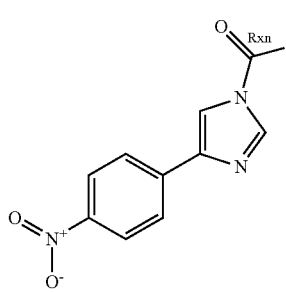

Yield (%) [25.3%]
Product Name N-cyclopentyl-N-methyl-4-(4-nitrophenyl)-1H-imidazole-1-carboxamide
NMR Solvent CDCl3
13C NA
1H 8.28 (2H, md, J=9.0 Hz), 7.96 (3H, m), 7.69 (1H, d, J=1.3 Hz), 4.45 (1H, m), 3.02 (3H, s), 1.98 (2H, m), 1.80 (2H, m), 1.73 (2H, m), 1.65 (2H, m)
Mp ND

EXAMPLE 6.66

Structure

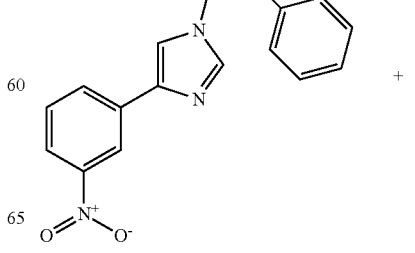

+

-continued

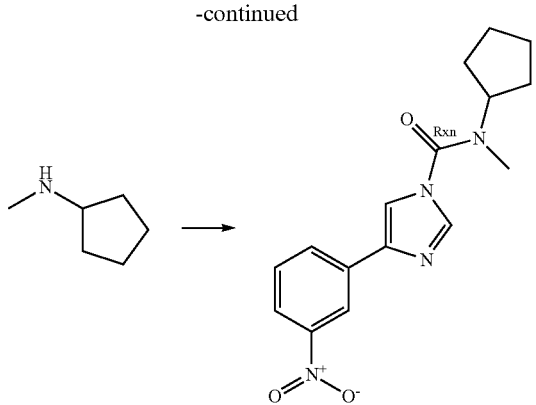

Yield (%) [44%]
Product Name N-cyclopentyl-N-methyl-4-(3-nitrophenyl)-1H-imidazole-1-carboxamide
NMR Solvent CDCl3
13C NA
1H 8.63 (1H, t, J=1.9 Hz), 8.15 (2H, m), 7.96 (1H, d, J=1.3 Hz), 7.65 (1H, d, J=1.3 Hz), 7.59 (1H, t, J=8.0 Hz), 4.46 (1H, m), 3.03 (3H s), 1.98 (2H m), 1.79 (2H, m), 1.73 (2H, m), 1.65 (2H, m)
Mp ND

EXAMPLE 6.67

Structure

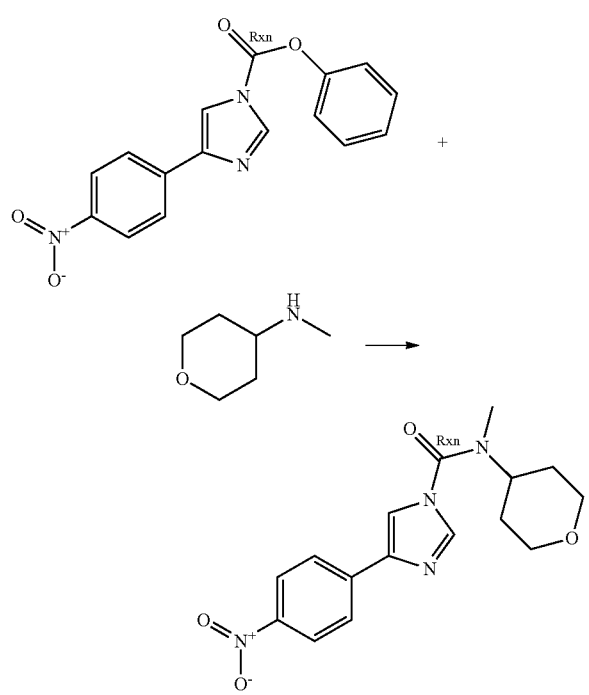

Yield (%) [27%]
Product Name [N-methyl-4-(4-nitrophenyl)-N-(tetrahydro-2H-pyran-4-yl)-1H-imidazole-1-carboxamide, tert-butyl 2-(chlorosulfonylcarbamoyl)-1H-pyrrole-1-carboxylate], [N-methyl-4-(4-nitrophenyl)-N-(tetrahydro-2H-pyran-4-yl)-1H-imidazole-1-carboxamide, tert-butyl 2-(chlorosulfonylcarbamoyl)-1H-pyrrole-1-carboxylate]
NMR Solvent DMSO
13C NA
1H 8.35 (1H, m), 8.27 (2H, m d, J=9.0 Hz), 8.25 (1H, d, J=1.2 Hz), 8.12 (2H, m d J=9.0 Hz), 4.11 (1H, m br), 3.94 (2H, dd, J=4.5, 11.3 Hz), 3.39 (2H, t, J=11.5 Hz), 2.96 (3H, s), 1.86 (2H, d q, J=4.7, 12.4 Hz), 1.70 (2H, m d, J=12.5 Hz)
Mp ND

EXAMPLE 6.68

Structure

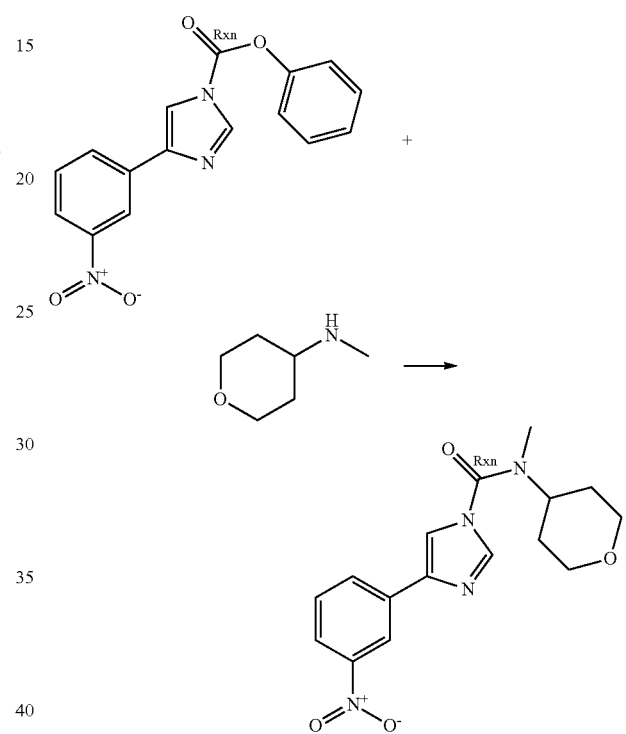

Yield (%) [21%]
Product Name [N-methyl-4-(3-nitrophenyl)-N-(tetrahydro-2H-pyran-4-yl)-1H-imidazole-1-carboxamide]
NMR Solvent DMSO
13C NA
1H 8.67 (1H, t br, J=1.9 Hz), 8.35 (1H, s), 8.30 (1H, m d, J=8.0 Hz), 8.23 (1H, d, J=1.2 Hz), 8.12 (1H, m d, J=8.2 Hz), 7.7 (1H, t, J=8.0 Hz), 4.11 (1H, s br), 3.94 (2H, dd, J=4.4, 11.5 Hz), 3.3 (2H, m), 2.97 (3H, s), 1.86 (2H, m), 1.70 (2H, m d, J=12.5 Hz)
Mp ND

EXAMPLE 7

Characterisation of Crystal Forms of Compound A

FIG. 1 shows X-ray powder diffraction (XRPD) results of a series of samples of crystal Form A of compound A. By way of comparison, FIG. 2 shows XRPD results for a series of samples, all of which were crystallised from HFIPA. The polymorph results are as follows (from top to bottom in FIG. 2):
1. Form B+Form A
2. Form B
3. Form B+Form A 4. Form B
5. Form A (trace from FIG. 1 (second from bottom therein)) for comparison The samples apparently containing Form B only were initially crystallised from a capillary experiment. Following removal from the capillary, conversion to Form A was readily observed, as shown in the samples exhibiting Form A+Form B characteristics.

All documents cited herein are hereby incorporated herein by way of reference in their entirety.

The invention claimed is:

1. A process of preparing a substituted urea compound of Formula IIa:

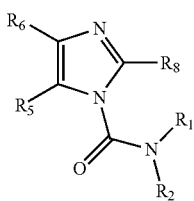

Formula IIa or a pharmaceutically acceptable salt or ester thereof, the process comprising the reaction of a carbamate of Formula IIa':

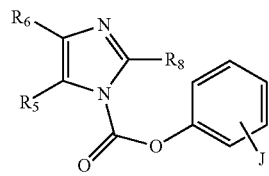

Formula IIa' with a secondary amine of the formula R1R2NH, wherein:

R1 is $C_{1-4}$ alkyl,

R2 is selected from aryl, heteroaryl, heterocyclyl, and $C_{3-10}$ cycloalkyl, each of which may optionally be substituted with one or more groups selected from R2a, halogen, OH, OR2a, OCOR2a, SH, SR2a, SCOR2a, $NH_2$, NHR2a, $NHSO_2NH_2$, $NHSO_2R2a$, NR2aCOR2b, NHC(NH)$NH_2$, NHCOR2a, NR2aR2b, COR2a, CSR2a, CN, COOH, COOR2a, $CONH_2$, CONHOH, CONHR2a, CONHOR2a, C(NOH)$NH_2$, $SO_2R2a$, $SO_3H$, $SO_2NH_2$, CONR2aR2b, and $SO_2NR2aR2b$, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the optional substitution of R2 is selected from the group consisting of $C_{1-6}$ alkyl, substituted $C_{1-6}$ alkyl, aryl, heteroaryl, $C_{3-8}$ cycloalkyl, and heterocyclyl, each may optionally be substituted with one or more groups selected from R2c, halogen, OH, OR2c, OCOR2c, SH, SR2c, SCOR2c, $NH_2$, NHR2c, $NHSO_2NH_2$, $NHSO_2R2c$, NR2cCOR2d, NHC(NH)$NH_2$, NHCOR2c, NR2cR2d, COR2c, CSR2c, CN, COOH, COOR2c, $CONH_2$, CONHOH, CONHR2c, CONHOR2c, C(NOH)$NH_2$, $SO_2R2c$, $SO_3H$, $SO_2NH_2$, CONR2cR2d, and $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, R5 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, NHC(NH)$NH_2$, NHCOR5a, NR5aR5b, COR5a, CSR5a, CN, COOH, COOR5a, $CONH_2$, CONHOH, CONHR5a, CONHOR5a, C(NOH)$NH_2$, $SO_2R5a$, $SO_3H$, $SO_2NH_2$, CONR5aR5b, and $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, R6 is selected from aryl, heteroaryl, heterocyclyl, and $C_{3-10}$ cycloalkyl, each of which may optionally be substituted with one or more groups selected from R6a, halogen, OH, OR6a, OCOR6a, SH, SR6a, SCOR6a, $NO_2$, $NH_2$, NHR6a, $NHSO_2NH_2$, $NHSO_2R6a$, NR6aCOR6b, NHC(NH)$NH_2$, NHCOR6a, NR6aR6b, COR6a, CSR6a, CN, COOH, COOR6a, $CONH_2$, CONHOH, CONHR6a, CONHOR6a, C(NOH)$NH_2$, $SO_2R6a$, $SO_3H$, $SO_2NH_2$, CONR6aR6b, and $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, and wherein, when R6 is heteroaryl or heterocyclyl, each of these moieties may optionally be substituted with one or more oxygen atoms, wherein, when the optional substitution of R6 is selected from the group consisting of $C_{1-6}$ alkyl, substituted $C_{1-6}$ alkyl, aryl, heteroaryl, $C_{3-8}$ cycloalkyl, and heterocyclyl, each may optionally be substituted with one or more groups selected from R6c, halogen, OH, OR6c, OCOR6c, SH, SR6c, SCOR6c, $NH_2$, NHR6c, $NHSO_2NH_2$, $NHSO_2R6c$, NR6cCOR6d, NHC(NH)$NH_2$, NHCOR6c, NR6cR6d, COR6c, CSR6c, CN, COOH, COOR6c, $CONH_2$, CONHOH, CONHR6c, CONHOR6c, C(NOH)$NH_2$, $SO_2R6c$, $SO_3H$, $SO_2NH_2$, CONR6cR6d, and $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, and wherein, when the substituent of R6 is heteroaryl or heterocyclyl, each of these moieties may optionally be substituted with one or more oxygen atoms, R8 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, NHC(NH)$NH_2$, NHCOR5a, NR5aR5b, COR5a, CSR5a, CN, COOH, COOR5a, $CONH_2$, CONHOH, CONHR5a, CONHOR5a, C(NOH)$NH_2$, $SO_2R5a$, $SO_3H$, $SO_2NH_2$, CONR5aR5b, and $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, and J is H or a nitro group and is attached at any available position on the phenyl ring.

2. The process according to claim 1, wherein R1 is selected from methyl and ethyl.

3. The process according to claim 1, wherein R2 is selected from fully saturated heterocyclyl and $C_{5-8}$ cycloalkyl, each of which are monocyclic and may be substituted or unsubstituted.

4. The process according to claim 3, wherein R2 is an unsubstituted cyclopentyl or unsubstituted cyclohexyl.

5. The process according to claim 3, wherein R2 is a fully saturated heterocyclyl, and wherein the heterocyclyl ring contains a single heteroatom.

6. The process according to claim 5, wherein the heterocyclyl R2 is six membered and the heteroatom in the said heterocyclyl group is at the 4-position relative to the position of attachment of the heterocyclyl group R2 to the urea nitrogen.

7. The process according to claim 6, wherein the heteroatom in heterocyclyl R2 is a nitrogen heteroatom which is substituted with a group selected from CN, $CONH_2$, $C(NOH)NH_2$, $SO_2-C_{1-4}$alkyl, $SO_2$-aryl, CO-heteroaryl, CO—$C_{1-4}$ alkyl, COO-$C_{1-4}$alkyl, COO-aryl, $C_{1-4}$ alkyl, aryl $C_{1-3}$ alkyl, heteroaryl $C_{1-3}$ alkyl, heterocyclyl $C_{1-3}$ alkyl, aryl, heteroaryl, and heterocyclyl, wherein the $C_{1-4}$ alkyl may optionally be substituted with OH, CN, COOH, the $SO_2$-aryl may optionally be substituted with a $C_{1-4}$ alkyl or $C_{1-4}$ haloalkyl, the CO-heteroaryl may optionally be substituted with a heteroaryl or halogen, the heteroaryl $C_{1-3}$ alkyl may optionally be substituted with COO—$C_{1-3}$ alkyl, and the heteroaryl may optionally be substituted with one or more halogens.

8. The process according to claim 7, wherein the nitrogen heteroatom is substituted with phenyl $C_{1-3}$ alkyl.

9. The process according to claim 1, wherein R6 is selected from monocyclic aryl, monocyclic heteroaryl, and heterocyclyl, each of which may be substituted or unsubstituted.

10. The process according to claim 9, wherein R6 is a substituted aryl, and wherein said aryl is substituted with one or more groups selected from halogen, R6a, OH, OR6a, $NH_2$, $NO_2$, $NHC(NH)NH_2$, NHR6a, NR6aR6b, C(NOH)$NH_2$, COR6a, COOH, COOR6a, $CONH_2$, CONHOH, $SO_2$R6a, and $SO_2$NR6aR6b, wherein R6a and R6b are independently selected from $C_{1-6}$ alkyl, substituted $C_{1-6}$ alkyl, aryl, heteroaryl, $C_{3-8}$ cycloalkyl and heterocyclyl, wherein, when the substituent of R6 is selected from the group consisting of $C_{1-6}$ alkyl, substituted $C_{1-6}$ alkyl, aryl, heteroaryl, $C_{3-8}$ cycloalkyl, and heterocyclyl, each substituent of R6 may optionally be substituted with one or more groups selected from OR6c, OH, and $CONH_2$, wherein R6c is selected from $C_{1-6}$ alkyl, substituted $C_{1-6}$ alkyl, aryl, heteroaryl, $C_{3-8}$ cycloalkyl and heterocyclyl, and wherein, when the substituent of R6 is heteroaryl or heterocyclyl, each of these moieties may optionally be substituted with one or more oxygen atoms.

11. The process according to claim 10, wherein R6 is a substituted aryl which is substituted with one or more groups selected from halogen, OH, $NO_2$, $C_{1-4}$ alkoxy, $CONH_2$, $C(NOH)NH_2$, CONHOH, $SO_2$—$C_{1-4}$ alkyl, heterocyclyl, and aryl, wherein the heterocyclyl may optionally be substituted with an oxygen atom and the aryl may optionally be substituted with $CONH_2$.

12. The process according to claim 9, wherein R6 is a heterocyclyl which is optionally substituted with an oxygen atom.

13. The process according to claim 9, wherein R6 is a monocyclic heteroaryl which is optionally substituted with an oxygen atom.

14. The process according to claim 1, wherein R8 is H.

15. The process according to claim 1, wherein R5 is H.

16. The process according to claim 1, wherein J is a nitro group, and is attached at any available position on the phenyl ring.

17. A process according to claim 1, wherein R2 is $C_{3-10}$ cycloalkyl.

18. A process according to claim 1, wherein R6 is heteroaryl.

19. A process according to claim 18, wherein R6 is pyridyl.

20. A process according to claim 19, wherein the urea of Formula IIa is subjected to a further step of N-oxidation of the pyridine R6.

21. A process according to claim 20, wherein the N-oxidation is conducted using a peroxyacid.

22. A process according to claim 20, wherein the substituted urea compound is 3-(1-(cyclohexyl(methyl)carbamoyl-1H-imidazol-4-yl)pyridine 1-oxide.

23. A process according to claim 1, wherein the reaction between the carbamate of Formula IIa' and the amine R1R2NH is conducted in tetrahydrofuran.

24. A process according to claim 1, wherein the carbamate of Formula IIa' is prepared by reacting a heteroaryl intermediate having a structure corresponding with Formula IIa' in which the -C(O)O-Ph-J group is replaced with H, with phenyl chloroformate, the phenyl group of which bears J as a substituent.

25. A process according to claim 24, wherein the heteroaryl intermediate is reacted with the phenyl chloroformate in tetrahydrofuran in the presence of an organic base.

26. A process according to claim 24, wherein the carbamate of Formula IIa' is not isolated before addition of the amine R1R2NH.

* * * * *